United States Patent
Kashiwamura et al.

(10) Patent No.: US 10,217,945 B2
(45) Date of Patent: Feb. 26, 2019

(54) COMPOUND, ORGANIC ELECTROLUMINESCENT ELEMENT MATERIAL USING SAME, ORGANIC ELECTROLUMINESCENT ELEMENT USING THIS MATERIAL, AND ELECTRONIC DEVICE

(71) Applicant: IDEMITSU KOSAN CO., LTD., Chiyoda-ku (JP)

(72) Inventors: Takashi Kashiwamura, Ichihara (JP); Kiyoshi Ikeda, Sodegaura (JP); Hironori Kawakami, Katsushika-ku (JP); Masahiro Kawamura, Chiba (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 286 days.

(21) Appl. No.: 14/917,832

(22) PCT Filed: Sep. 30, 2014

(86) PCT No.: PCT/JP2014/076180
§ 371 (c)(1),
(2) Date: Mar. 9, 2016

(87) PCT Pub. No.: WO2015/050140
PCT Pub. Date: Apr. 9, 2015

(65) Prior Publication Data
US 2016/0226002 A1    Aug. 4, 2016

(30) Foreign Application Priority Data
Oct. 3, 2013   (JP) .................................. 2013-208531

(51) Int. Cl.
*H01L 51/00* (2006.01)
*H01L 51/50* (2006.01)
(Continued)

(52) U.S. Cl.
CPC ........ *H01L 51/0072* (2013.01); *C07D 239/70* (2013.01); *C07D 401/14* (2013.01);
(Continued)

(58) Field of Classification Search
CPC ............. H01L 51/0072; H01L 51/0085; H01L 51/0052; H01L 51/0058; H01L 51/0054;
(Continued)

(56) References Cited

U.S. PATENT DOCUMENTS 6,835,469 B2 * 12/2004 Kwong ................ C07D 215/04
313/504
2009/0247753 A1    10/2009 Takasu et al.
(Continued)

FOREIGN PATENT DOCUMENTS

CN    103329299 A    9/2013
JP    2005-68367 A    3/2005
(Continued)

OTHER PUBLICATIONS

Xiaopeng Chen, "Four Iodine-Mediated Electrophilic Cyclizations of Rigid Parallel TriplebBonds Mapped from 1,8-Dialkynylnaphthalenes" Chem. Eur. J. 2011, 17, 8105-8114.*
(Continued)

*Primary Examiner* — Jeffrey T Barton
*Assistant Examiner* — Michael Y Sun
(74) *Attorney, Agent, or Firm* — Oblon, McClelland, Maier & Neustadt, L.L.P.

(57) ABSTRACT

A compound having a structure wherein at least 8-position or 9-position of fluoranthene is replaced by a nitrogen atom, a material for organic electroluminescence devices including the compound, and an organic electroluminescence device and an electronic equipment each including the material are provided. The compound is represented by formula (1):
(Continued)

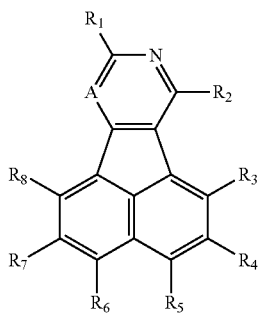

(1)

wherein A represents $CR_0$ or N; $R_0$ to $R_8$ each independently represent a hydrogen atom or a substituent; at least one selected from $R_0$ to $R_8$ represents a substituent other than hydrogen atom; and groups selected from $R_0$ to $R_8$ which are bonded to adjacent carbon atoms may be bonded to each other to form a saturated or unsaturated ring structure.

17 Claims, 3 Drawing Sheets

(51) Int. Cl.
C07D 239/70 (2006.01)
C07D 401/14 (2006.01)
C07D 403/14 (2006.01)
C07D 405/10 (2006.01)
C07D 405/14 (2006.01)
C07D 409/14 (2006.01)
C09K 11/02 (2006.01)
C09K 11/06 (2006.01)

(52) U.S. Cl.
CPC ......... C07D 403/14 (2013.01); C07D 405/10 (2013.01); C07D 405/14 (2013.01); C07D 409/14 (2013.01); C09K 11/025 (2013.01); C09K 11/06 (2013.01); H01L 51/0052 (2013.01); H01L 51/0054 (2013.01); H01L 51/0058 (2013.01); H01L 51/0061 (2013.01); H01L 51/0065 (2013.01); H01L 51/0073 (2013.01); H01L 51/0074 (2013.01); H01L 51/0085 (2013.01); H01L 51/0087 (2013.01); C09K 2211/1007 (2013.01); C09K 2211/1011 (2013.01); C09K 2211/1029 (2013.01); C09K 2211/1044 (2013.01); C09K 2211/1088 (2013.01); C09K 2211/1092 (2013.01); C09K 2211/185 (2013.01); H01L 51/0088 (2013.01); H01L 51/5012 (2013.01); H01L 51/5016 (2013.01); H01L 51/5056 (2013.01); H01L 51/5072 (2013.01)

(58) Field of Classification Search
CPC .......... H01L 51/0055; H01L 51/0067; C09K 11/025; C09K 11/06; C07D 403/14; C07D 403/04; C07D 209/86; C07D 209/60; C07D 471/04; H05B 33/14
See application file for complete search history.

(56) References Cited

U.S. PATENT DOCUMENTS

2012/0080670 A1* 4/2012 Park .................... C07D 209/82
257/40

2012/0223295 A1* 9/2012 Inoue .................... C09K 11/06
257/40
2013/0306955 A1 11/2013 Mizutani et al.
2014/0048784 A1 2/2014 Inoue et al.
2014/0107338 A1 4/2014 Ahn et al.

FOREIGN PATENT DOCUMENTS

| JP | 2009-256348 A | 11/2009 |
|---|---|---|
| WO | 2012/108388 A1 | 8/2012 |
| WO | 2012/121561 A1 | 9/2012 |
| WO | 2013/032278 A1 | 3/2013 |
| WO | 2013/094921 A1 | 6/2013 |
| WO | WO 2015-020217 A1 | 2/2015 |

OTHER PUBLICATIONS

Kausik Panda "Efficient Routes to Acenaphthylene-Fused Polycyclic Arenes/Heteroarenes andvHeterocyclic Fluoranthene Analogues" Eur. J. Org. Chem. 2005, 2045-2055.*
Combined Office Action and Search Report dated Jun. 28, 2017 in Chinese Patent Application No. 201480054335.X (with English translation of categories of cited documents).
Chen, Xiaopeng, et al., "Four Iodine-Mediated Electrophilic Cyclizations of Rigid Parallel Triple Bonds Mapped from 1,8-Dialkynylnaphthalenes", Chemistry—A European Journal, 2011, vol. 17, No. 29, pp. 8105-8114.
Some, Surajit, et al., "New protocols for the synthesis of 3,4-annulated and 4-substituted quinolines from β-bromo α, β-unsaturated aldehydes and 1-bromo-2-nitrobensene or 2-bromoacetanilide", Tetrahedron Letters, 2007, vol. 48, No. 20, pp. 3609-3612.
Tatsugi, Jiro, et al, "Unusual Products of the Leuckart Reaction of 1-Acenaphthenone", Bulletin of the Chemical Society of Japan, 1978, vol. 51, No. 4, pp. 1227-1228.
Jacquignon, P., et al, "Carcinogenic nitrogen compounds. LXXXIV. New heterocyclic compounds derived from 2-azafluorene and 7-amino-2-azafluorene", Collection of Czechoslovak Chemical Communications, 1976, vol. 41, No. 4, pp. 1208-1211.
Gubergrits, M. Ya., Polynuclear heterocyclic compounds. II. SI-S0 transition frequency, Zhurnal Obshchei Khimii, 1987, vol. 57, No. 12, pp. 2763-2765, (5 pages).
Prostakov, N. S., "Benzo[f]-3-aza-and-10-azafluoranthenes", Khimiya Geterotsiklicheskikh Soedinenii, 1977, No. 9, pp. 1245-1247, (5 pages).
Tatsugi, Jiro, et al., "3-Methyl-Oyobi 5-Methyl-1-Acenaphthenone no Ijo Leuckart Hanno", Journal of the Chemical Society of Japan, 1982, No. 5, pp. 876-879.
Tsuge, Otohiko, et al, "Studies on N-(α-Chlorobenzylidene)carbamoyl Chloride. II. Reaction of N-(α-chlorobenzylidene) carbamoyl Chloride with Active Methylene Compounds", Journal of Organic Chemistry, 1974, vol. 39, No. 9, pp. 1228-1232.
Panda, Kausik, et al, "Efficient Routes to Acenaphthylene-Fused Polycyclic Arenes/Heteroarenes and Heterocyclic Fluoranthene Analogues", European Journal of Organic Chemistry, 2005, No. 10, pp. 2045-2055.
Gatehouse, D., "Mutagenicity of 1,2-ring-fused Acenaphthenes against S. typhimurium TA1537 and TA1538: Structure-Activity Relationships", Mutation Research, Genetic Toxicology Testing, 1980, vol. 78, No. 2, pp. 121-135.
International Search Report dated Dec. 22, 2014 for PCT/JP2014/076180 filed on Sep. 30, 2014.
Office Action dated Jun. 5, 2018 in Japanese Patent Application No. 2015-540513 (with English language translation) citing document AO therein, 9 pages.
Office Action dated Aug. 21, 2018 in corresponding Japanese Patent Application No. 2015-540513 (with English Translation), 7 pages.

* cited by examiner

COMPOUND, ORGANIC ELECTROLUMINESCENT ELEMENT MATERIAL USING SAME, ORGANIC ELECTROLUMINESCENT ELEMENT USING THIS MATERIAL, AND ELECTRONIC DEVICE

TECHNICAL FIELD

The present invention relates to compounds, materials for organic electroluminescence devices comprising the compounds, and organic electroluminescence devices and electronic equipment each employing the materials.

BACKGROUND ART

An organic electroluminescence device (also referred to as "organic EL device") made of organic substances is promising for use as an inexpensive large-area, solid-state full-color display device and many efforts have been directed to the development thereof. An organic EL device is generally composed of a light emitting layer and a pair of opposite electrodes sandwiching the light emitting layer. When a voltage is applied between the pair of electrodes, electrons are injected from the cathode and holes are injected from the anode. The injected electrons recombine with the injected holes in the light emitting layer to form excited states. When the excited states return to the ground state, the energy is released as light.

Many researches have been made on the applications of organic EL device to display, etc. because of its possibility of a wide selection of emission colors by using various emitting materials in a light emitting layer. Particularly, the research on the materials which emit three primary red, green, and blue colors has been made most actively, and the intensive research has been made to improve their properties.

Patent Literature 1 discloses to use a compound having a fluoranthene skeleton in which the carbon atom(s) at 7-position and/or 10-position is(are) replaced by a nitrogen atom or nitrogen atoms in an organic EL device.

However, a useful material is still required to be developed in the field of organic EL device to further improve the device performance.

CITATION LIST

Patent Literature

PATENT LITERATURE 1: JP 2005-68367A

SUMMARY OF INVENTION

Technical Problem

The present invention has been made to solve the above problem and an object of the invention is to provide a compound useful as a material for organic EL devices and an organic EL device employing the compound.

Solution to Problem

As a result of extensive research in view of achieving the above object, the inventors have found that a compound having a structure wherein 8-position or 9-position of fluoranthene is replaced by a nitrogen atom is effective as a material for organic EL devices for improving device performance.

In an aspect of the present invention, a compound described below is provided:
(1) a compound represented by formula (1):

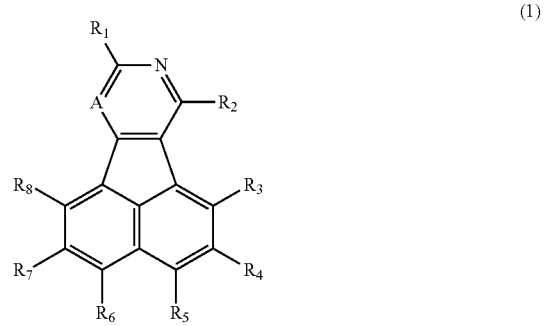

(1)

wherein:
A represents $CR_0$ or N;
$R_0$ to $R_8$ each independently represent a hydrogen atom or a substituent, and at least one selected from $R_0$ to $R_8$ represents a substituent other than hydrogen atom; and
groups selected from $R_0$ to $R_8$ which are bonded to adjacent carbon atoms may be bonded to each other to form a saturated or unsaturated ring structure;
(2) a material for organic electroluminescence devices comprising the compound mentioned above:
(3) an organic electroluminescence device comprising an organic thin film layer between a cathode and an anode, wherein the organic thin film layer comprises one or more layers and comprises a light emitting layer, and at least one layer of the organic thin film layer comprises the compound mentioned above; and
(4) an electronic equipment comprising the organic electroluminescence device mentioned above.

Advantageous Effects of Invention

The present invention provides a novel material useful for producing organic EL devices and an organic EL device employing the material.

DESCRIPTION OF EMBODIMENTS

Figure 1:
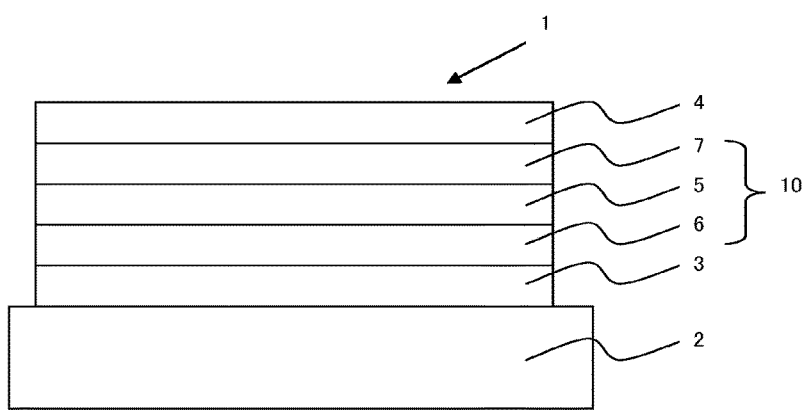
FIG. 1 is a schematic illustration of the structure of an organic EL device in an aspect of the present invention.

The term "a to b carbon atoms" referred to by "a substituted or unsubstituted group X having a to b carbon atoms" used herein is the number of carbon atoms of the unsubstituted group X and does not include any carbon atom in the substituent of the substituted group X.

When adjacent groups are bonded to each other to form a ring, any carbon atom of a group having a to b carbon atoms may be bonded to any carbon atom of another group having a to b carbon atoms.

The number of "ring carbon atoms" referred to herein means the number of the carbon atoms included in the atoms which are members forming the ring itself of a compound in which a series of atoms or molecules is bonded to form the ring, for example, a monocyclic compound, a fused ring compound, a cross-linked compound, a spiro ring compound, a carbocyclic compound, and a heterocyclic compound. If the ring has a substituent, the carbon atom in the substituent is not included in the ring carbon atom. The same applies to the number of "ring carbon atom" described below, unless otherwise noted.

The number of "ring atom" referred to herein means the number of the atoms which are members forming the ring itself of a compound in which a series of atoms or molecules is bonded to form the ring, for example, a monocyclic compound, a fused ring compound, a cross-linked compound, a spiro ring compound, a carbocyclic compound, and a heterocyclic compound. The atom not forming the ring, for example, hydrogen atom(s) for saturating the valence of the atom which forms the ring, and the atom in a substituent on the ring are not counted as the ring atom. The same applies to the number of "ring atoms" described below, unless otherwise noted.

The definition of "hydrogen atom" used herein includes isotopes different in the neutron numbers, i.e., light hydrogen (protium), heavy hydrogen (deuterium), and tritium.

The optional substituent referred to by "substituted or unsubstituted" used herein is preferably selected from the group consisting of an alkyl group having 1 to 50, preferably 1 to 18, more preferably 1 to 8 carbon atoms; a cycloalkyl group having 3 to 50, preferably 3 to 10, more preferably 3 to 8, still more preferably 5 or 6 ring carbon atoms; an aryl group having 6 to 50, preferably 6 to 25, more preferably 6 to 18 ring carbon atoms; an aralkyl group having 7 to 51, preferably 7 to 30, more preferably 7 to 20 carbon atoms which includes an aryl group having 6 to 50, preferably 6 to 25, more preferably 6 to 18 ring carbon atoms; an amino group; a mono- or disubstituted amino group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; an alkoxy group having an alkyl group having 1 to 50, preferably 1 to 18, more preferably 1 to 8 carbon atoms; an aryloxy group having an aryl group having 6 to 50, preferably 6 to 25, more preferably 6 to 18 ring carbon atoms; a mono-, di- or tri-substituted silyl group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; a heteroaryl group having 5 to 50, preferably 5 to 24, more preferably 5 to 13 ring atoms; a haloalkyl group having 1 to 50, preferably 1 to 18, more preferably 1 to 8 carbon atoms; a halogen atom selected from a fluorine atom, a chlorine atom, a bromine atom and an iodine atom; a cyano group; a nitro group; a substituted sulfonyl group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; a di-substituted phosphoryl group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; an alkylsulfonyloxy group; an arylsulfonyloxy group; an alkylcarbonyloxy group; an arylcarbonyloxy group; a boron-containing group; a zinc-containing group; a tin-containing group; a silicon-containing group; a magnesium-containing group; a lithium-containing group; a hydroxyl group; an alkyl-substituted or aryl-substituted carbonyl group; a carboxyl group; a vinyl group; a (meth) acryloyl group; an epoxy group; and an oxetanyl group.

These groups may have a substituent selected from the above optional substituents.

Compound

The compound in an aspect of the invention is represented by formula (1):

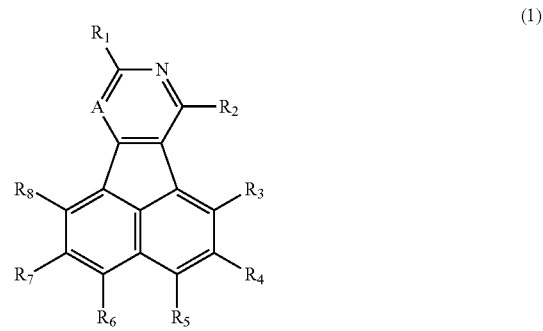

(1)

wherein:

A represents $CR_0$ or N;

$R_0$ to $R_8$ each independently represent a hydrogen atom or a substituent, and at least one selected from $R_0$ to $R_8$ represents a substituent other than hydrogen atom; and groups selected from $R_0$ to $R_8$ which are bonded to adjacent carbon atoms may be bonded to each other to form a saturated or unsaturated ring structure.

In formula (1), each substituent represented by $R_0$ to $R_8$ is independently selected preferably from the following group consisting of a substituted or unsubstituted alkyl group having 1 to 50, preferably 1 to 18, more preferably 1 to 8 carbon atoms; a substituted or unsubstituted cycloalkyl group having 3 to 50, preferably 3 to 10, more preferably 3 to 8 ring carbon atoms; a substituted or unsubstituted aryl group (also referred to as "aromatic hydrocarbon group") having 6 to 50, preferably 6 to 25, more preferably 6 to 18 ring carbon atoms; a substituted or unsubstituted aralkyl group having 7 to 61, preferably 7 to 25, more preferably 7 to 18 carbon atoms; amino group; a mono- or di-substituted amino group, wherein the substituent is selected from a substituted or unsubstituted alkyl group having 1 to 50, preferably 1 to 18, more preferably 1 to 8 carbon atoms and a substituted or unsubstituted aryl group having 6 to 50, preferably 6 to 25, more preferably 6 to 18 ring carbon atoms; a substituted or unsubstituted alkoxy group having an alkyl group having 1 to 50, preferably 1 to 18, more preferably 1 to 8 carbon atoms; a substituted or unsubstituted cycloalkoxy group having 3 to 50, preferably 3 to 10, more preferably 3 to 8 ring carbon atoms; a substituted or unsubstituted aryloxy group having 6 to 50, preferably 6 to 25, more preferably 6 to 18 ring carbon atoms; a substituted or unsubstituted alkylthio group having 1 to 50, preferably 1 to 18, more preferably 1 to 8 carbon atoms; a substituted or unsubstituted arylthio group having 6 to 50, preferably 6 to 25, more preferably 6 to 18 ring carbon atoms; a mono-, di- or tri-substituted silyl group, wherein the substituent is selected from a substituted or unsubstituted alkyl group having 1 to 50, preferably 1 to 18, more preferably 1 to 8 carbon atoms and a substituted or unsubstituted aryl group having 6 to 50, preferably 6 to 25, more preferably 6 to 18 ring carbon atoms; a substituted or unsubstituted heteroaryl group (also referred to as "heterocyclic group") having 5 to 60, preferably 5 to 30, more preferably 5 to 26 ring atoms; a substituted or unsubstituted haloalkyl group having 1 to 50, preferably 1 to 18, more preferably 1 to 8 carbon atoms; a halogen atom, a cyano group; a nitro group; a substituted sulfonyl group, wherein the substituent is selected from a substituted or unsubstituted alkyl group having 1 to 50, preferably 1 to 18, more preferably 1 to 8 carbon atoms and a substituted or unsubstituted aryl group having 6 to 50, preferably 6 to 25, more preferably 6 to 18 ring carbon atoms; a di-substituted phosphoryl group, wherein the substituent is selected from a substituted or unsubstituted alkyl group having 1 to 50, preferably 1 to 18, more preferably 1 to 8 carbon atoms and a substituted or unsubstituted aryl group having 6 to 60, preferably 6 to 25, more preferably 6 to 18 ring carbon atoms; an alkylsulfonyloxy group; an arylsulfonyloxy group; an alkylcarbonyloxy group; an arylcarbonyloxy group; a boron-containing group; a zinc-containing group; a tin-containing group; a silicon-containing group; a magnesium-containing group; a lithium-containing group; a hydroxyl group; an alkyl-substituted or aryl-substituted carbonyl group; a carboxyl group; a vinyl group; a (meth)acryloyl group; an epoxy group; and an oxetanyl group.

Examples of the alkyl group referred to in the embodiment of the invention include a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), an octyl group (inclusive of isomeric groups), a nonyl group (inclusive of isomeric groups), a decyl group (inclusive of isomeric groups), an undecyl group (inclusive of isomeric groups), a dodecyl group (inclusive of isomeric groups), a tridecyl group, a tetradecyl group, an octadecyl group, a tetracosanyl group, and a tetracontanyl group. These groups may have a substituent.

More preferred are a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), an octyl group (inclusive of isomeric groups), a nonyl group (inclusive of isomeric groups), a decyl group (inclusive of isomeric groups), an undecyl group (inclusive of isomeric groups), a dodecyl group (inclusive of isomeric groups), a tridecyl group, a tetradecyl group, and an octadecyl group. These groups may have a substituent.

Still more preferred are a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), and an octyl group (inclusive of isomeric groups). These groups may have a substituent.

Examples of the cycloalkyl group referred to in the embodiment of the invention include a cyclopropyl group, a cyclobutyl group, a cyclopentyl group, a cyclohexyl group, a cycloheptyl group, a cyclooctyl group, and an adamantyl group. These groups may have a substituent.

More preferred are a cyclopentyl group and a cyclohexyl group. These groups may have a substituent.

Examples of the aryl group referred to in the embodiment of the invention include a phenyl group, a naphthyl group, a naphthylphenyl group, a biphenylyl group, a terphenylyl group, a quarterphenylyl group, a quinquephenylyl group, an acenaphthylenyl group, an anthryl group, a benzanthryl group, an aceanthryl group, a phenanthryl group, a benzophenanthryl group, a phenalenyl group, a fluorenyl group, a 9,9'-spirobifluorenyl group, a benzofluorenyl group, a dibenzofluorenyl group, a picenyl group, a pentaphenyl group, a pentacenyl group, a pyrenyl group, a chrysenyl group, a benzochrysenyl group, a s-indacenyl group, an as-indacenyl group, a fluoranthenyl group, a benzofluoranthenyl group, a tetracenyl group, a triphenylenyl group, a benzotriphenylenyl group, a perylenyl group, a coronyl group, a dibenzanthryl group, a 9,9-dimethylfluorenyl group, and a 9,9-diphenylfluorenyl group. These groups may have a substituent.

More preferred are a phenyl group, a naphthyl group, a biphenylyl group, a terphenylyl group, a phenanthryl group, a benzophenanthryl group, a fluorenyl group, a 9,9'-spirobifluorenyl group, a benzofluorenyl group, a dibenzofluorenyl group, a chrysenyl group, a benzochrysenyl group, a s-indacenyl group, an as-indacenyl group, a triphenylenyl group, a benzotriphenylenyl group, an anthryl group, a 9,9-dimethylfluorenyl group, and a 9,9-diphenylfluorenyl group. These groups may have a substituent.

Still more preferred are a phenyl group, a biphenylyl group, a terphenylyl group, a naphthyl group, a phenanthryl group, a fluorenyl group, a 9,9'-spirobifluorenyl group, a chrysenyl group, a triphenylenyl group, a 9,9-dimethylfluorenyl group, and a 9,9-diphenylfluorenyl group. These groups may have a substituent.

The heteroaryl group referred to in the embodiment of the invention includes at least one, preferably 1 to 5, more preferably 1 to 3, and still more preferably 1 or 2 hetero atoms, for example, a nitrogen atom, a sulfur atom, an oxygen atom, and a phosphorus atom. Examples of the heteroaryl group include a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, a tetrazolyl group, an indolyl group, an isoindolyl group, a benzofuranyl group, an isobenzofuranyl group, a benzothiophenyl group, an isobenzothiophenyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a dibenzothiophenyl group, a carbazolyl group, a bicarbazolyl group, a phenanthridinyl group, an acridinyl group, a phenanthrolinyl group, a phenazinyl group, a phenothiazinyl group, a phenoxazinyl group, an azatriphenylenyl group, a diazatriphenylenyl group, a xanthenyl group, an azacarbazolyl group, an azadibenzofuranyl group, an azadibenzothiophenyl group, a benzofuranobenzothiophenyl group, a benzothienobenzothiophenyl group, a dibenzofuranonaphthyl group, a dibenzothienonaphthyl group, a dinaphthothienothiophenyl group, and a dinaphto[2',3':2,3:2',3':6,7]carbazolyl group. These groups may have a substituent.

More preferred are a pyridyl group, a pyridazinyl group, a pyrimidinyl group, a pyrazinyl group, a triazinyl group, an imidazolyl group, an indolyl group, an isoindolyl group, a benzofuranyl group, an isobenzofuranyl group, a benzothiophenyl group, an isobenzothiophenyl group, an indolizinyl group, a quinolizinyl group, a quinolyl group, an isoquinolyl group, a quinazolinyl group, a quinoxalinyl group, a benzimidazolyl group, a benzoxazolyl group, a benzothiazolyl group, a benzisoxazolyl group, a benzisothiazolyl group, a dibenzofuranyl group, a dibenzothiophenyl group, a carbazolyl group, a bicarbazolyl group, a phenanthridinyl group, an acridinyl group, a phenanthrolinyl group, an azatriphenylenyl group, a diazatriphenylenyl group, a xanthenyl group, an azacarbazolyl group, an azadibenzofuranyl group, and an azadibenzothiophenyl group. These groups may have a substituent.

Still more preferred are a pyridyl group, a pyrimidinyl group, a triazinyl group, a benzofuranyl group, an isobenzofuranyl group, a quinolyl group, an isoquinolyl group, a quinazolinyl group, a benzothiophenyl group, an isobenzothiophenyl group, an indolizinyl group, a dibenzofuranyl group, a dibenzothiophenyl group, a carbazolyl group, a bicarbazolyl group, an azatriphenylenyl group, a diazatriphenylenyl group, a xanthenyl group, an azacarbazolyl group, an azadibenzofuranyl group, and an azadibenzothiophenyl group. These groups may have a substituent.

Examples of the aralkyl group referred to in the embodiment of the invention include those having the aryl group having 6 to 60 ring carbon atoms mentioned above. These groups may have a substituent. Preferred are aralkyl groups each having the aryl group having 6 to 25 ring carbon atoms mentioned above, and more preferred are aralkyl groups each having the aryl group having 6 to 18 ring carbon atoms mentioned above. These groups may have a substituent.

Examples of the mono- or di-substituted amino group referred to in the embodiment of the invention include those having a substituent selected from the alkyl group having 1 to 50 carbon atoms and the aryl group having 6 to 60 ring carbon atoms, each described above, with a di-substituted amino group being preferred and a di-substituted amino group having a substituent selected from the aryl group mentioned above being more preferred. These groups may have a substituent. More preferred are mono- or di-substituted amino groups each having a substituent selected from the alkyl group having 1 to 18 carbon atoms and the aryl group having 6 to 25 ring carbon atoms, each described above. These groups may have a substituent. Still more preferred are mono- or di-substituted amino groups each having a substituent selected from the alkyl group having 1 to 8 carbon atoms and the aryl group having 6 to 18 ring carbon atoms, each described above. These groups may have a substituent.

Examples of the alkoxy group referred to in the embodiment of the invention include those having the alkyl group having 1 to 50 carbon atoms mentioned above. These groups may have a substituent. More preferred are alkoxy groups each having the alkyl group having 1 to 18 carbon atoms mentioned above. These groups may have a substituent. Still more preferred are alkoxy groups each having the alkyl group having 1 to 8 carbon atoms mentioned above. These groups may have a substituent.

Examples of the cycloalkoxy group referred to in the embodiment of the invention include those having the cycloalkyl group having 3 to 50 carbon atoms mentioned above. These groups may have a substituent.

Examples of the aryloxy group referred to in the embodiment of the invention include those having the aryl group having 6 to 60 ring carbon atoms mentioned above. These groups may have a substituent. More preferred are aryloxy groups each having the aryl group having 6 to 25 ring carbon atoms mentioned above. These groups may have a substituent. Still more preferred are aryloxy groups each having the aryl group having 6 to 18 ring carbon atoms mentioned above, with a phenoxy group being preferred. These groups may have a substituent.

Examples of the alkylthio group referred to in the embodiment of the invention include those having the alkyl group having 1 to 50 carbon atoms mentioned above. These groups may have a substituent. More preferred are alkylthio groups each having the alkyl group having 1 to 18 carbon atoms mentioned above. These groups may have a substituent. Still more preferred are alkylthio groups each having the alkyl group having 1 to 8 carbon atoms mentioned above. These groups may have a substituent.

Examples of the arylthio group referred to in the embodiment of the invention include those having the aryl group having 6 to 60 ring carbon atoms mentioned above. These groups may have a substituent. More preferred are arylthio groups each having the aryl group having 6 to 25 ring carbon atoms mentioned above. These groups may have a substituent. Still more preferred are arylthio groups each having the aryl group having 6 to 18 ring carbon atoms mentioned above. These groups may have a substituent.

Examples of the mono-, di-, or trisubstituted silyl group referred to in the embodiment of the invention include those having a substituent selected from the alkyl group having 1 to 50 carbon atoms and the aryl group having 6 to 60 ring carbon atoms, each described above. These groups may have a substituent. More preferred are mono-, di-, or trisubstituted silyl groups each having a substituent selected from the alkyl group having 1 to 18 carbon atoms and the aryl group having 6 to 25 ring carbon atoms, each described above. These groups may have a substituent. Still more preferred are mono-, di-, or trisubstituted silyl groups each having a substituent selected from the alkyl group having 1 to 8 carbon atoms and the aryl group having 6 to 18 ring carbon atoms, each described above. These groups may have a substituent. Specific examples thereof include a trimethylsilyl group, a triethylsilyl group, a t-butyldimethylsilyl group, a vinyldimethylsilyl group, a propyldimethylsilyl group, an isopropyldimethylsilyl group, a triphenylsilyl group, a phenyldimethylsilyl group, a t-butyldiphenylsilyl group, and a tritolylsilyl group. These groups may have a substituent.

Examples of the haloalkyl group referred to in the embodiment of the invention include those derived from the alkyl group having 1 to 50 carbon atoms mentioned above by replacing one or more hydrogen atoms with a halogen atom, such as a fluorine atom, a chlorine atom, a bromine atom and an iodine atom. These groups may have a substituent. More preferred are those derived from the alkyl group having 1 to 18 carbon atoms mentioned above by replacing one or more hydrogen atoms with the halogen atom. These groups may have a substituent. Still more preferred are those derived from the alkyl group having 1 to 8 carbon atoms mentioned above by replacing one or more hydrogen atoms with the halogen atom. These groups may have a substituent. Specific examples include a trifluoromethyl group, a pentafluoroethyl group, and a heptafluoropropyl group.

Examples of the sulfonyl group referred to in the embodiment of the invention include those having a substituent selected from the alkyl group having 1 to 50 carbon atoms and the aryl group having 6 to 60 ring carbon atoms, each described above. These groups may have a substituent. More preferred are sulfonyl groups each having a substituent selected from the alkyl group having 1 to 18 carbon atoms and the aryl group having 6 to 25 ring carbon atoms, each described above. These groups may have a substituent. Still more preferred are sulfonyl groups each having a substituent selected from the alkyl group having 1 to 8 carbon atoms and the aryl group having 6 to 18 ring carbon atoms, each described above. These groups may have a substituent.

Examples of the di-substituted phosphoryl group referred to in the embodiment of the invention include those having a substituent selected from the alkyl group having 1 to 50 carbon atoms and the aryl group having 6 to 60 ring carbon atoms, each described above. These groups may have a substituent. More preferred are di-substituted phosphoryl groups each having a substituent selected from the alkyl group having 1 to 18 carbon atoms and the aryl group having 6 to 25 ring carbon atoms, each described above. These groups may have a substituent. Still more preferred are di-substituted phosphoryl groups each having a substituent selected from the alkyl group having 1 to 8 carbon atoms and the aryl group having 6 to 18 ring carbon atoms, each described above. These groups may have a substituent.

Examples of the alkylsulfonyloxy group, the arylsulfonyloxy group, the alkylcarbonyloxy group, the arylcarbonyloxy group, and the alkyl- or aryl-substituted carbonyl group include those having a substituent selected from the alkyl group and the aryl group mentioned above.

Of the above substituents, preferred are a fluorine atom, a cyano group, the alkyl group, the aryl group, the heteroaryl group, the di-substituted amino group, and a trifluoromethyl group, a pentafluoroethyl group, and a heptafluoropropyl group.

In a preferred embodiment of the invention, $R_0$ to $R_8$ each independently represent a hydrogen atom, a substituted or unsubstituted alkyl group having 1 to 50 carbon atoms, a substituted or unsubstituted cycloalkyl group having 3 to 50 ring carbon atoms, a substituted or unsubstituted alkoxy group having 1 to 50 carbon atoms, a substituted or unsubstituted aryl group having 6 to 60 ring carbon atoms, a substituted or unsubstituted heteroaryl group having 5 to 60 ring atoms, a substituted or unsubstituted amino group, a substituted or unsubstituted aryloxy group having 6 to 60 ring carbon atoms, a substituted silyl group, a substituted or unsubstituted haloalkyl group having 1 to 50 carbon atoms, a halogen atom, a cyano group, or a nitro group. Examples of these groups are as described above.

In the embodiment of the invention, the substituent other than hydrogen atom which is represented by at least one selected from $R_0$ to $R_8$ is preferably a substituted or unsubstituted aryl group having 6 to 60 ring carbon atoms or a substituted or unsubstituted heteroaryl group having 5 to 60 ring atoms, and more preferably a substituted or unsubstituted phenyl group, a substituted or unsubstituted naphthyl group, a substituted or unsubstituted anthracenyl group, a substituted or unsubstituted phenanthryl group, a substituted or unsubstituted fluorenyl group, a substituted or unsubstituted dibenzofuranyl group, a substituted or unsubstituted dibenzothiophenyl group, a substituted or unsubstituted carbazolyl group, or an aza-substituted analogue thereof.

In the embodiment of the invention, two selected from $R_0$ to $R_8$ each preferably represent the substituent other than hydrogen atom mentioned above.

The substituent other than hydrogen atom represented by two selected from $R_0$ to $R_8$ is preferably a substituted or unsubstituted aryl group having 6 to 60 ring carbon atoms or a substituted or unsubstituted heteroaryl group having 5 to 60 ring atoms, and more preferably a substituted or unsubstituted phenyl group, a substituted or unsubstituted naphthyl group, a substituted or unsubstituted anthracenyl group a substituted or unsubstituted phenanthryl group, a substituted or unsubstituted fluorenyl group, a substituted or unsubstituted dibenzofuranyl group, a substituted or unsubstituted dibenzothiophenyl group, a substituted or unsubstituted carbazolyl group, or an aza-substituted analogue thereof.

Examples of the ring which may be formed by the adjacent groups selected from $R_0$ to $R_8$ of formula (1) which are bonded to each other include a substituted or unsubstituted aryl group having 6 to 60 ring carbon atoms or a substituted or unsubstituted heteroaryl group having 5 to 60 ring atoms.

Examples of the substituted or unsubstituted aryl group having 6 to 60 ring carbon atoms include those mentioned above with respect to the substituent represented by $R_0$ to $R_8$.

Examples of the substituted or unsubstituted heteroaryl group having 5 to 60 ring atoms include those mentioned above with respect to the substituent represented by $R_0$ to $R_8$.

In the embodiment of the invention, the substituent other than hydrogen atom represented by at least one selected from $R_0$ to $R_8$ of formula (1) is preferably represented by formula (a), more preferably represented by formula (b), and still more preferably represented by formula (c):

wherein:

* represents a bonding site to the carbon atom in formula (1) to which each of $R_0$ to $R_8$ is bonded;

$L_0$ and $L_1$ each independently represent a single bond, an arylene group having 6 to 60 ring carbon atoms, or a heteroarylene group having 5 to 60 ring atoms;

$L_2$ represents a hydrogen atom, an aryl group having 6 to 60 ring carbon atoms or a heteroaryl group having 5 to 60 ring atoms;

$L_0$, $L_1$ and $L_2$ may have a substituent independently selected from an alkyl group having 1 to 20 carbon atoms, a cycloalkyl group having 3 to 18 ring carbon atoms, an alkoxy group having 1 to 20 carbon atoms, a cycloalkoxy group having 3 to 20 ring carbon atoms, an aryloxy group having 6 to 18 ring carbon atoms, an amino group, a silyl group, a fluorine atom, a cyano group, an aryl group having 6 to 18 ring carbon atoms, and a heteroaryl group having 5 to 18 ring atoms;

n represents an integer of 1 to 5, and when n is 2 or more, groups ($L_1$-$L_2$) may be the same or different; and $L_0$ and $L_1$, or $L_1$ and $L_2$ may be bonded to each other to form a saturated or unsaturated ring, respectively, for example, the ring mentioned above with respect to the ring optionally formed by adjacent groups of $R_0$ to $R_8$ of formula (1);

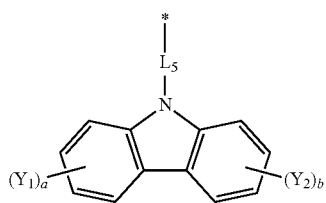

(b)

wherein
* represents a bonding site to the carbon atom in formula (1) to which each of $R_0$ to $R_8$ is bonded;
$L_5$ is the same as defined in formula (a) with respect to $L_0$;
$Y_1$ and $Y_2$ each represent a hydrogen atom or a substituent;
a and b each represent an integer of 1 to 4, and when a or b is 2 or more, groups $Y_1$ or groups $Y_2$ may be the same or different; and
adjacent groups $Y_1$ and adjacent groups $Y_2$ may be bonded to each other to form a saturated or unsaturated ring, respectively, for example, the ring mentioned above with respect to the ring optionally formed by adjacent groups of $R_0$ to $R_8$ of formula (1); and

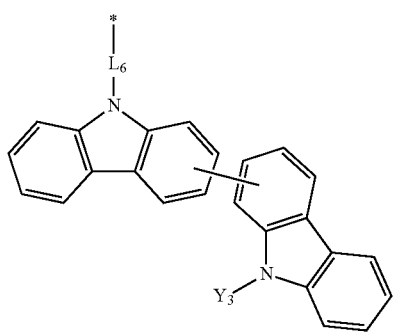

(c)

wherein:
* represents a bonding site to the carbon atom in formula (1) to which each of $R_0$ to $R_8$ is bonded;
$L_6$ is the same as defined in formula (a) with respect to $L_0$; and
$Y_3$ represents a hydrogen atom or a substituent.

In the embodiment of the invention, the substituent other than hydrogen atom represented by two selected from $R_0$ to $R_8$ of formula (1) is preferably represented by formula (c).

Examples of the aryl group having 6 to 60 ring carbon atoms and the heteroaryl group having 5 to 60 ring atoms for $L_2$ include those mentioned above with respect to the substituent represented by $R_0$ to $R_8$.

Examples of the arylene group having 6 to 60 ring carbon atoms and the heteroarylene group having 5 to 60 ring atoms for $L_0$, $L_1$, $L_5$, and $L_6$ include arylene groups and heteroarylene groups corresponding to the aryl groups and the heteroaryl groups mentioned above with respect to the substituent represented by $R_0$ to $R_8$.

Examples of the optional substituent for $L_0$, $L_1$, $L_2$, $L_5$, and $L_6$, i.e., examples of the alkyl group having 1 to 20 carbon atoms, the cycloalkyl group having 3 to 18 ring carbon atoms, the alkoxy group having 1 to 20 carbon atoms, the cycloalkoxy group having 3 to 20 ring carbon atoms, the aryloxy group having 6 to 18 ring carbon atoms, the amino group, the silyl group, the aryl group having 6 to 18 ring carbon atoms and the heteroaryl group having 5 to 18 ring atoms include those having corresponding carbon atoms which are mentioned above with respect to the substituent represented by $R_0$ to $R_8$.

In the embodiment of the invention, formula (1) is preferably represented by formula (2) and more preferably represented by formula (3):

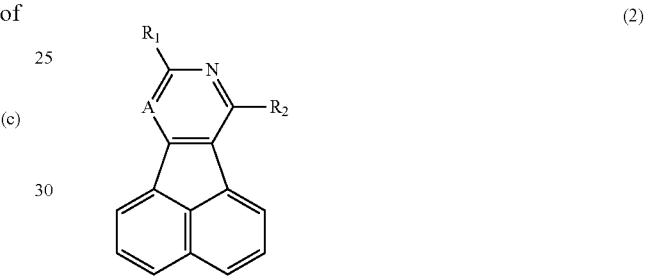

(2)

wherein A' represents CH or N and $R_1$ to $R_2$ are as defined above; and

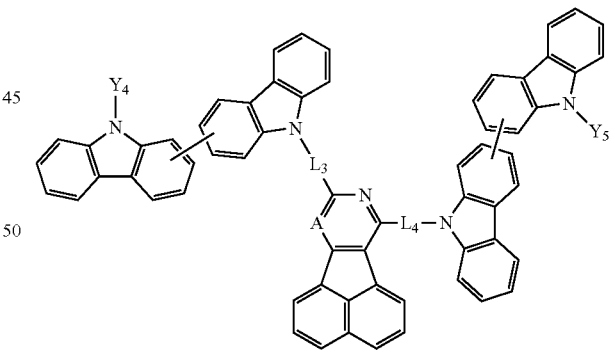

(3)

wherein A' is as defined above, $L_3$ and $L_4$ are each the same as defined above with respect to $L_0$, and $Y_4$ and $Y_5$ are each the same as defined above with respect to $Y_3$.

In the embodiment of the invention, a compound represented by formula (4) wherein A of formula (1) is N and a compound of formula (5) or (6) wherein A' of formula (2) or (3) is N are preferred.

(4)

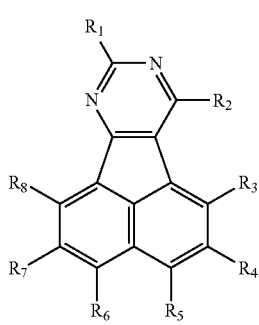

(5)

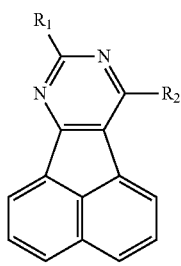

(6)

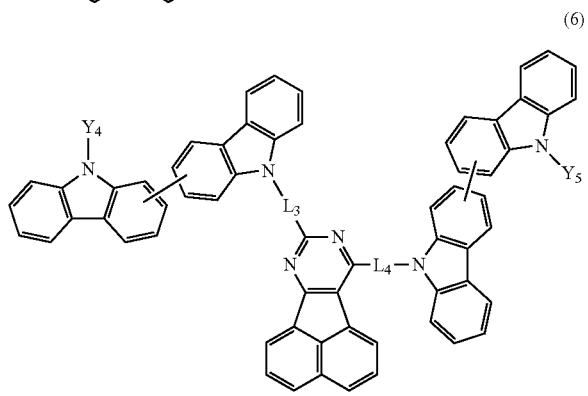

In the embodiment of the invention, three selected from $R_0$ to $R_8$ each preferably represent the substituent other than hydrogen atom.

The substituent other than hydrogen atom represented by three of $R_0$ to $R_8$ is preferably a substituted or unsubstituted aryl group having 6 to 60 ring carbon atoms or a substituted or unsubstituted heteroaryl group having 5 to 60 ring atoms and more preferably a substituted or unsubstituted phenyl group, a substituted or unsubstituted naphthyl group, a substituted or unsubstituted anthracenyl group a substituted or unsubstituted phenanthryl group, a substituted or unsubstituted fluorenyl group, a substituted or unsubstituted dibenzofuranyl group, a substituted or unsubstituted dibenzothiophenyl group, a substituted or unsubstituted carbazolyl group, or an aza-substituted analogue thereof.

In the embodiment of the invention, formula (4) is preferably represented by formula (7):

(7)

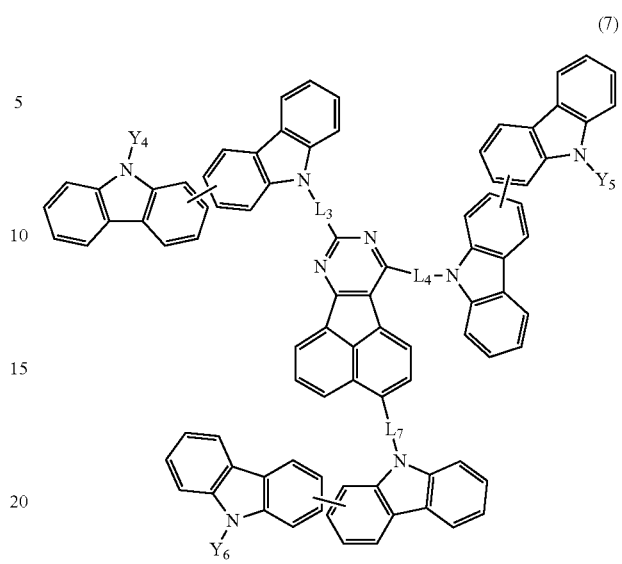

wherein $L_3$, $L_4$ and $L_7$ are each the same as defined with respect to $L_0$ and $Y_4$, $Y_5$ and $Y_6$ are each the same as defined with respect to $Y_3$.

Material for Organic Electroluminescence Devices

The material for organic electroluminescence devices in an aspect of the invention comprises the compound mentioned above. The content of the compound in an aspect of the invention is, for example, desirably 1% by mass or more, preferably 10% by mass or more, more preferably 50% by mass or more, still more preferably 80% by mass or more, and particularly preferably 90% by mass or more.

The compound and the material for organic EL devices each in an aspect of the invention are useful as a material for producing an organic EL device and may be used, for example, in a light emitting layer of a fluorescent emission unit as a host material or a dopant material and in a light emitting layer of a phosphorescent emission unit as a host material. In this case, the light emitting layer comprises the compound in an aspect of the invention together with a fluorescent emitting material or a phosphorescent emitting material. In addition, in either a fluorescent emission unit or a phosphorescent emission unit, the compound and the material for organic EL devices of the invention are also useful as a material for forming an anode-side organic thin film layer which is formed between an anode and a light emitting layer and a material for forming a cathode-side organic thin film layer which is formed between a cathode and a light emitting layer, i.e., also useful as a material for forming a hole transporting layer, a hole injecting layer, an electron transporting layer, an electron injecting layer, a hole blocking layer, and an electron blocking layer.

The "emission unit" referred to herein is the smallest unit for emitting light by the recombination of injected holes and injected electrons, which comprises one or more organic layers wherein one layer is a light emitting layer.

Examples of the compound in an aspect of the present invention are shown below, although not limited thereto.

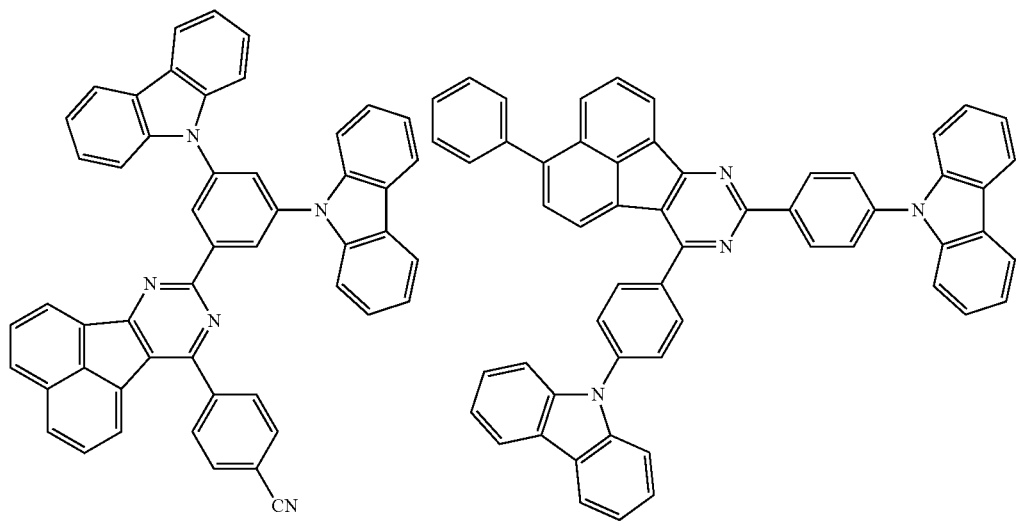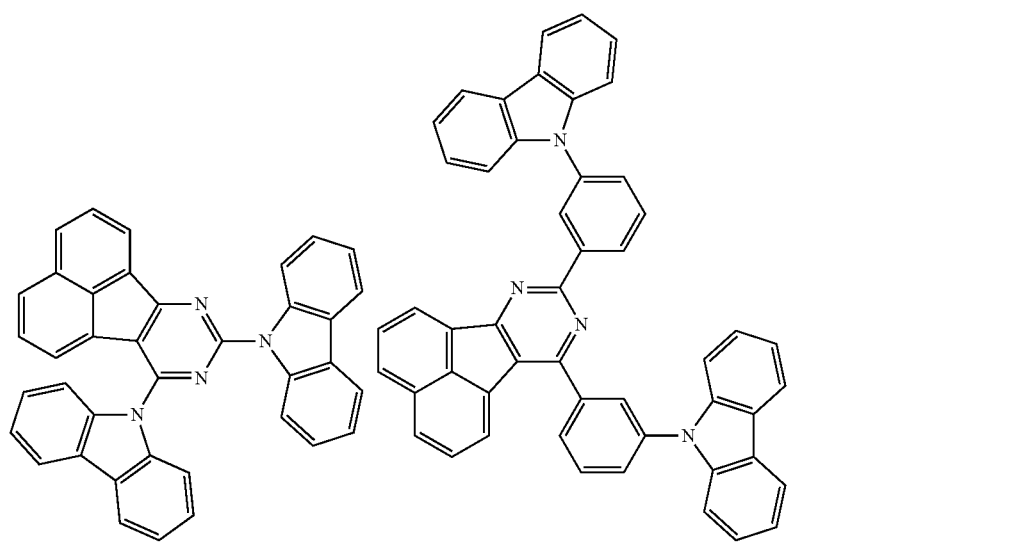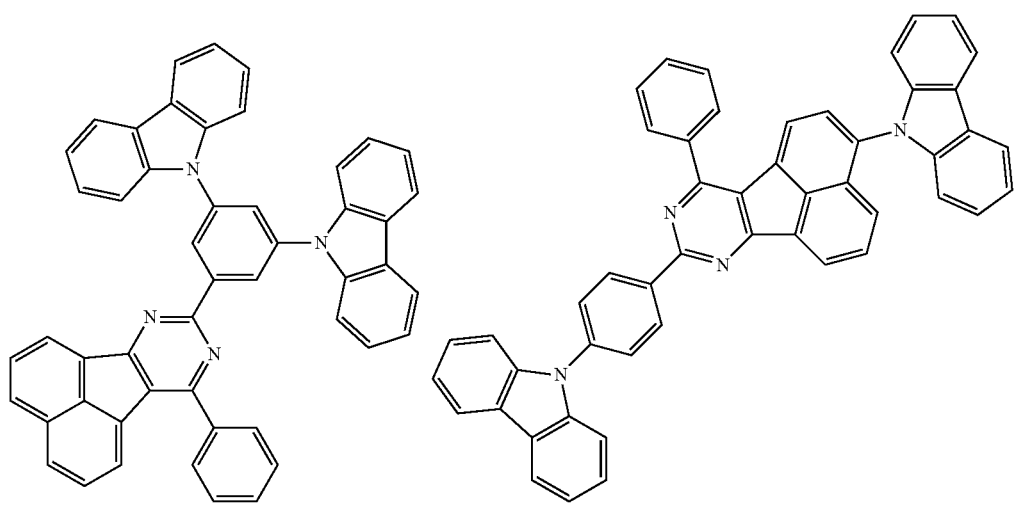

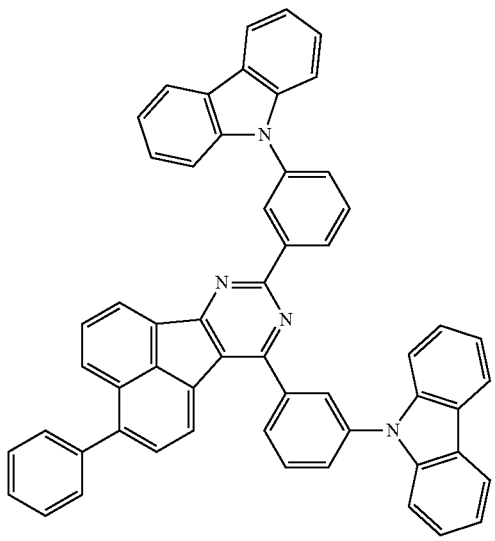
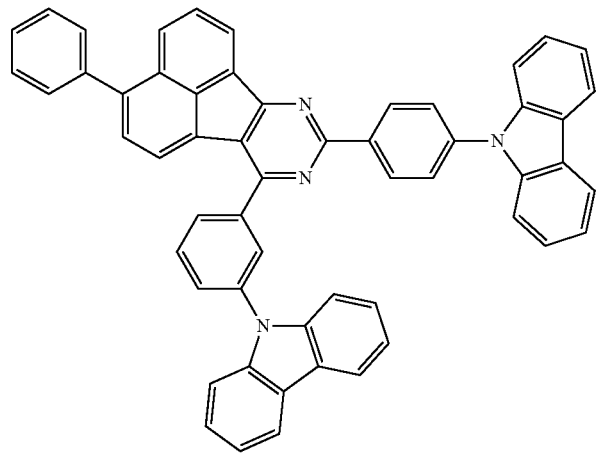
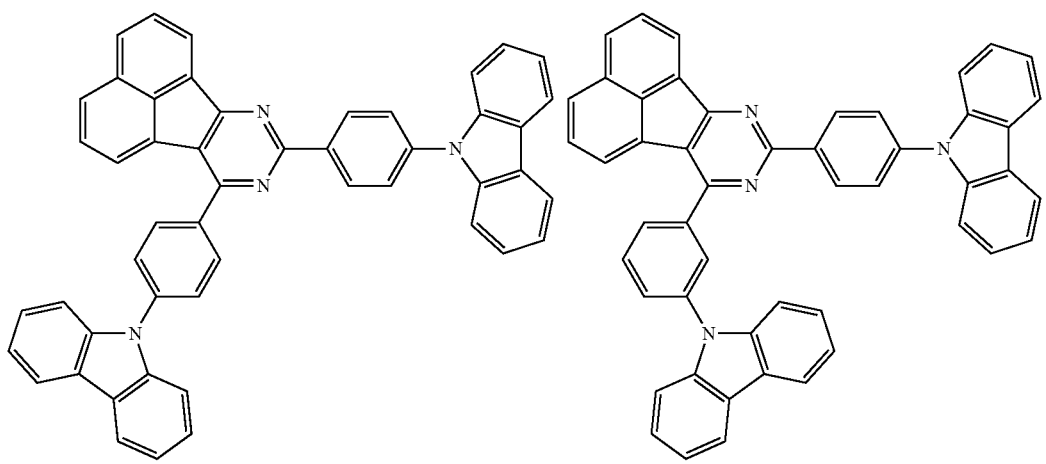
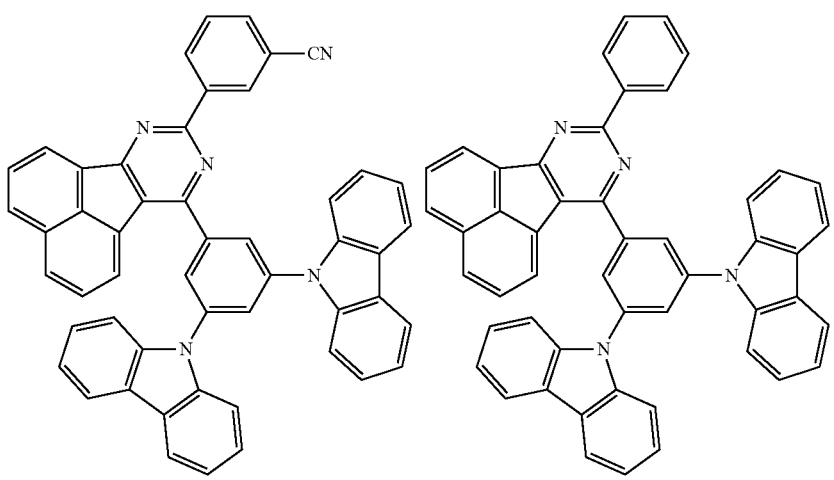

-continued
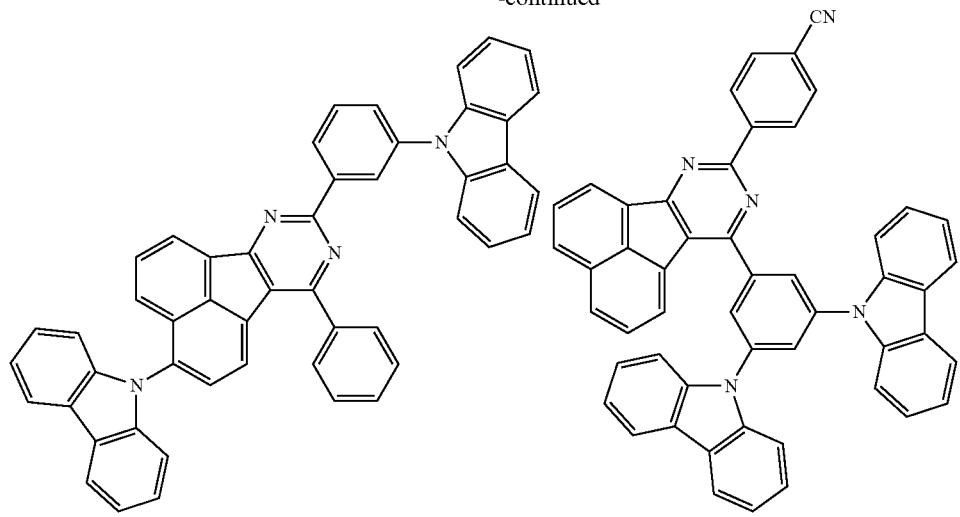
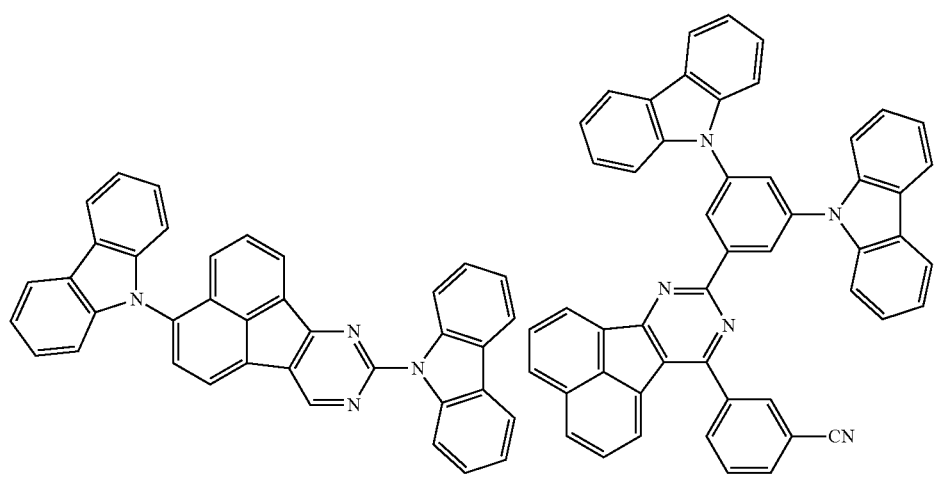
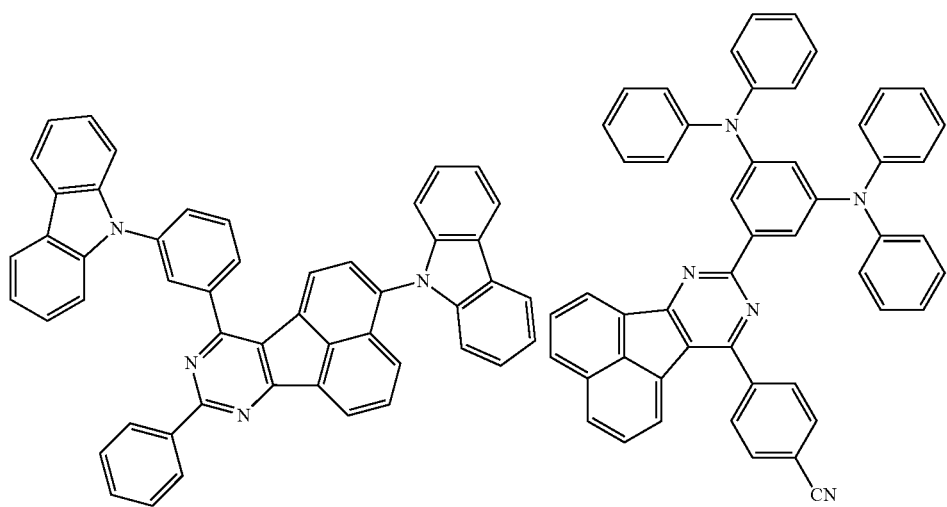

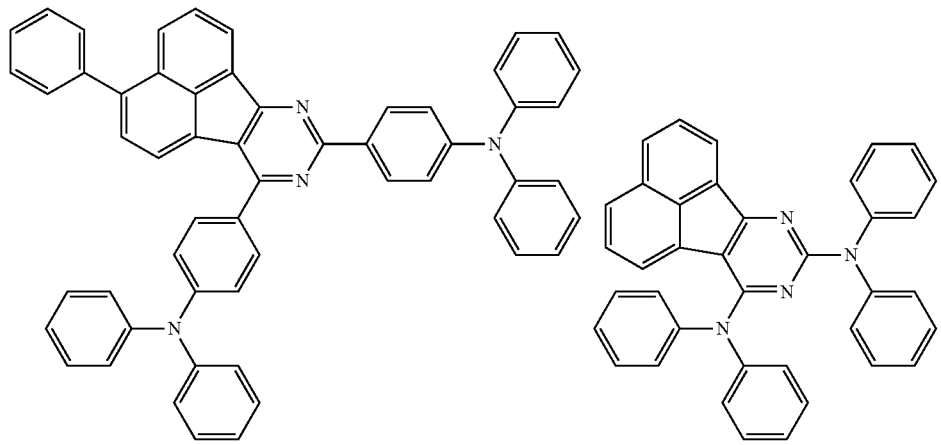
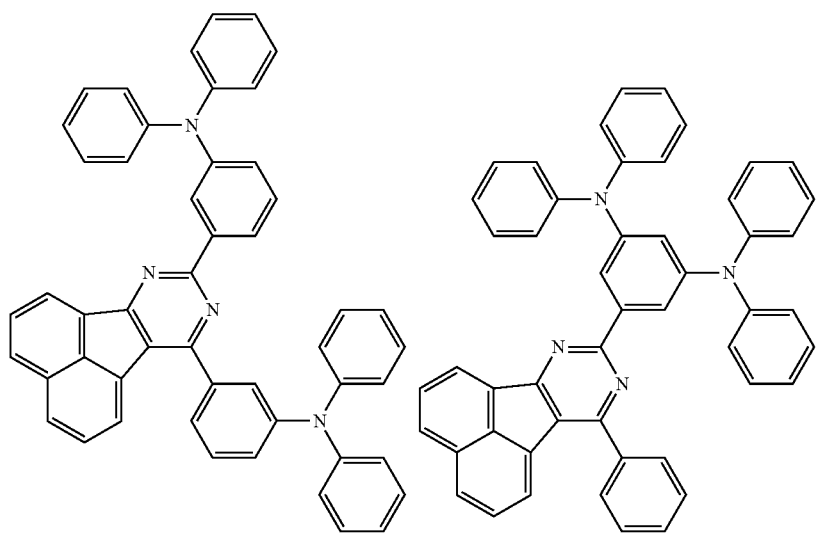
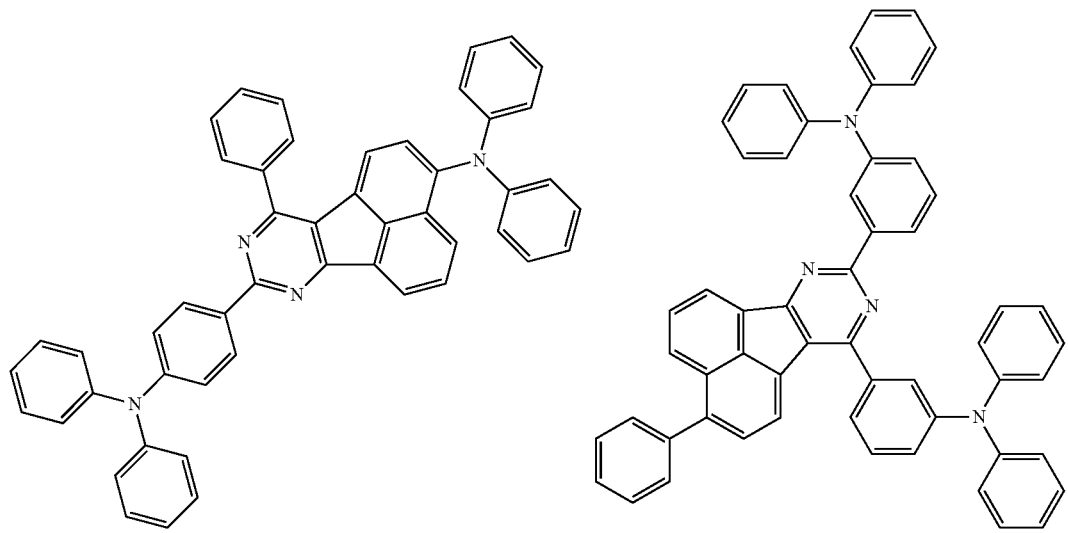

23 24
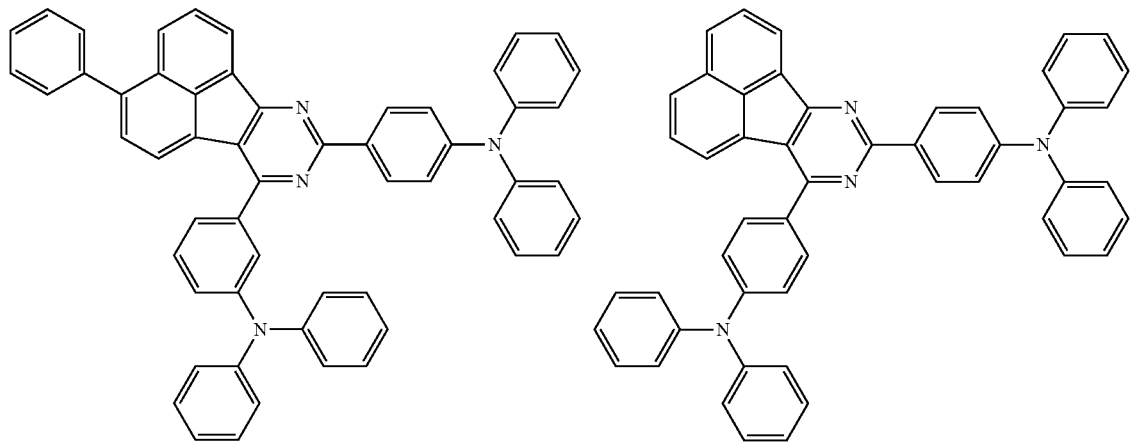
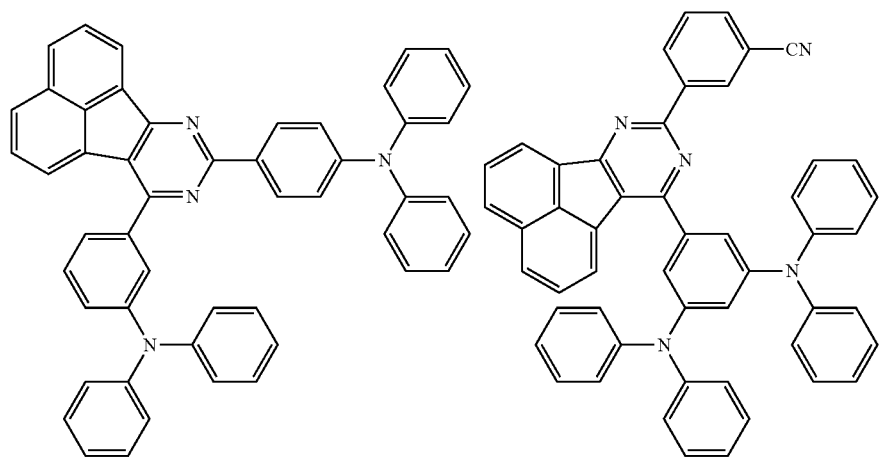
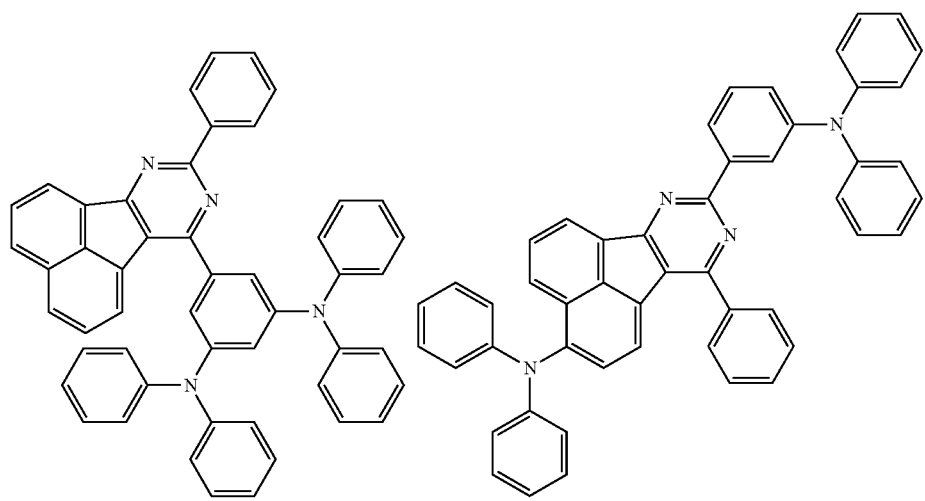

-continued
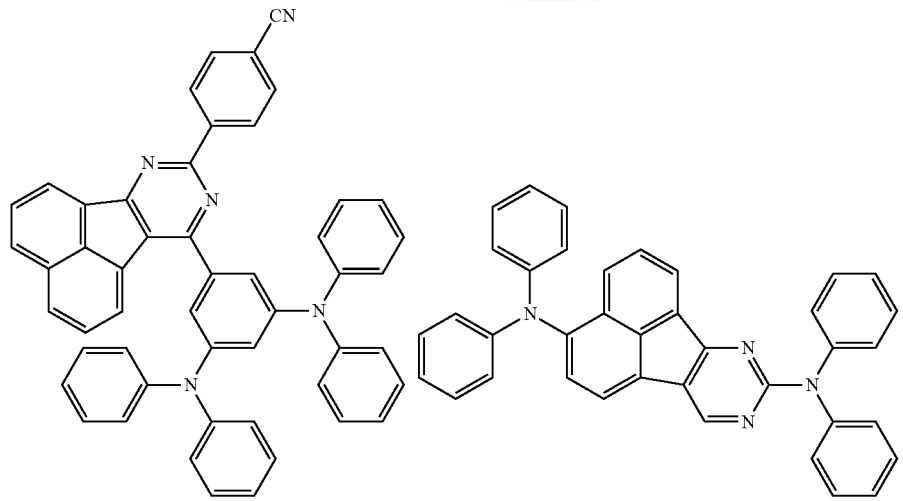
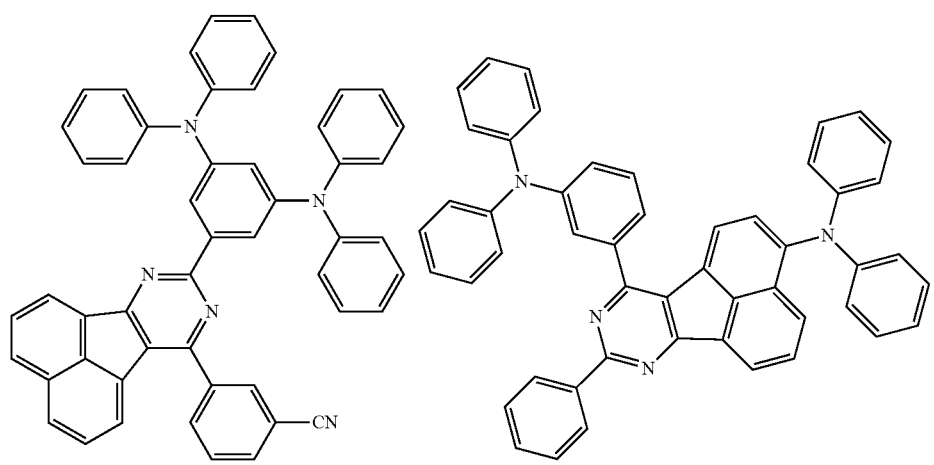
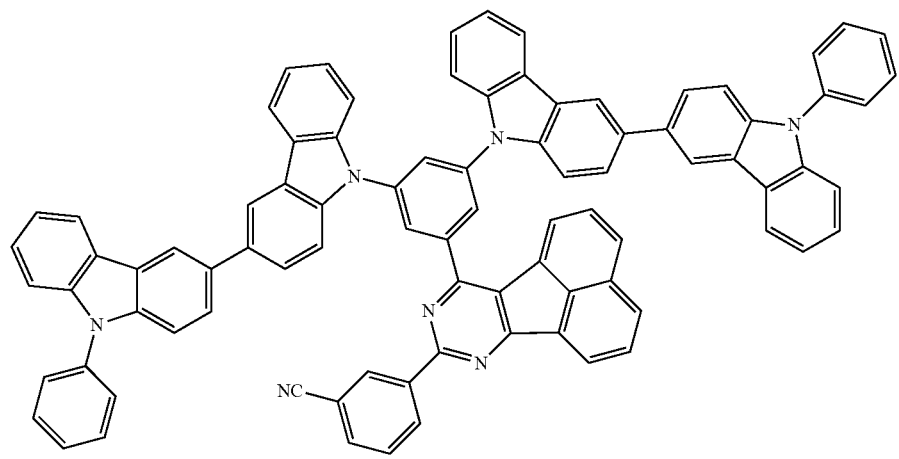

-continued
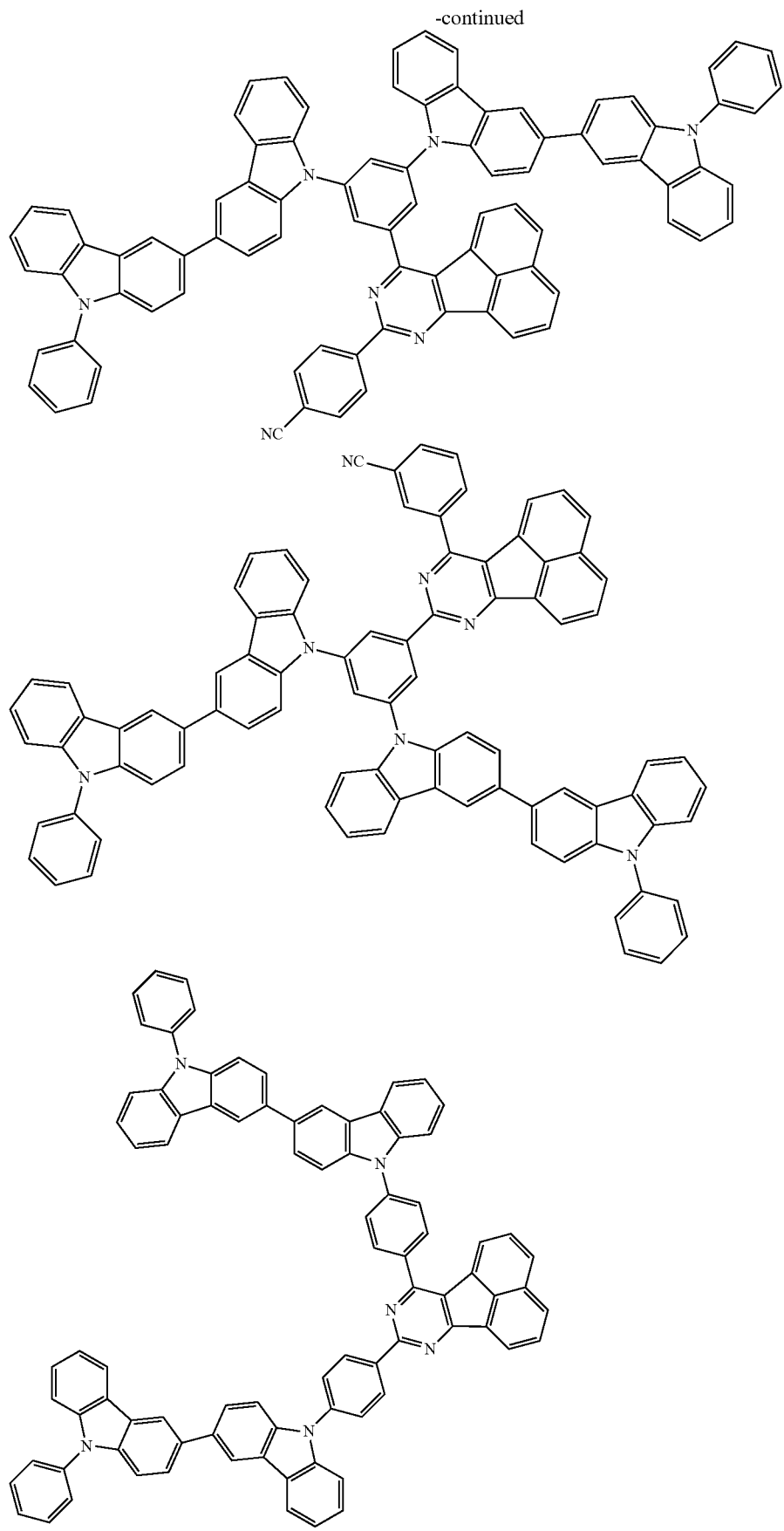

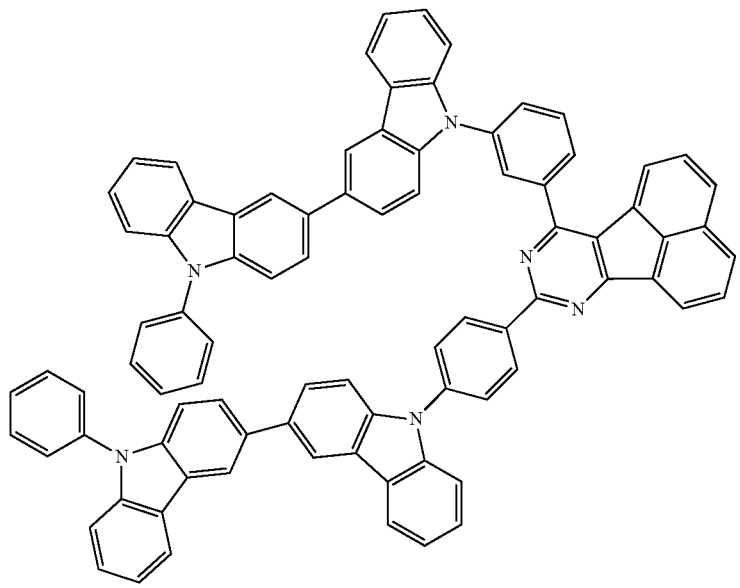
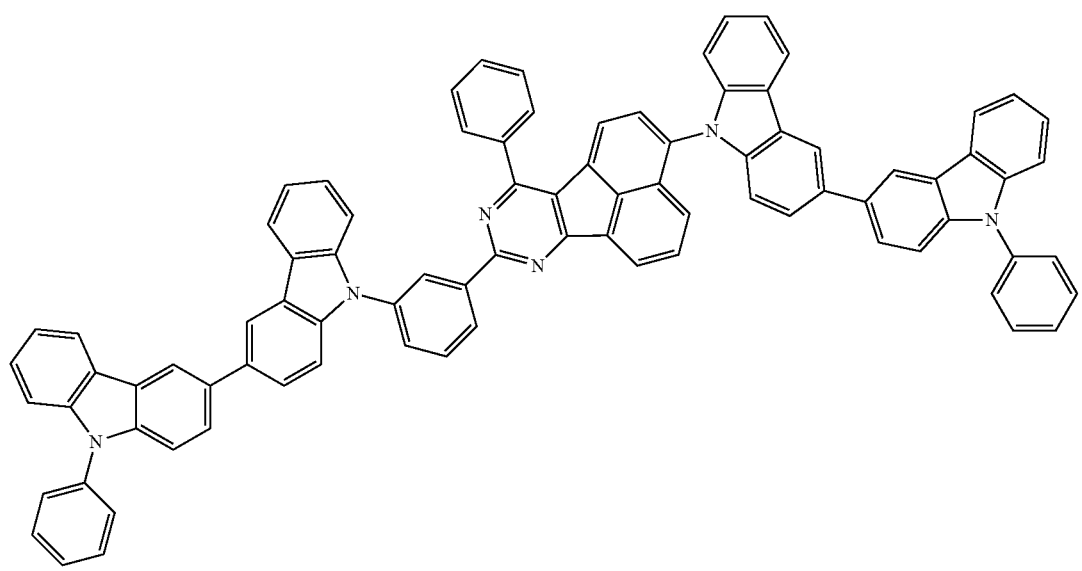

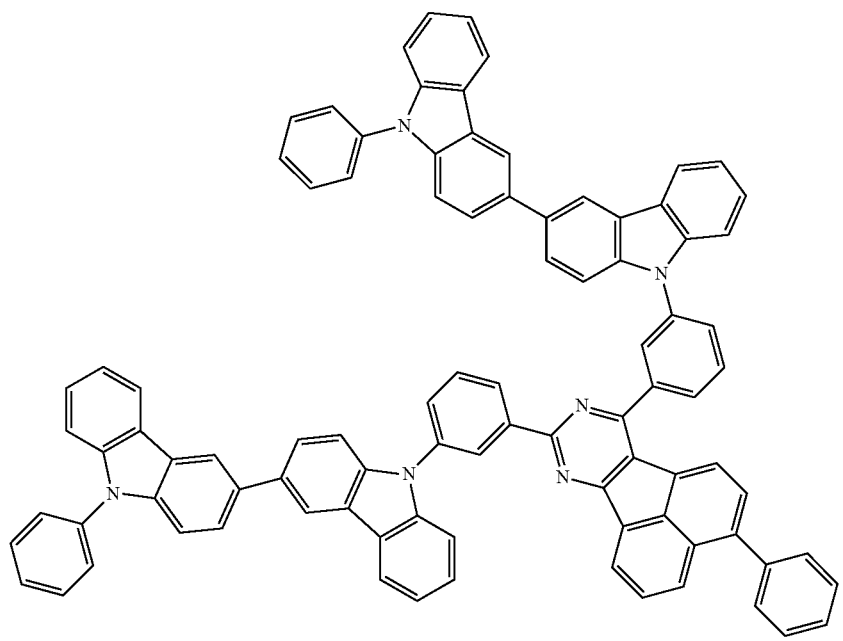
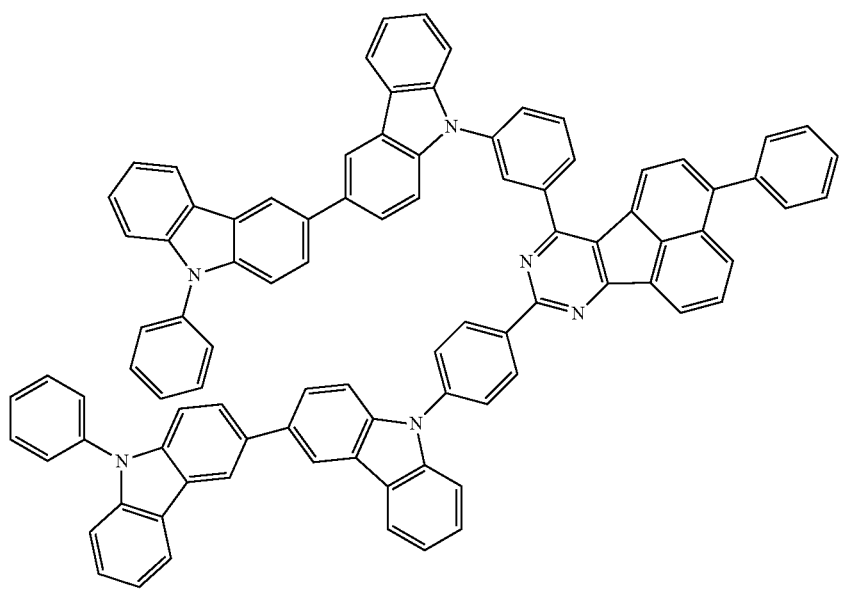

-continued
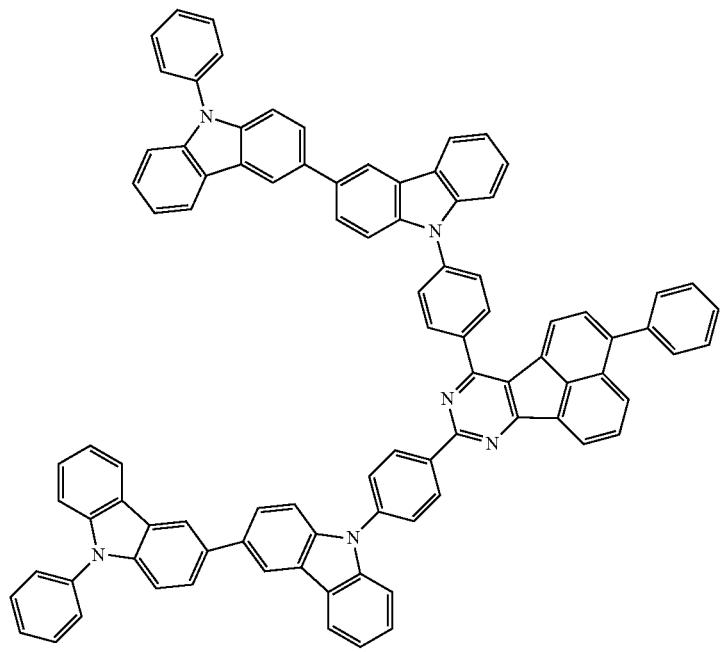

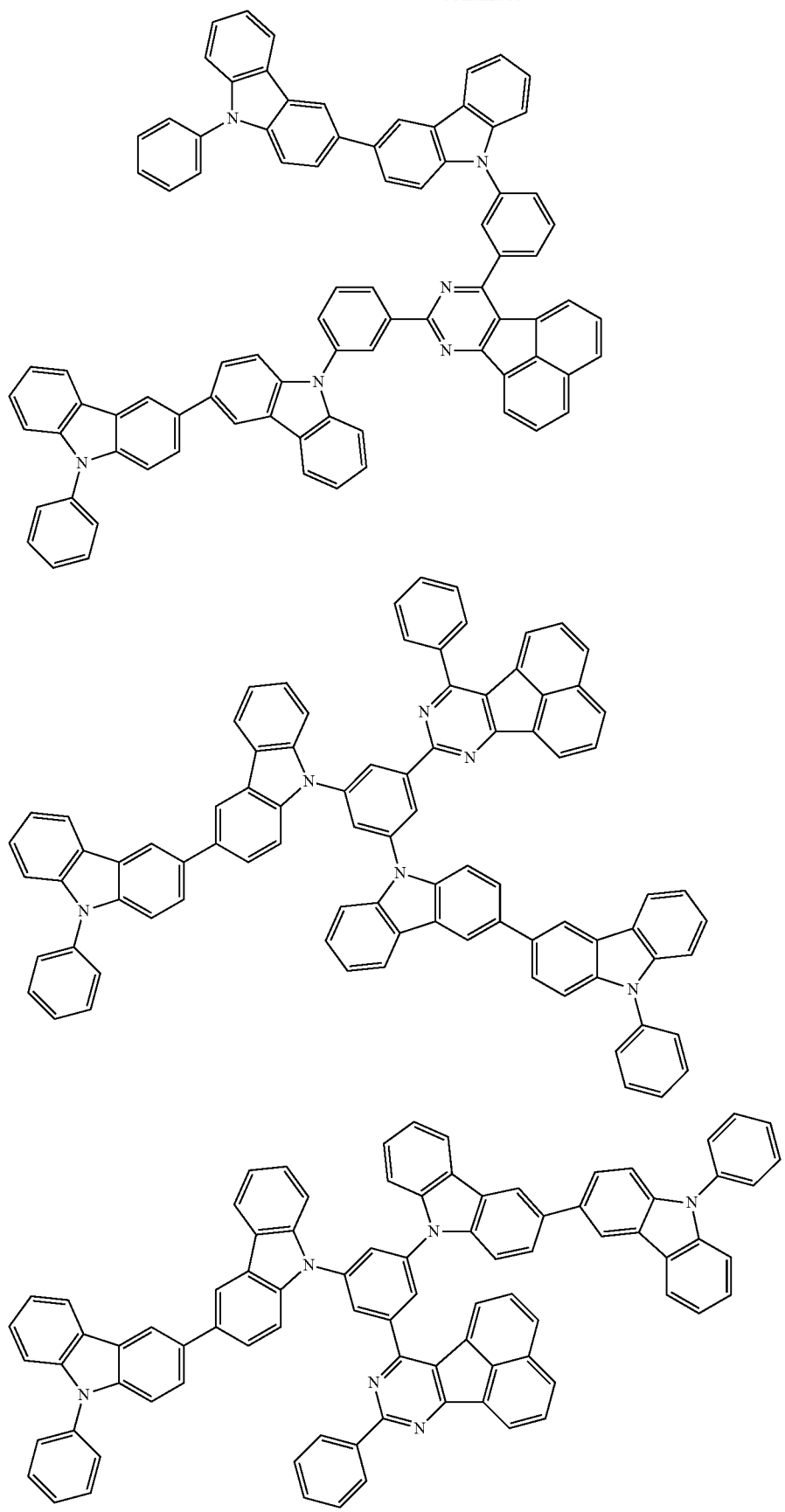

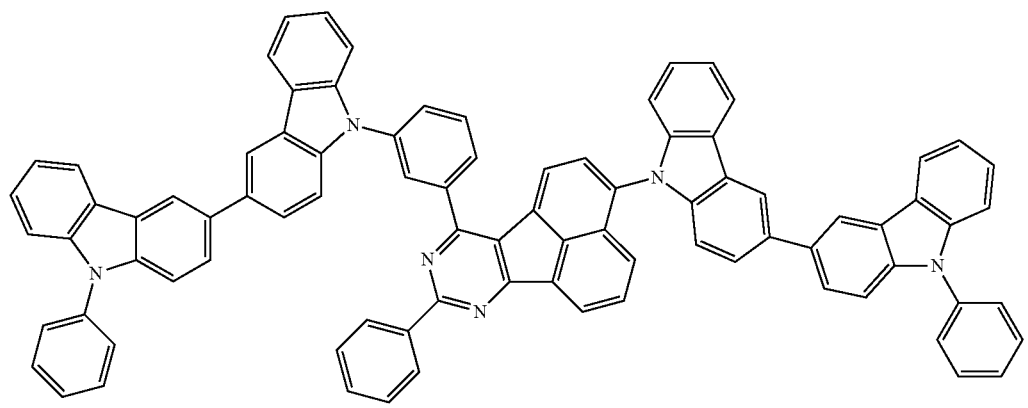
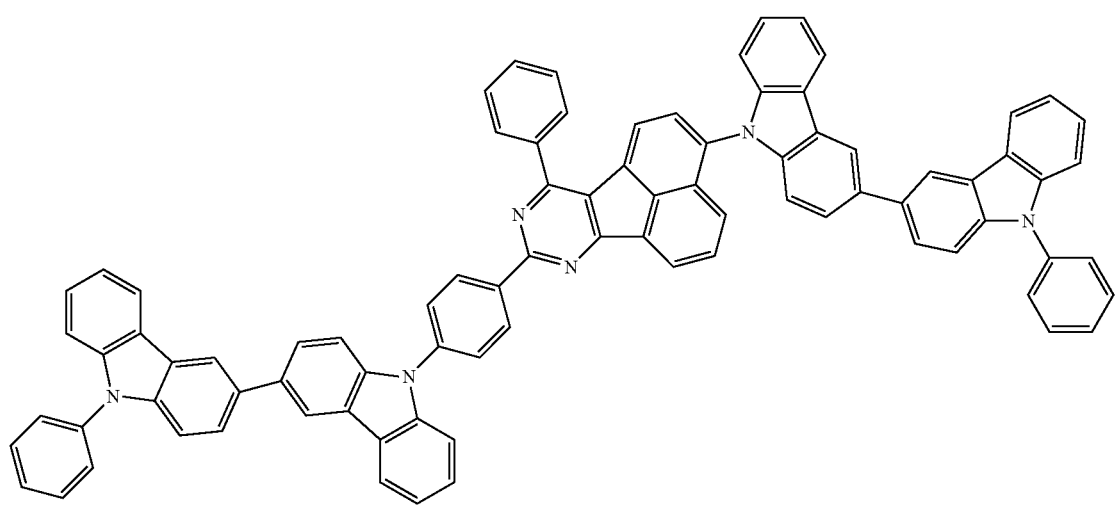
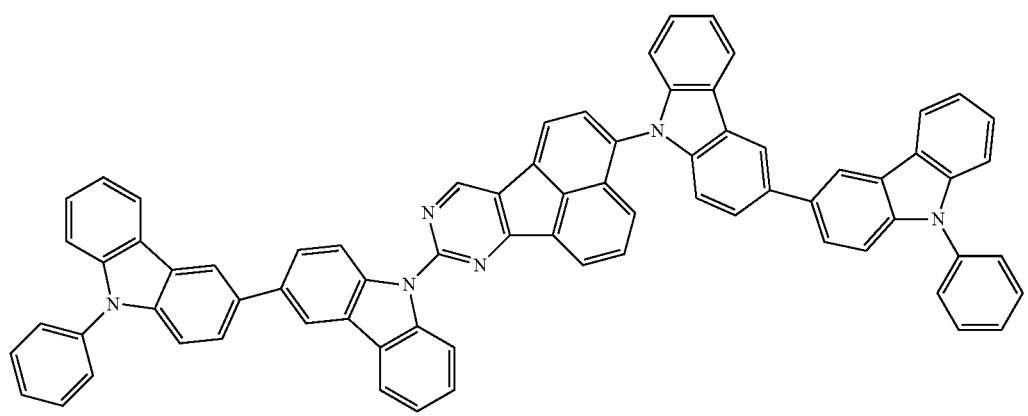

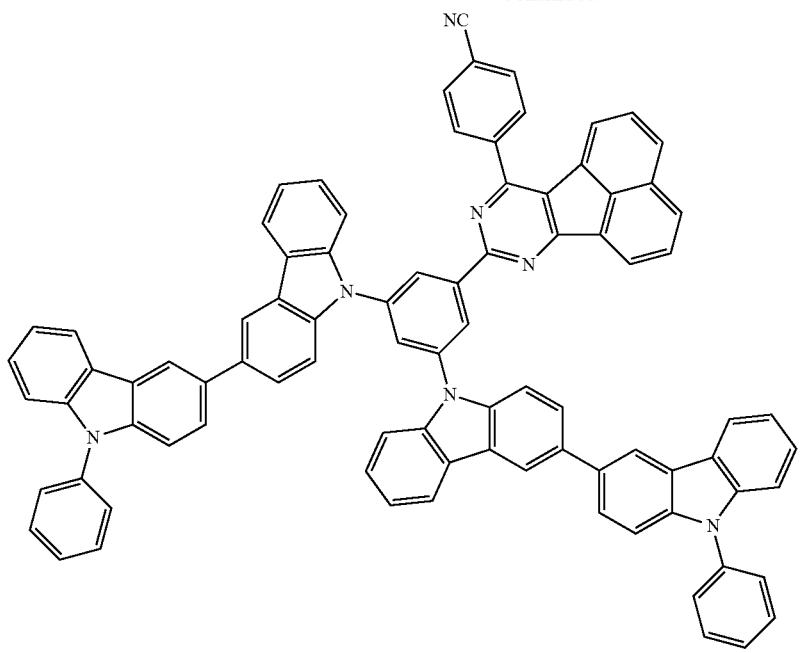
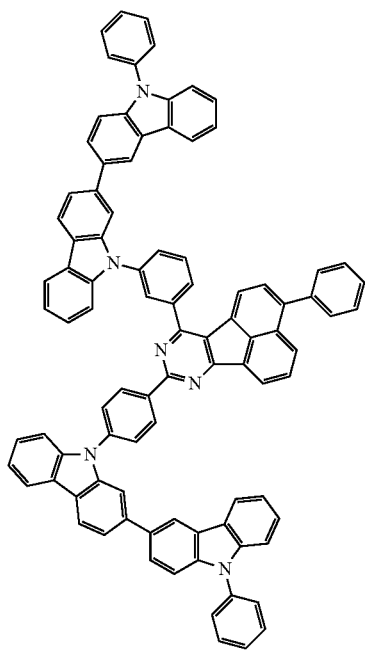

-continued
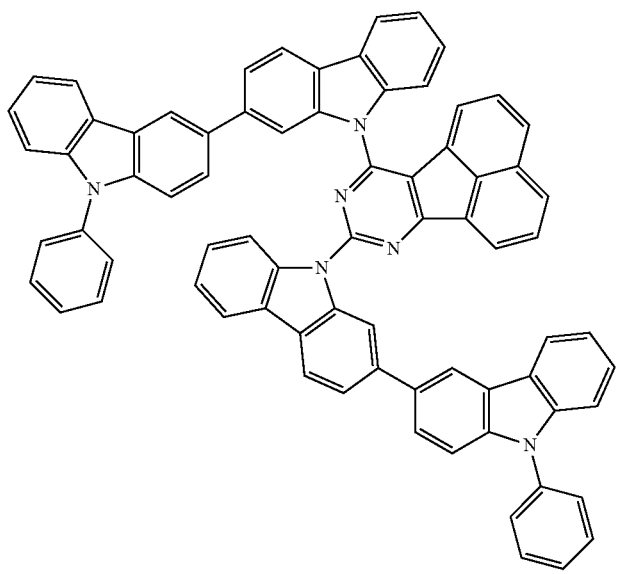
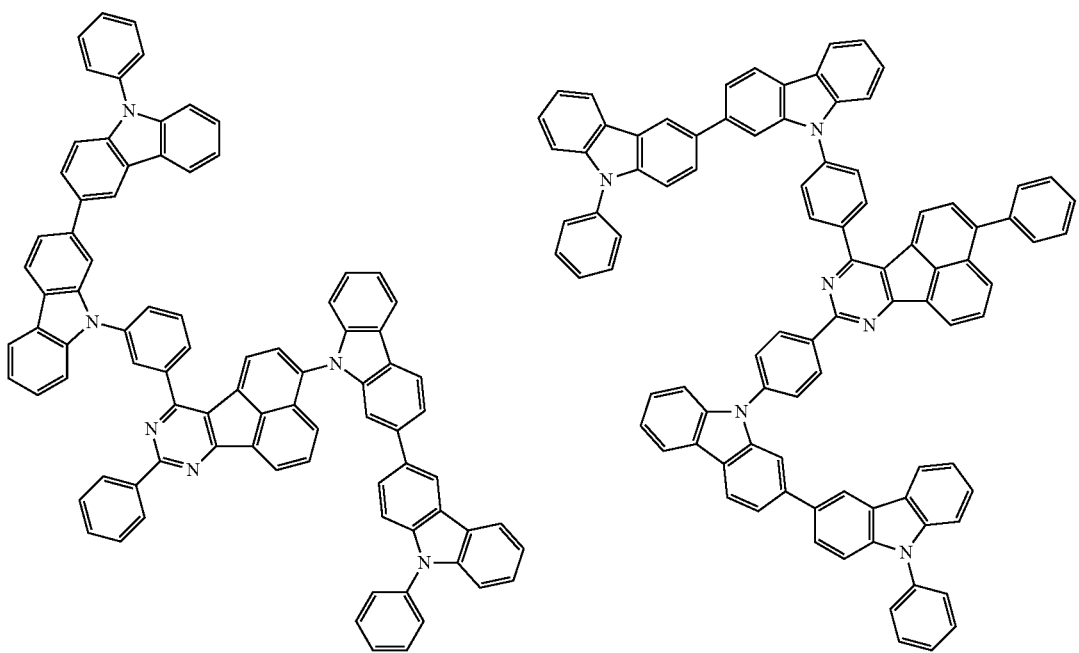

-continued
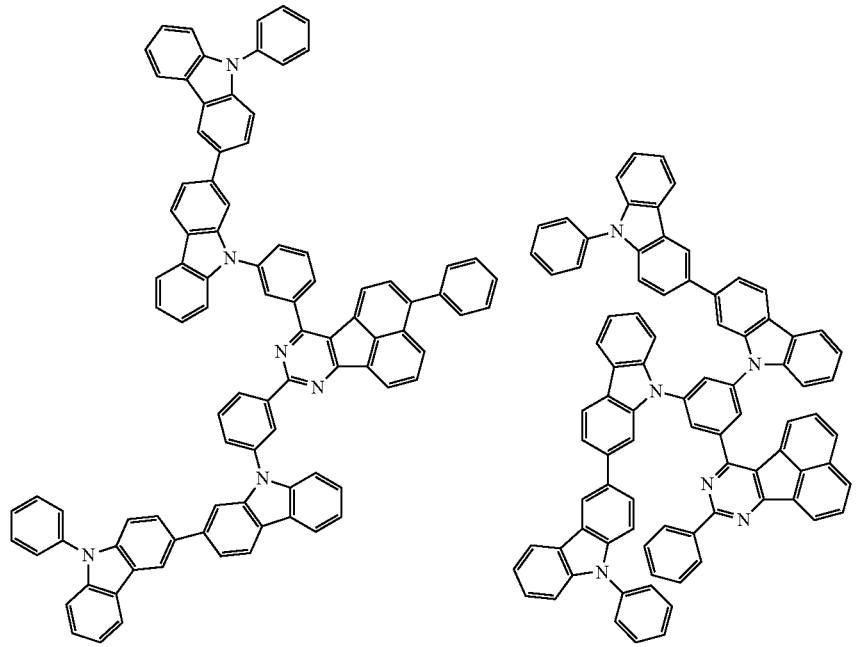
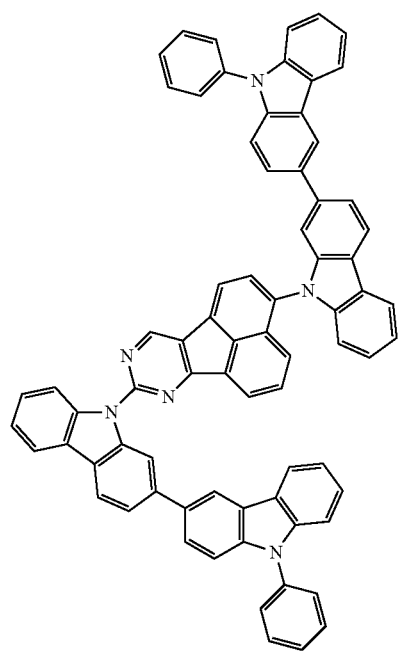

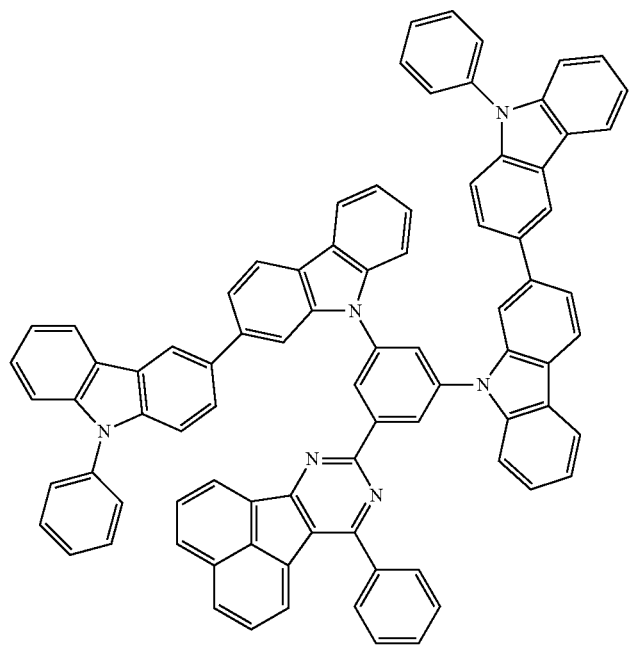
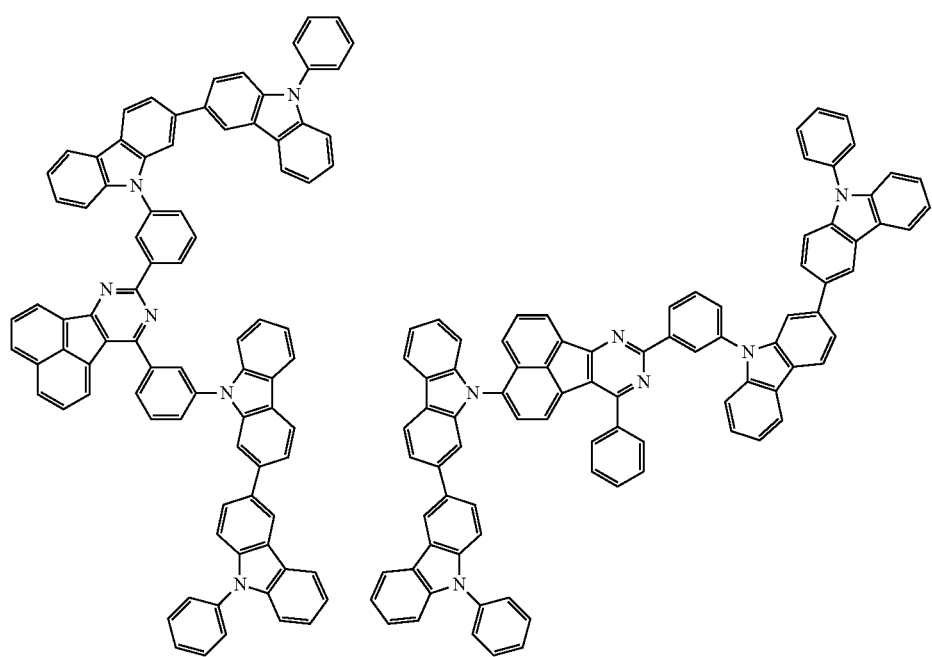

-continued
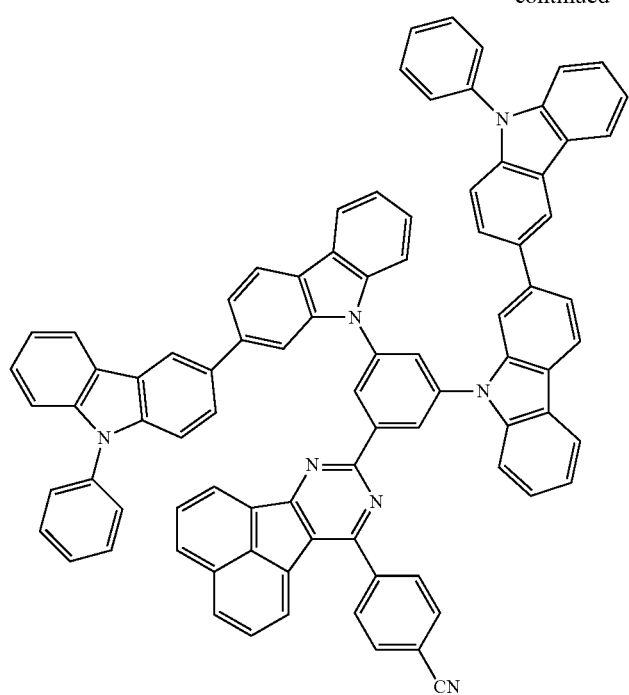
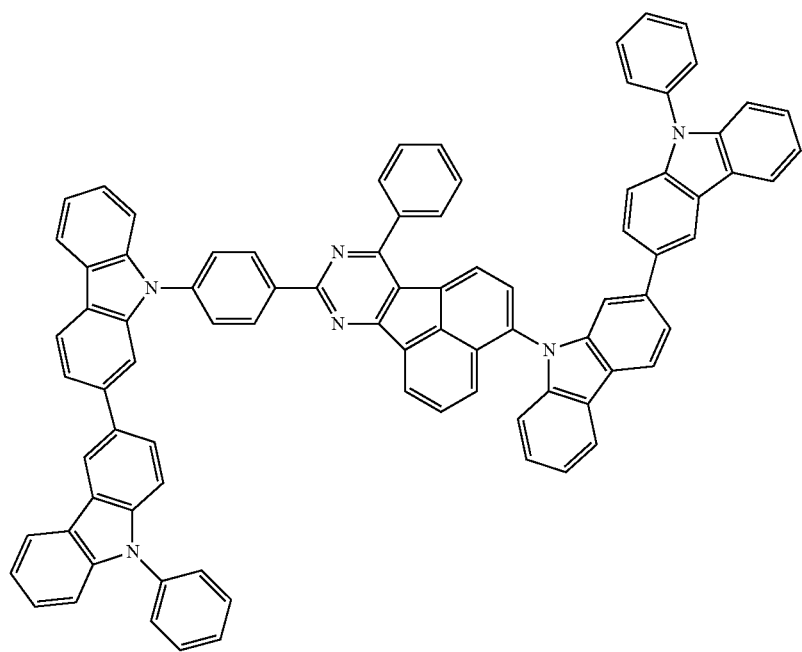

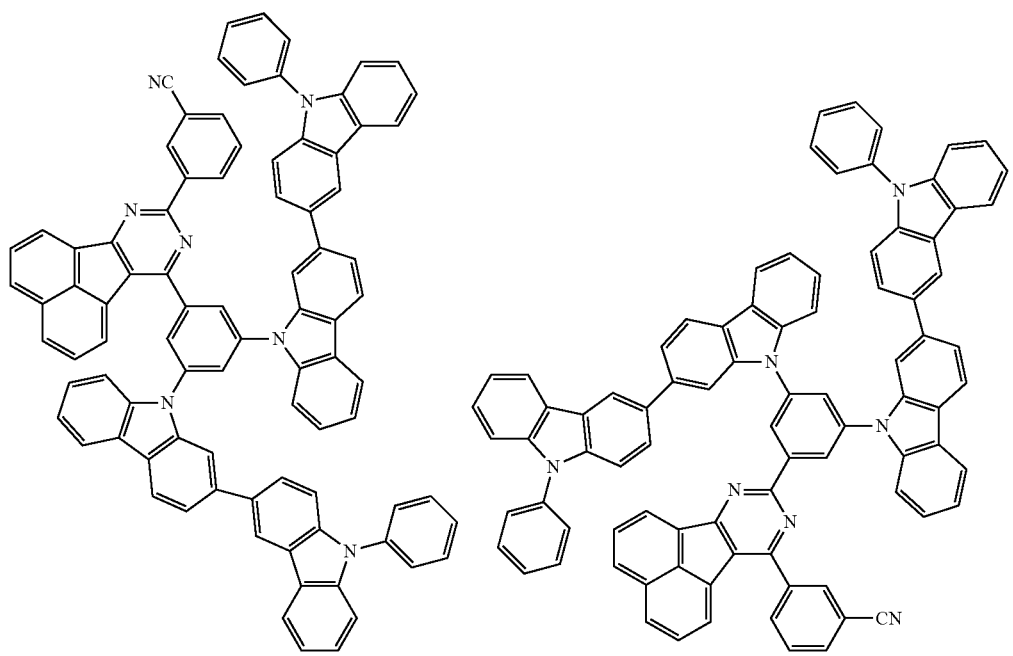
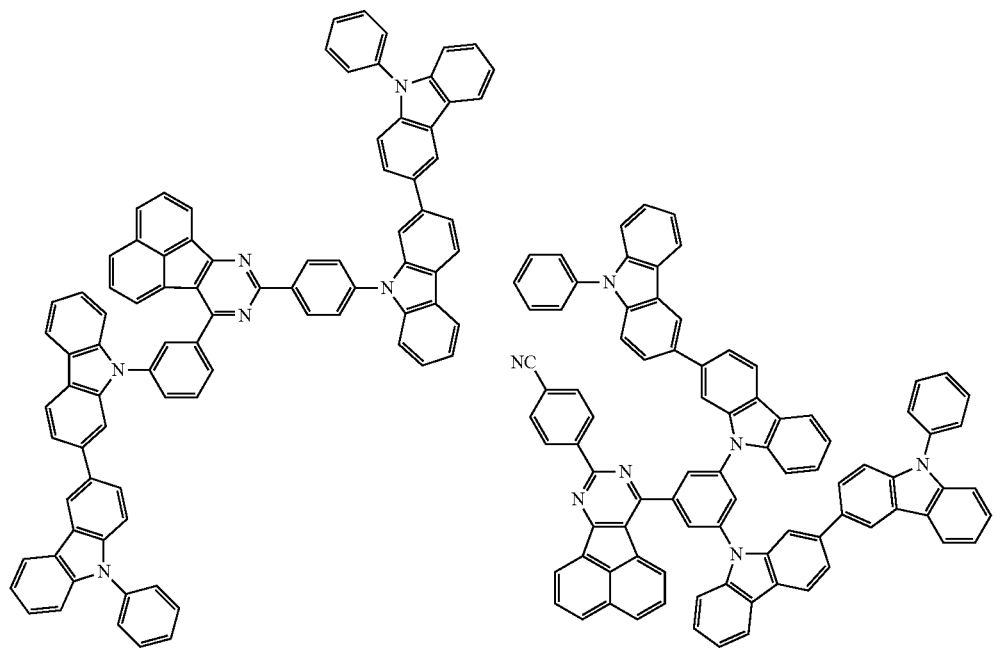

-continued
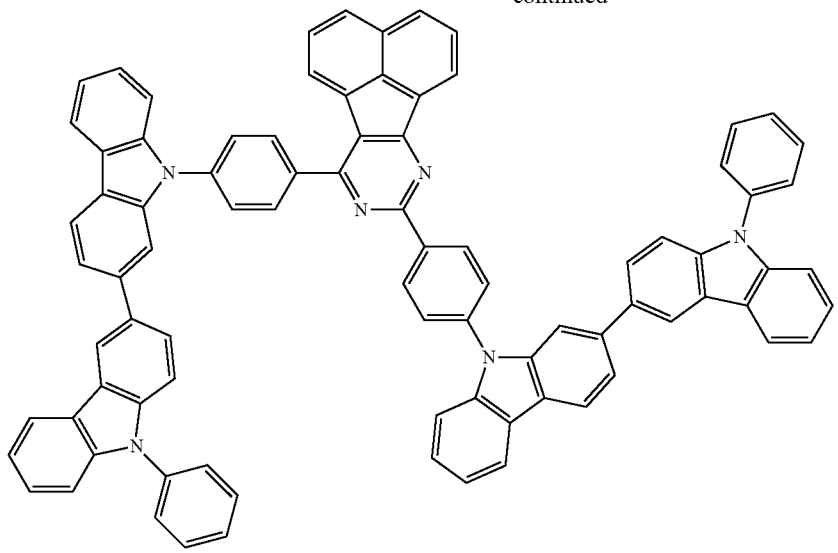
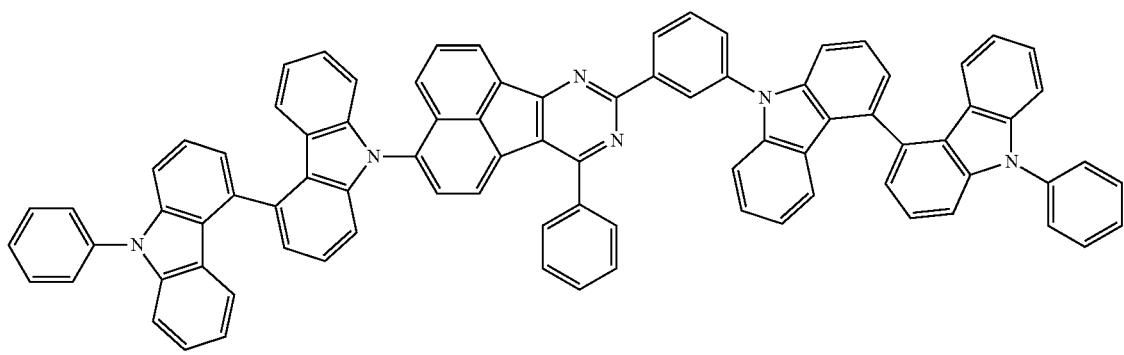
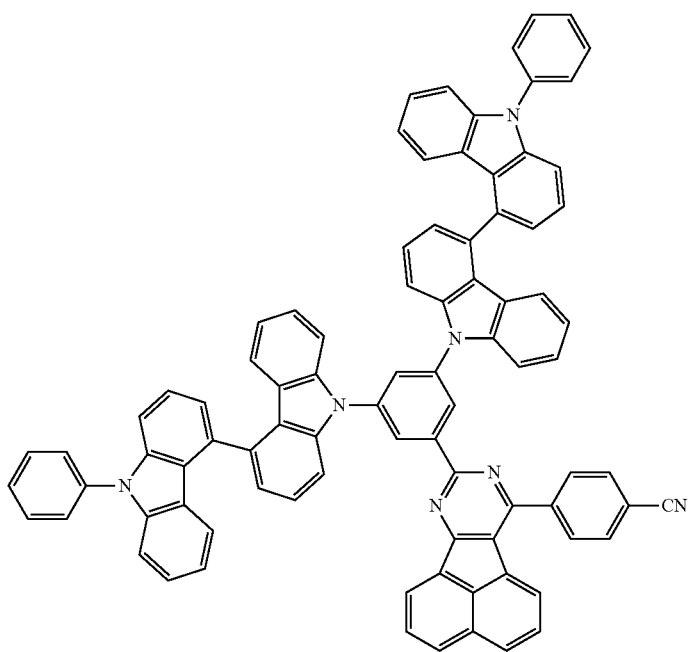

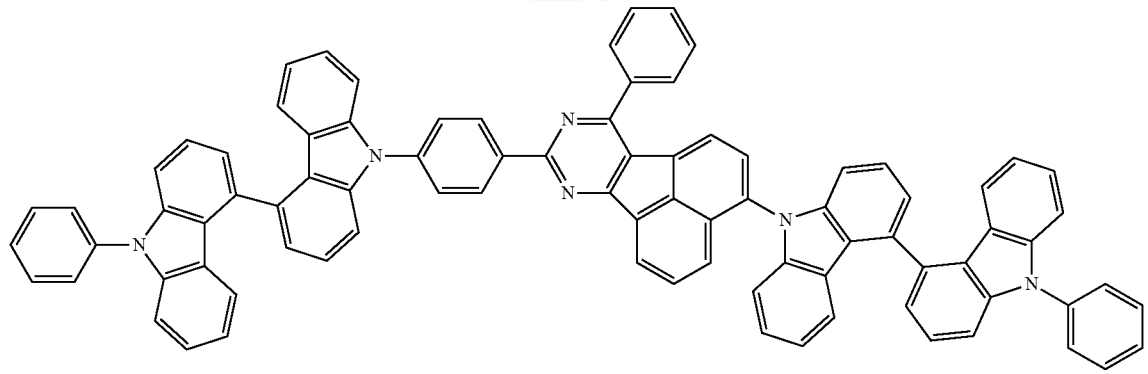
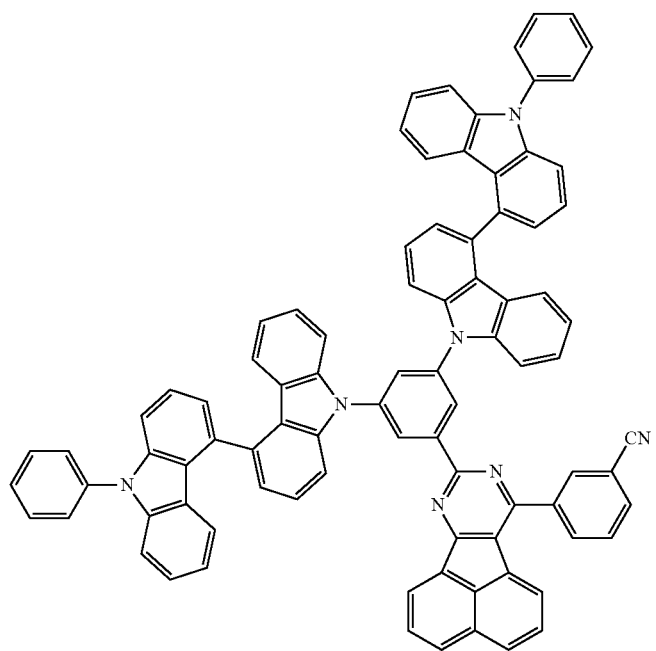
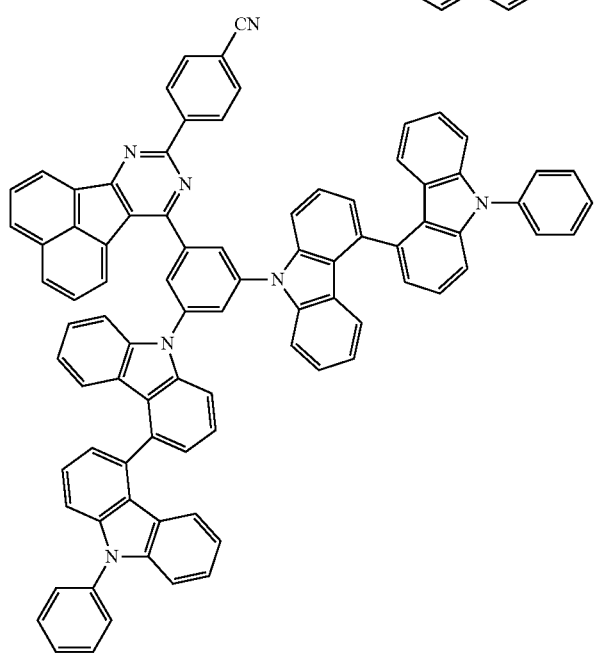

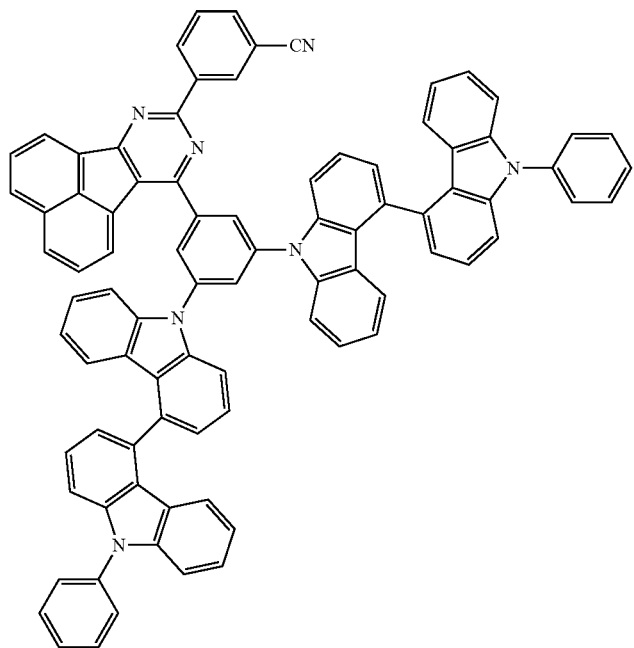
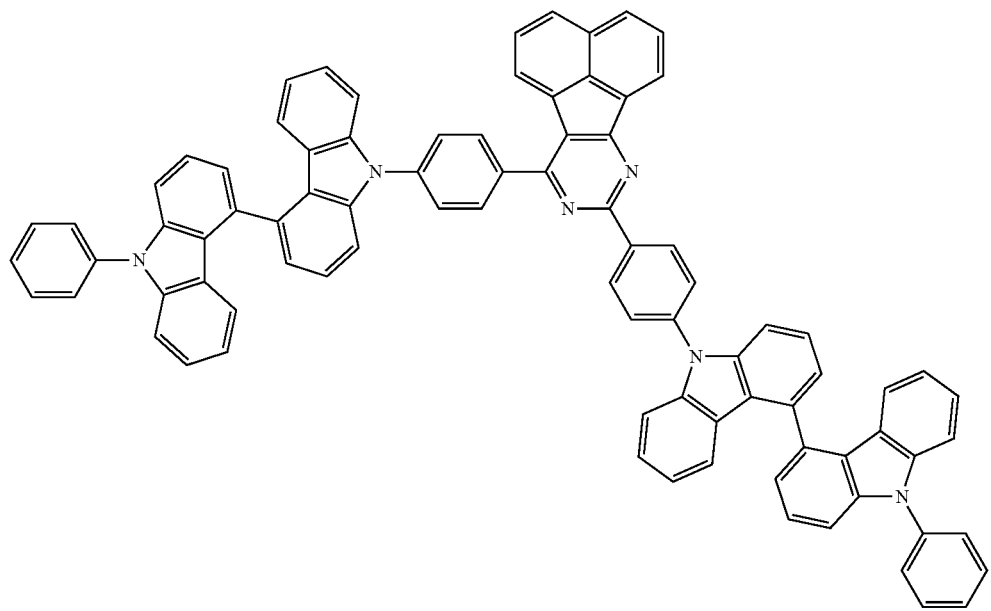

-continued
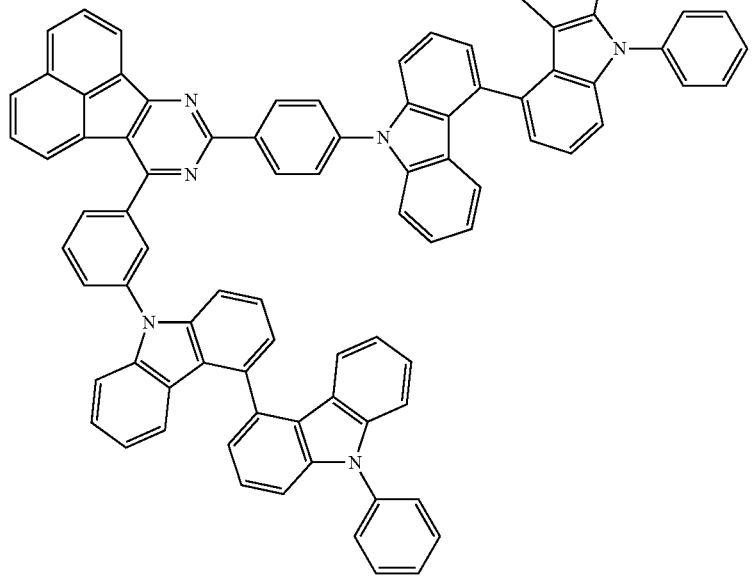
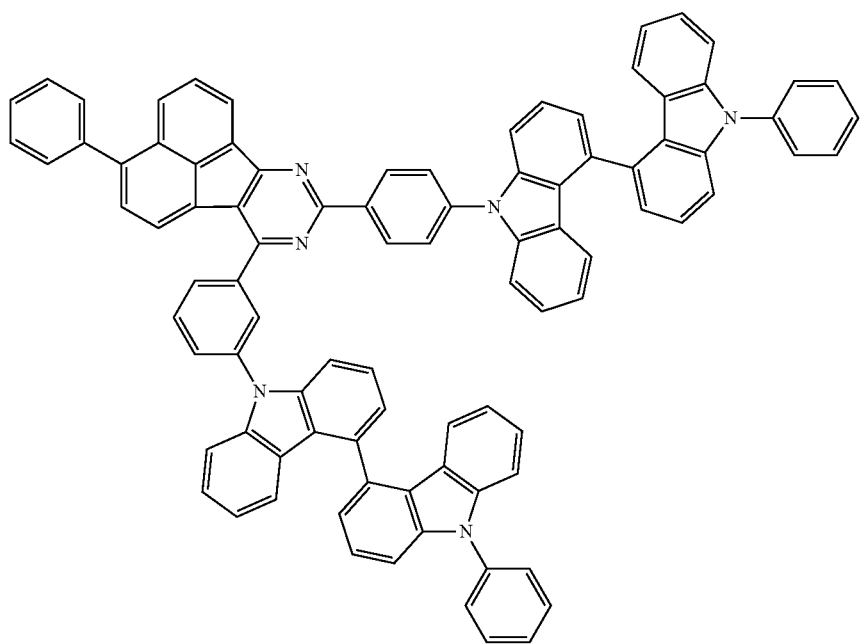

-continued
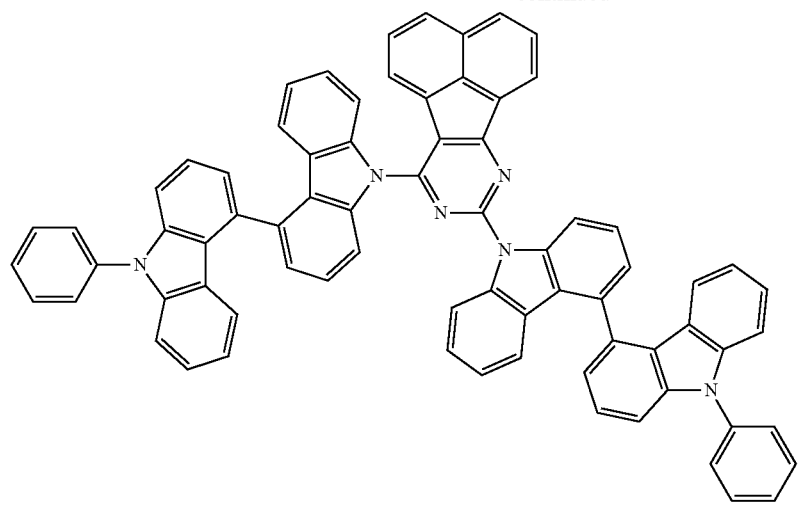
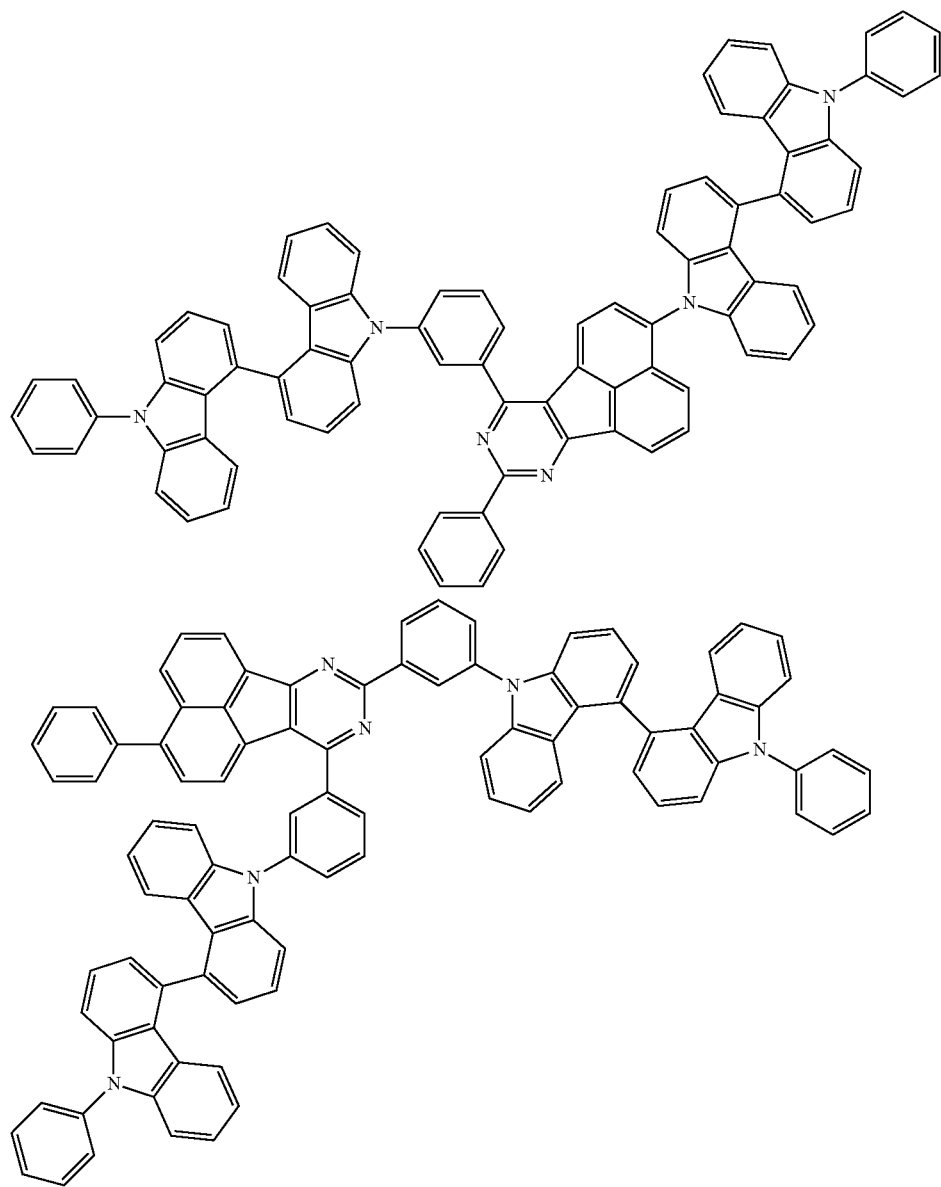

-continued
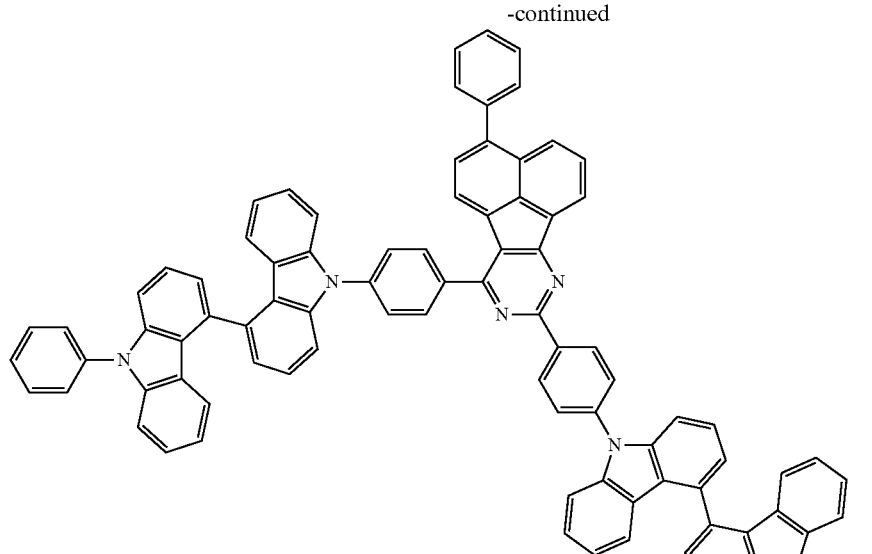
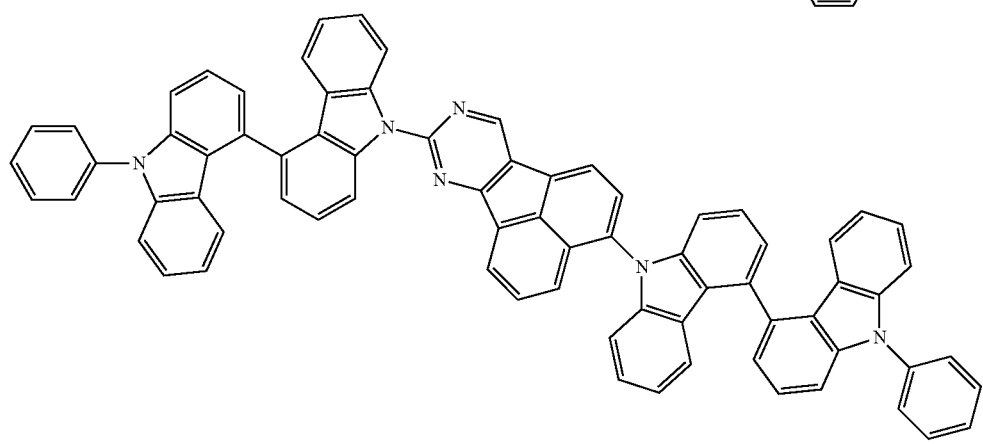
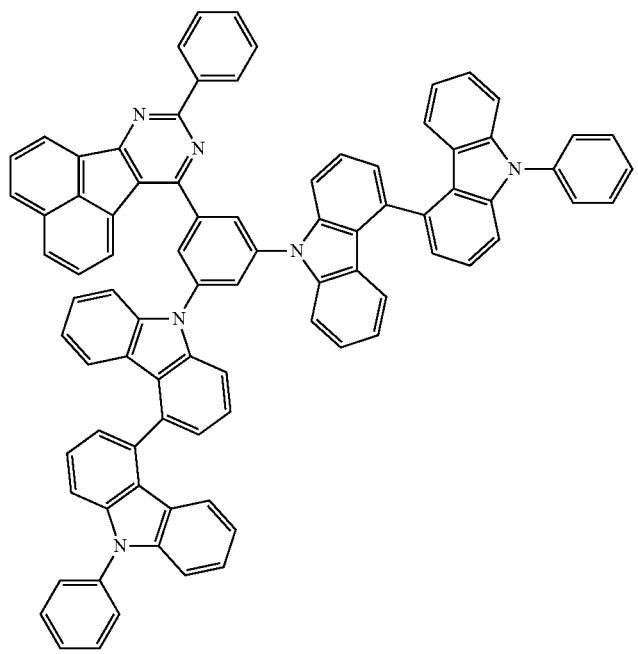

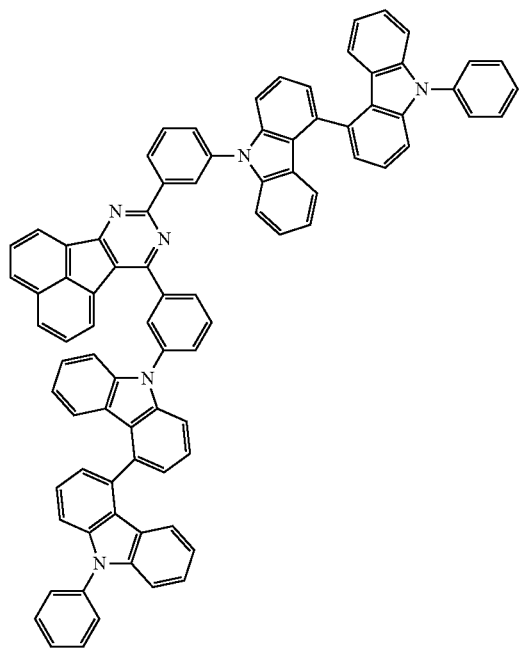
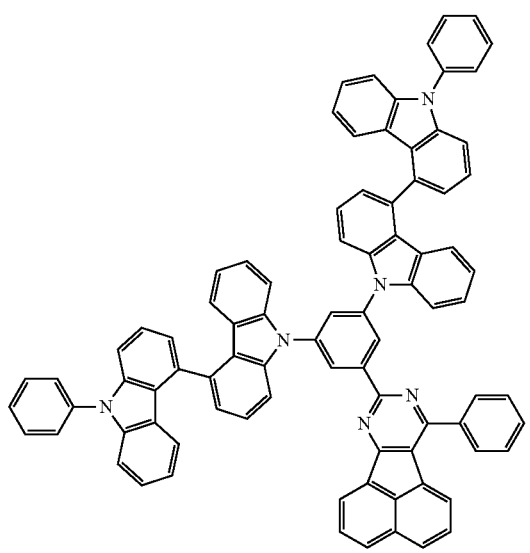
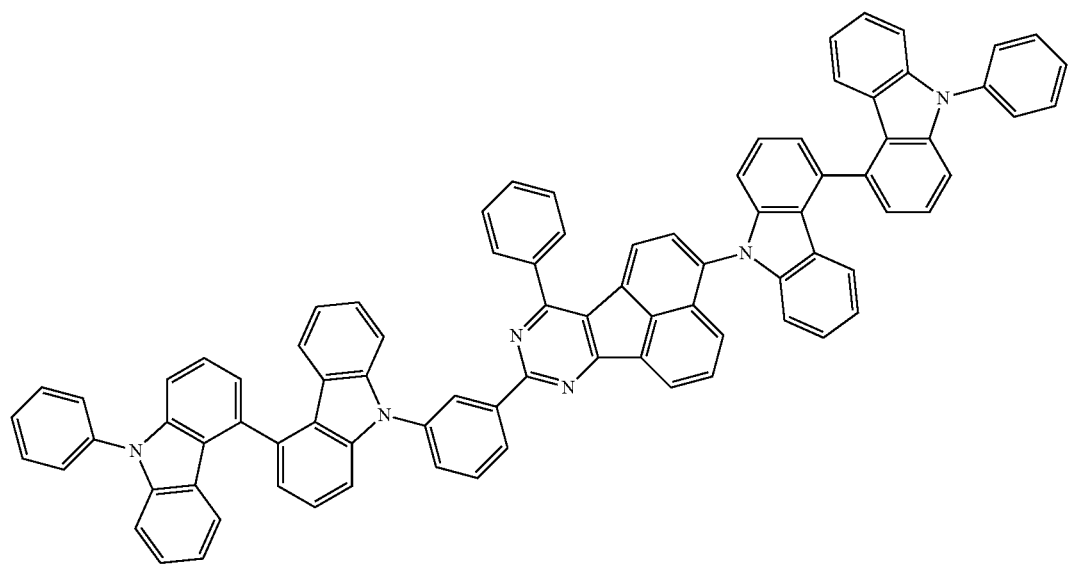

-continued
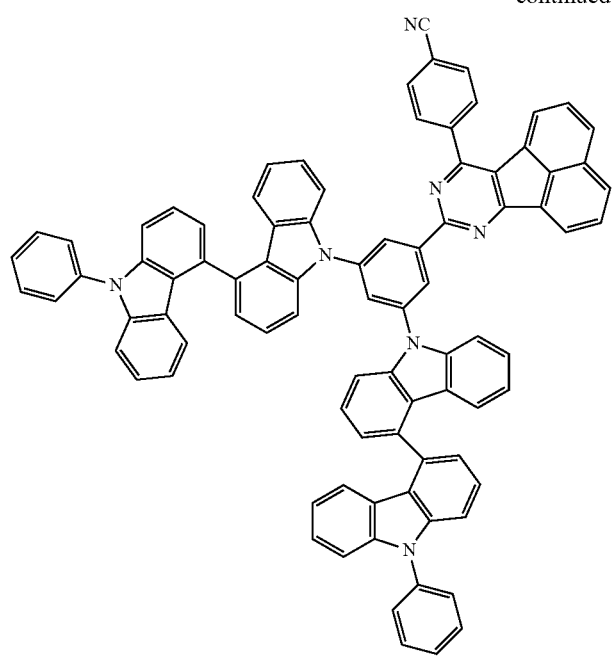
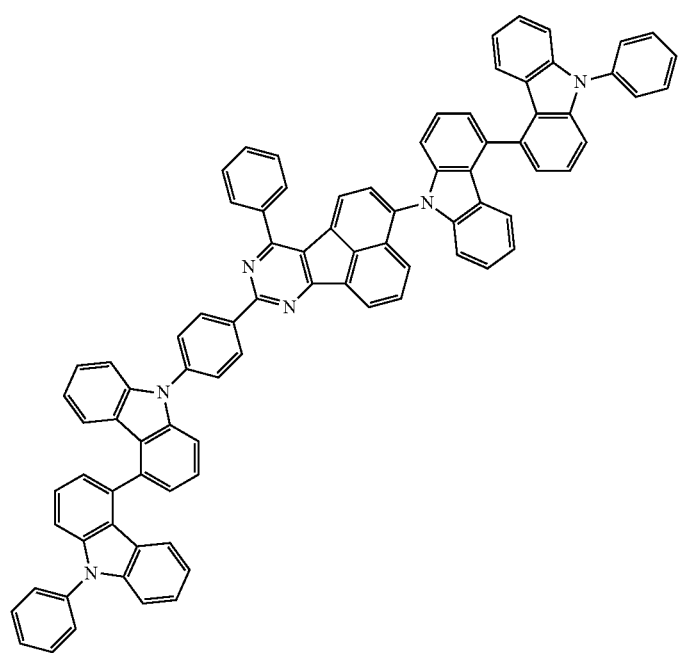

-continued
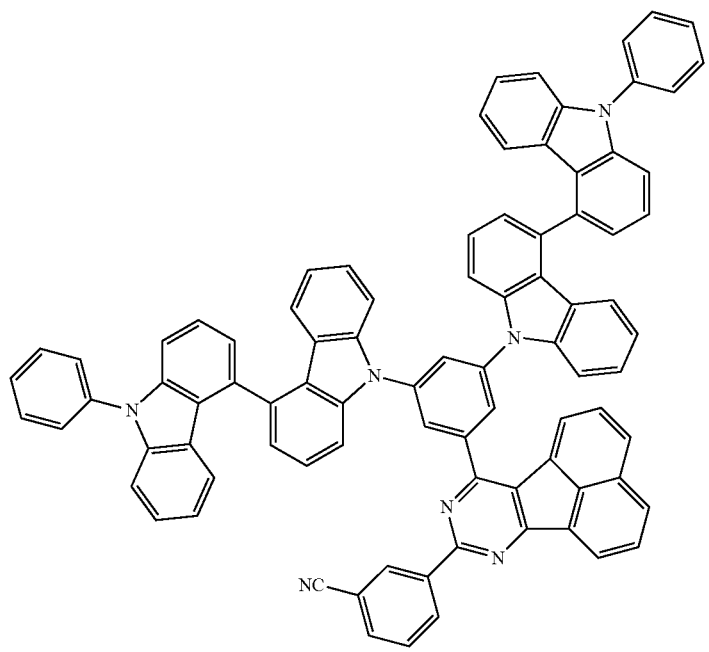
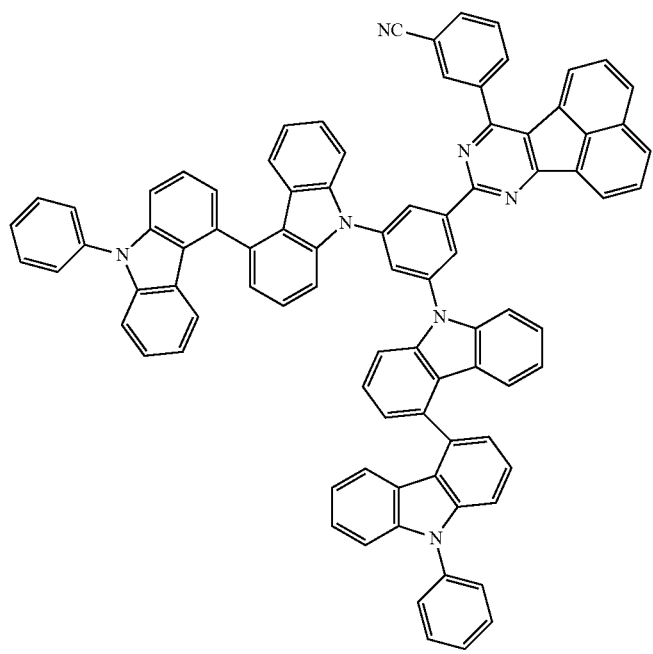

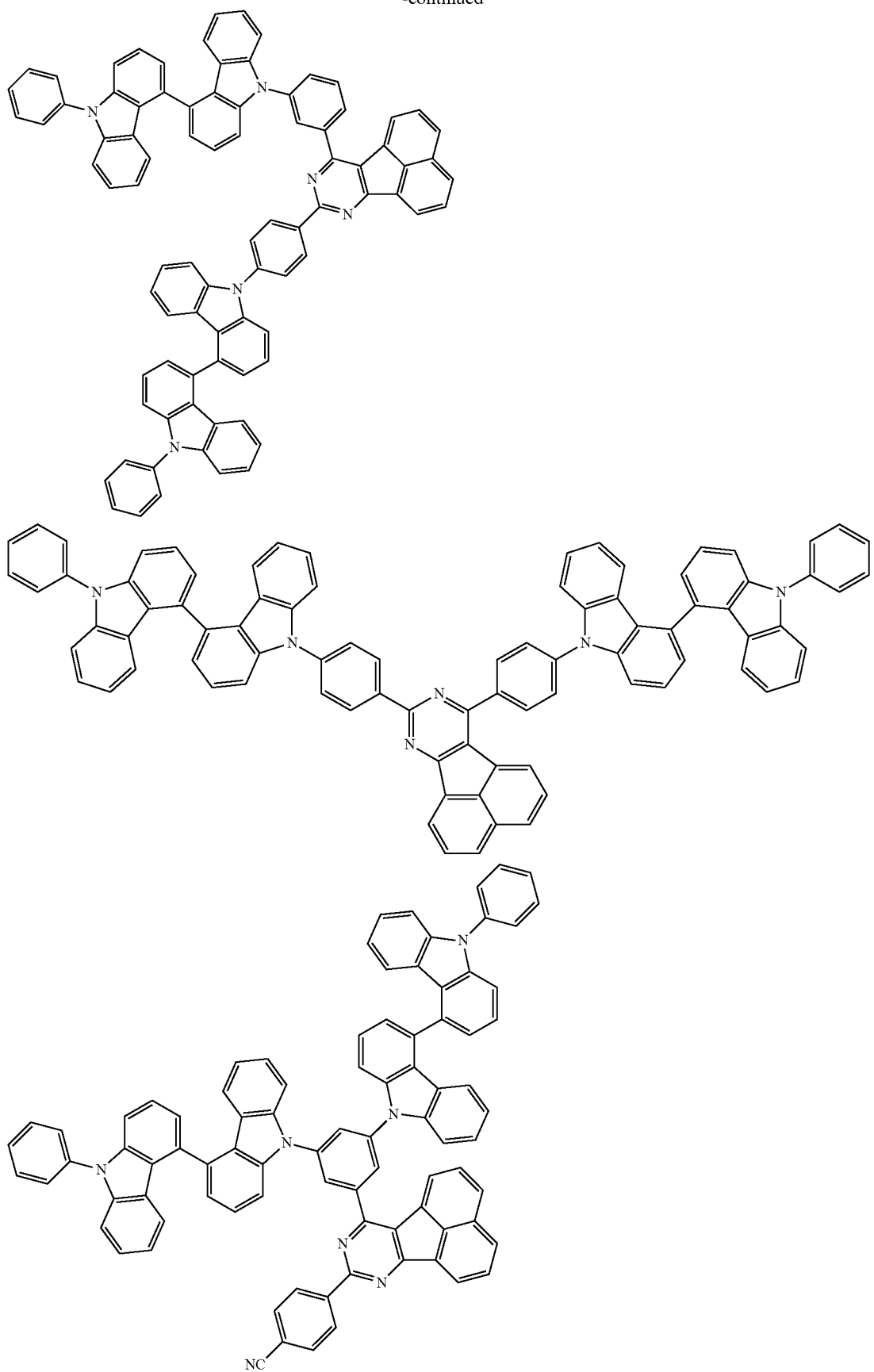

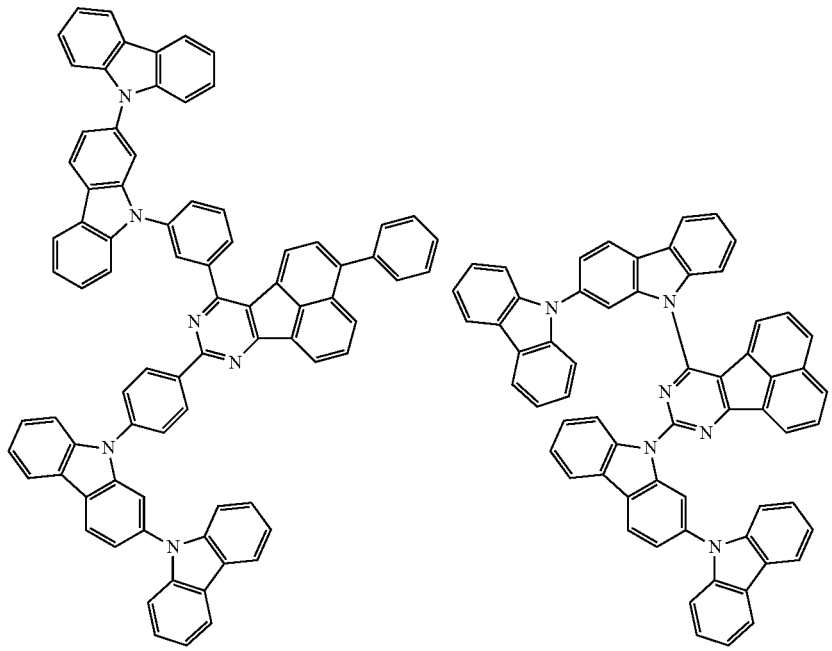
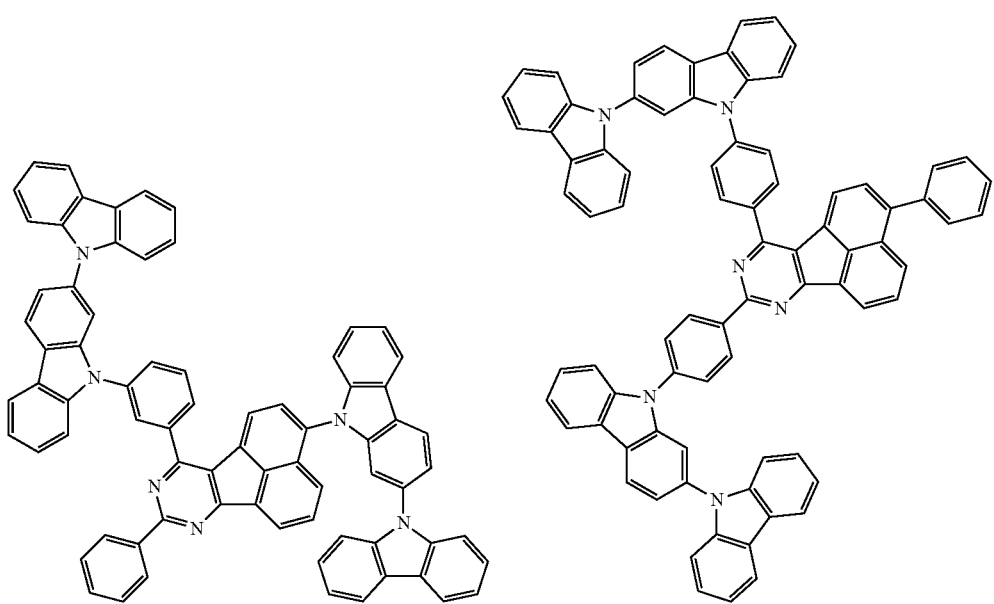

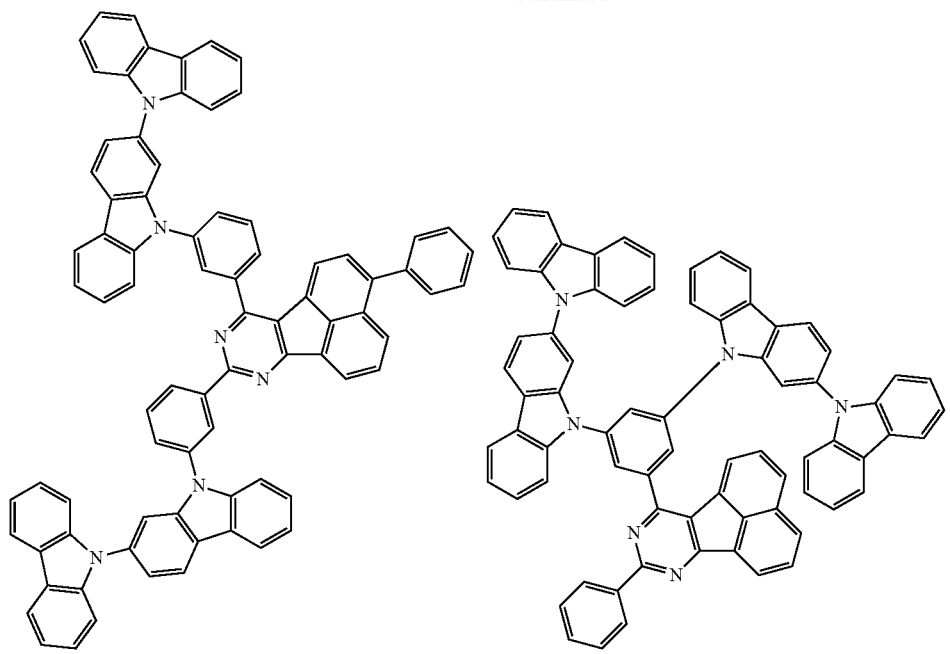
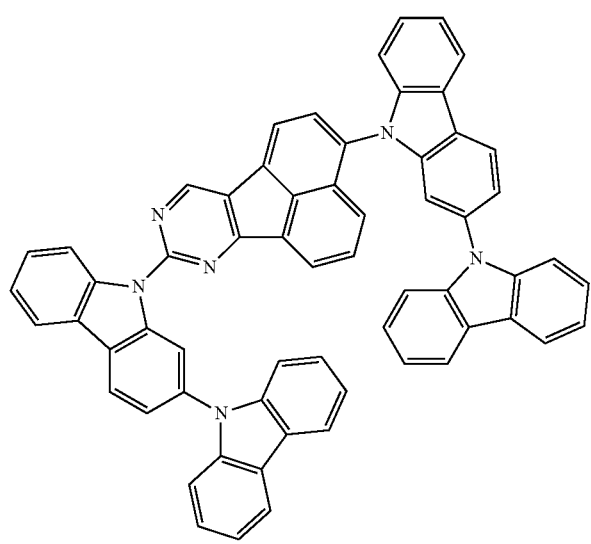

-continued
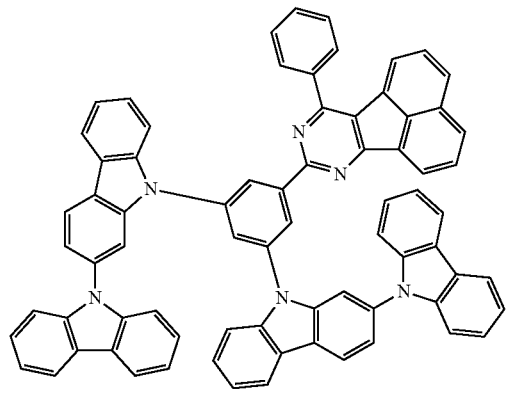
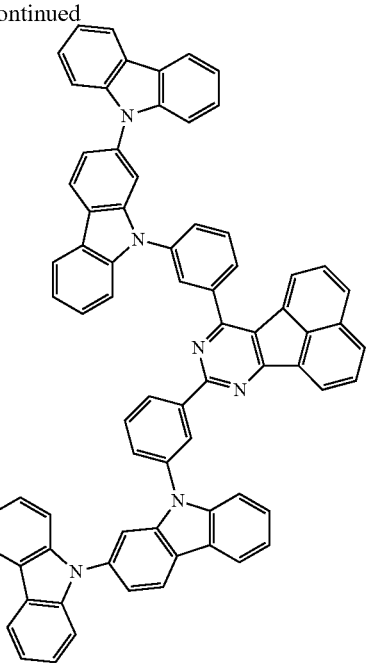
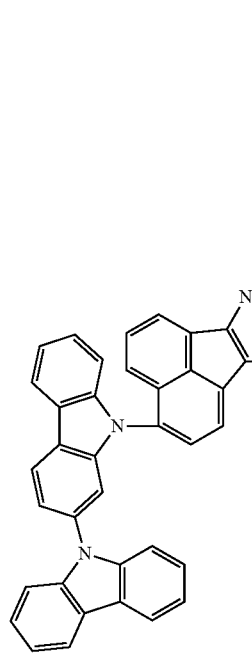
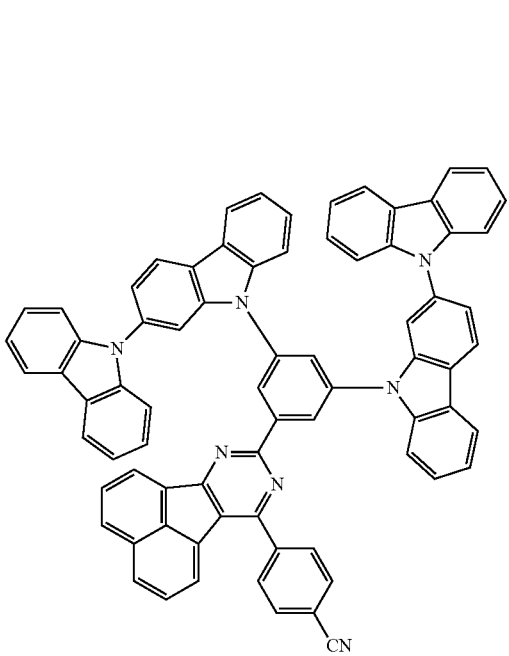

-continued
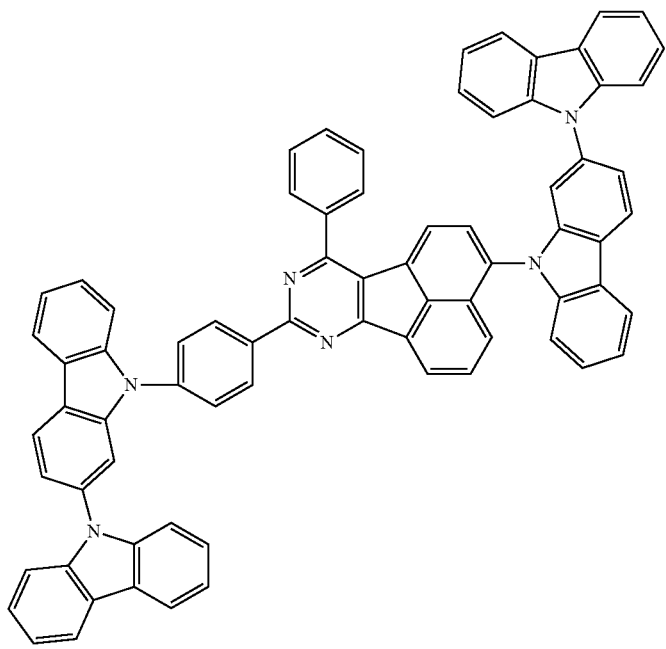
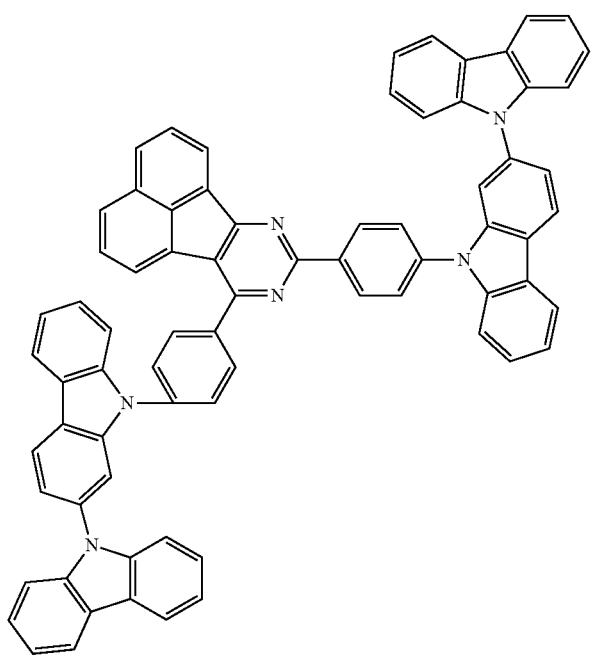

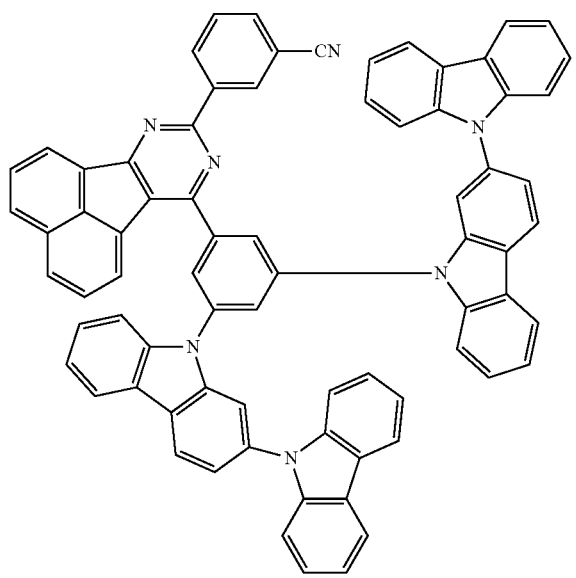
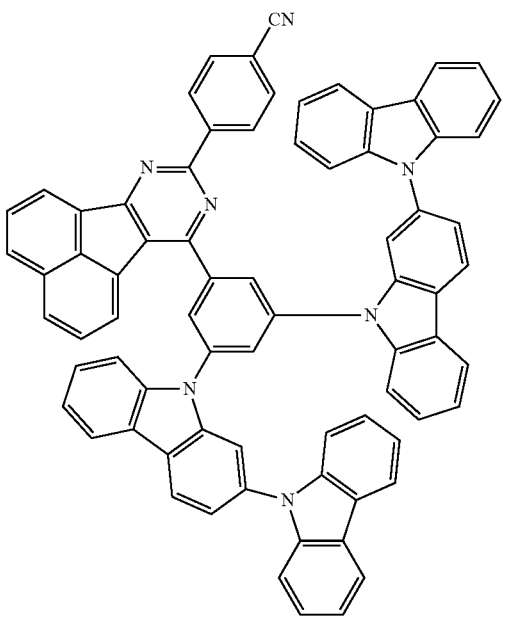
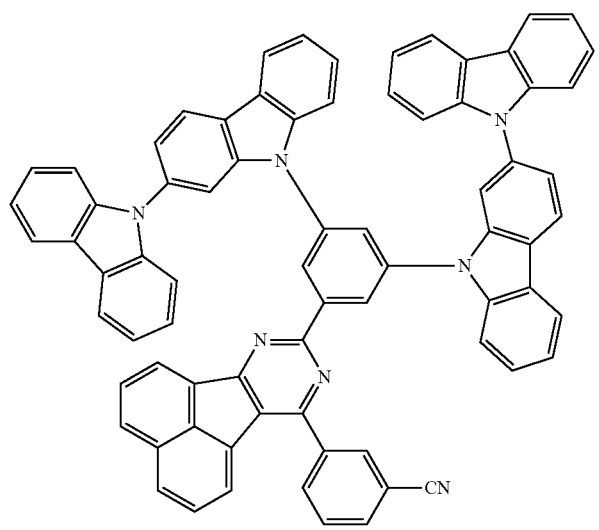

-continued
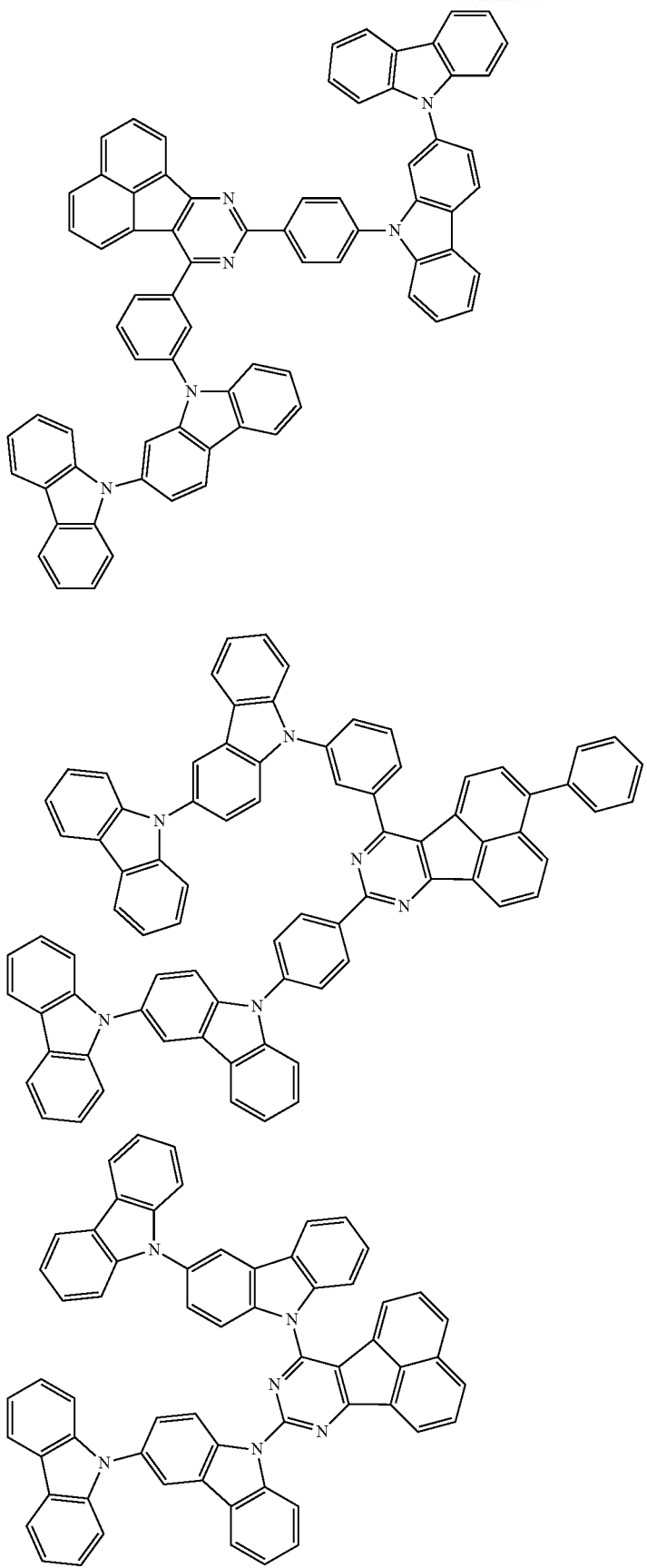

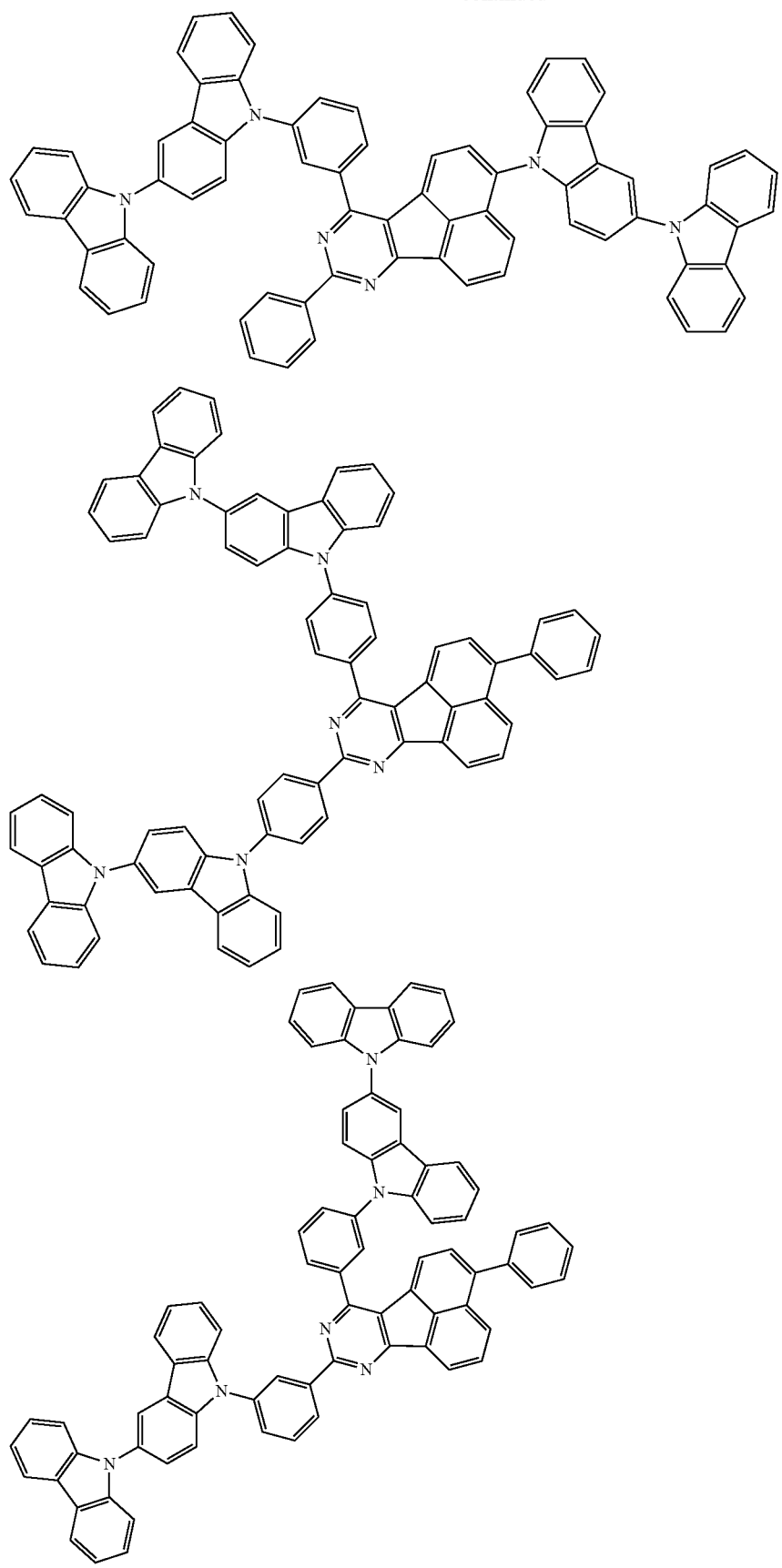

-continued
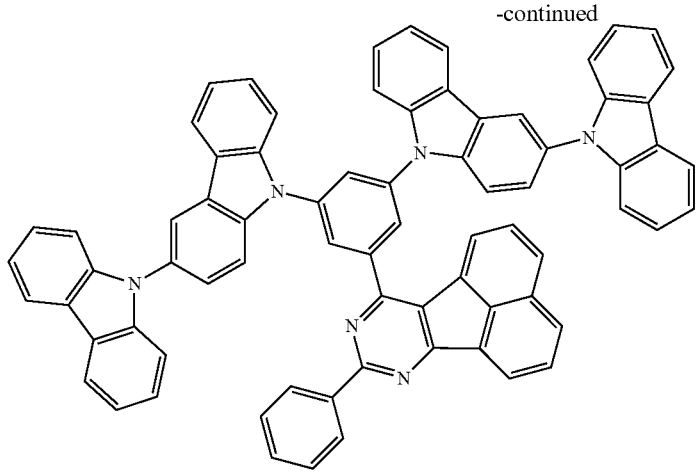
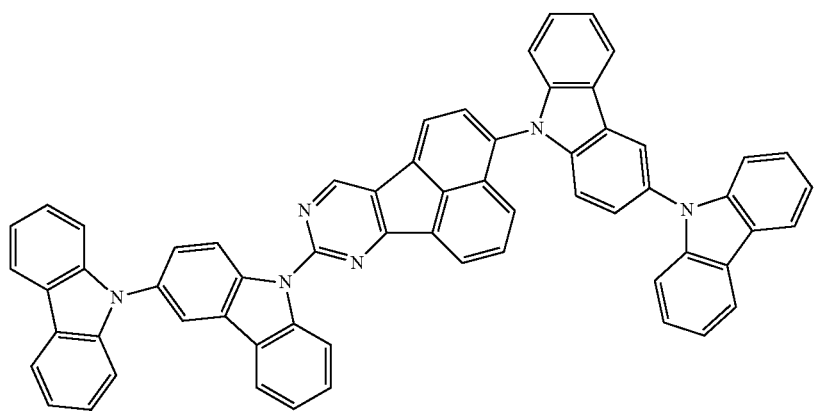
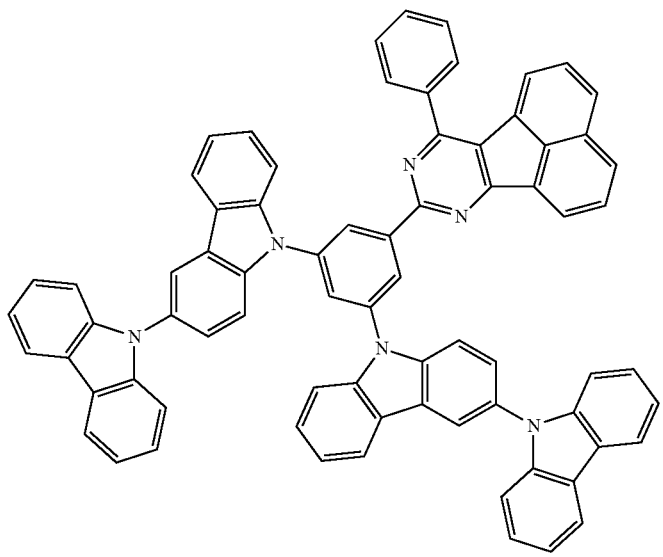

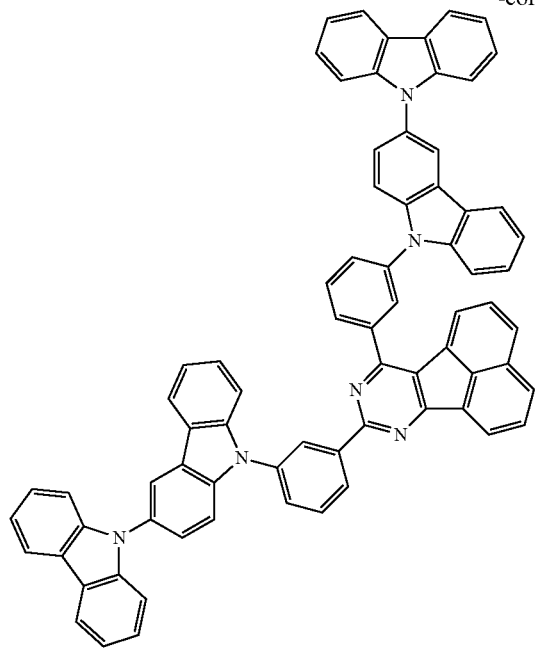
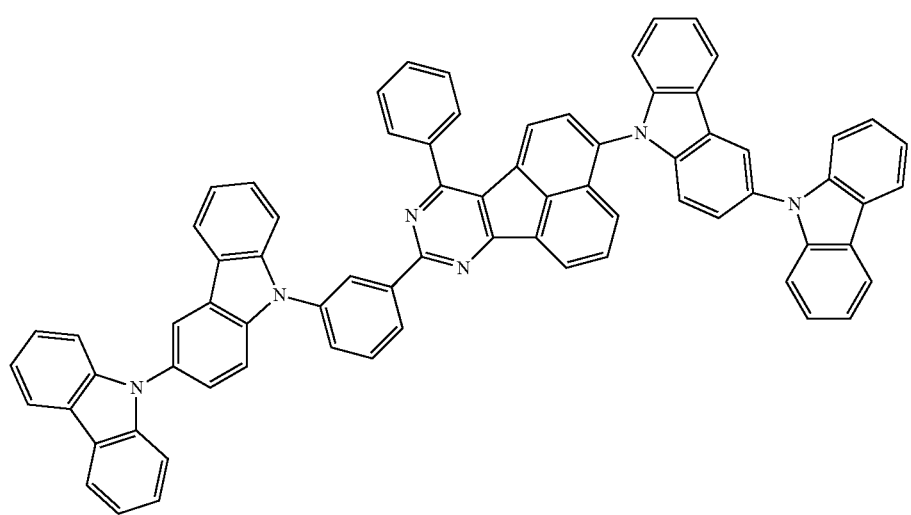

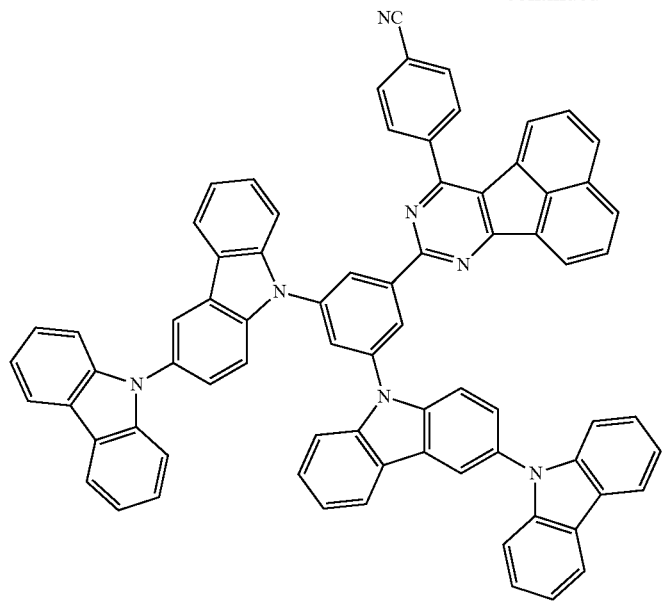
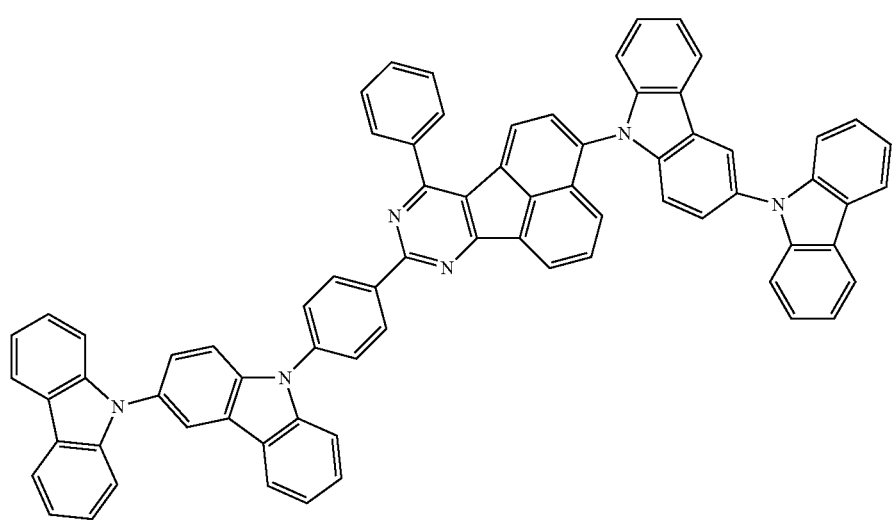

-continued
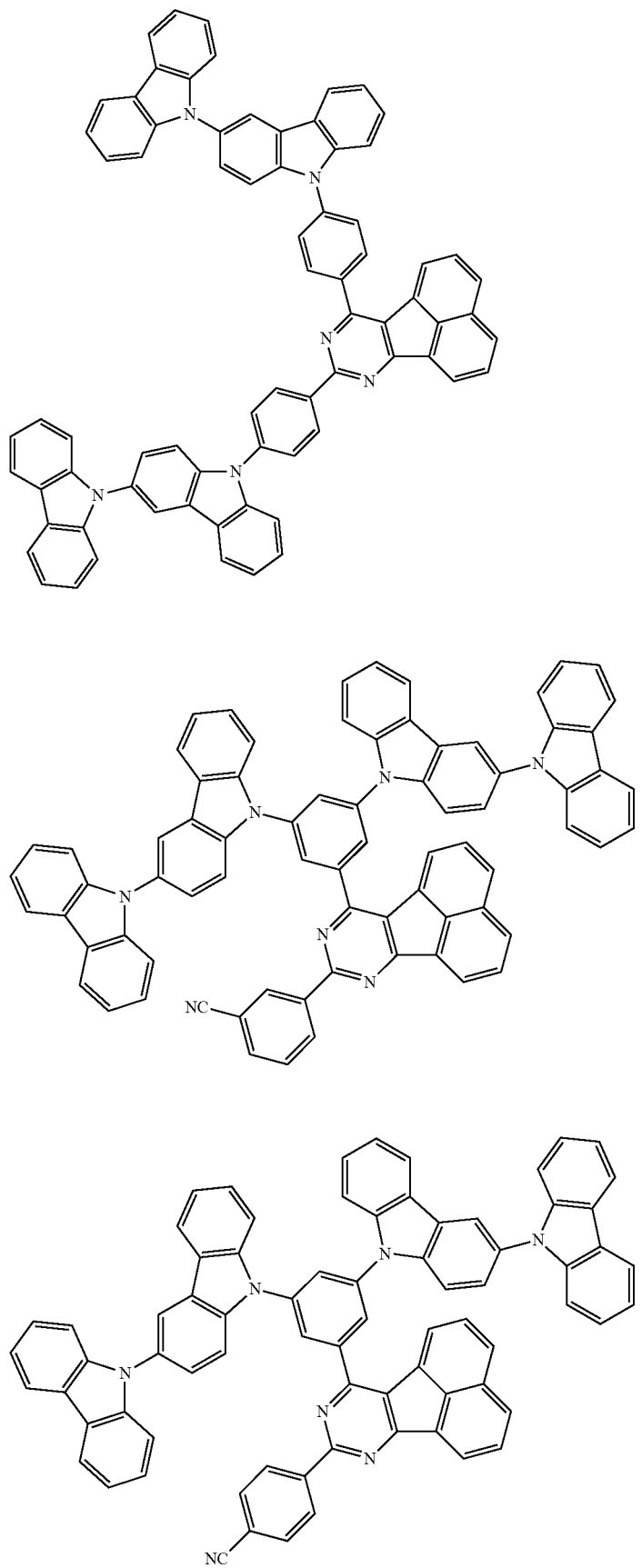 [SMILES: c1cc2c3c(cccc3c1)-c1c(-c3ccc(-n4c5ccccc5c5cc(-n6c7ccccc7c7ccccc76)ccc54)cc3)nc(-c3ccc(-n4c5ccccc5c5cc(-n6c7ccccc7c7ccccc76)ccc54)cc3)nc1-2 ; N#Cc1cccc(-c2nc(-c3cc(-n4c5ccccc5c5cc(-n6c7ccccc7c7ccccc76)ccc54)cc(-n4c5ccccc5c5cc(-n6c7ccccc7c7ccccc76)ccc54)c3)c3c(n2)-c2cccc4cccc-3c24)c1 ; N#Cc1ccc(-c2nc(-c3cc(-n4c5ccccc5c5cc(-n6c7ccccc7c7ccccc76)ccc54)cc(-n4c5ccccc5c5cc(-n6c7ccccc7c7ccccc76)ccc54)c3)c3c(n2)-c2cccc4cccc-3c24)cc1]

-continued
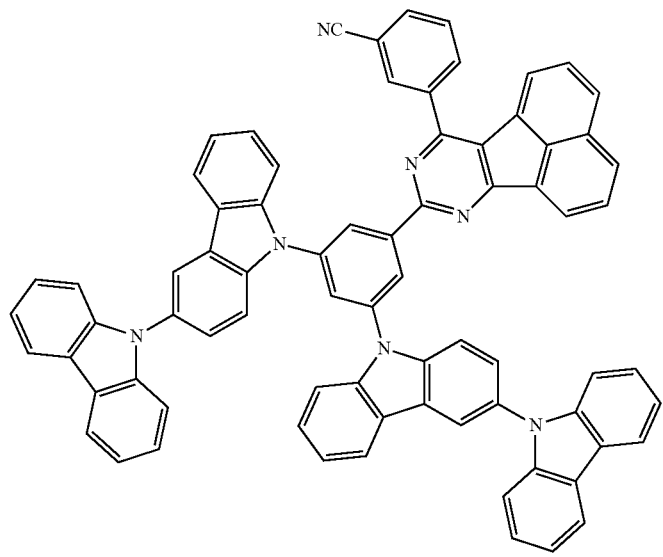
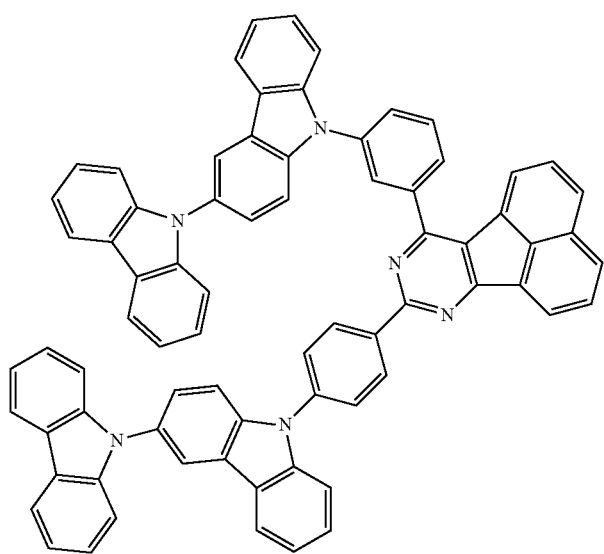

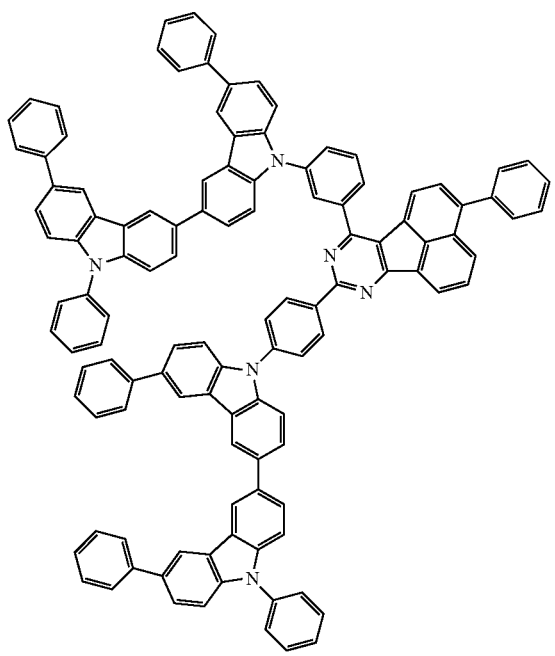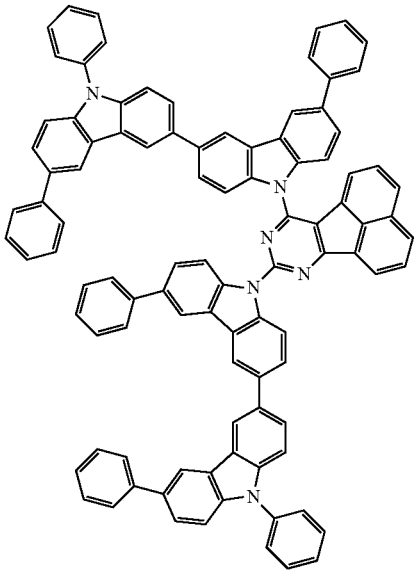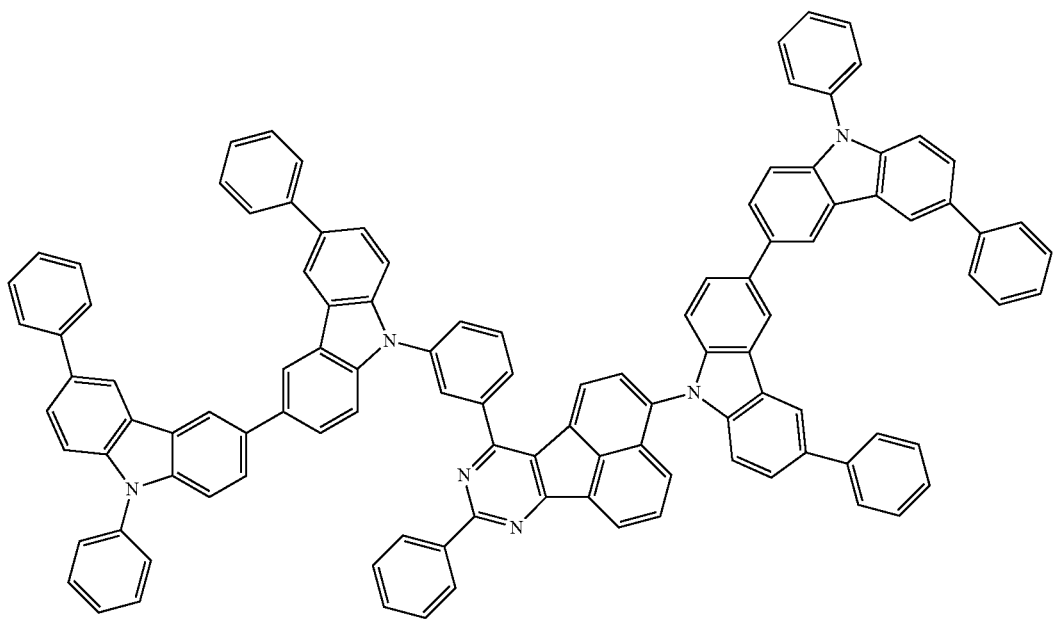

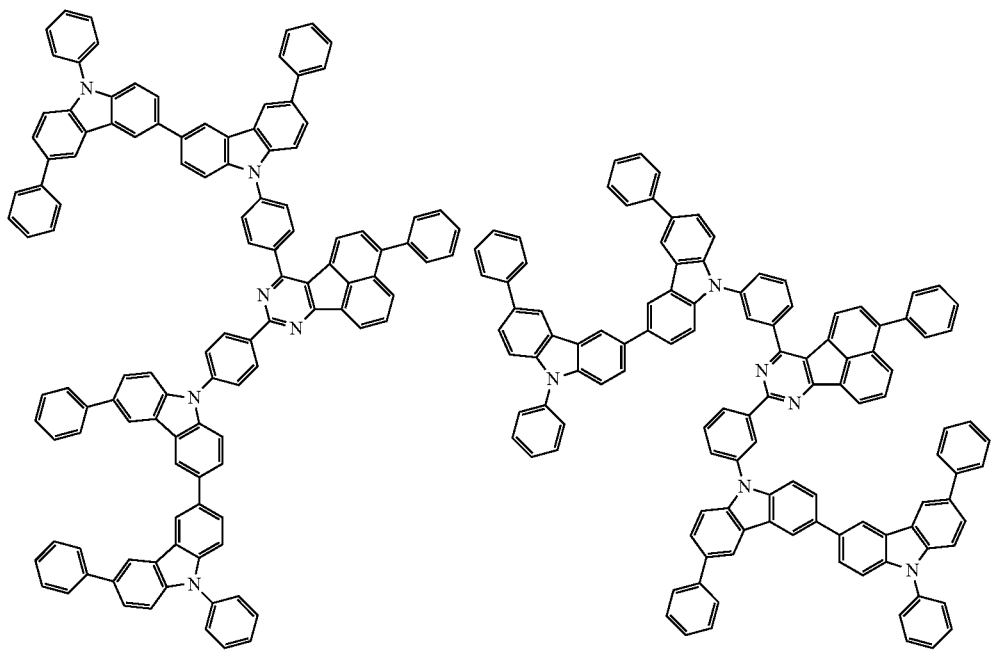
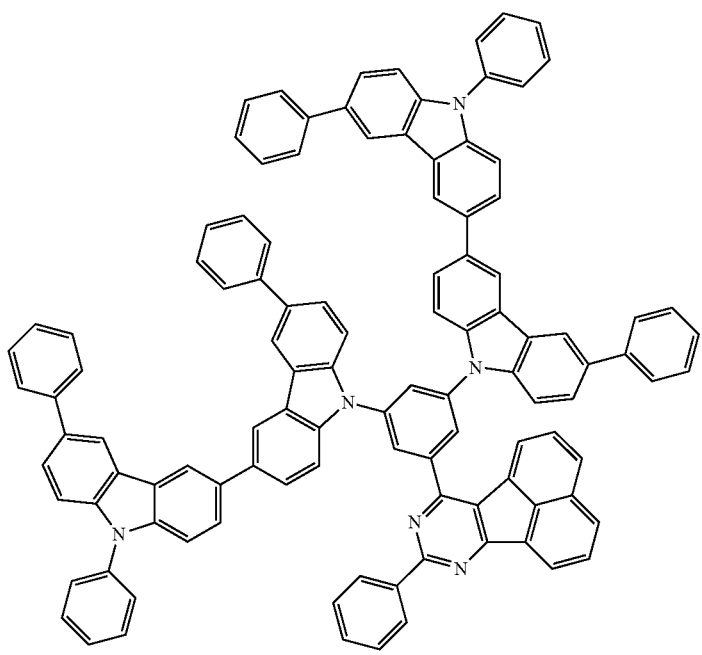

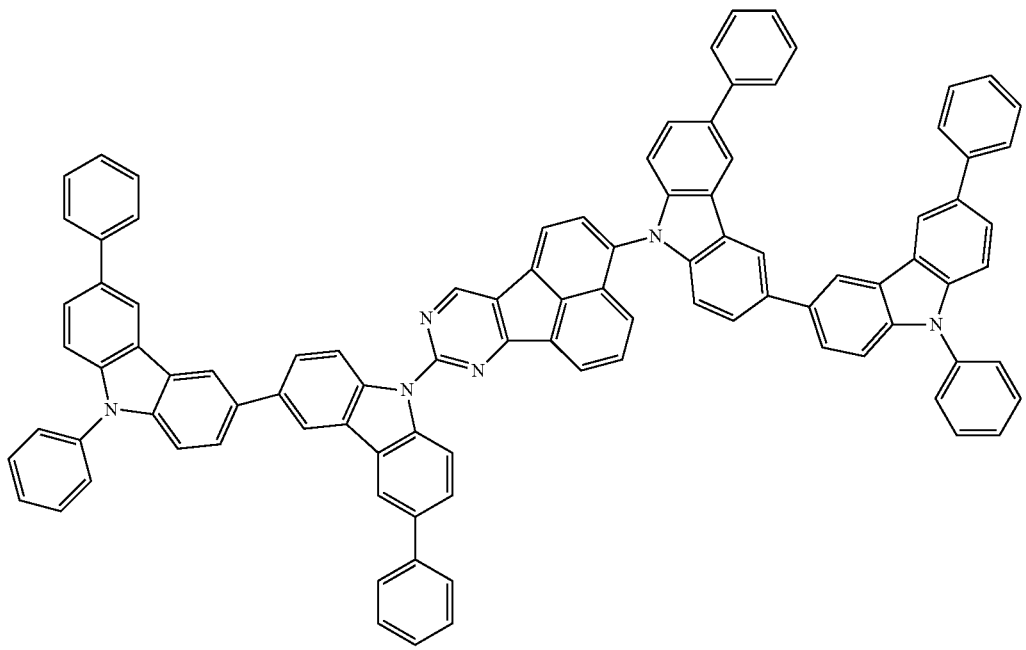
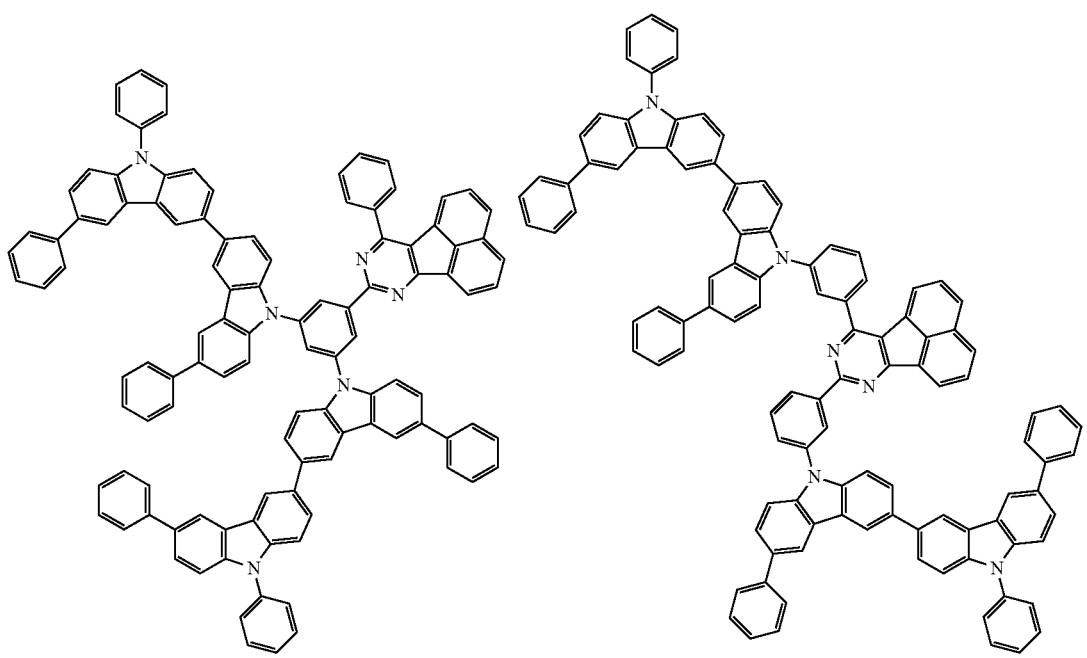

101
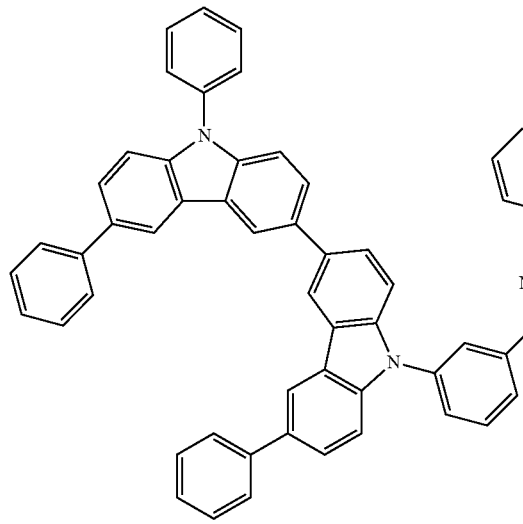
102
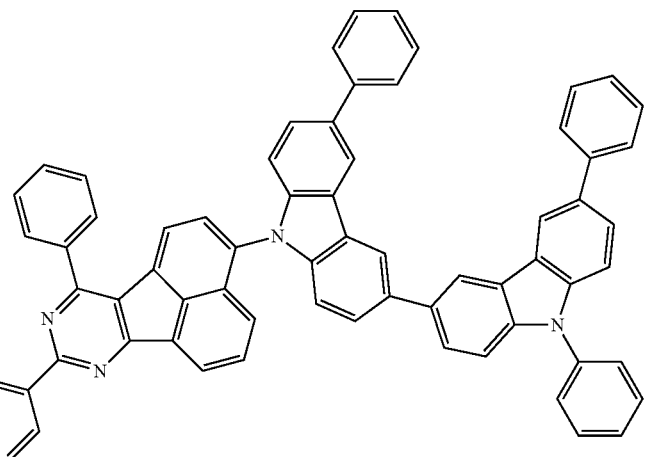
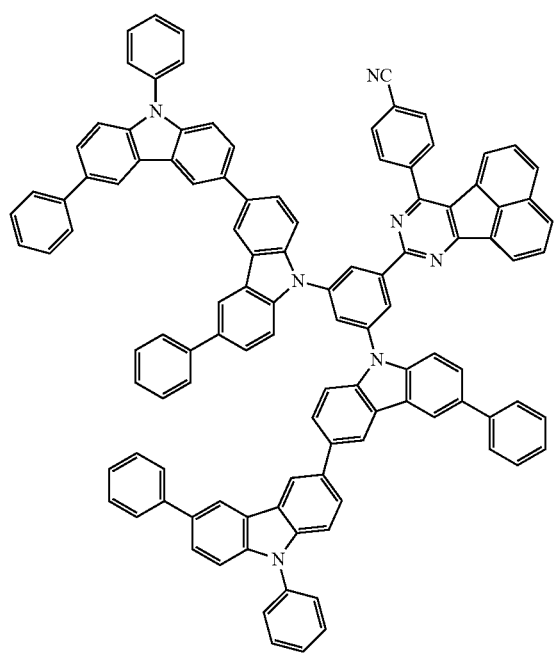

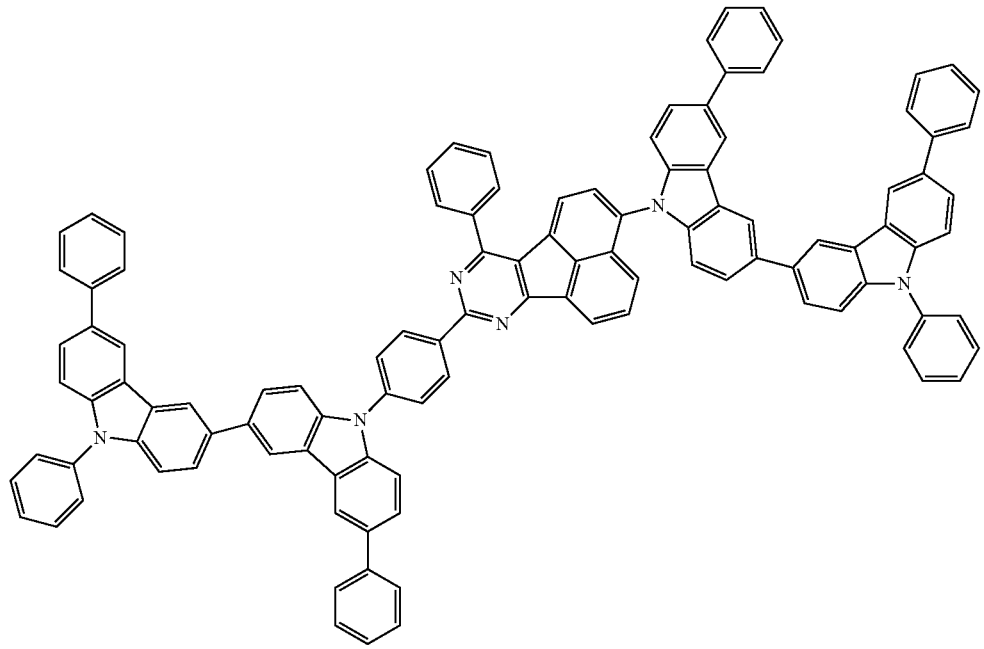
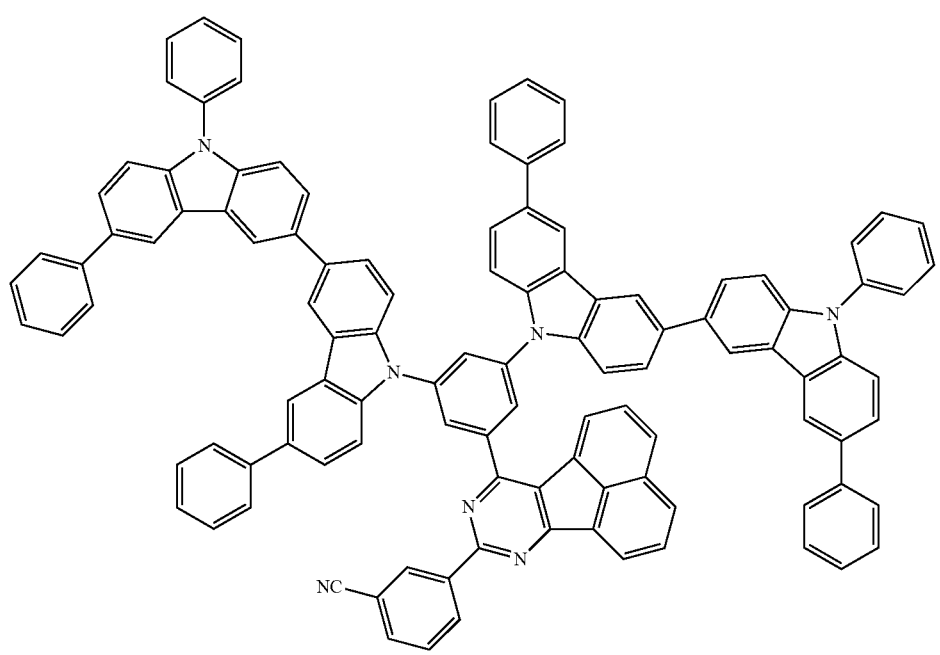

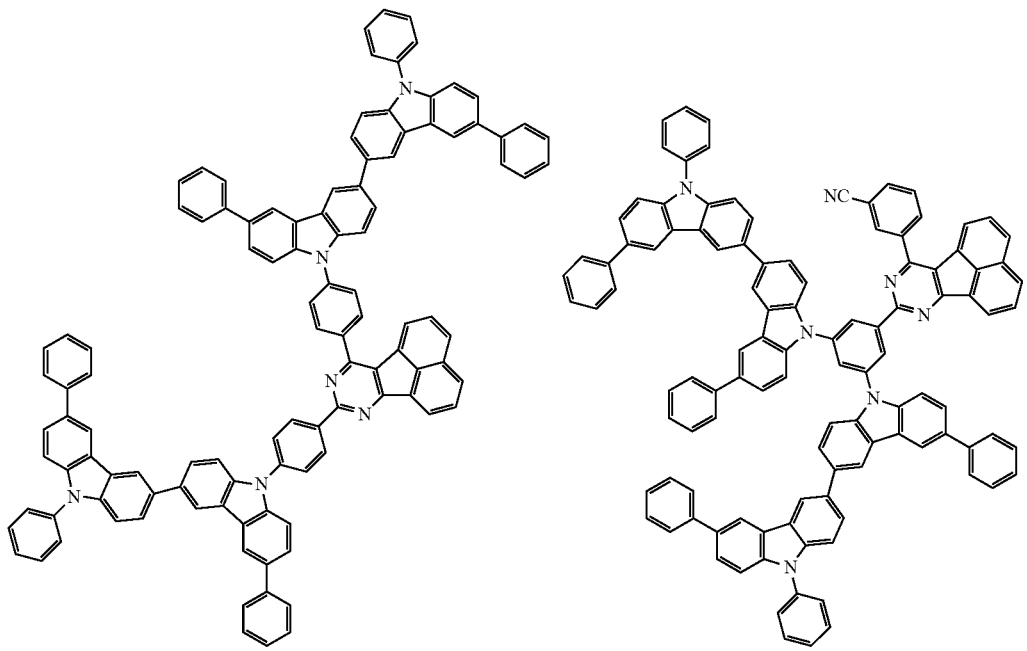
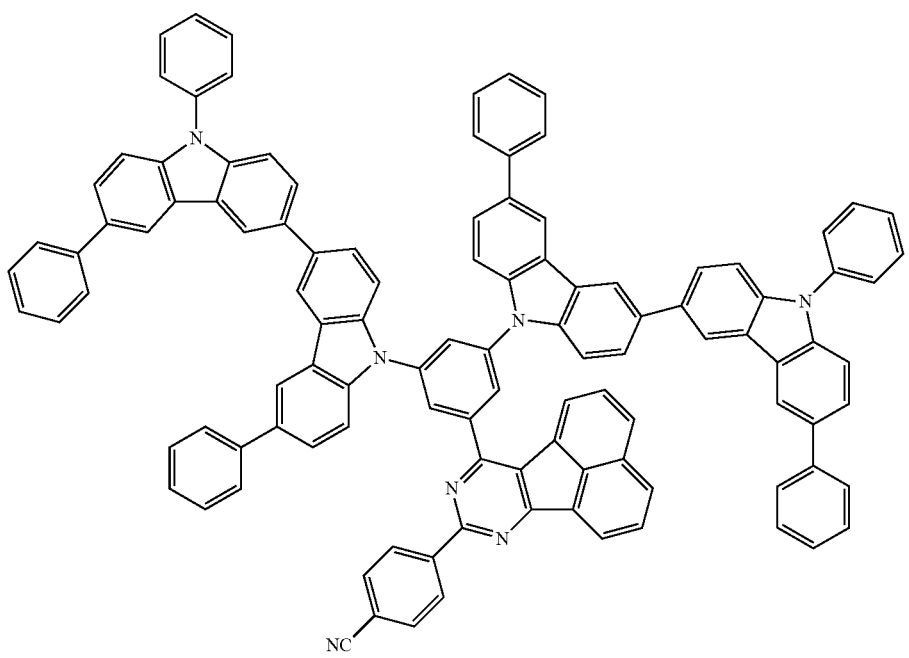

-continued
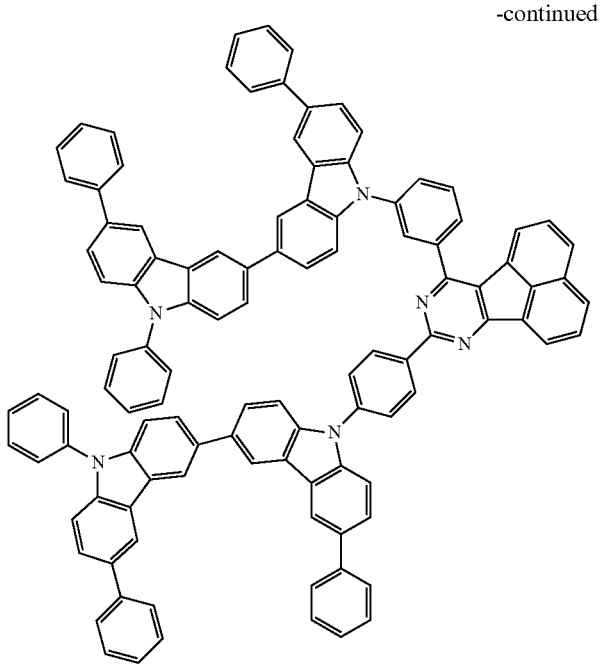
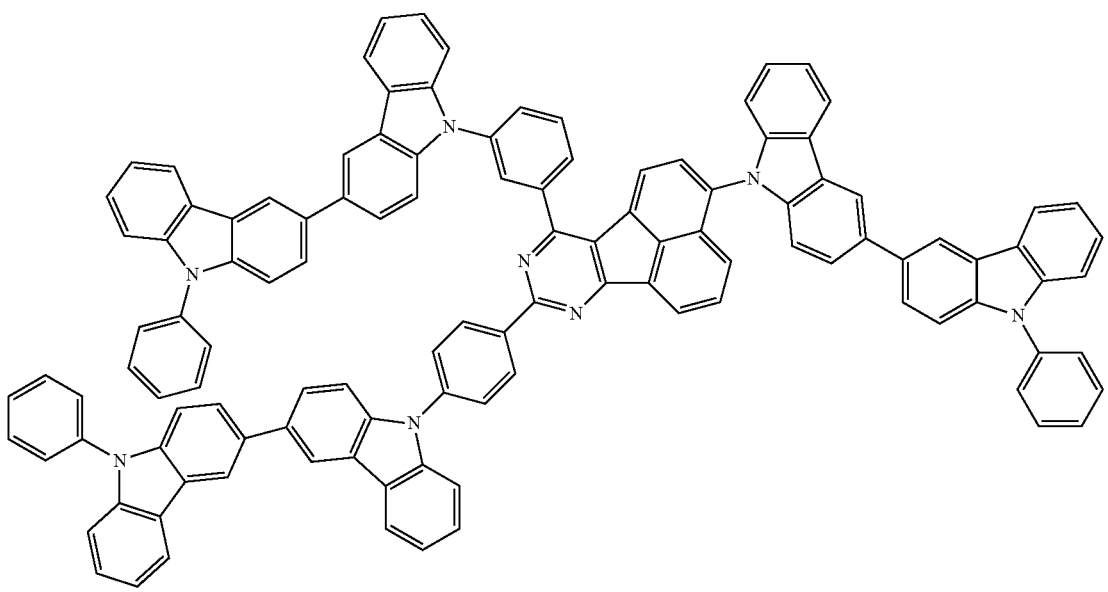

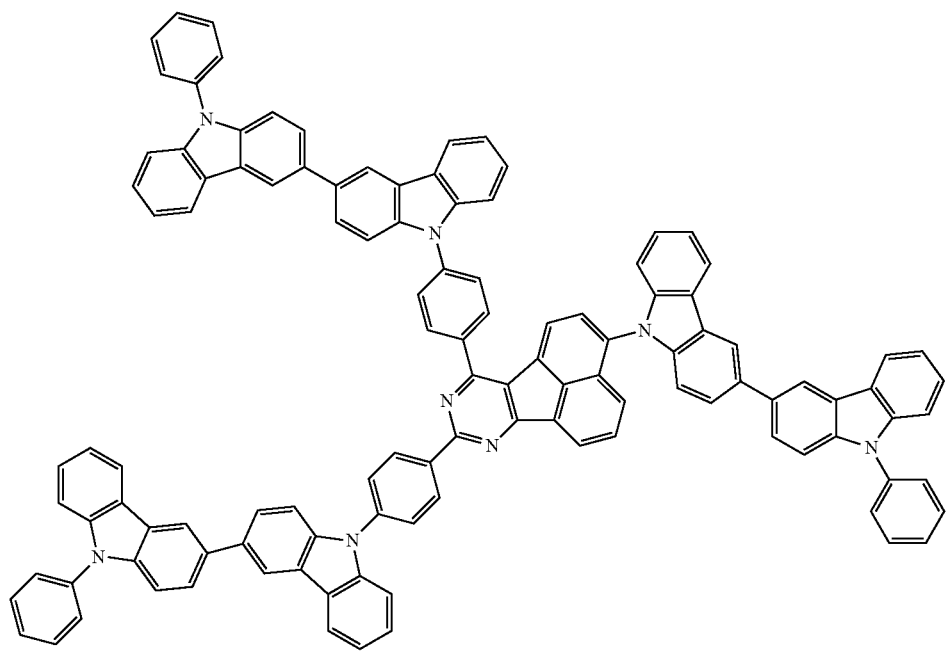
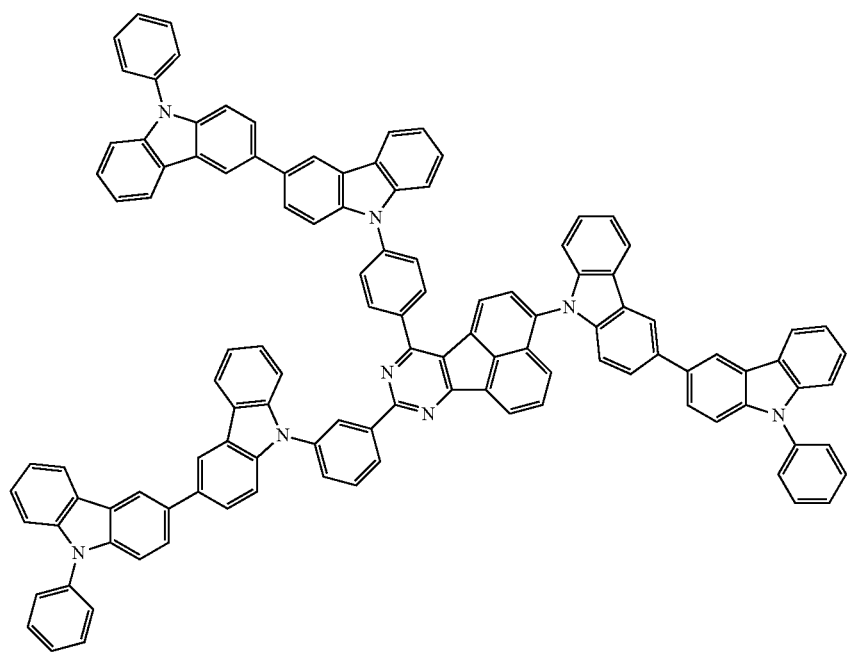

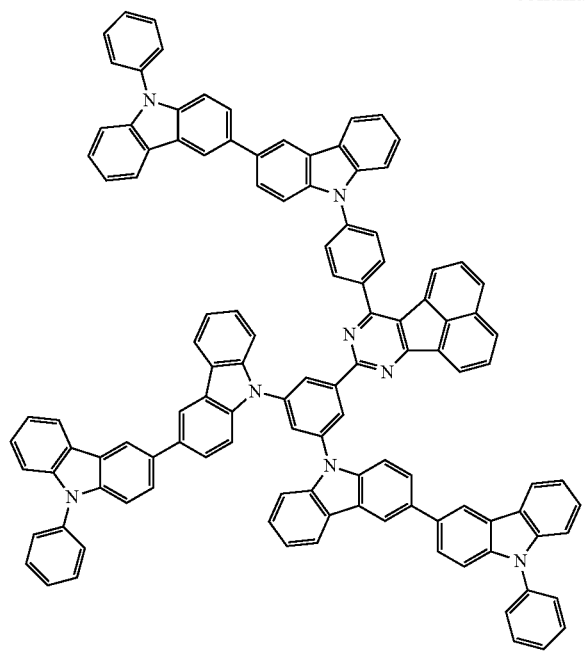
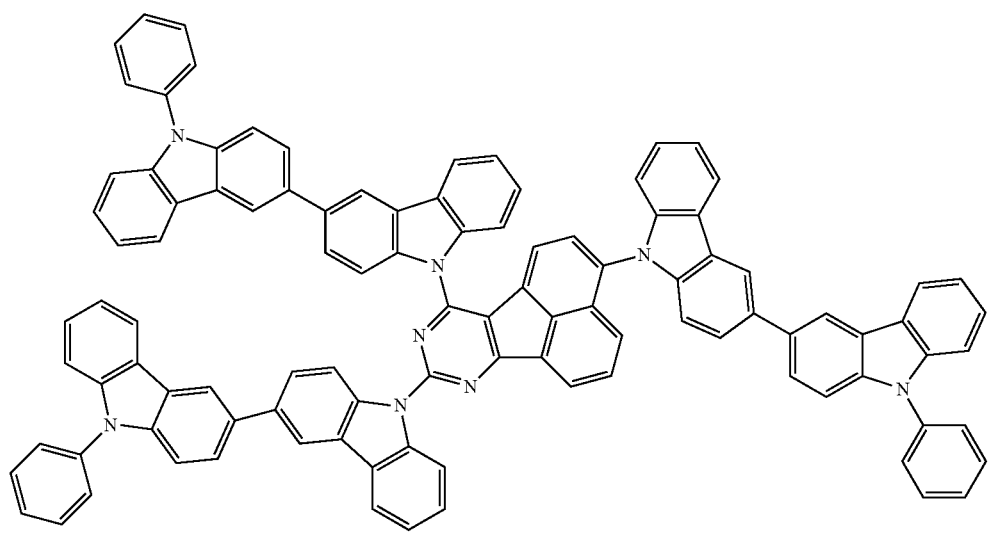

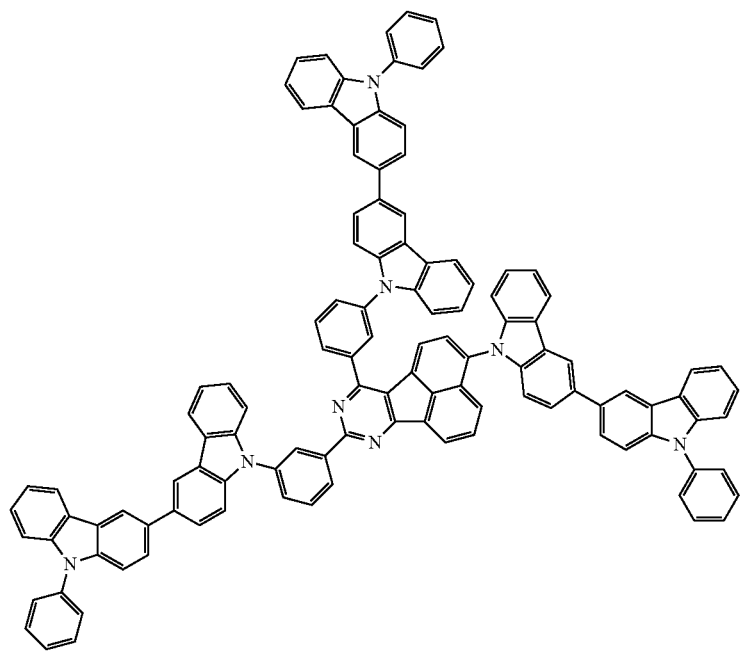
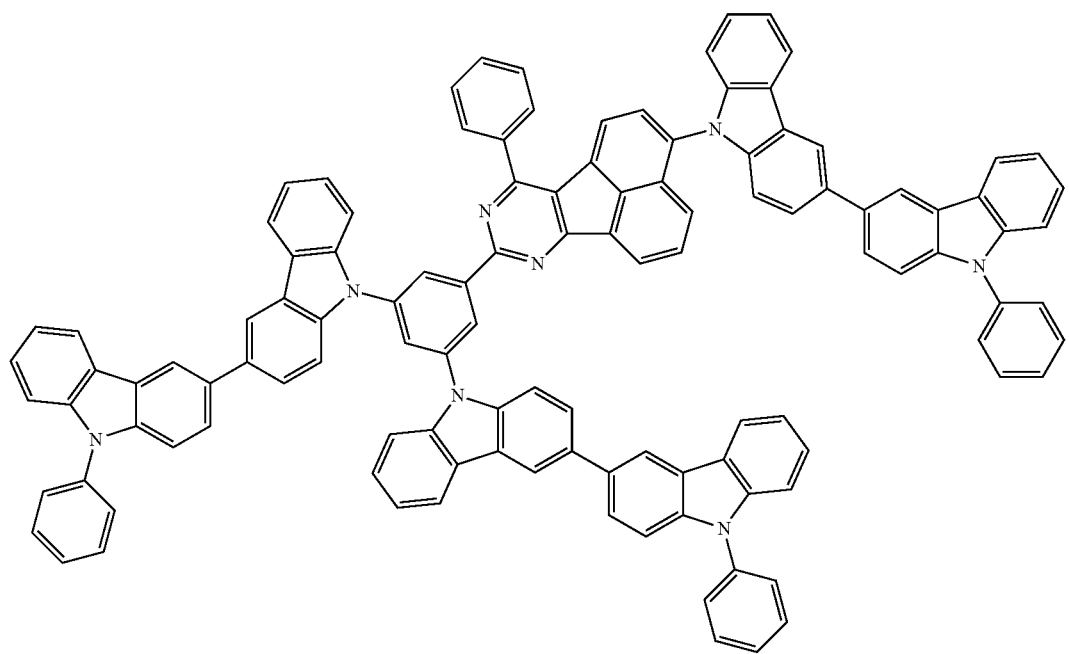

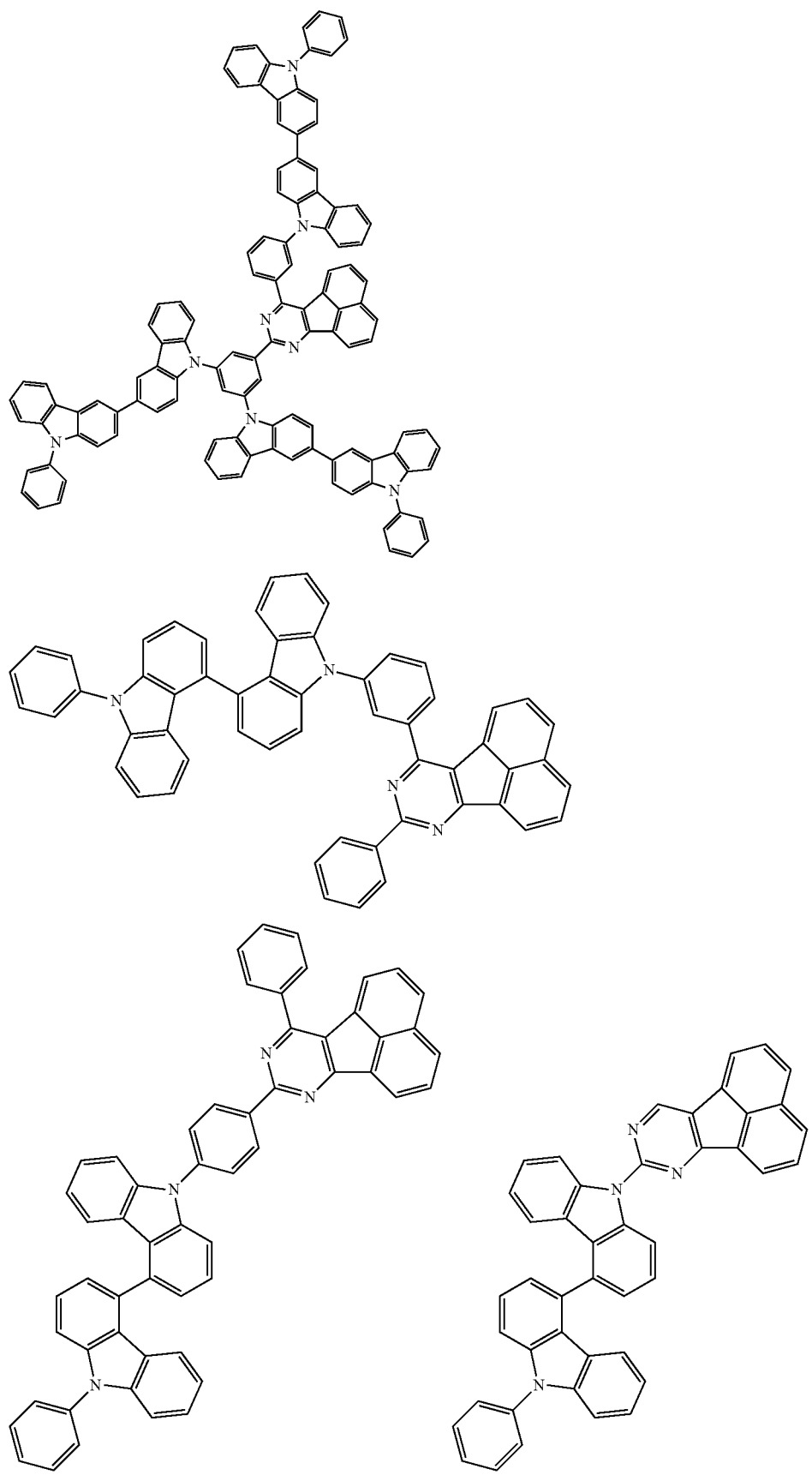

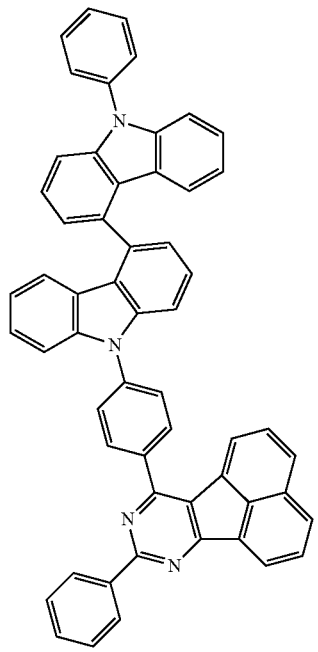
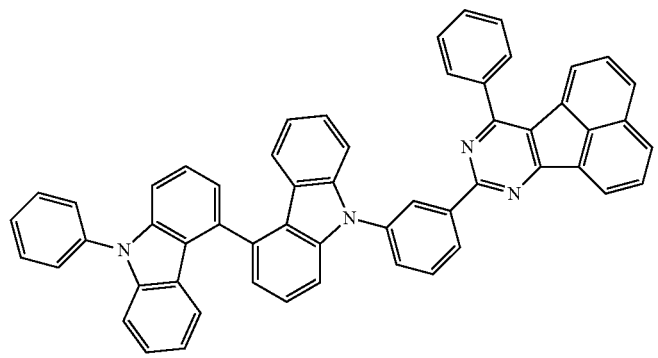
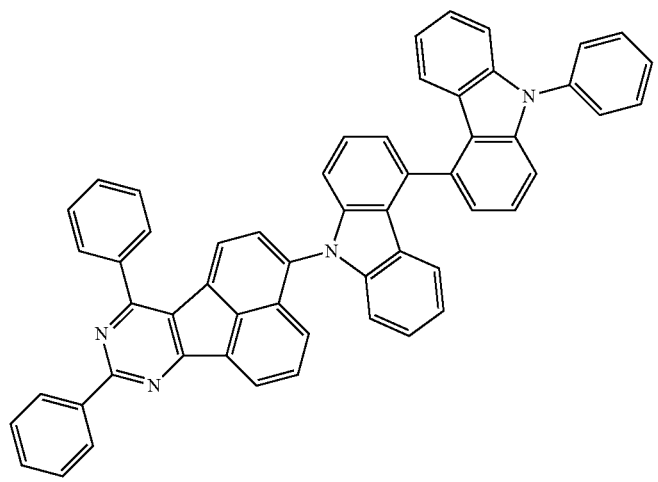

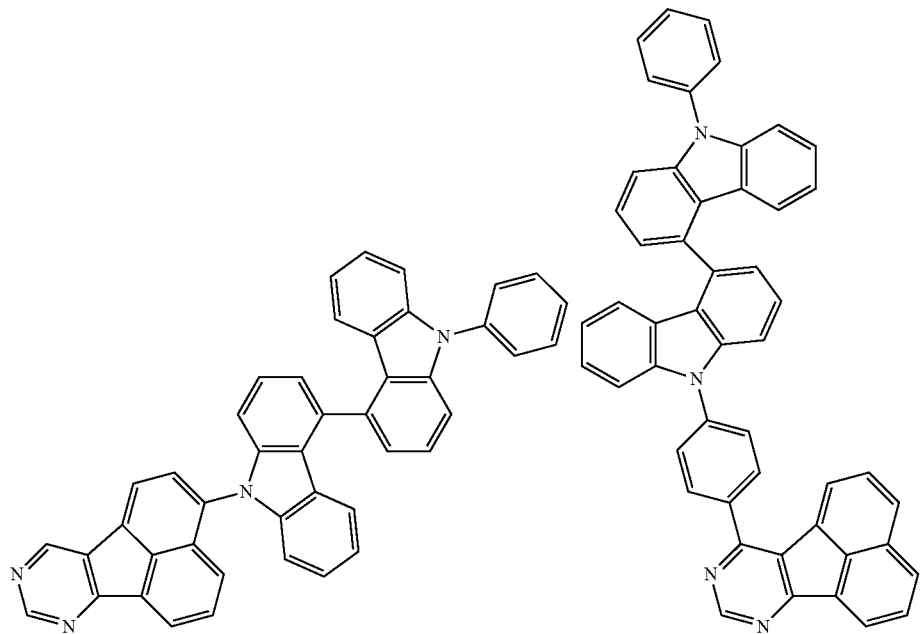
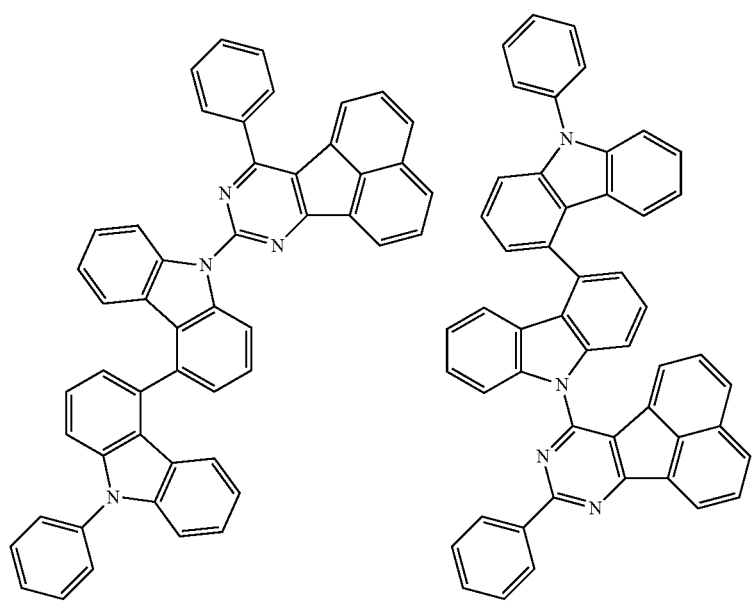

-continued
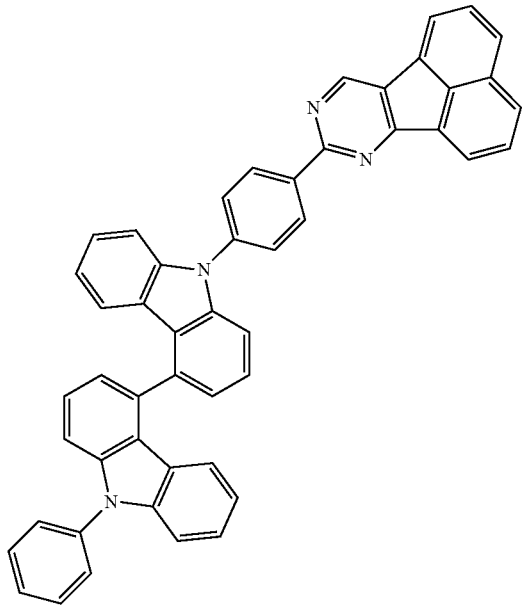
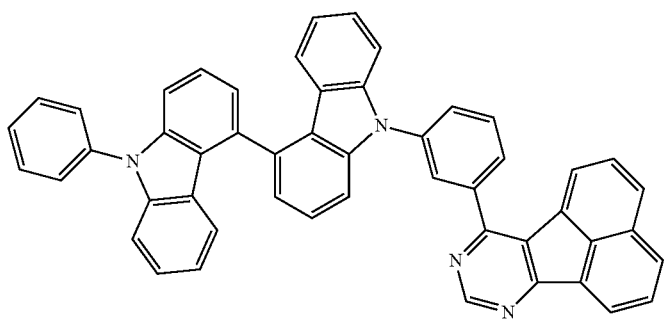
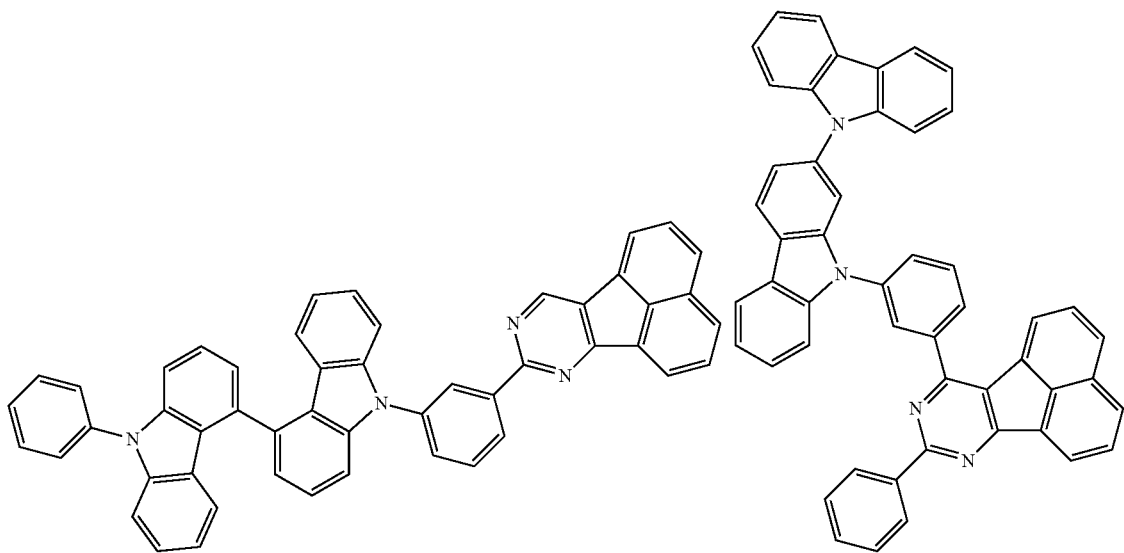

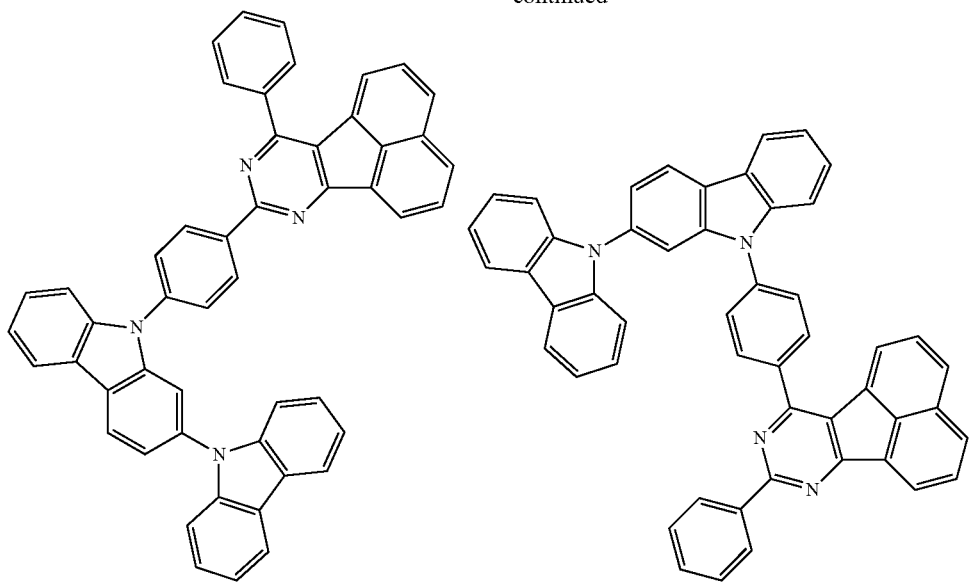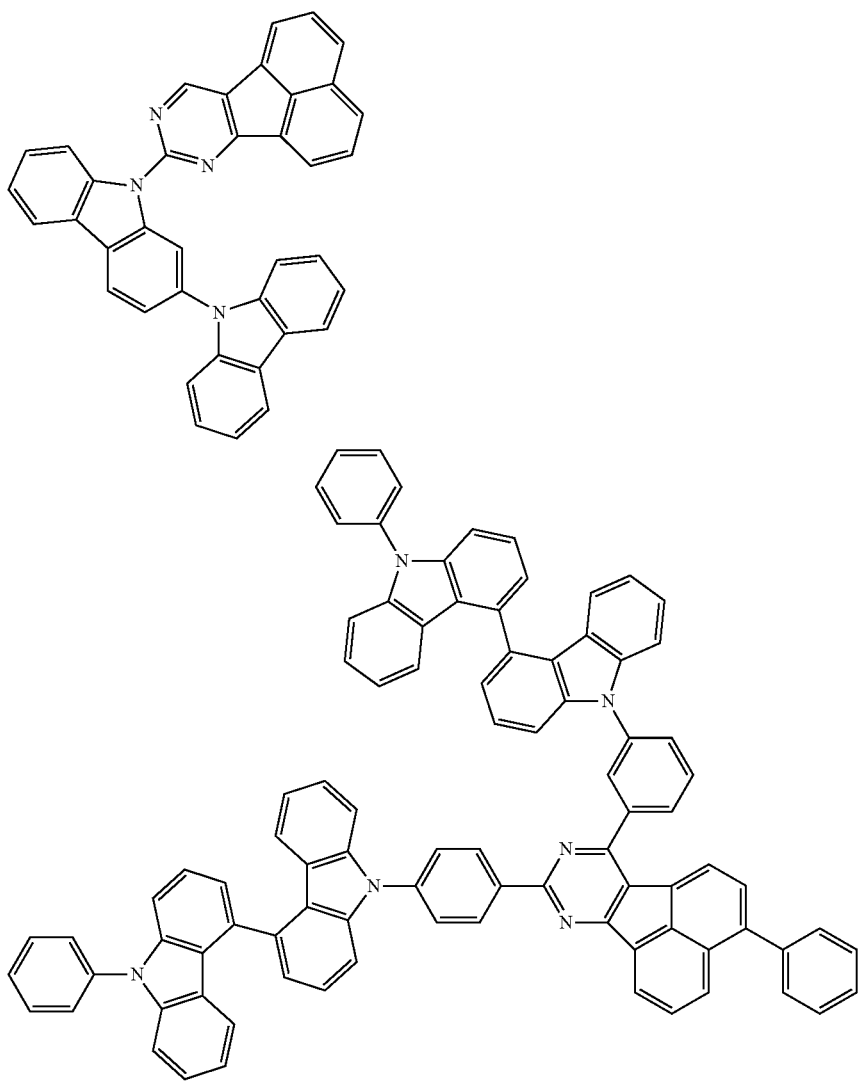

-continued
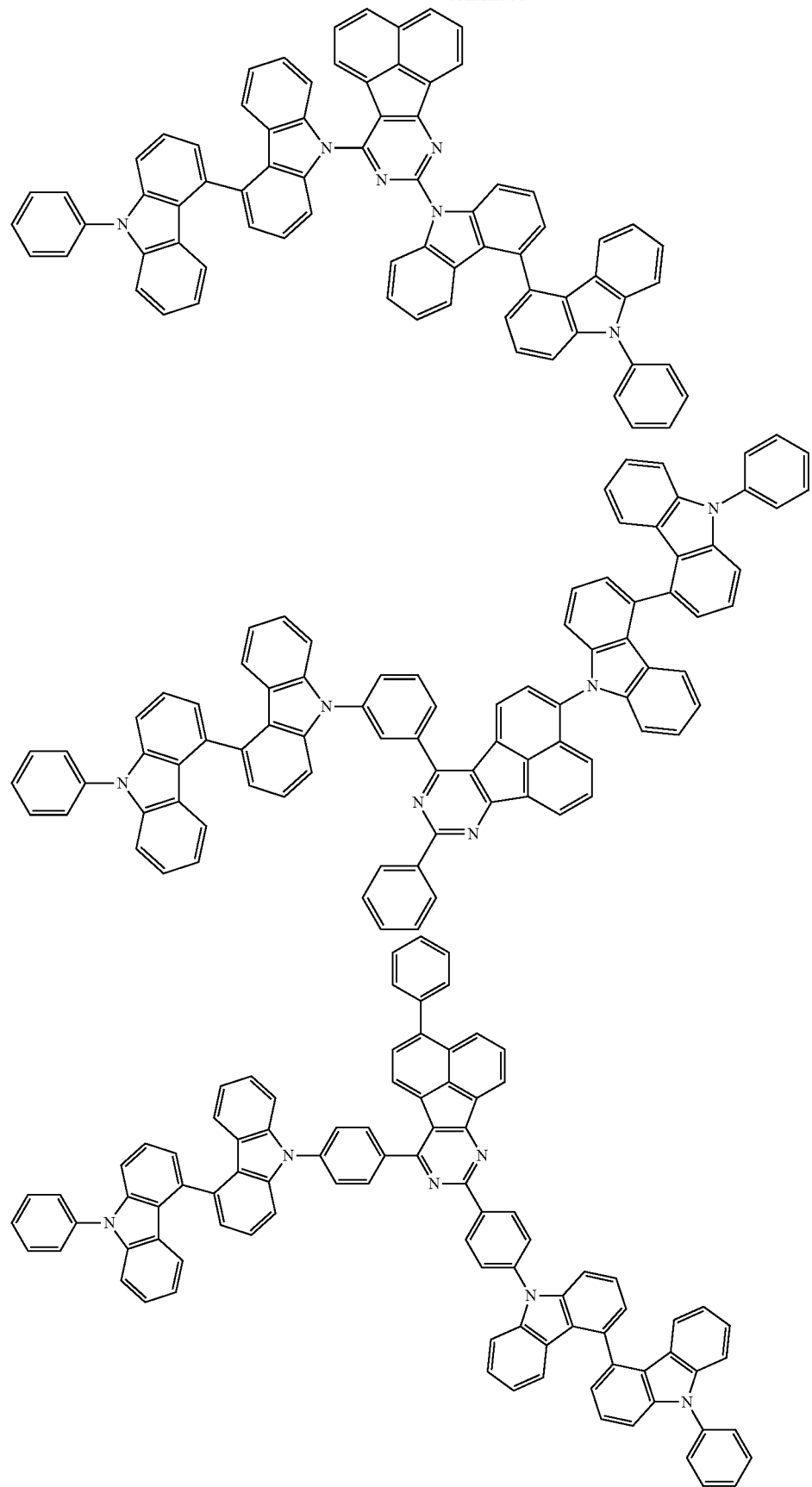

-continued
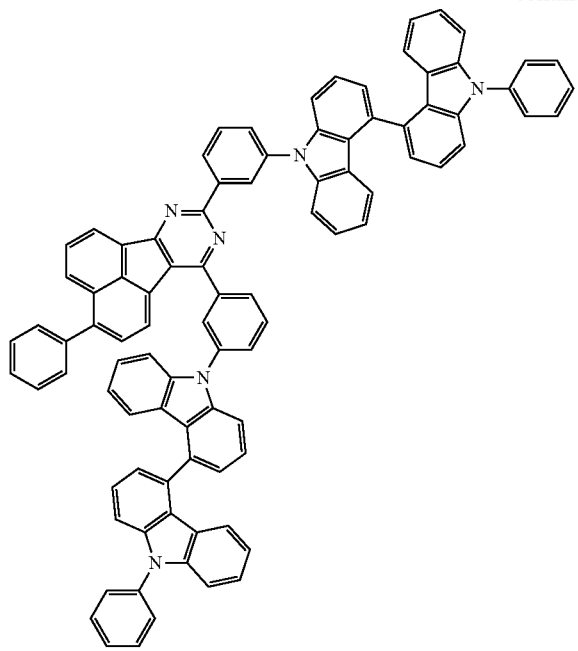
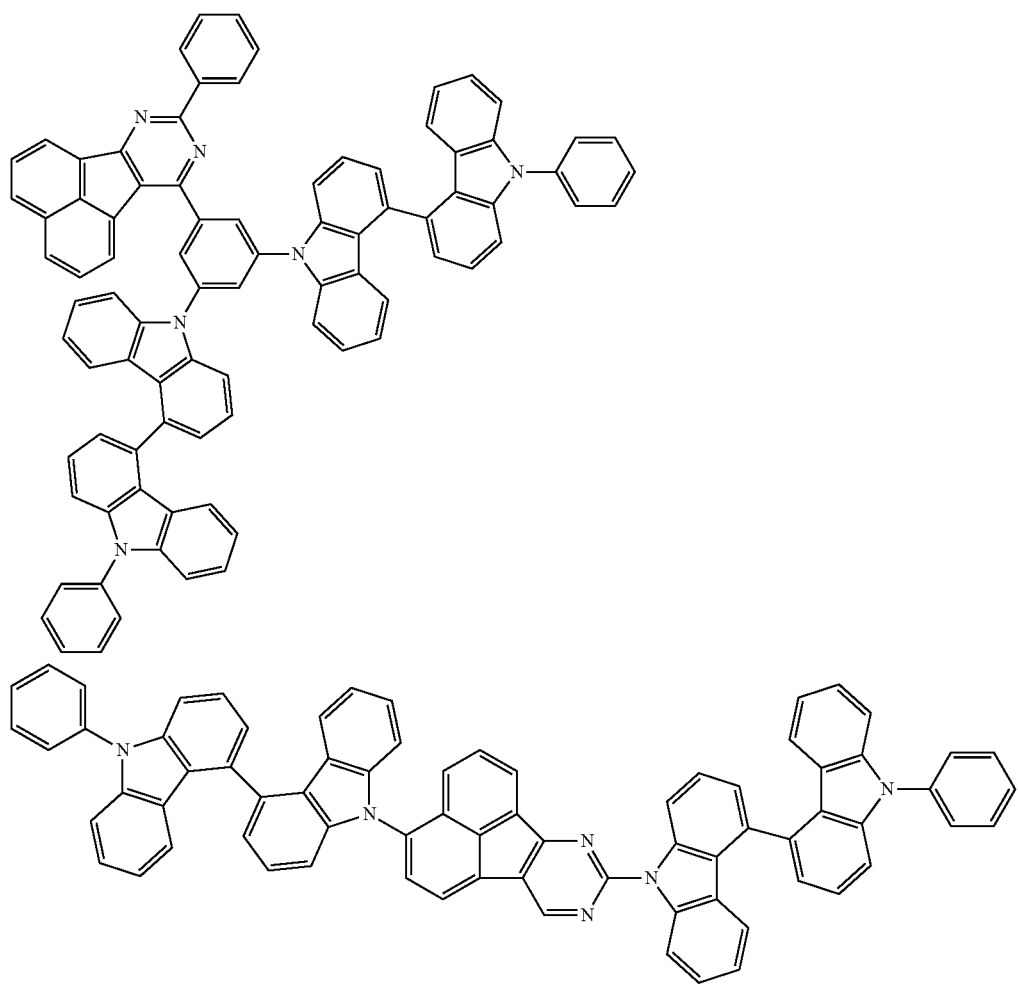

-continued
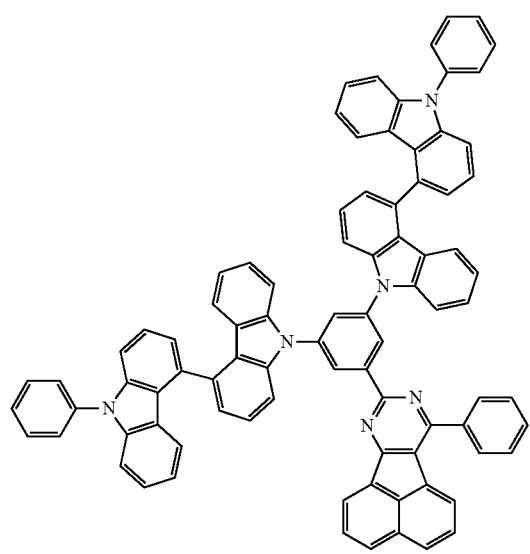
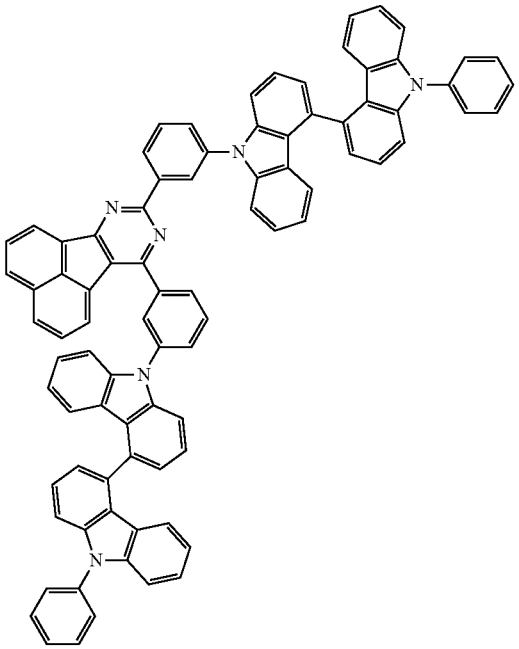
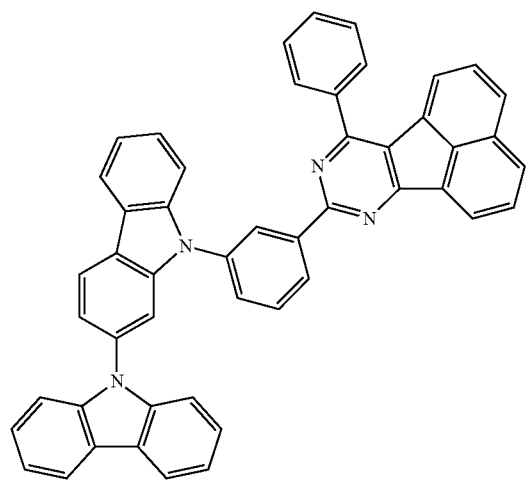
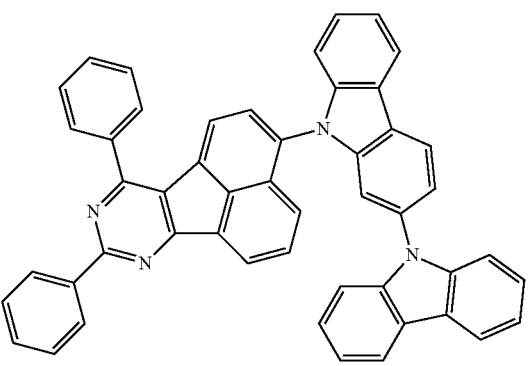
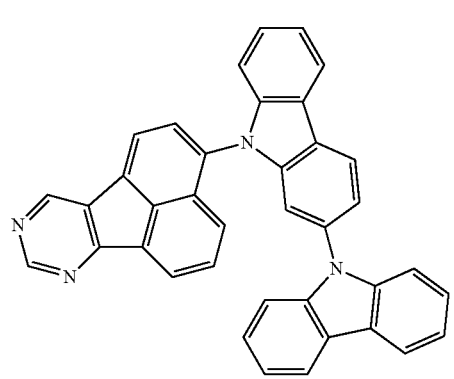
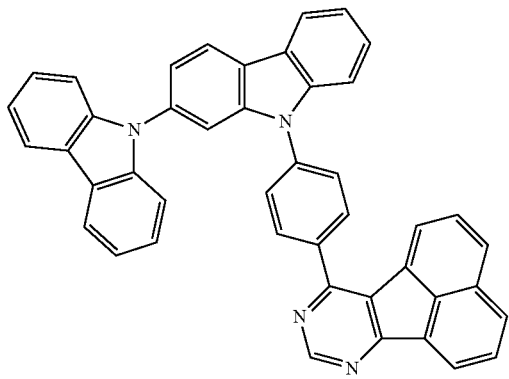

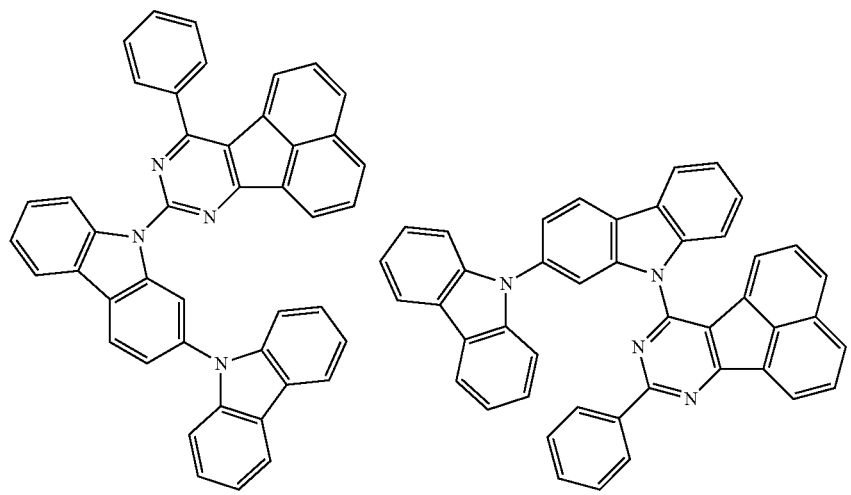
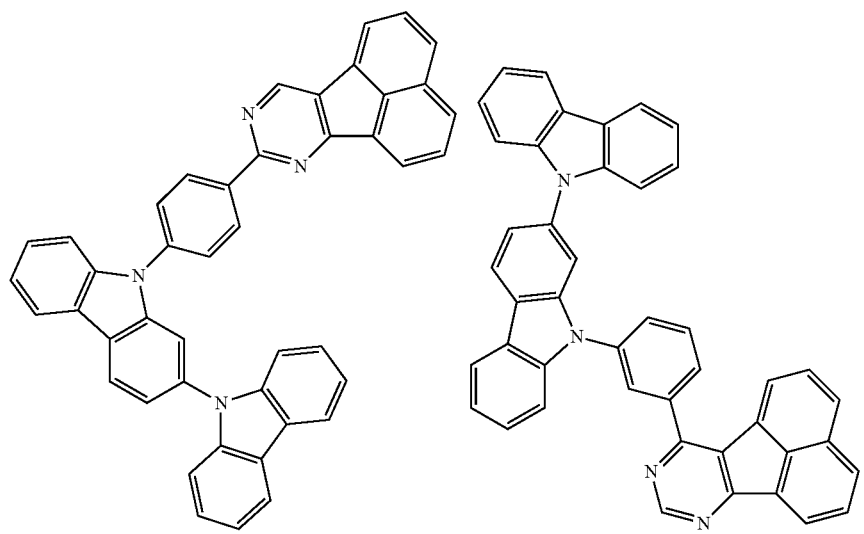
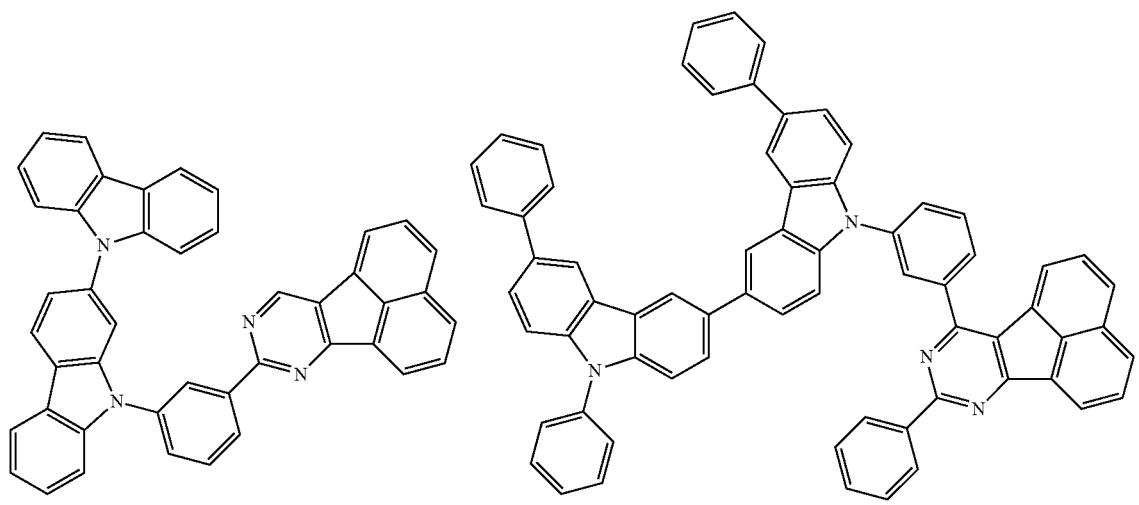

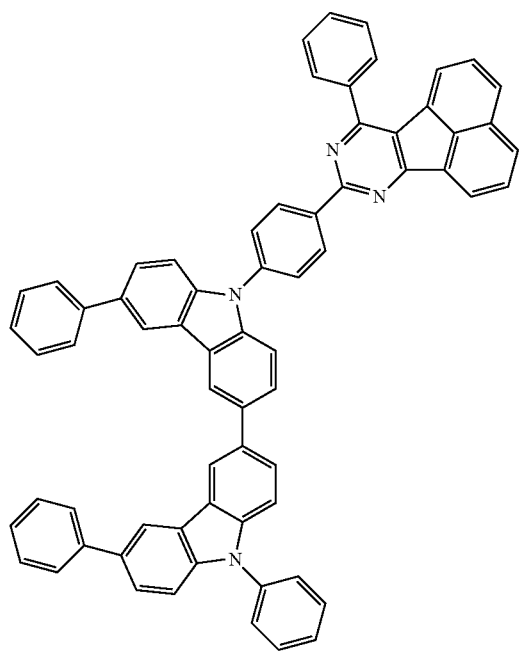
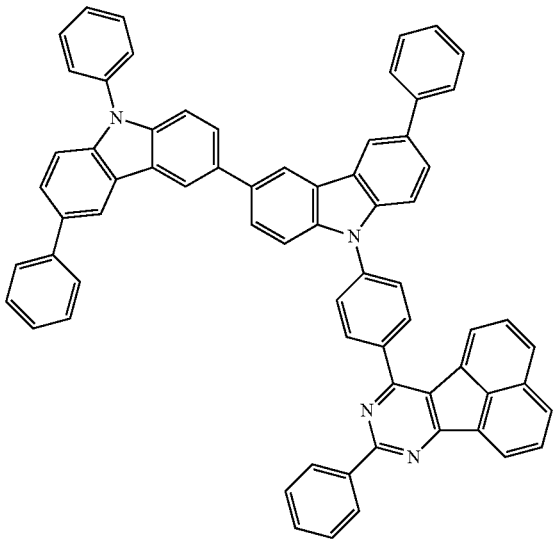
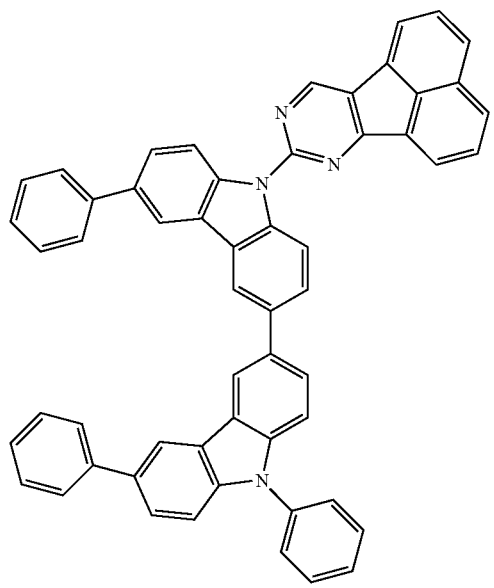

-continued
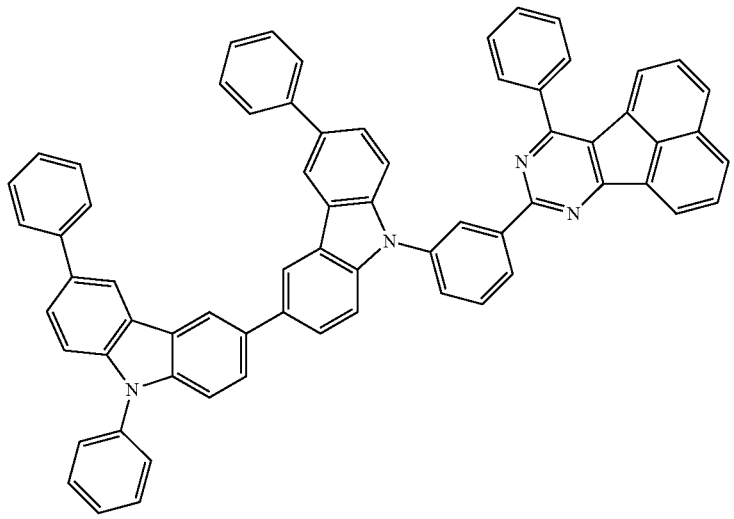
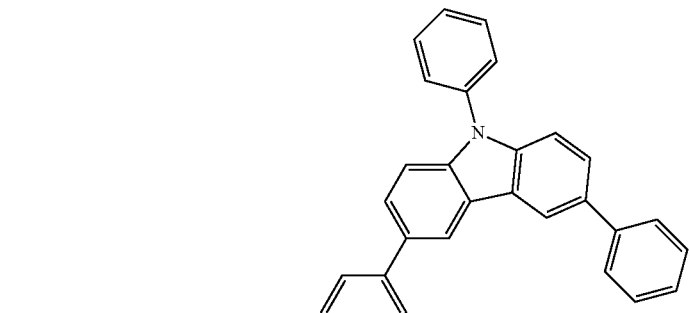
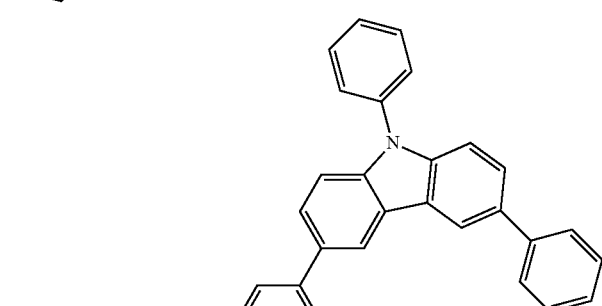
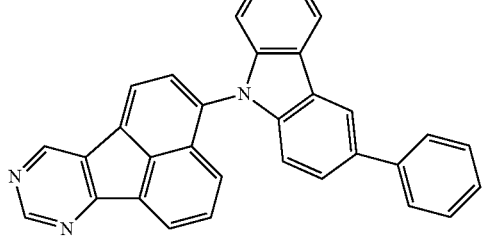

137 138
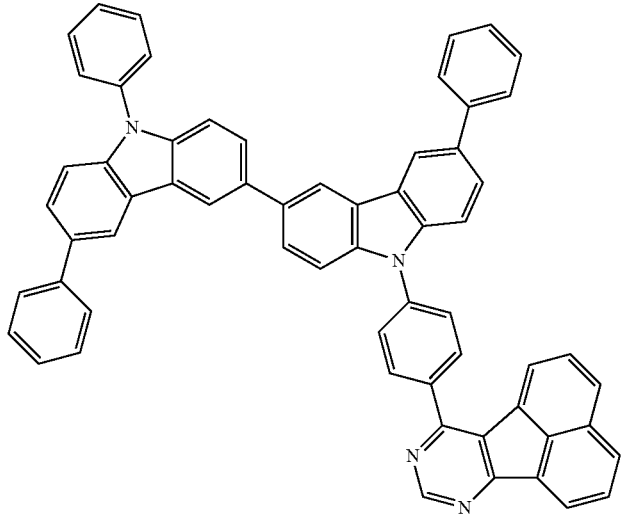
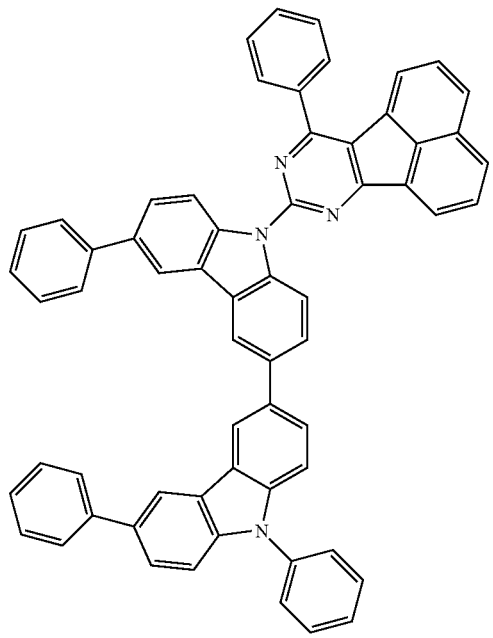
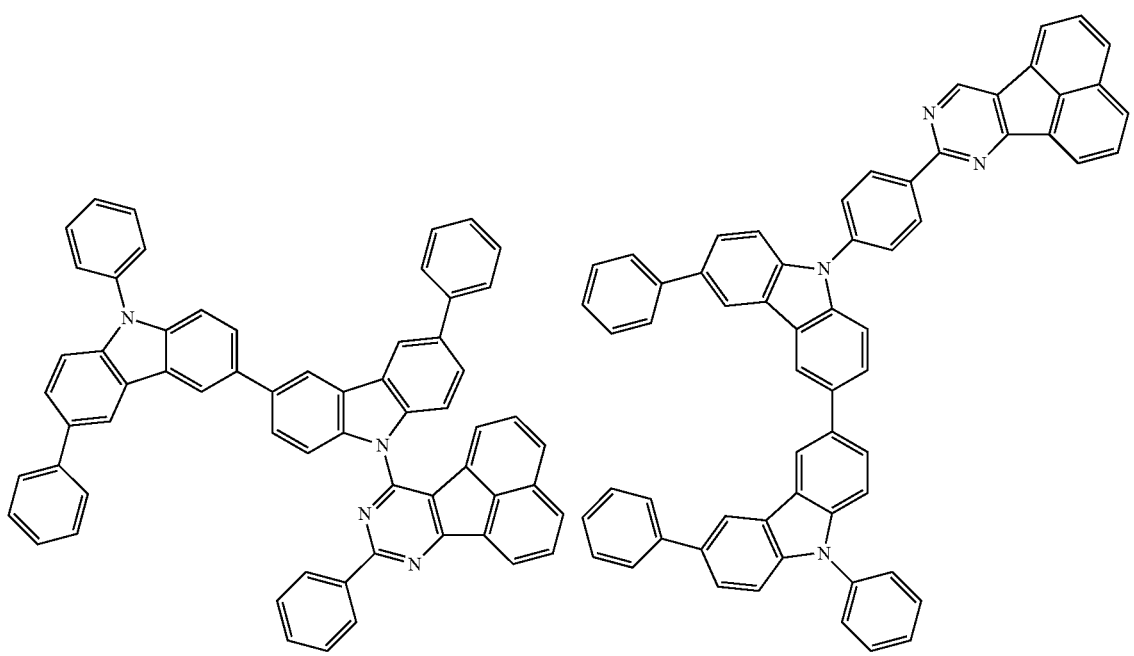

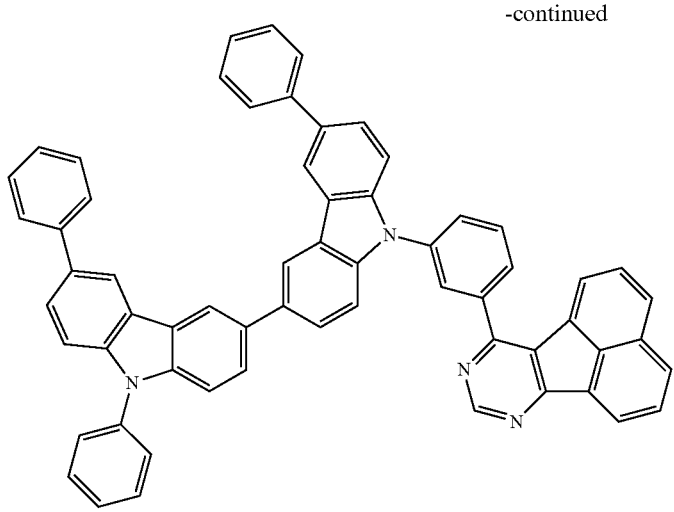
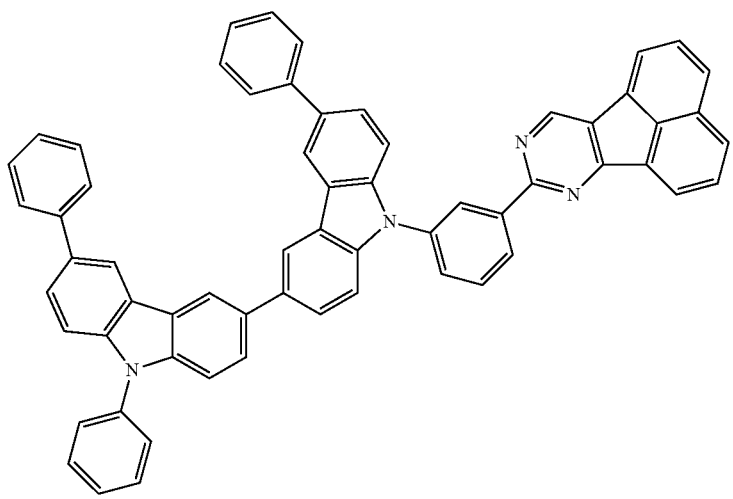
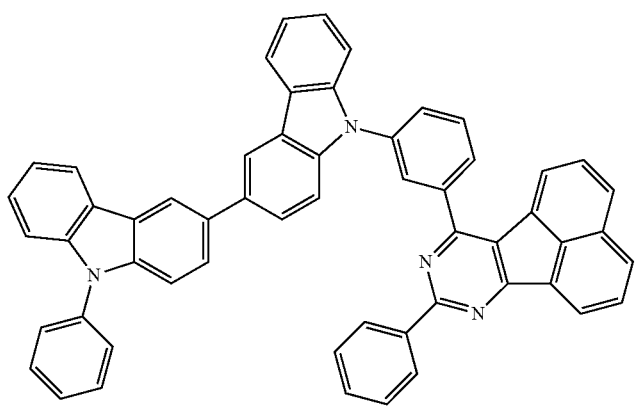

-continued
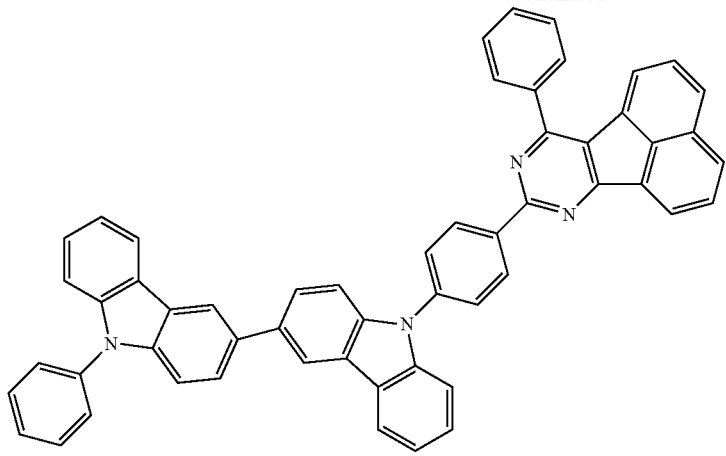
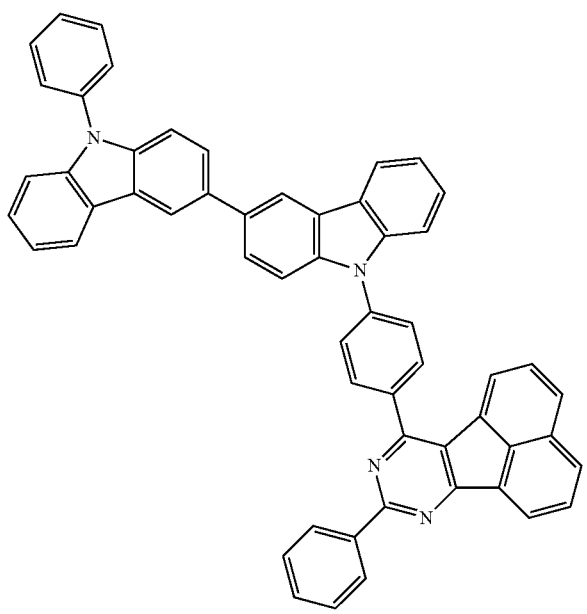
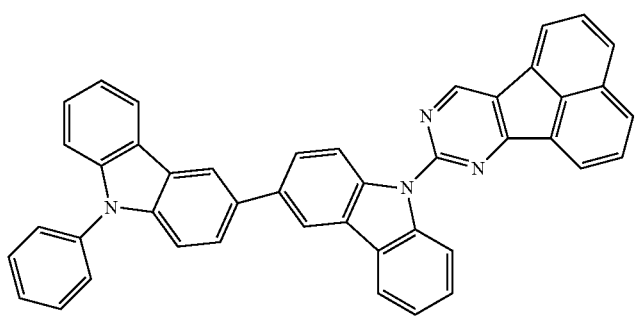

-continued
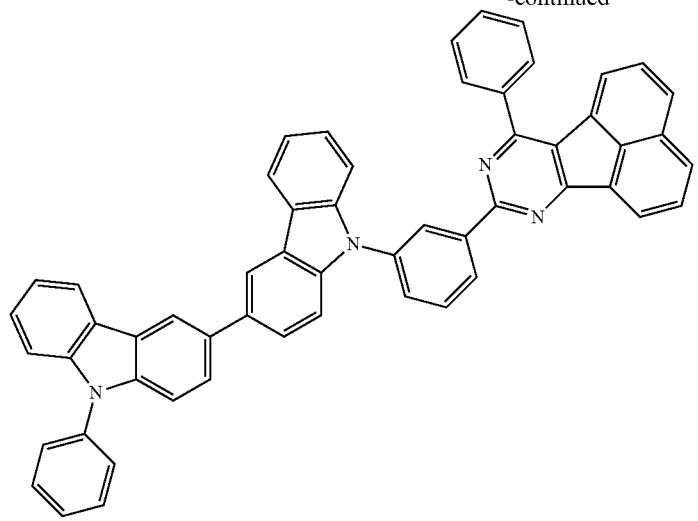
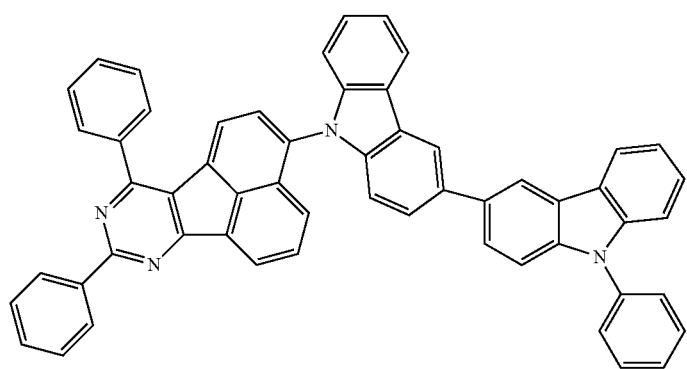
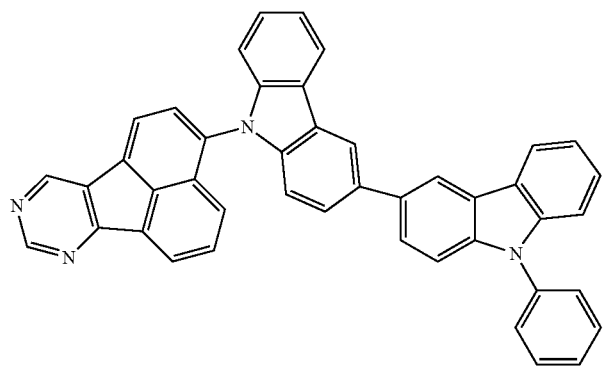

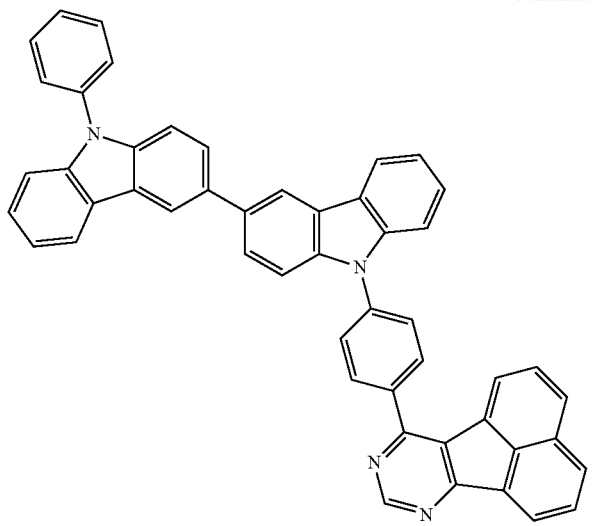
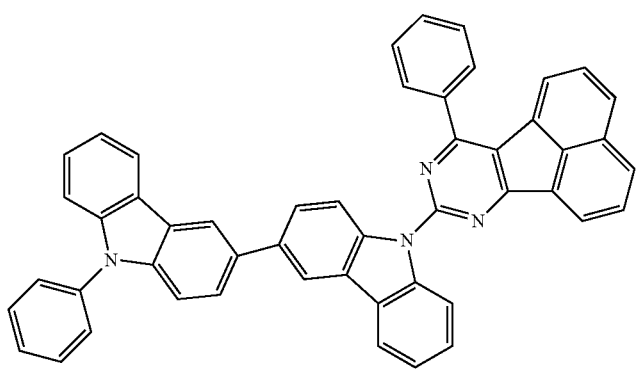
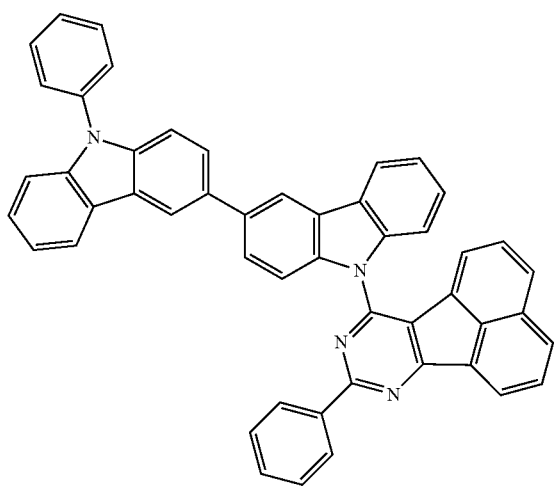

-continued
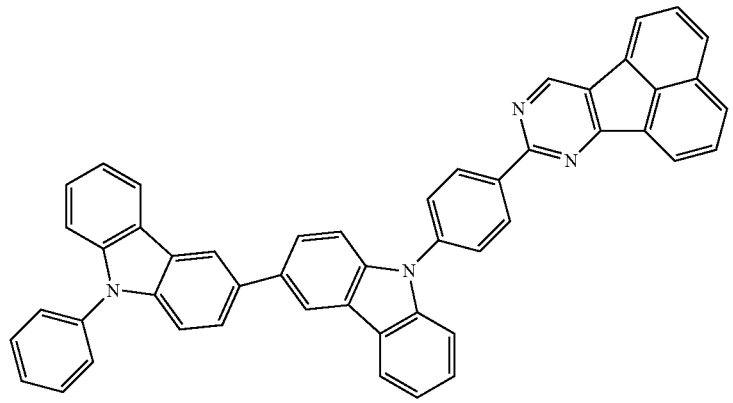
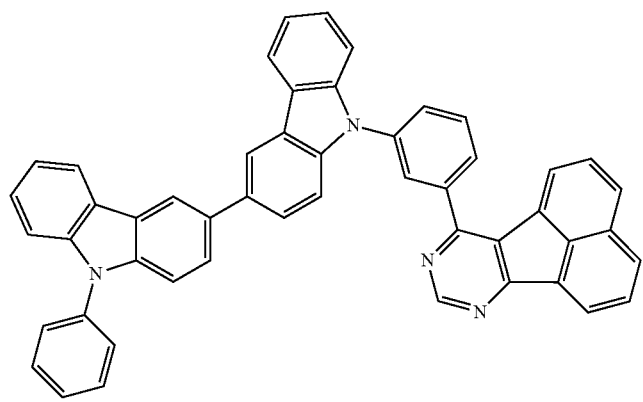
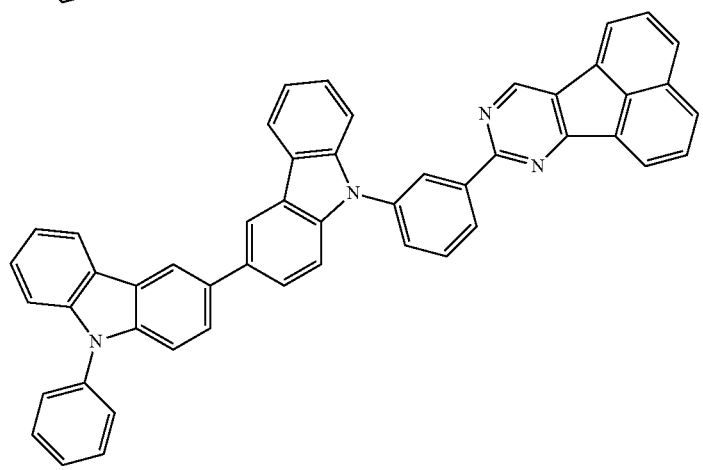
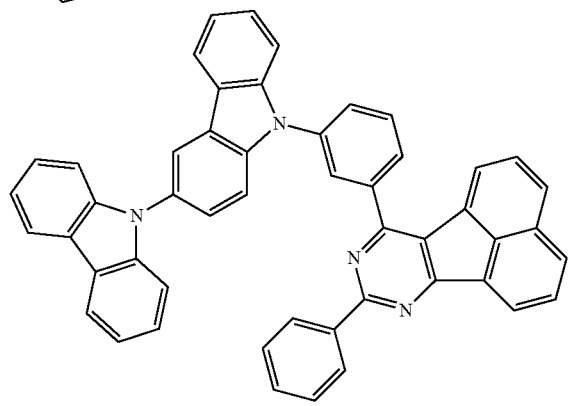

149 150
-continued
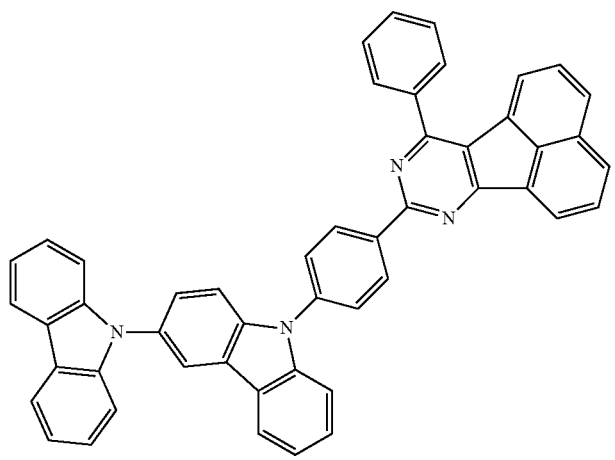
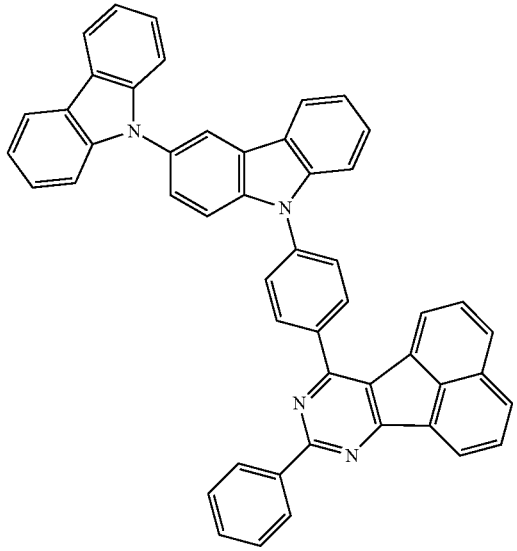
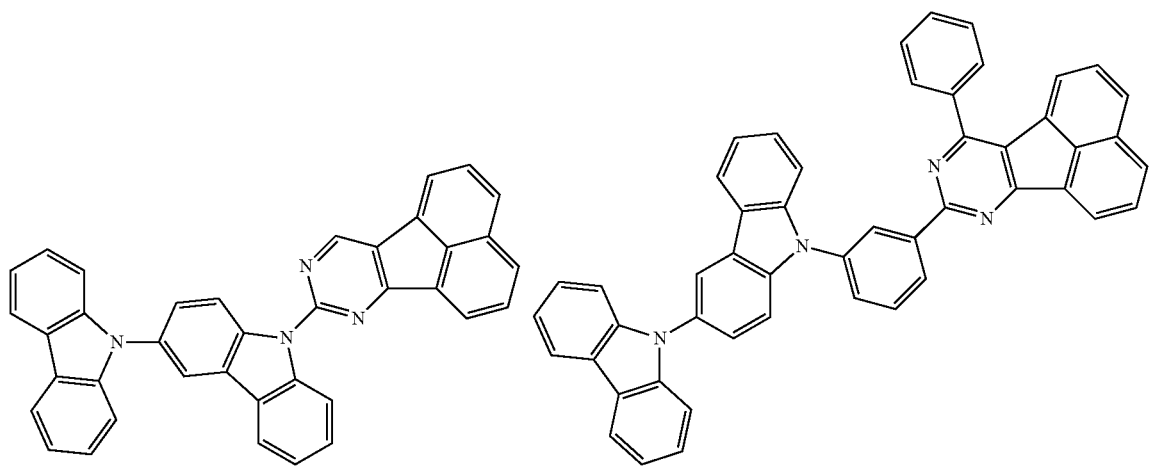
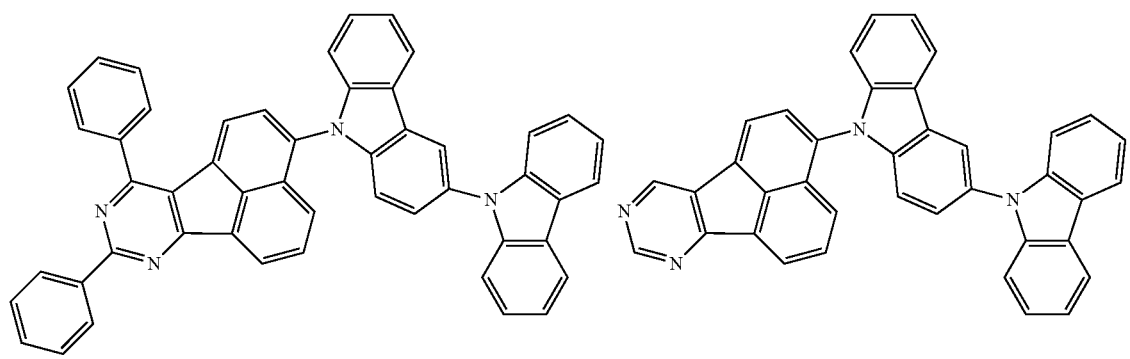

-continued
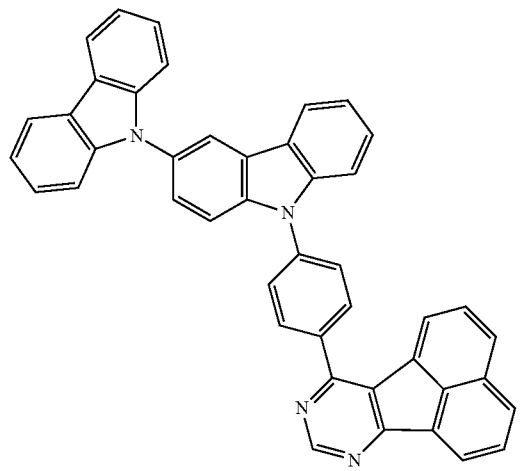
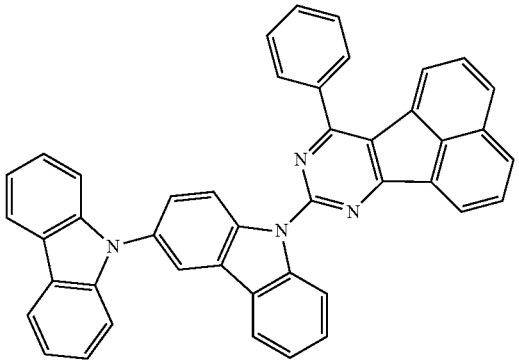
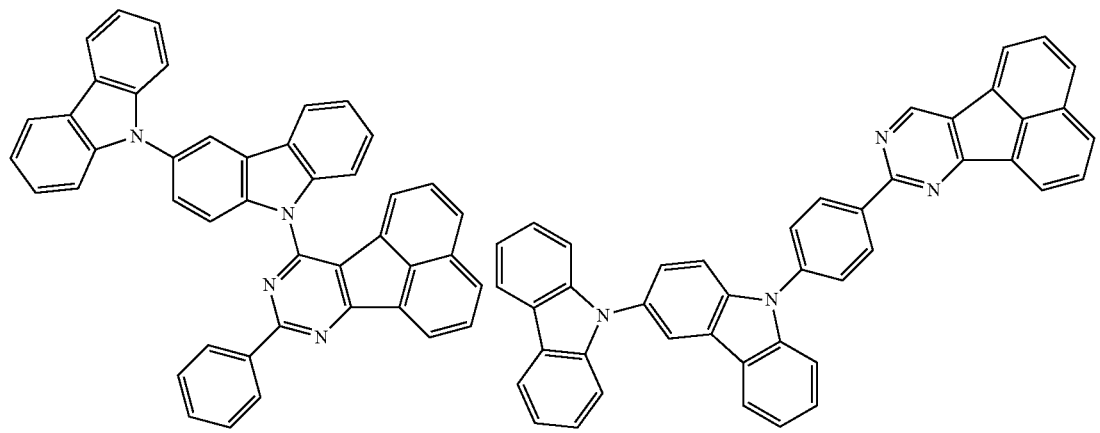
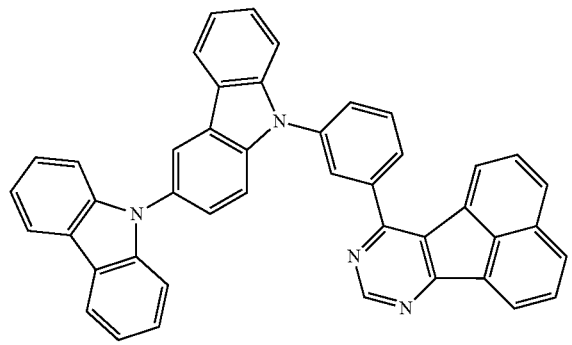
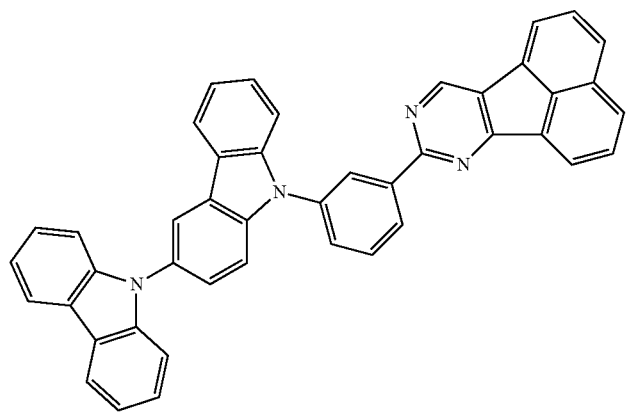

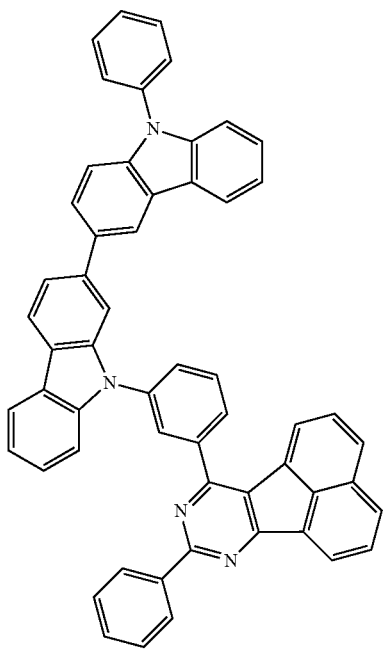
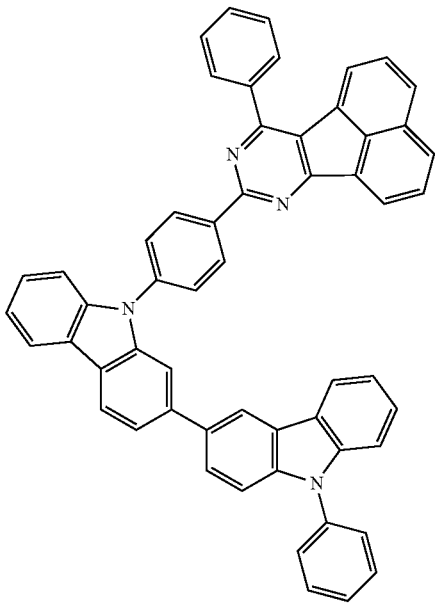
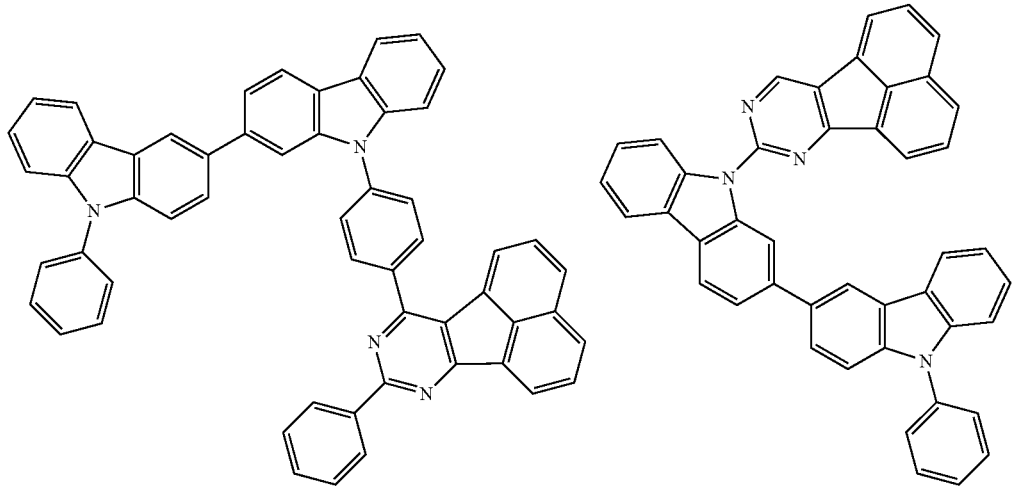

-continued
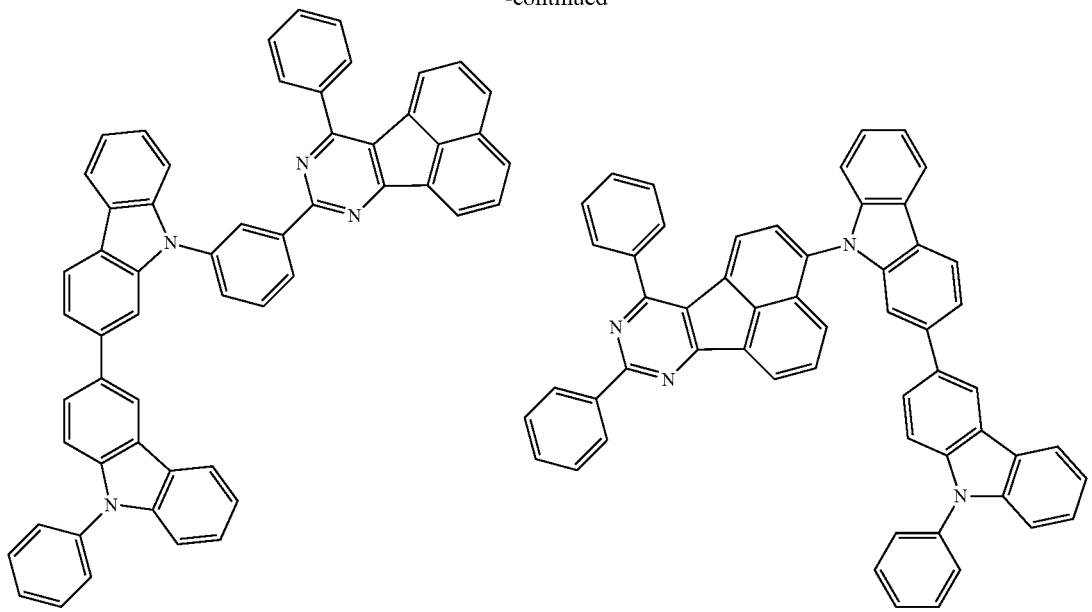
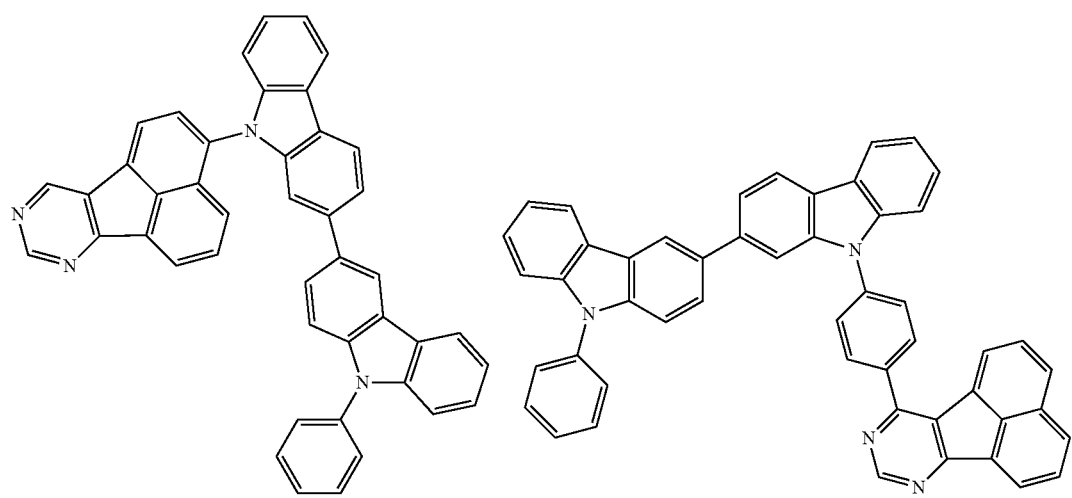
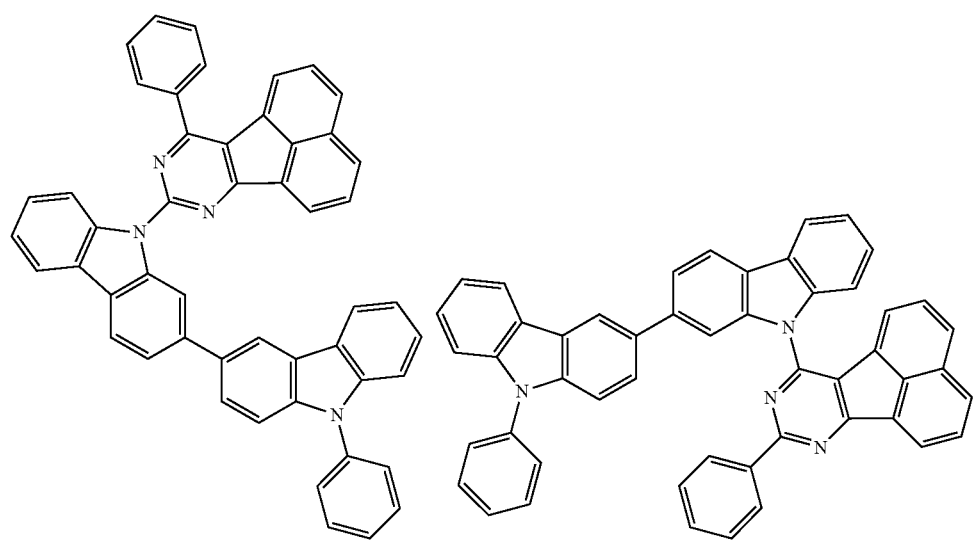

-continued
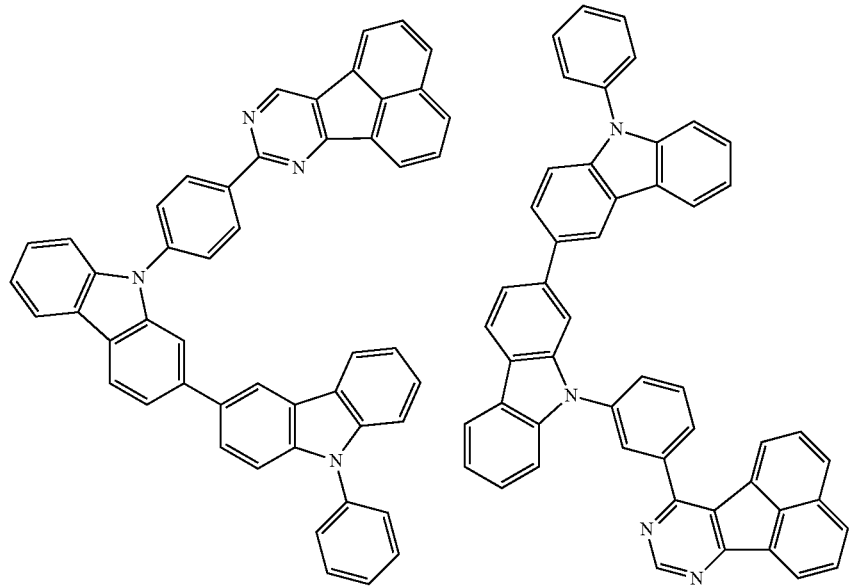
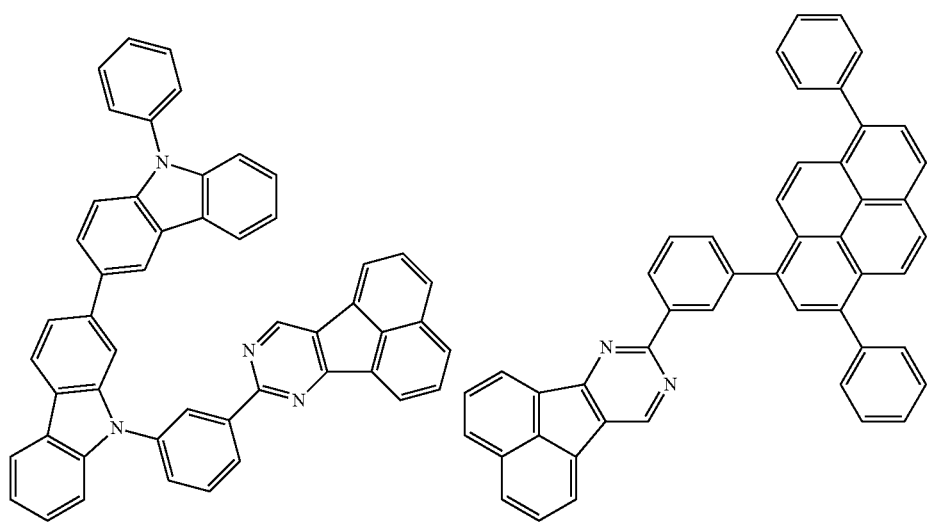
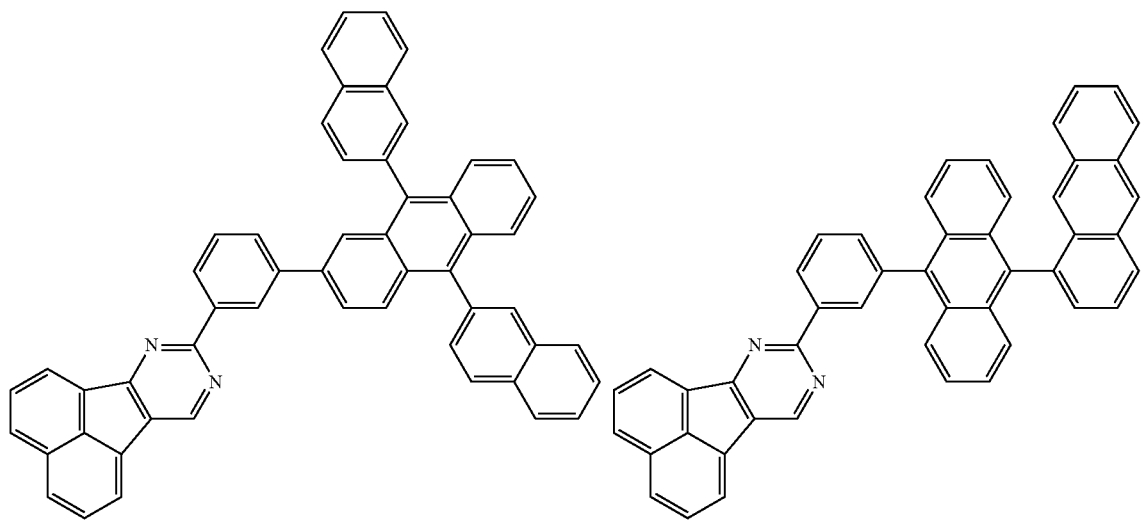

-continued
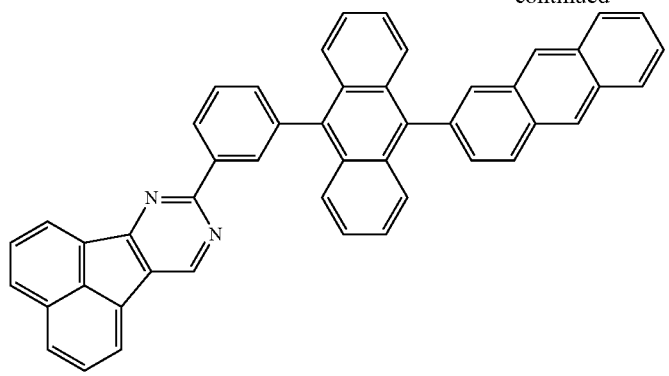
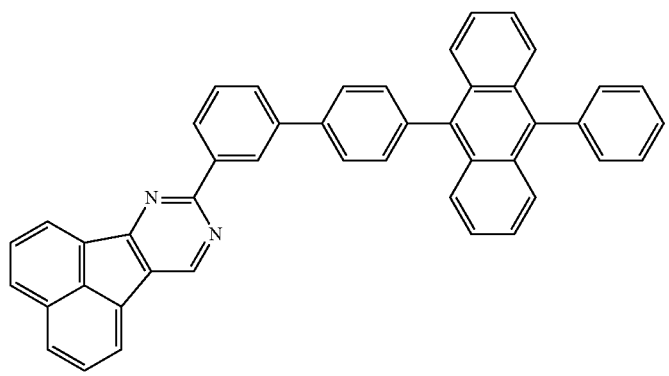
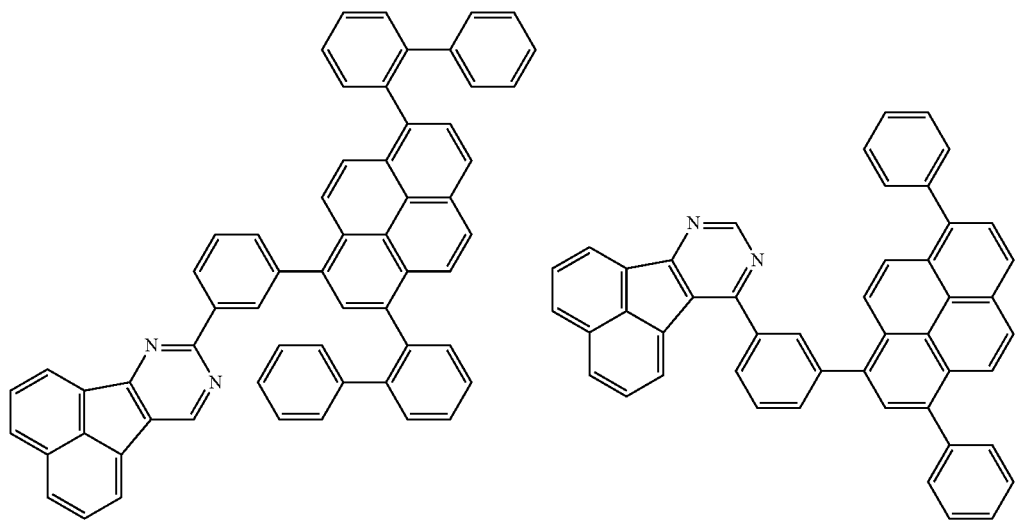
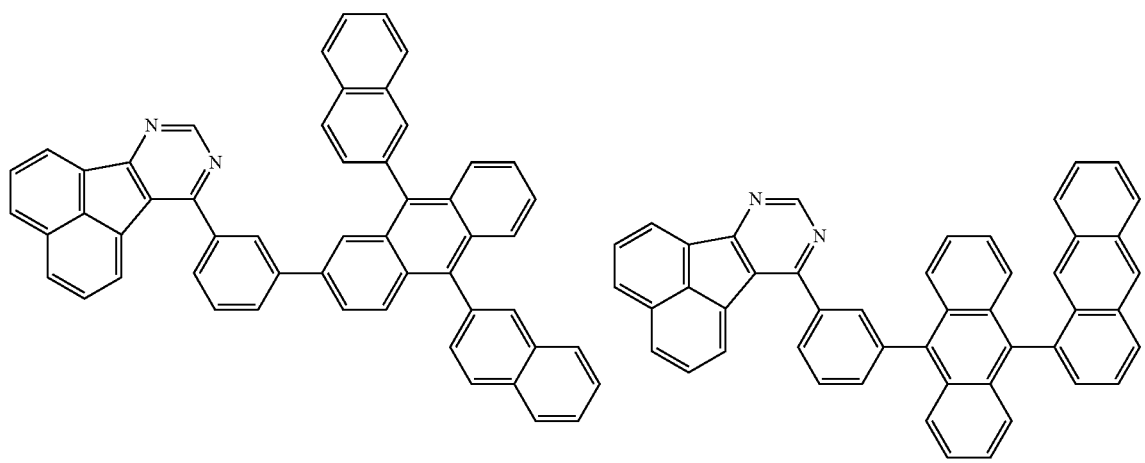

-continued
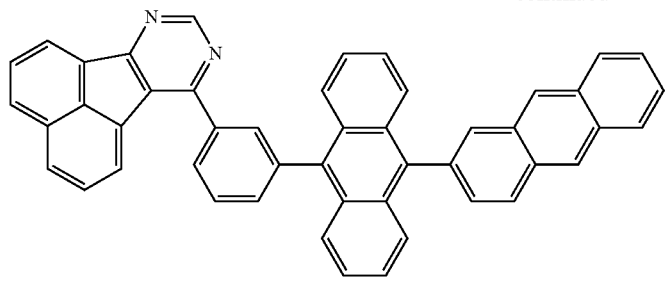
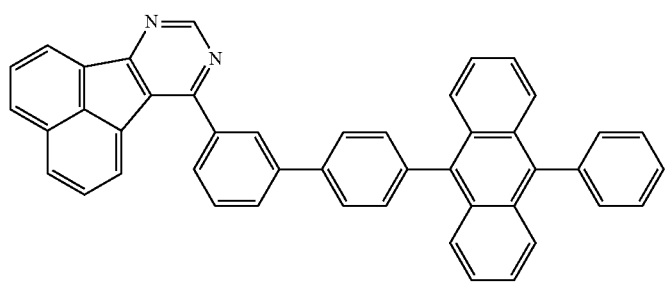
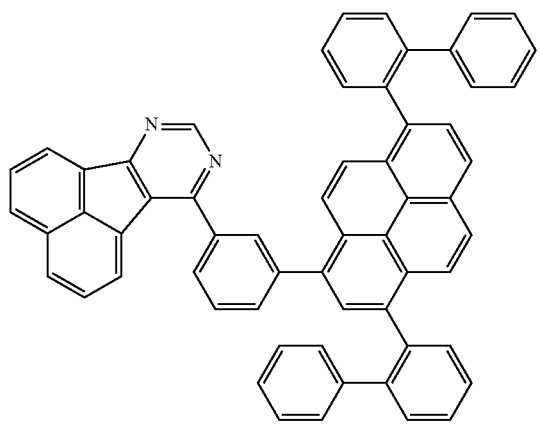
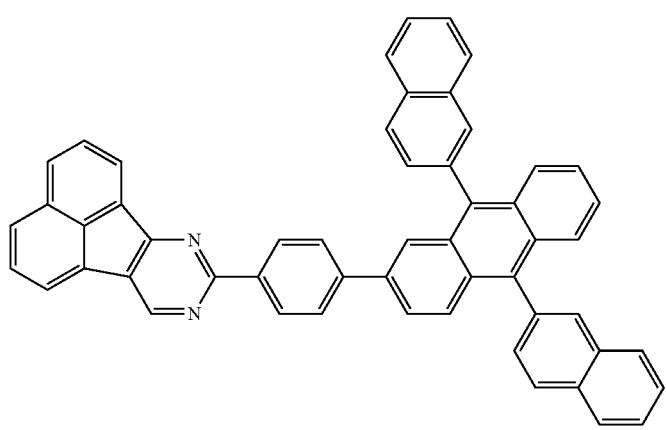

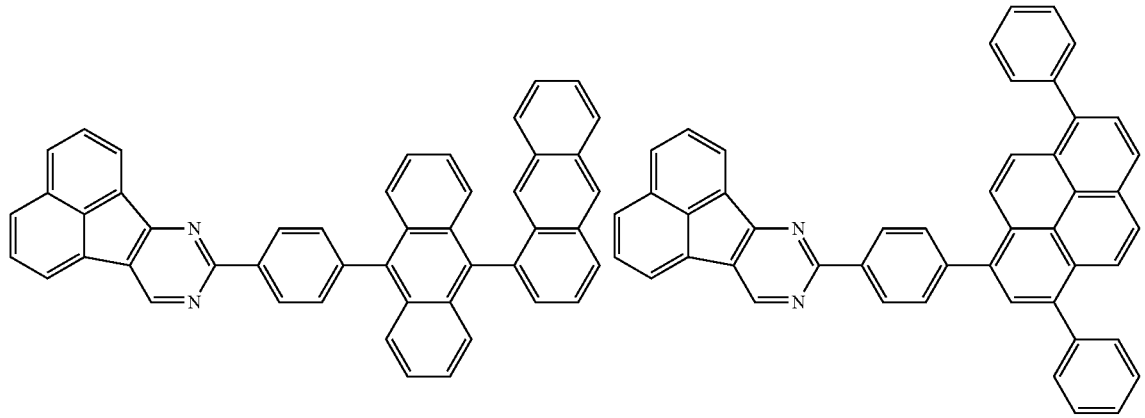
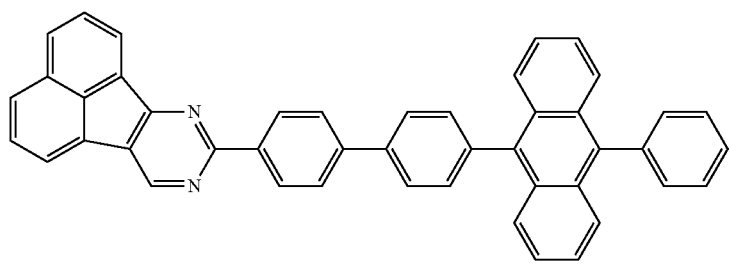
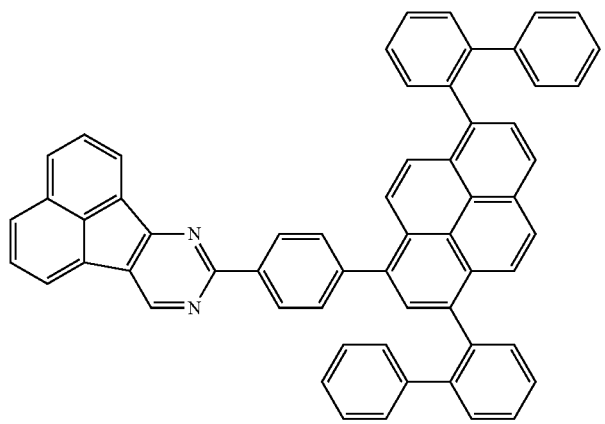
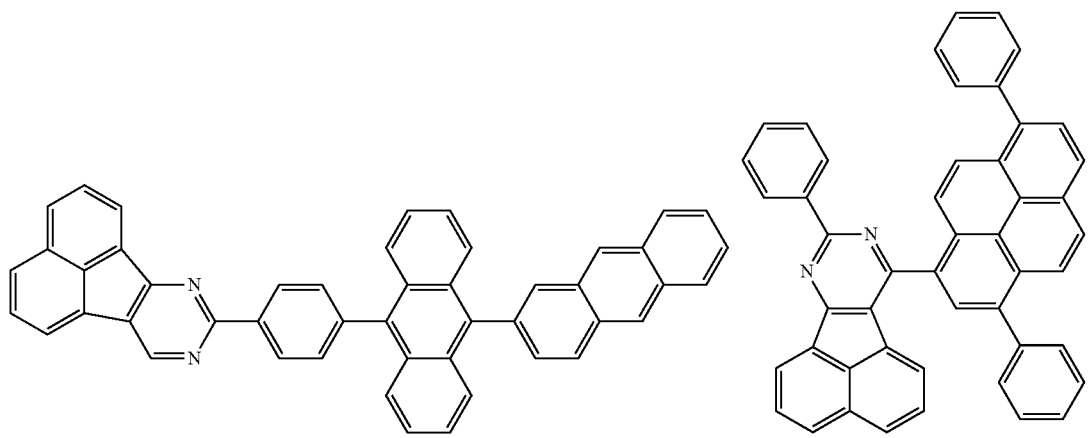

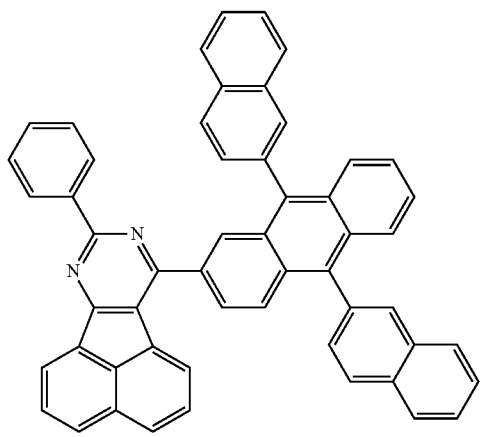
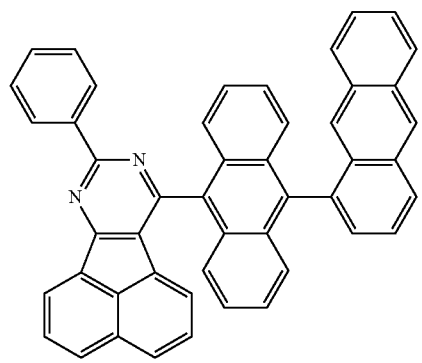
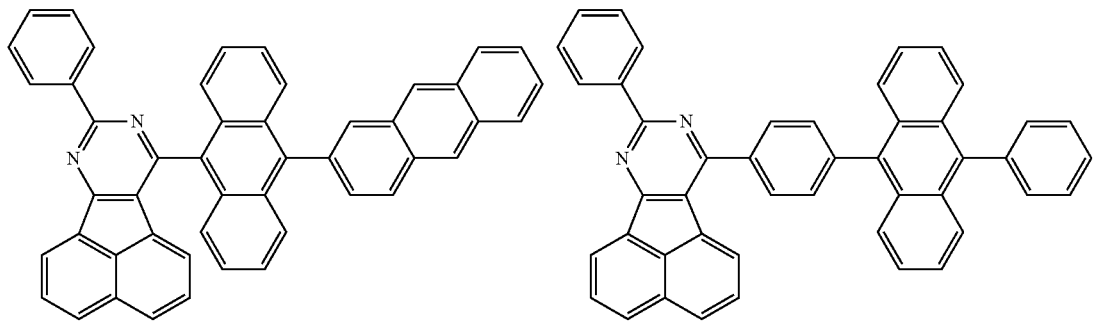
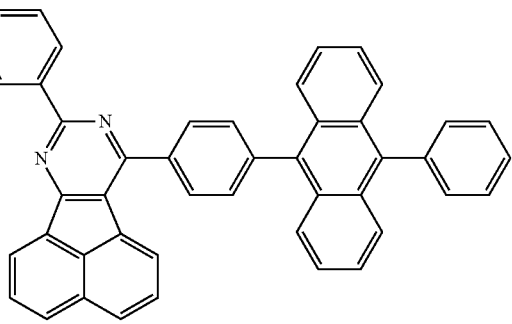
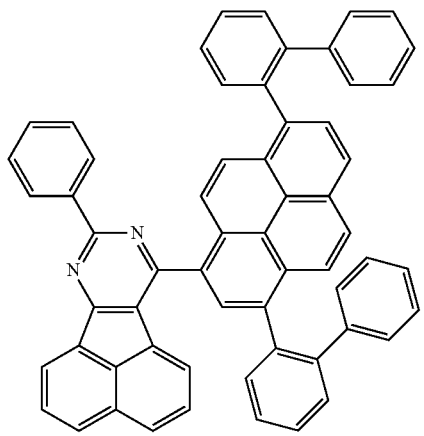
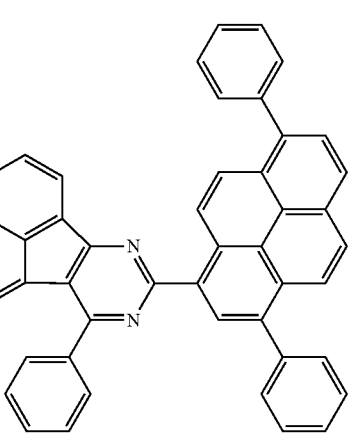
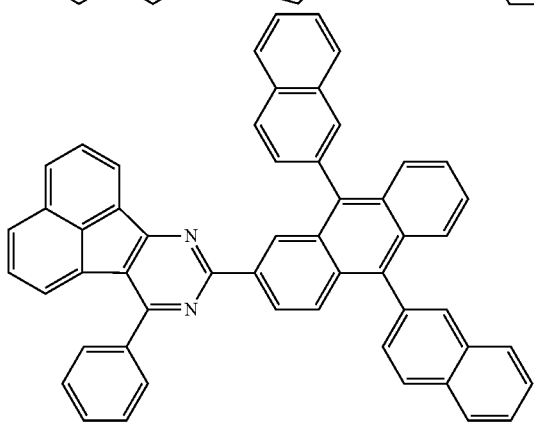
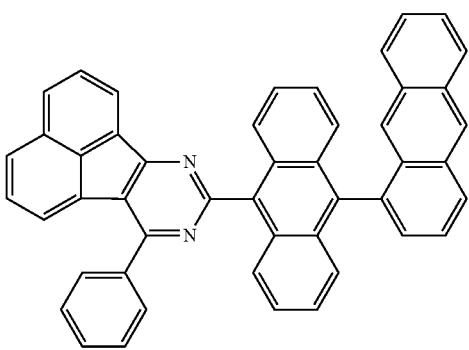

-continued
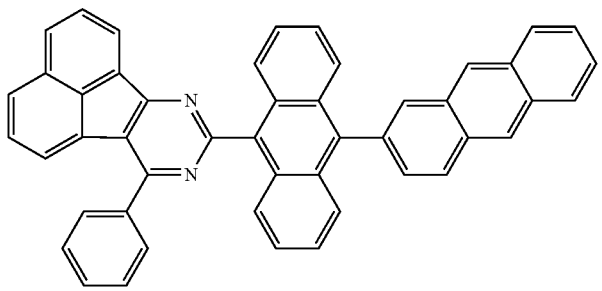
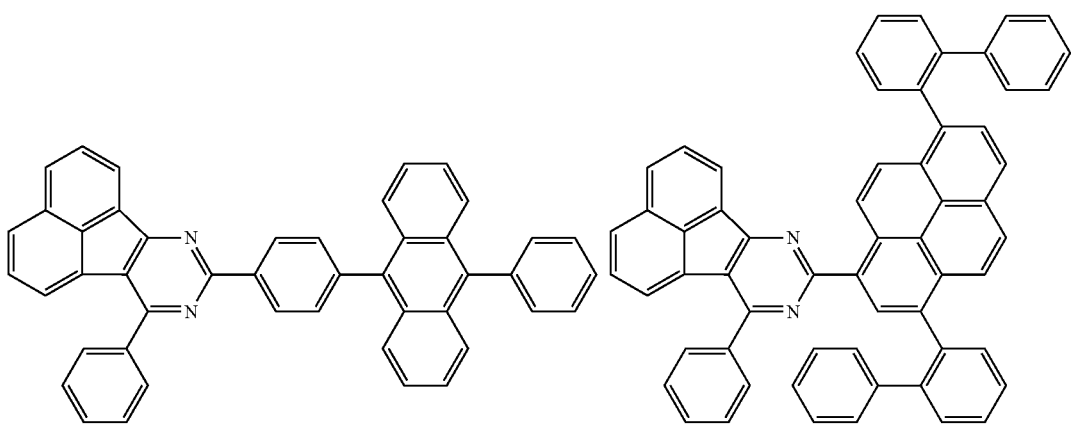
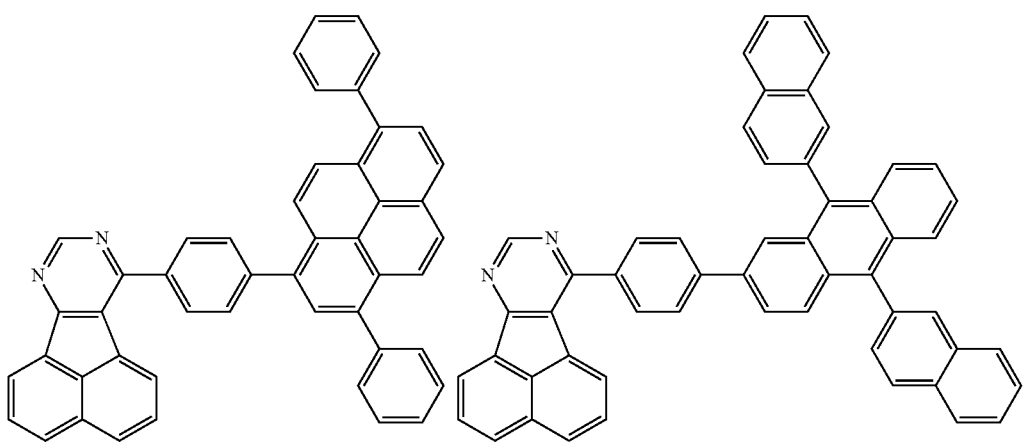
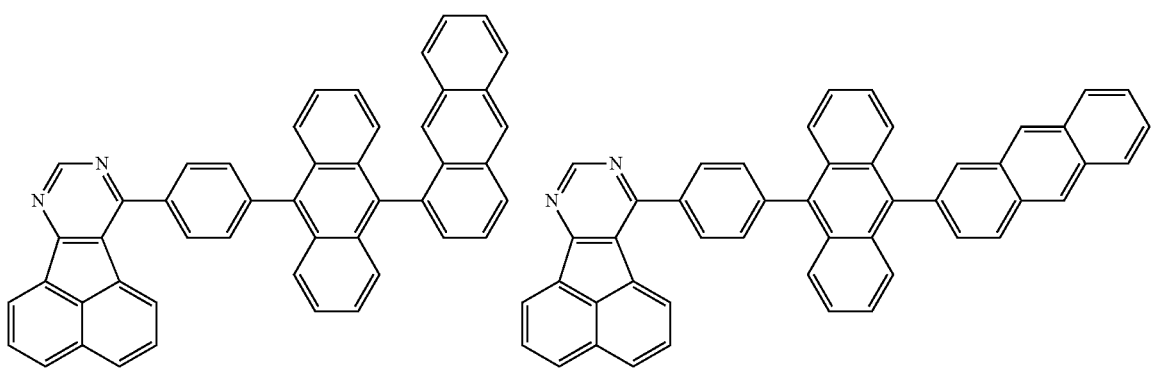

-continued
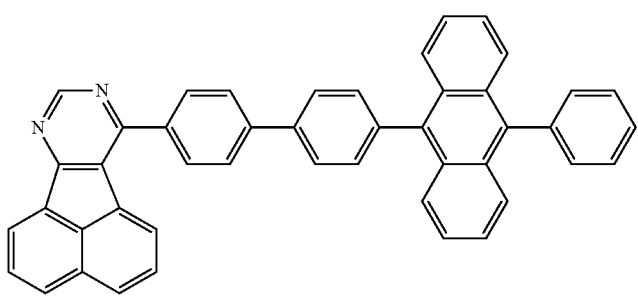
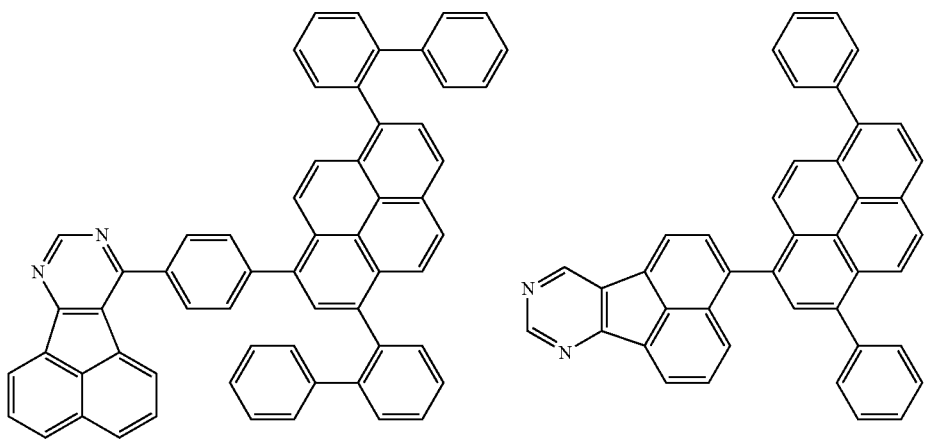
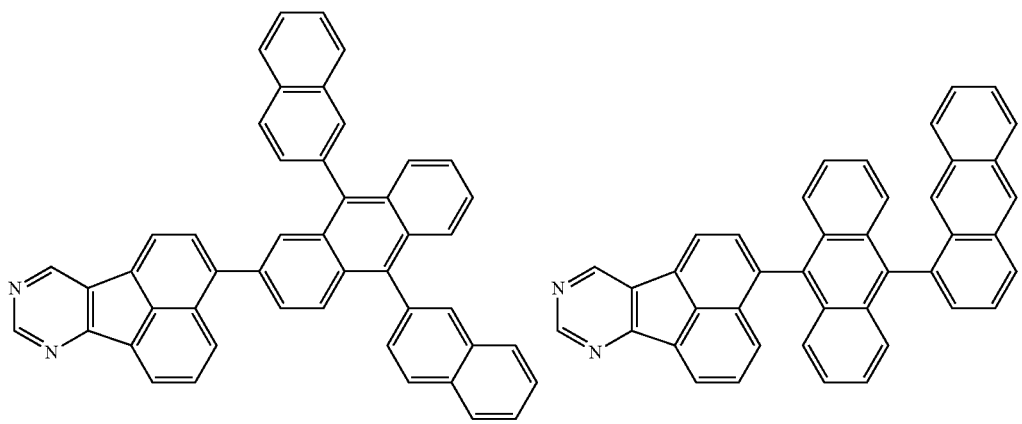
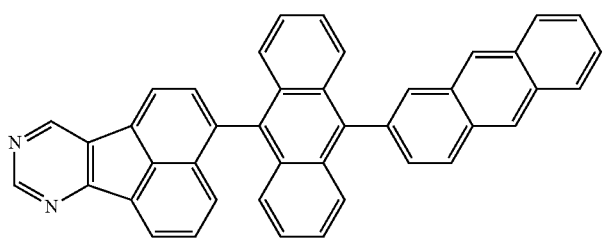

-continued
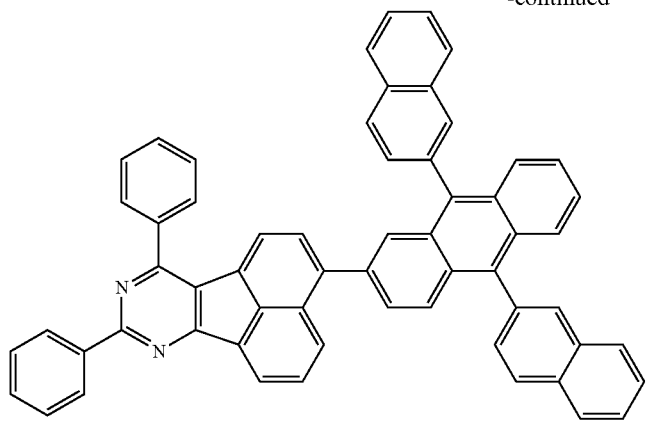
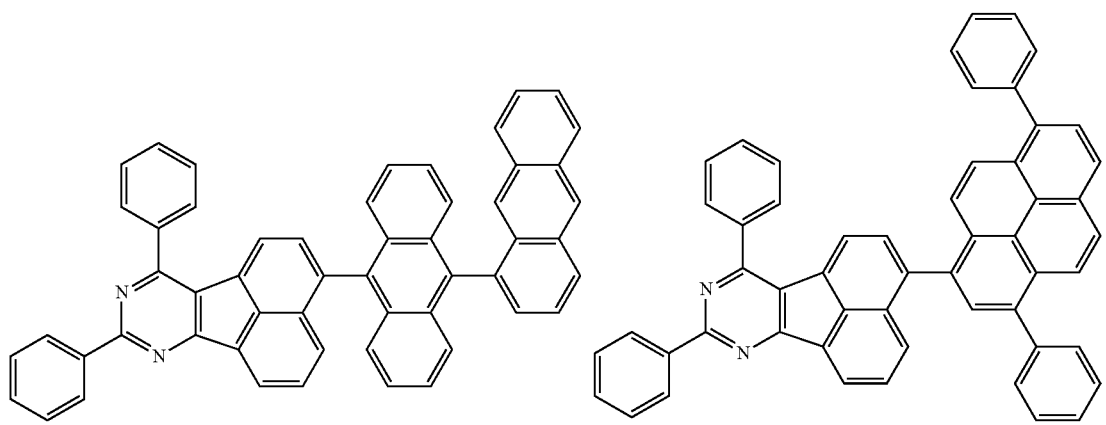
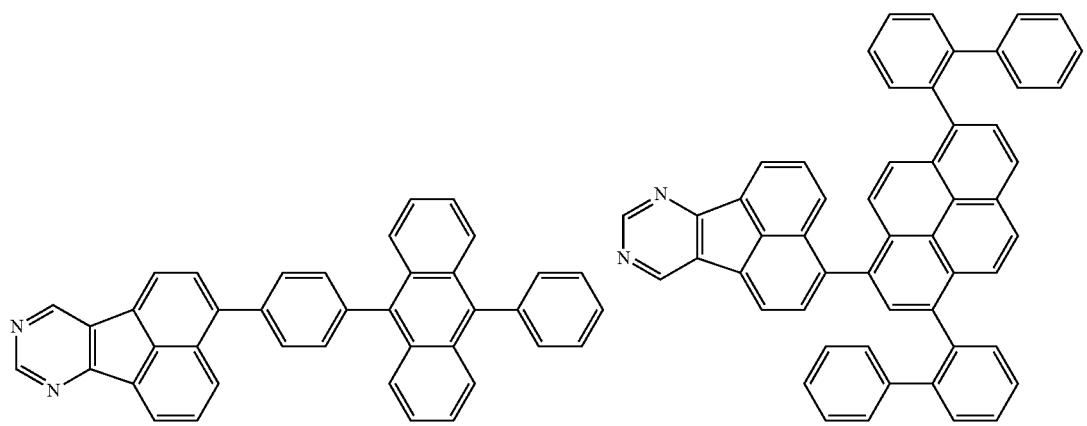
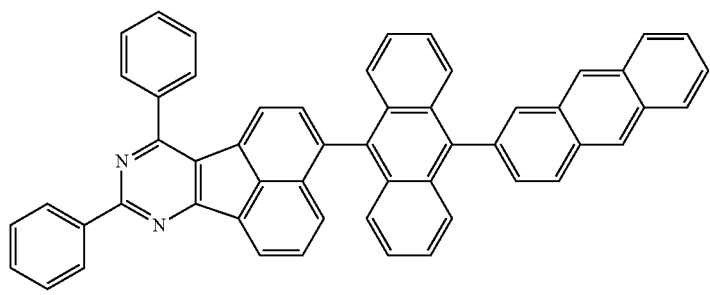

173
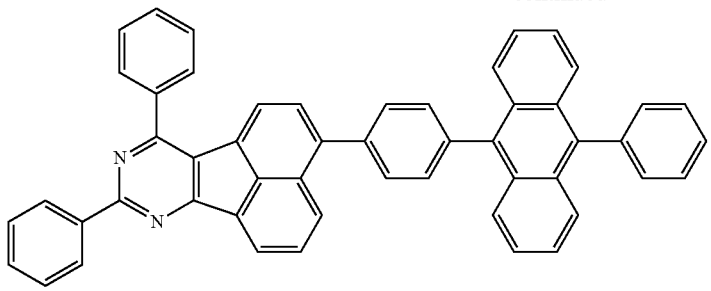
-continued
174
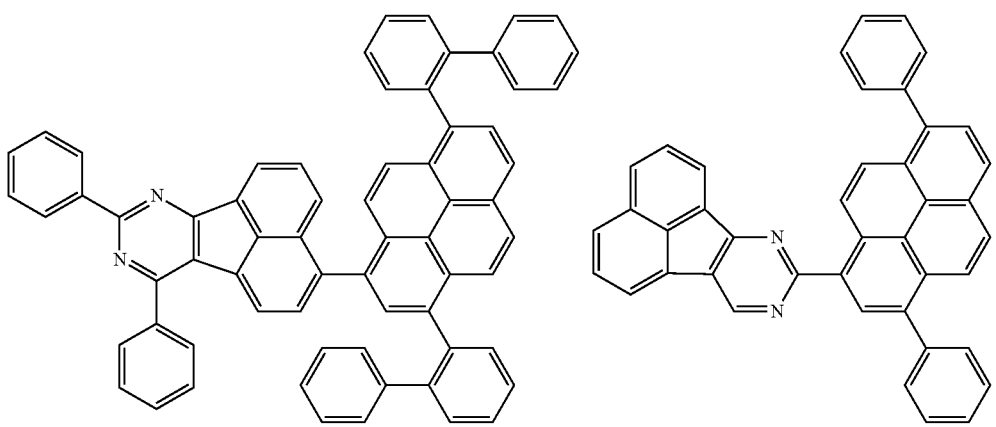
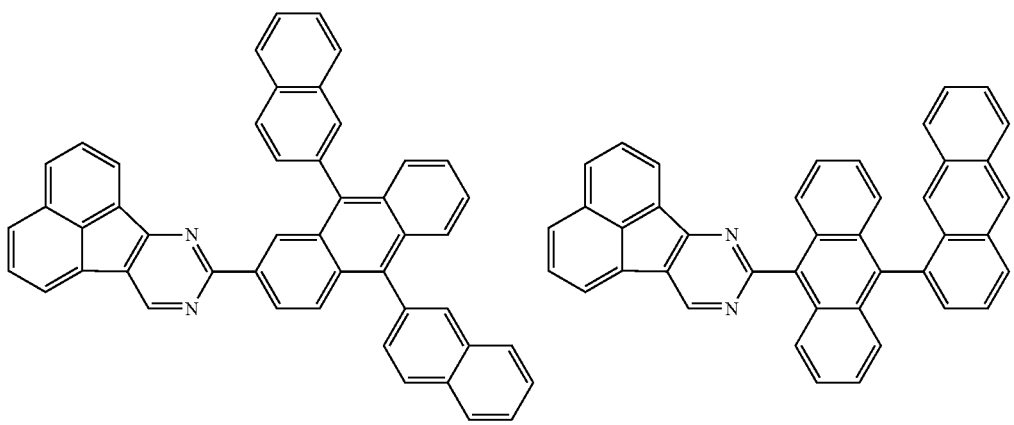
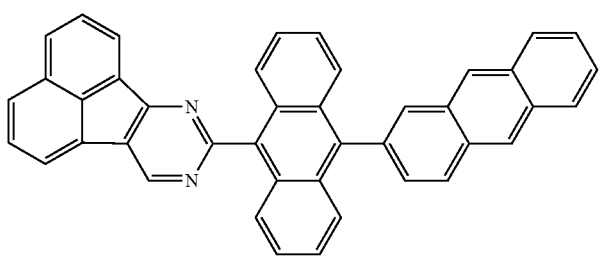

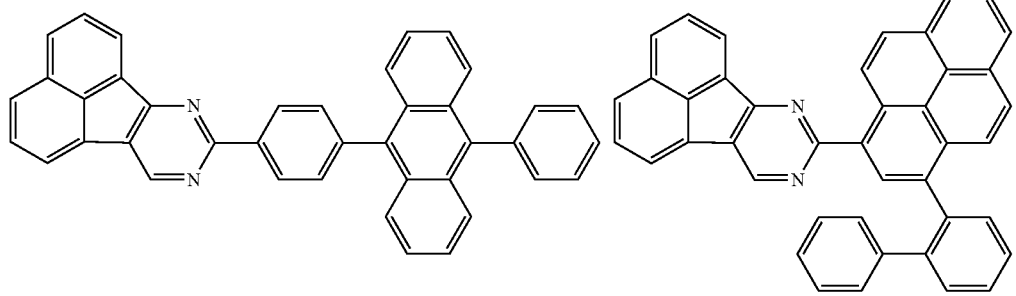
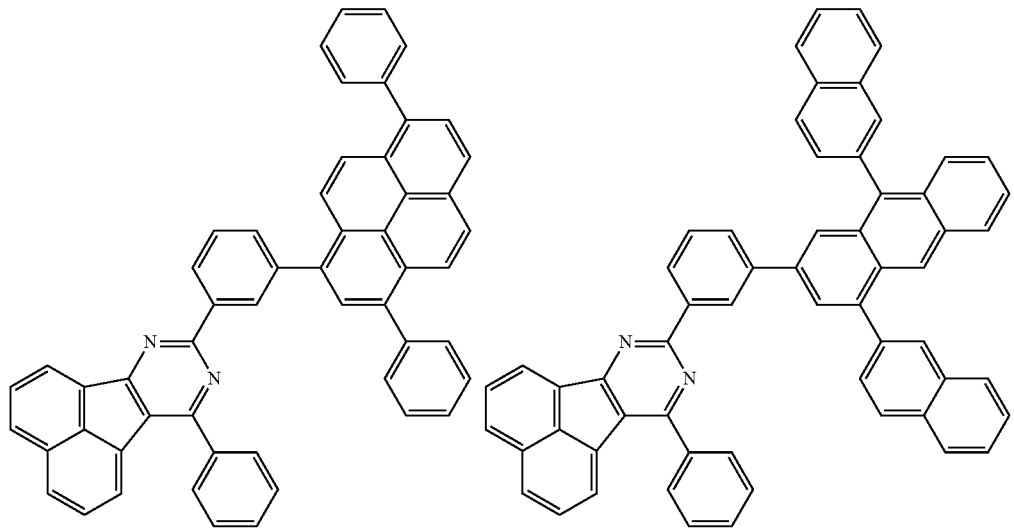
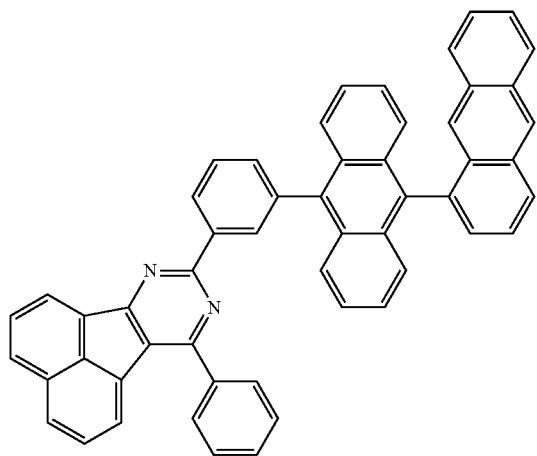

-continued
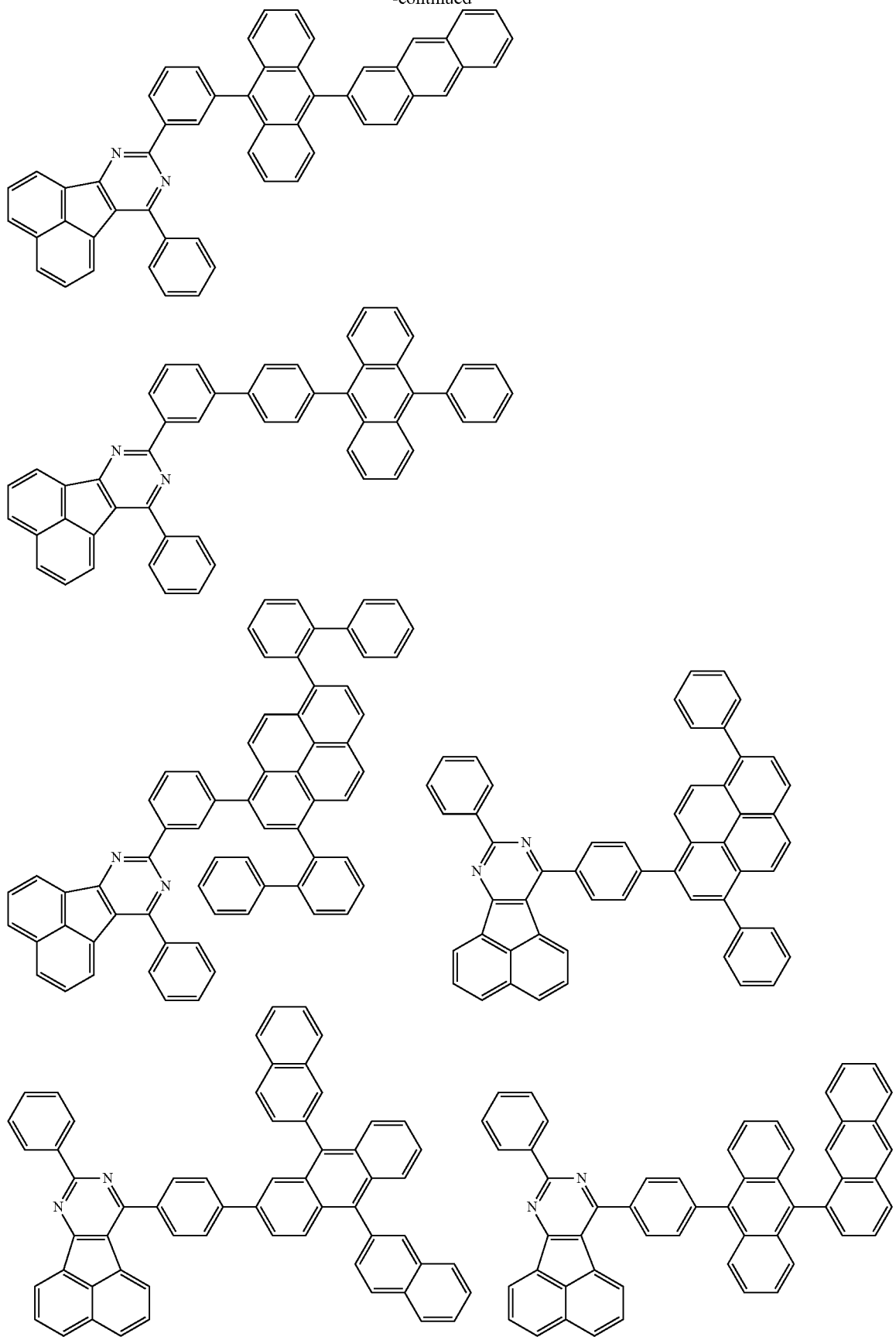

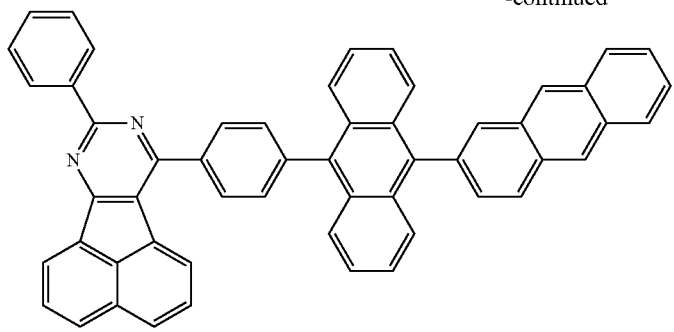
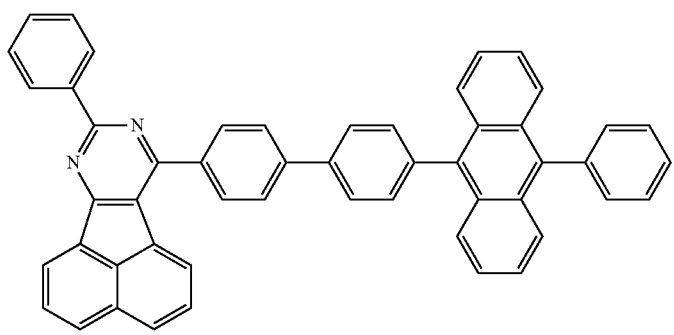
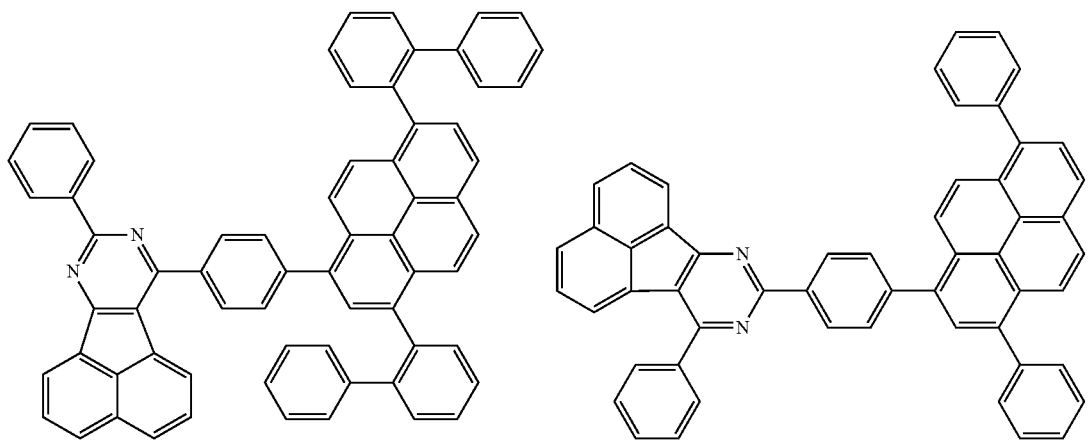
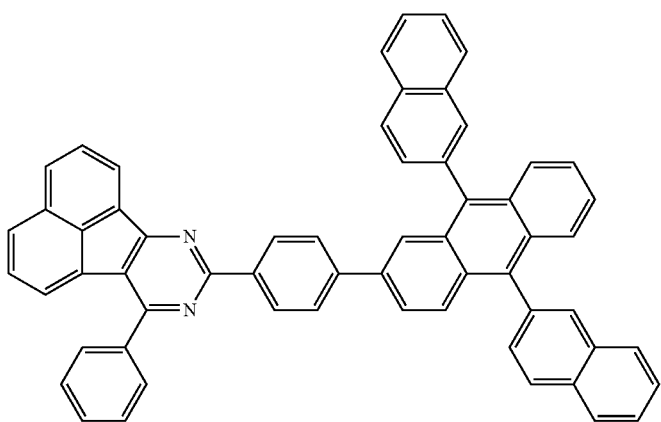

-continued
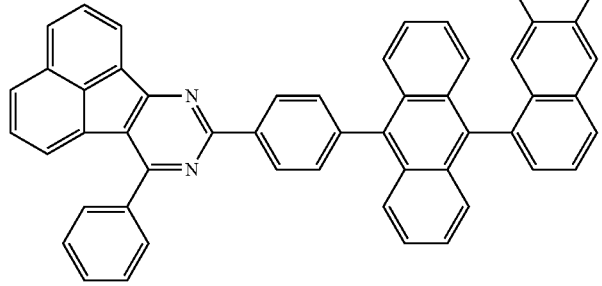
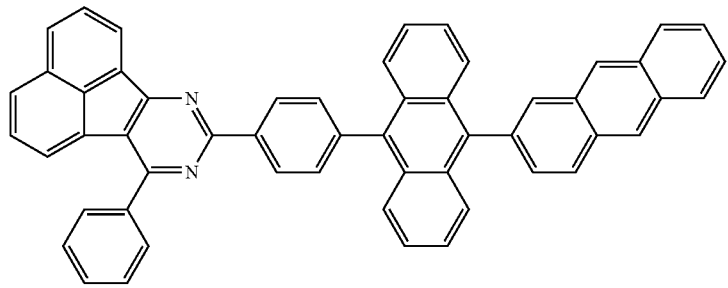
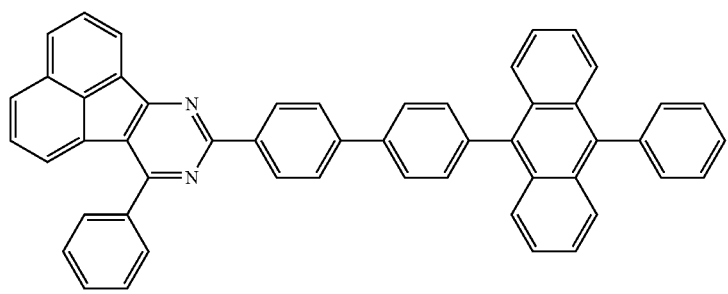
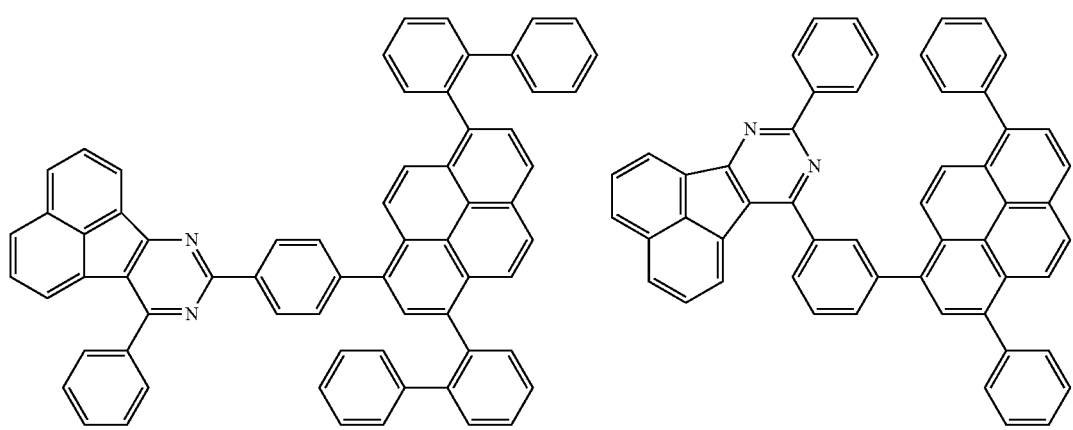

183 184
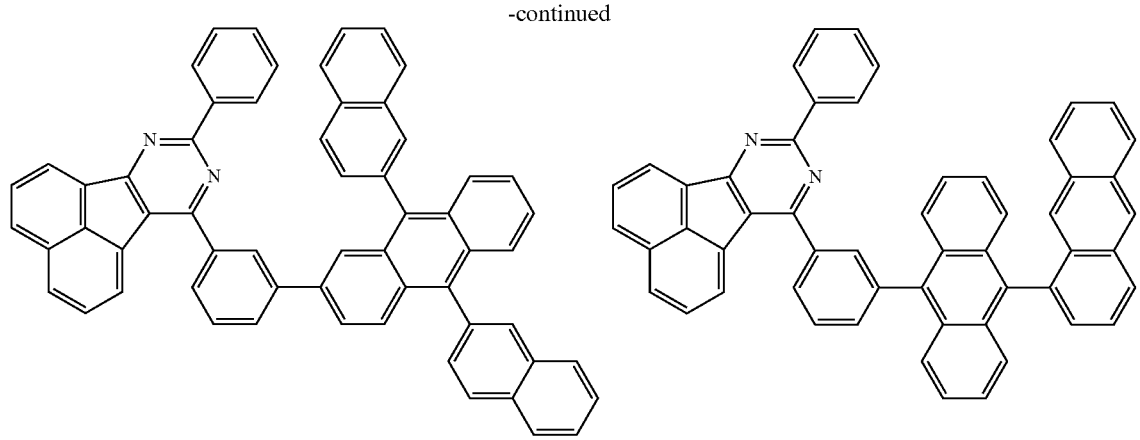
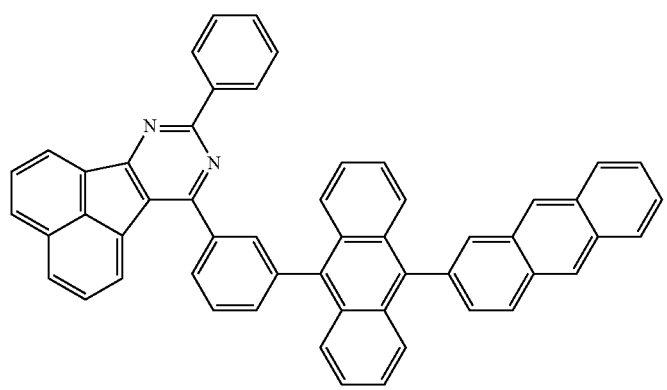
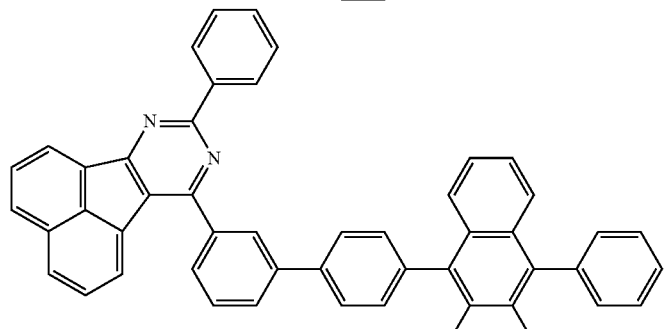
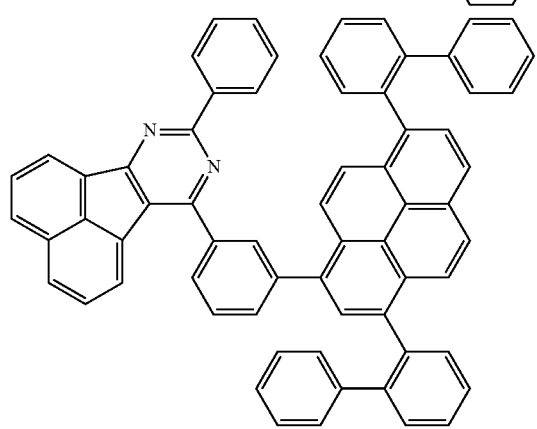
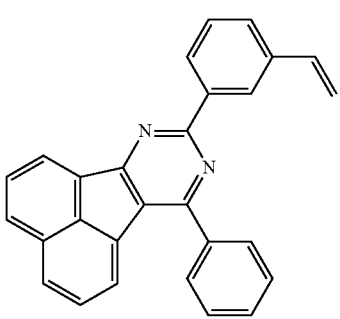

185
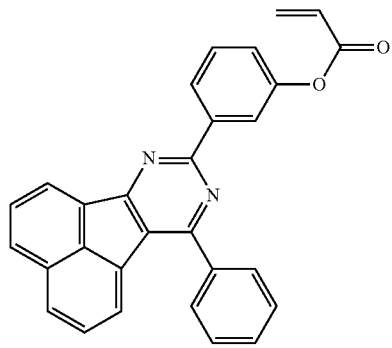 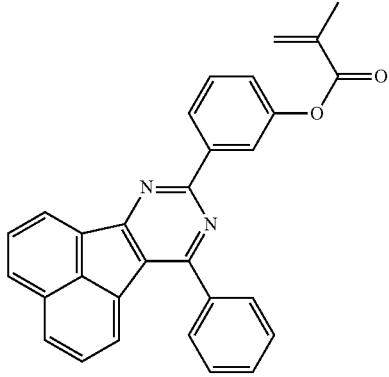 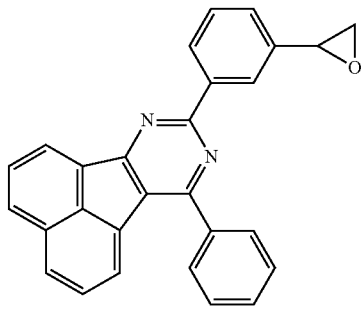
186
-continued
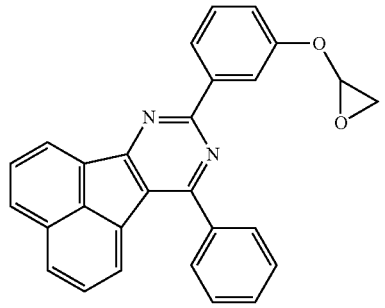 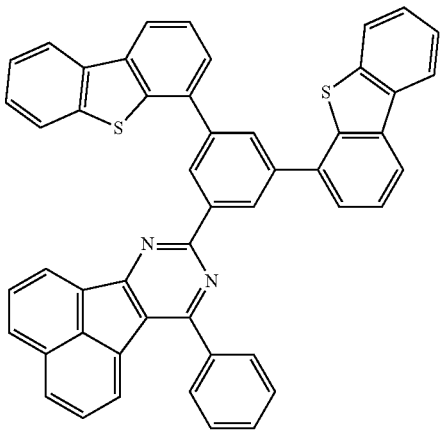
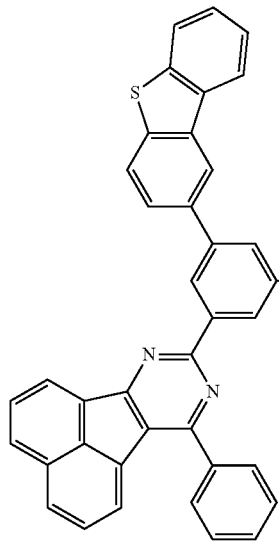 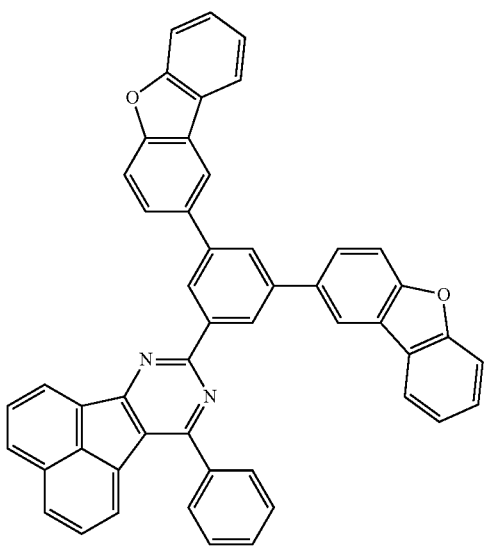

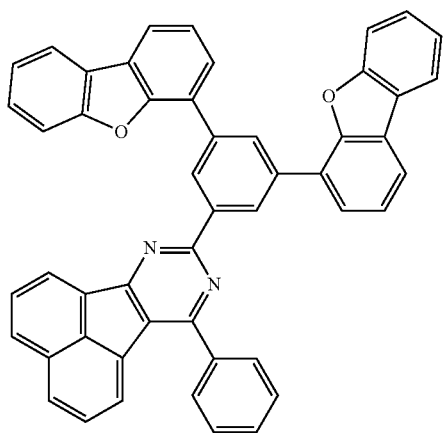
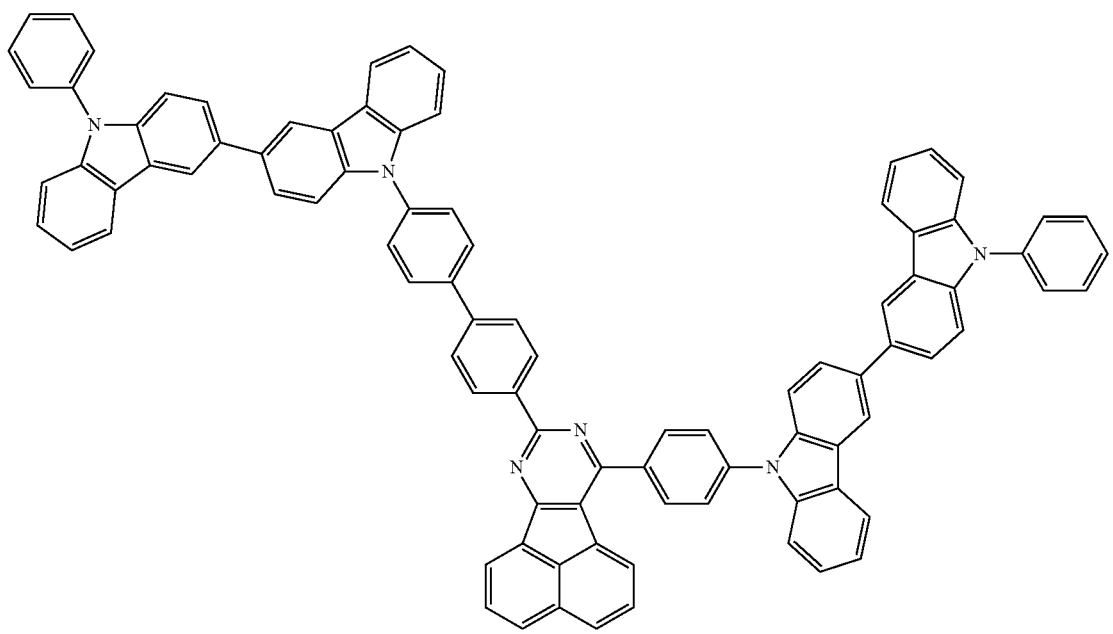
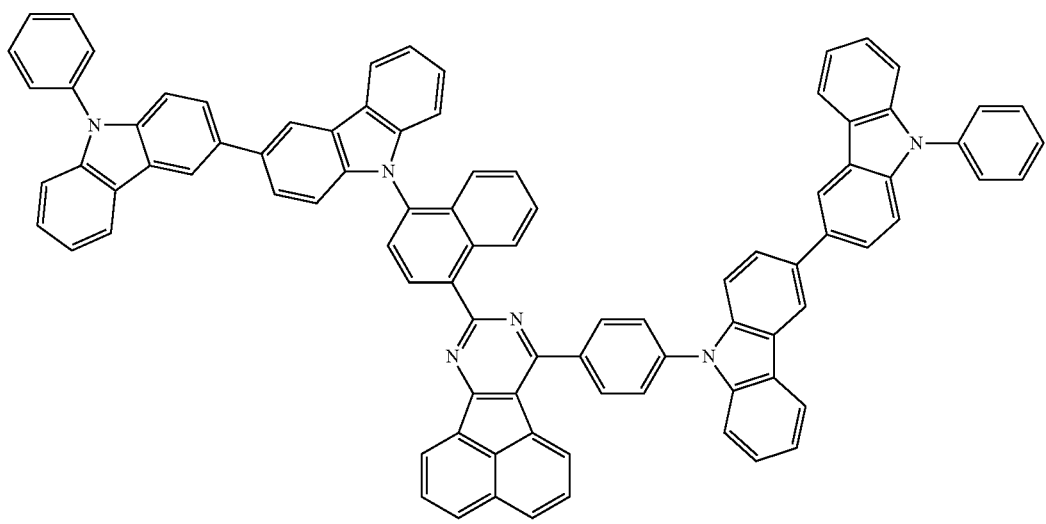

-continued
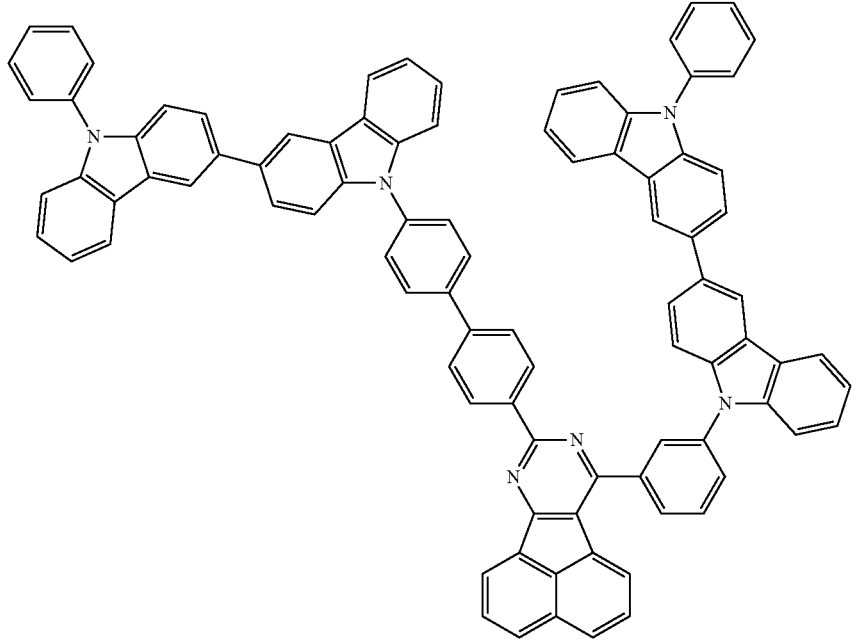
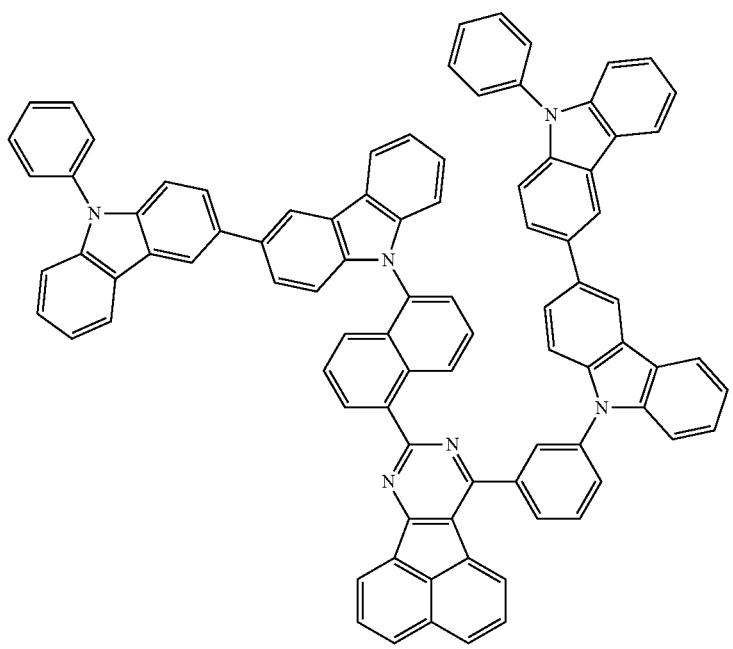

191
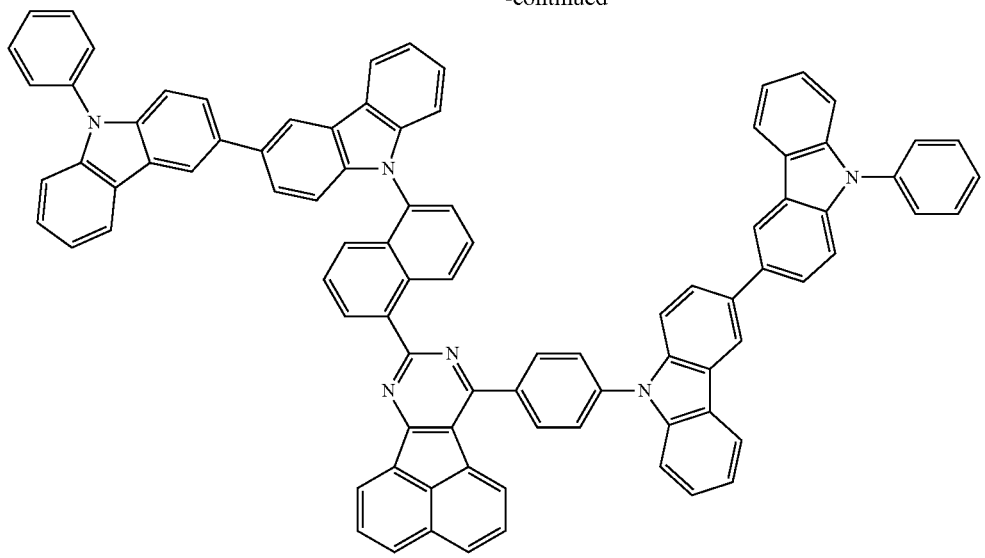
192
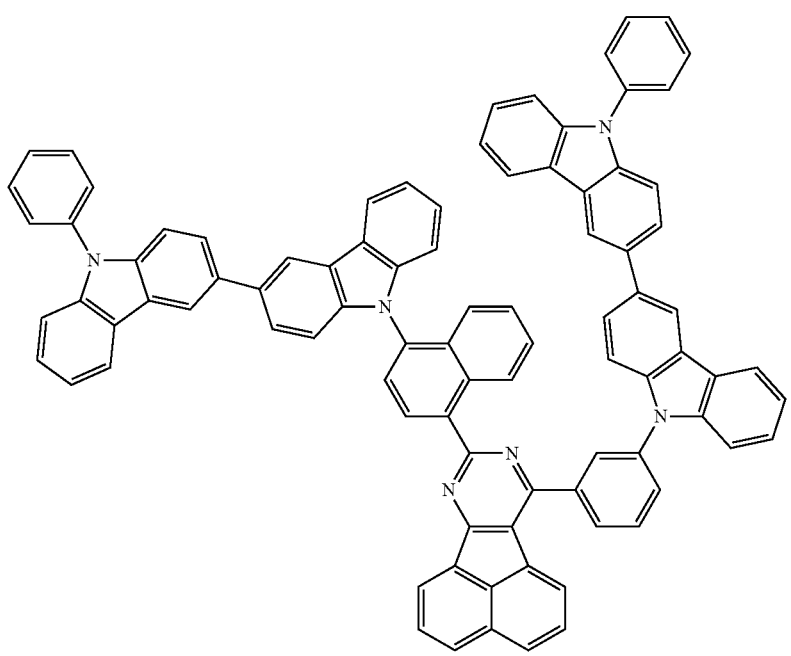

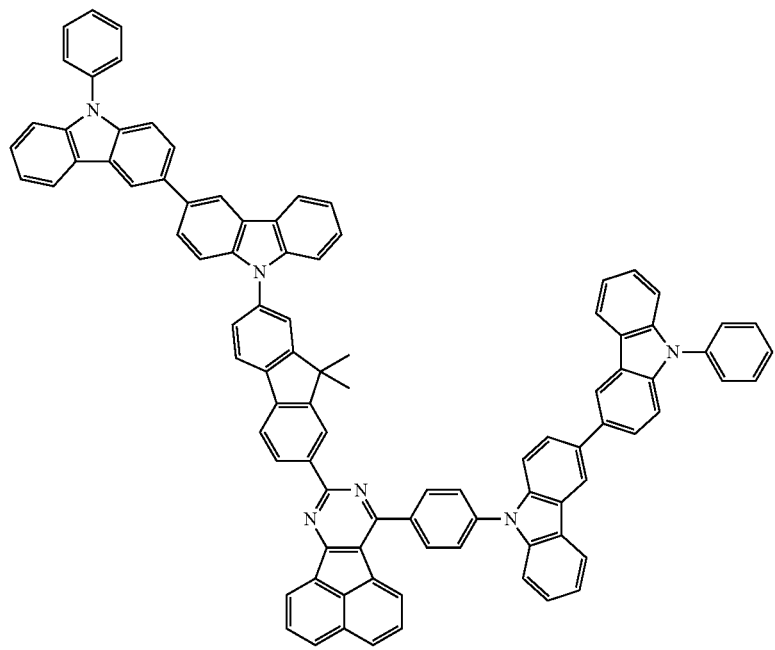
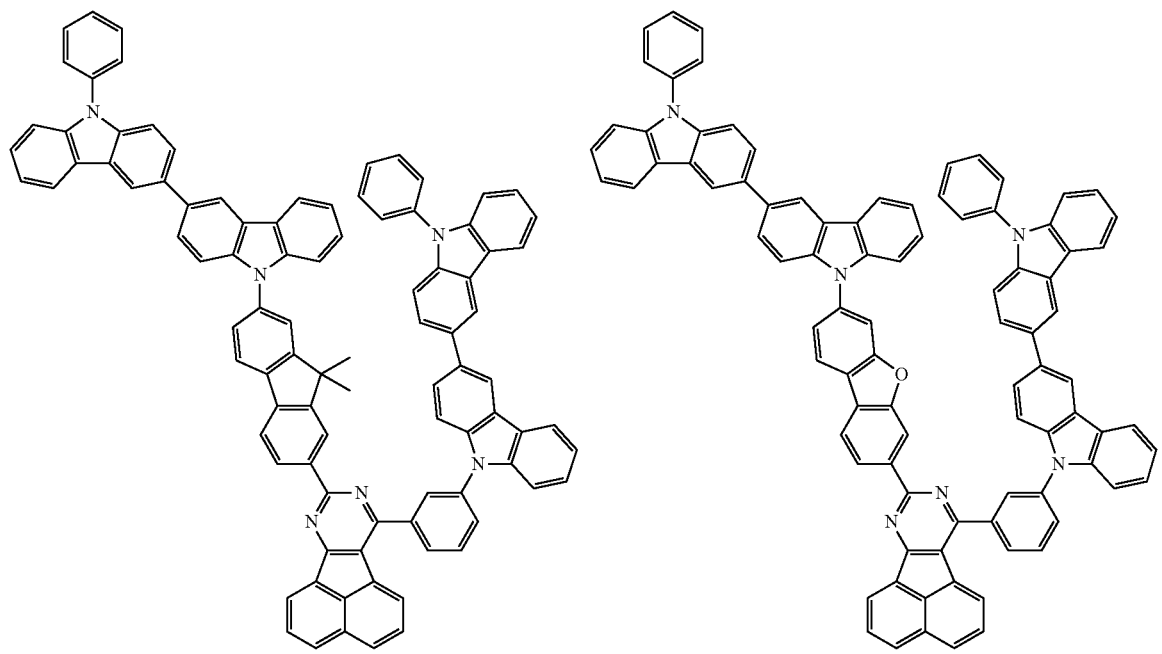

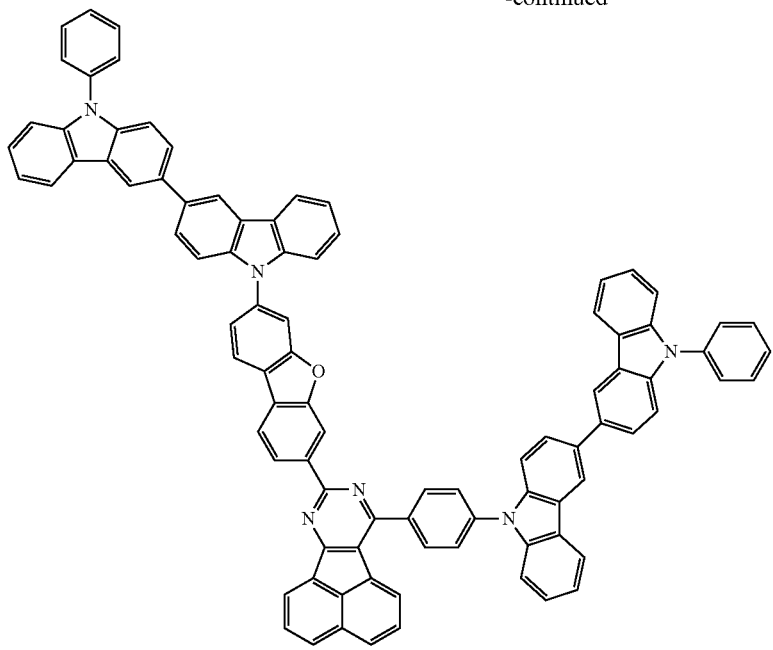
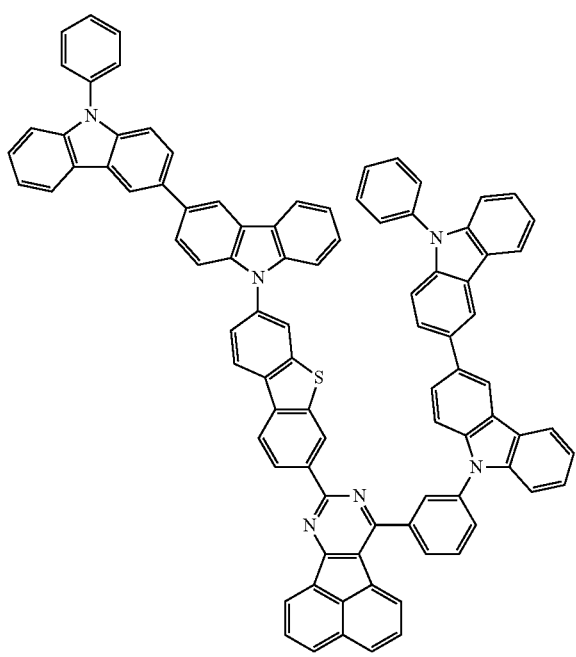

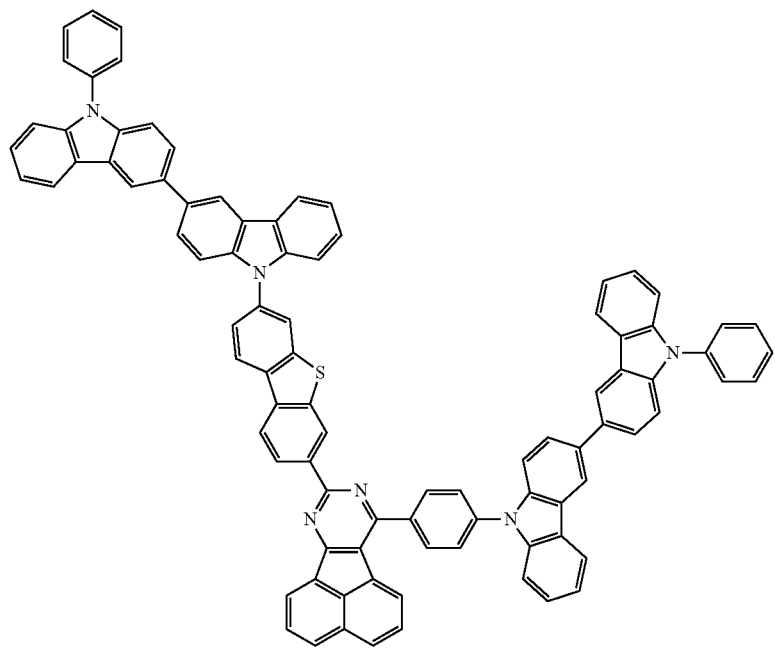
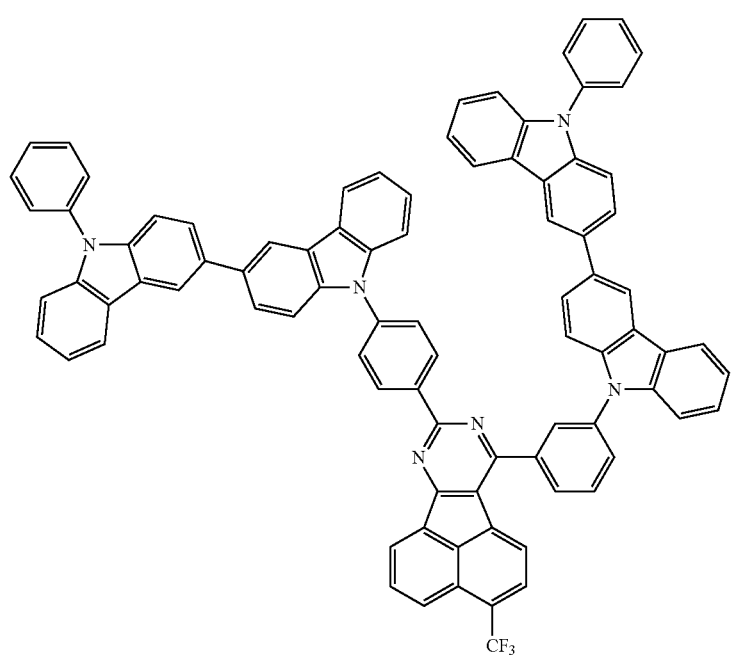

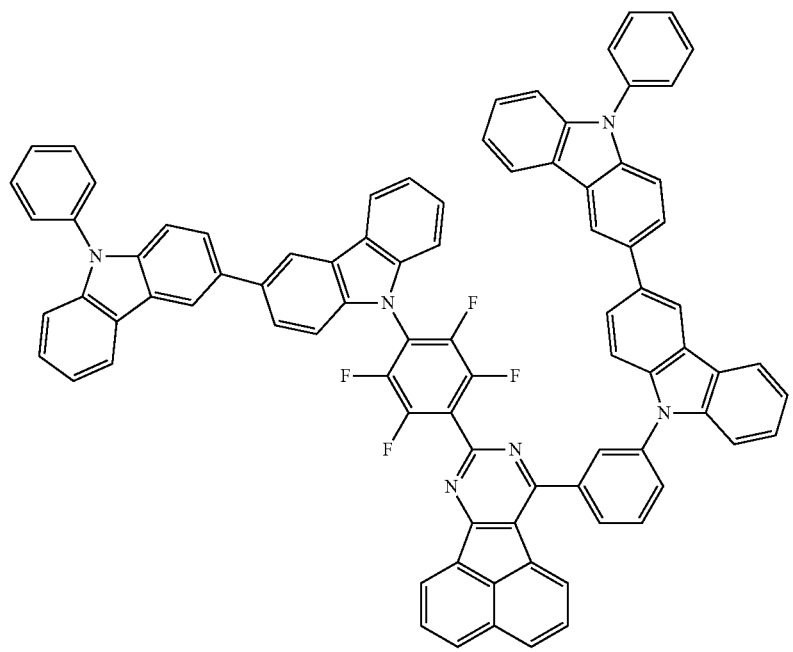
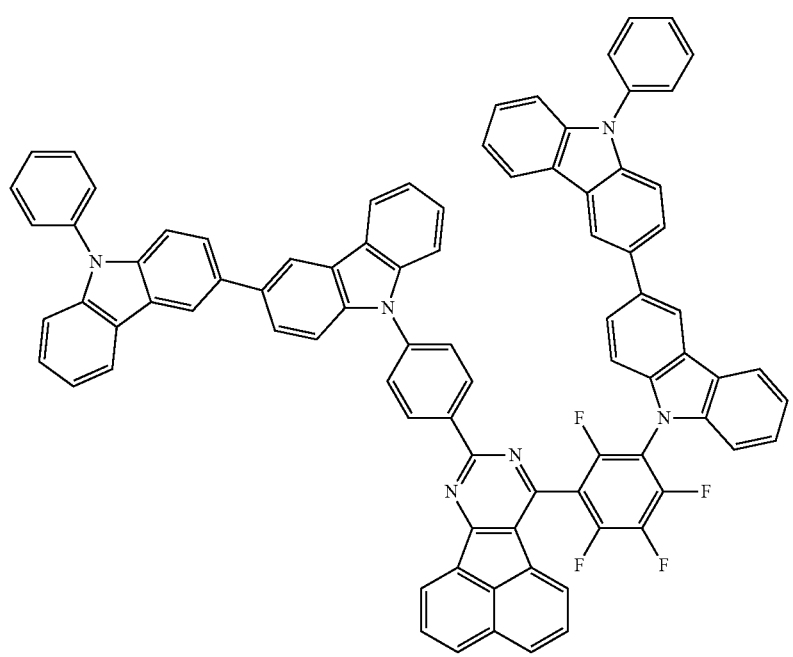

201
-continued
202
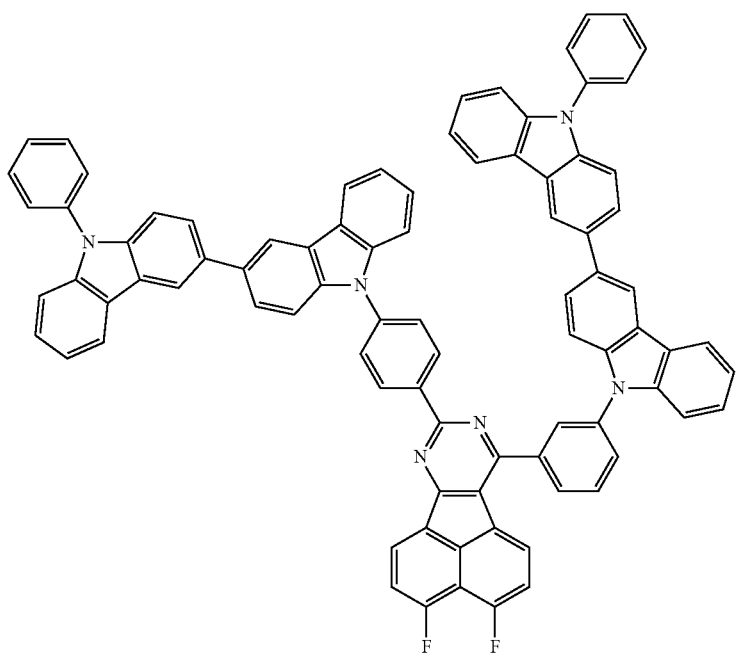
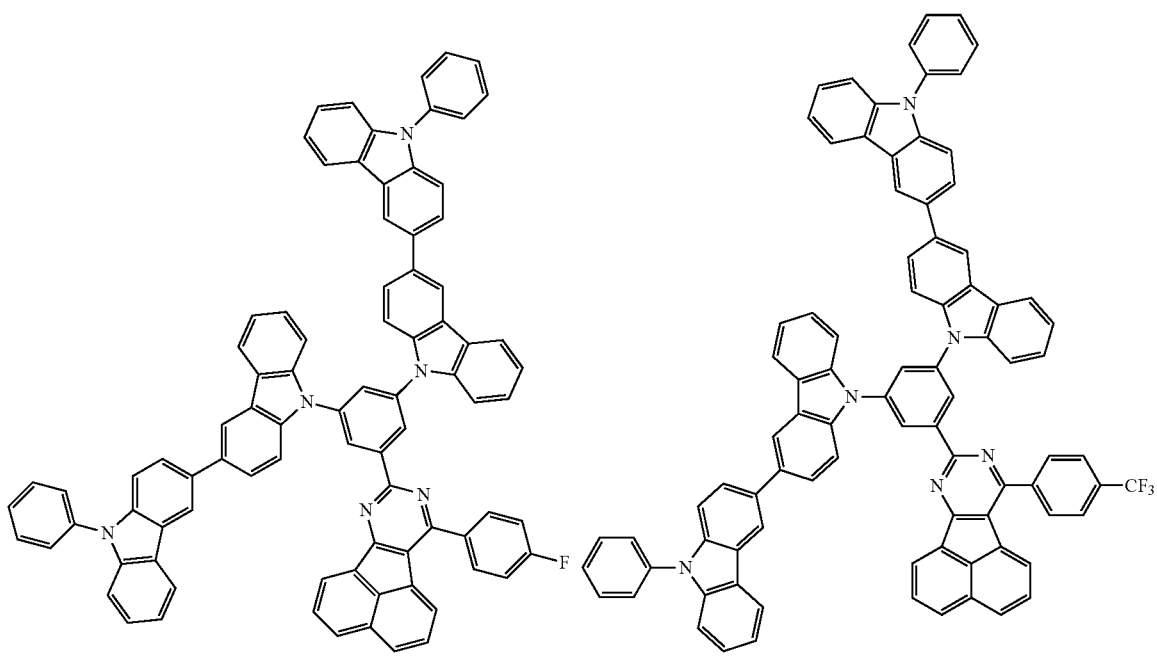

-continued
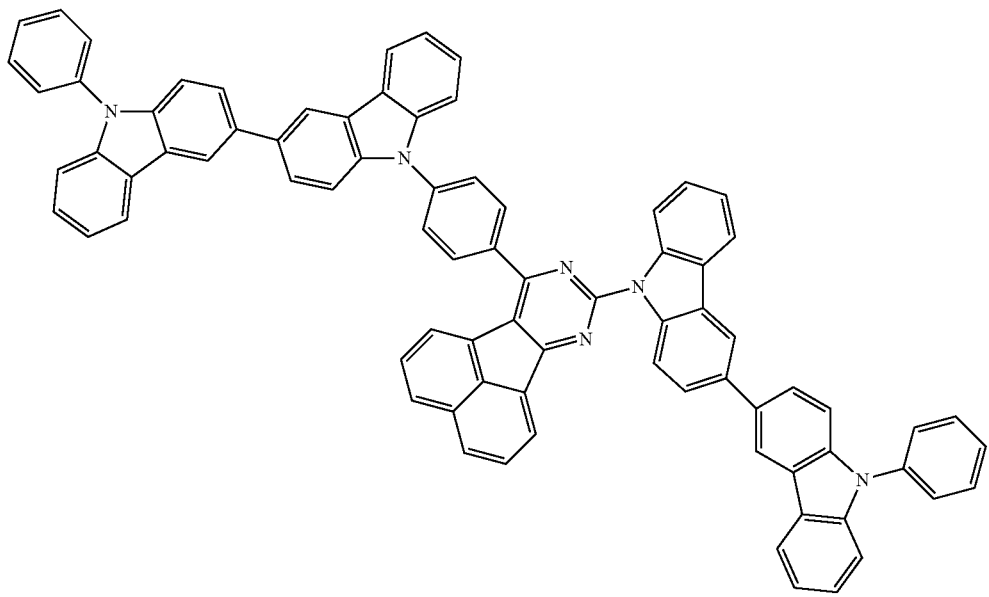
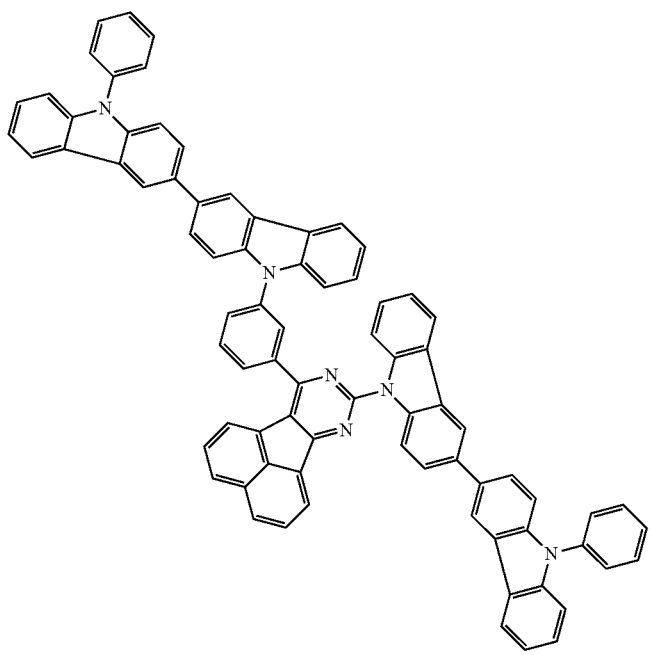
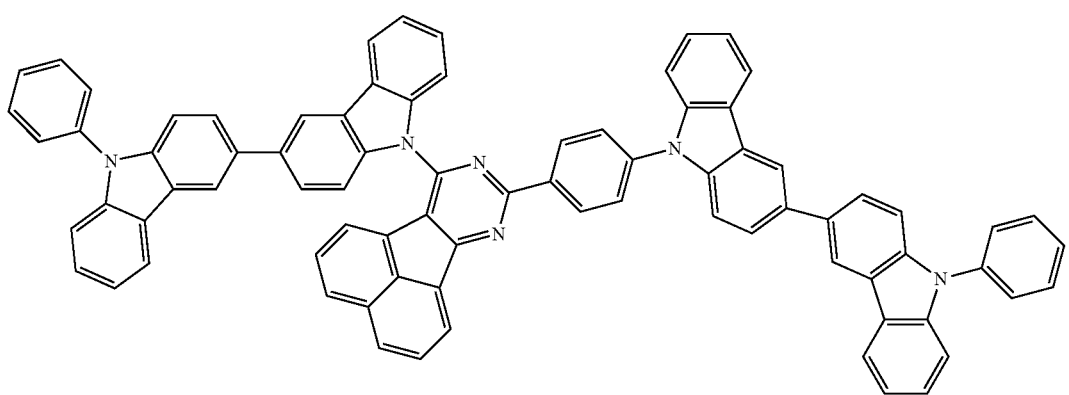

205
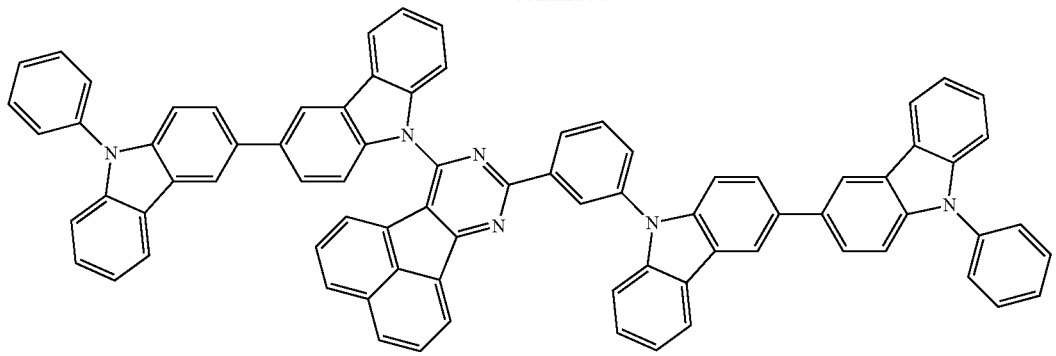
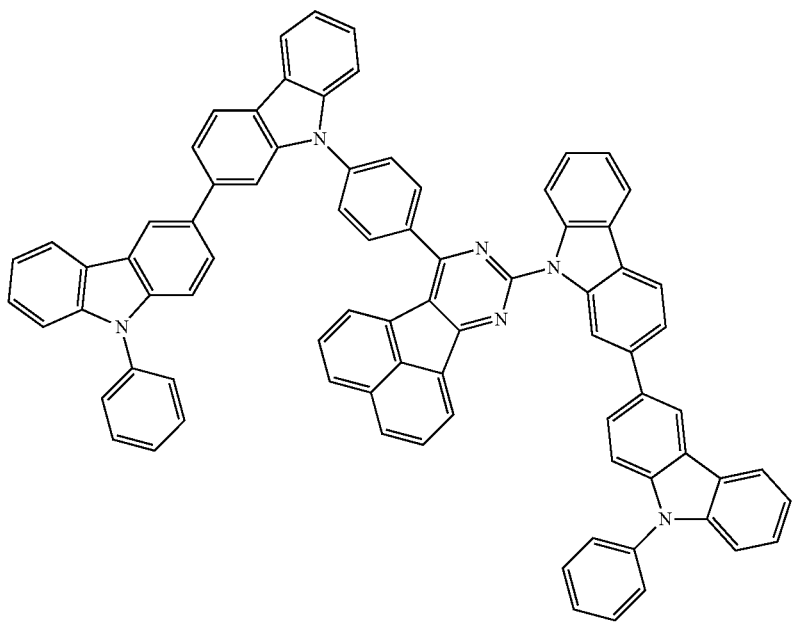
206
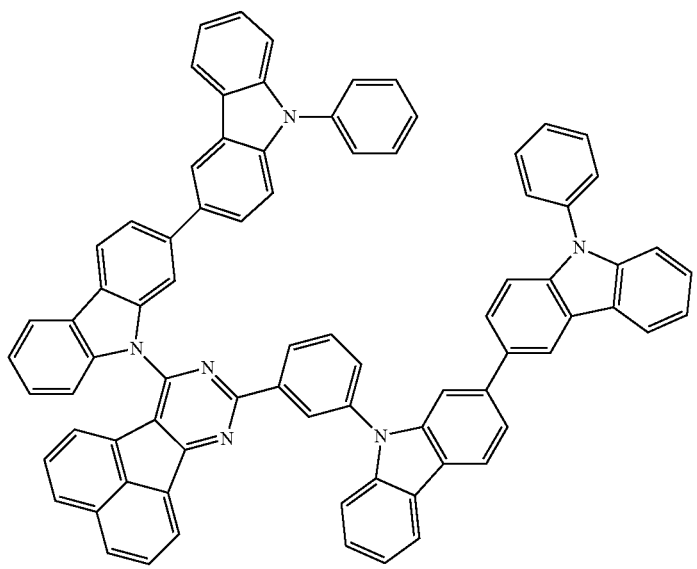

-continued
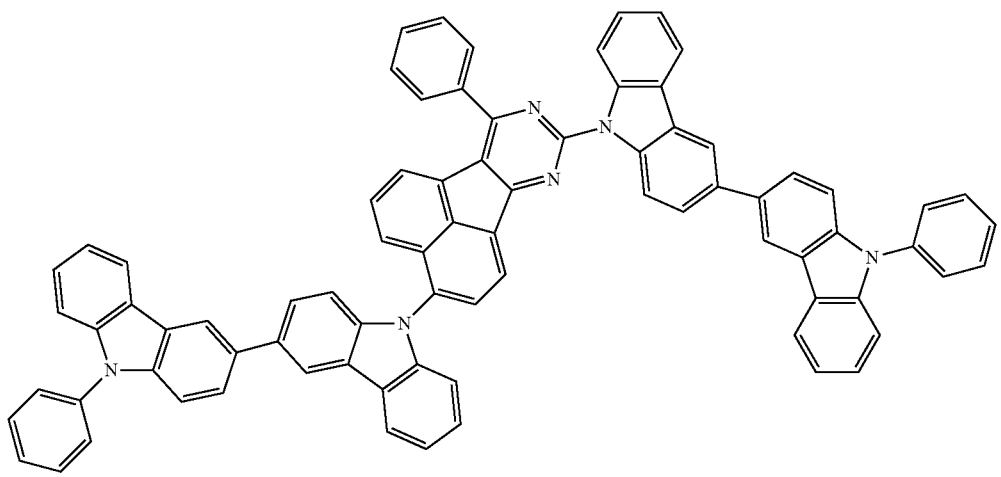
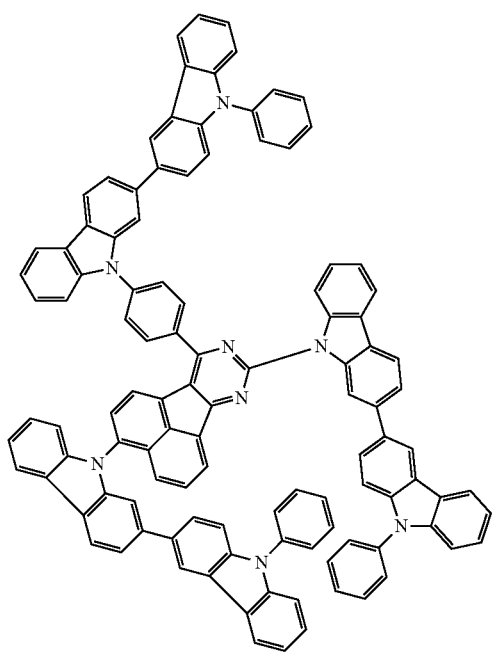
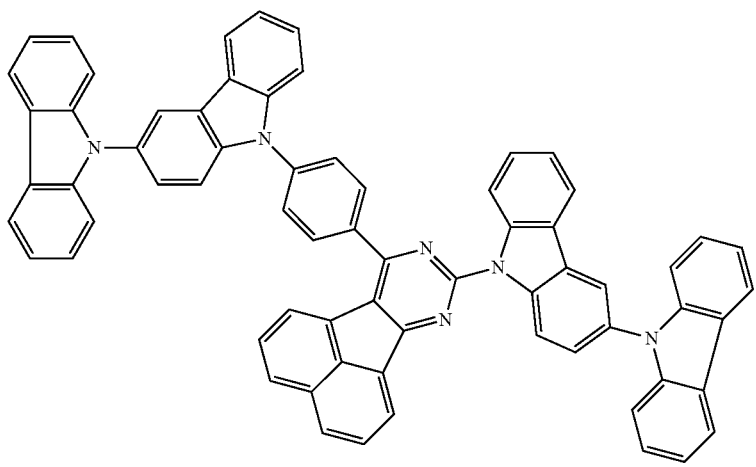

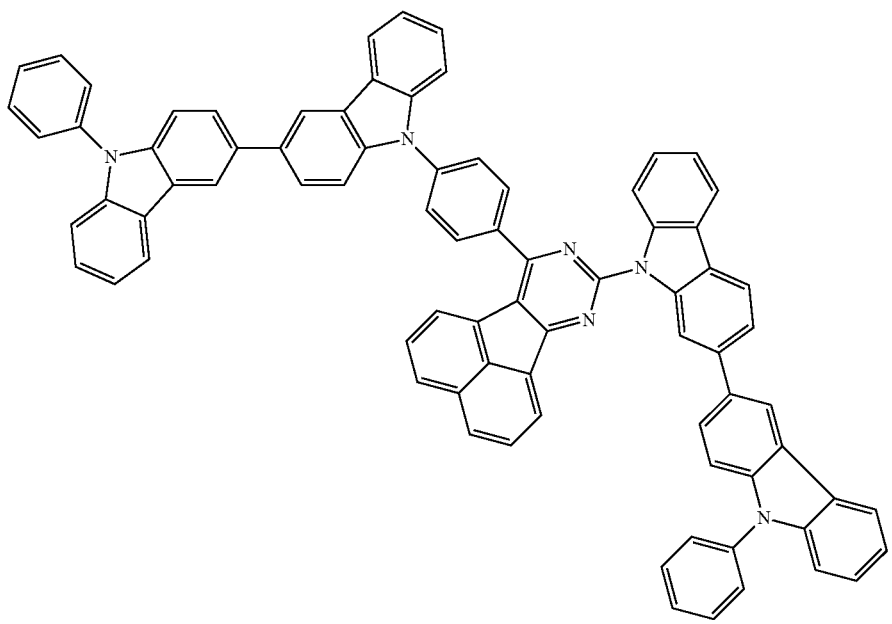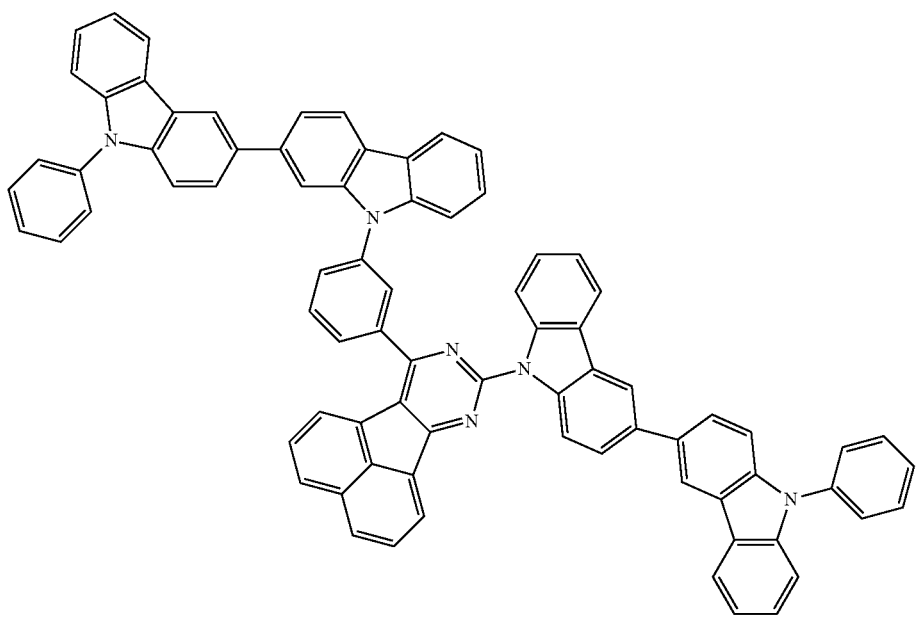

-continued

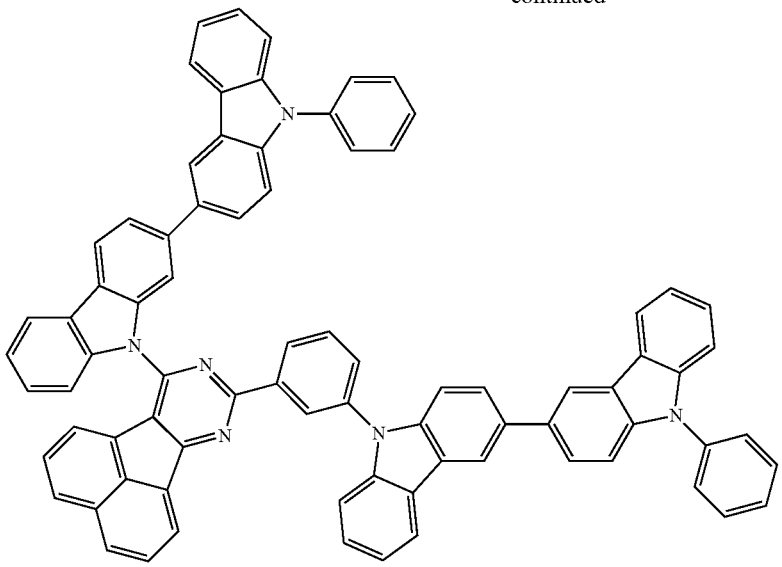 [SMILES: c1ccc(-n2c3ccccc3c3cc(-c4ccc5c(c4)c4ccccc4n5-c4cccc(-c5nc6c(c(-n7c8ccccc8c8ccc(-c9ccc%10c(c9)c9ccccc9n%10-c9ccccc9)cc87)n5)-c5cccc7cccc-6c57)c4)ccc32)cc1]

Organic EL Device

The organic EL device in an aspect of the invention will be described below.

The organic EL device comprises an organic thin film layer between a cathode and an anode. The organic thin film layer comprises a light emitting layer and at least one layer of the organic thin film layer comprises the material for organic EL devices described above.

Examples of the organic thin film layer comprising the material for organic EL devices include an anode-side organic thin film layer formed between an anode and a light emitting layer (hole transporting layer, hole injecting layer, etc.), a light emitting layer, a cathode-side organic thin film layer formed between a cathode and a light emitting layer (electron transporting layer, electron injecting layer, etc.), a space layer, and a blocking layer, although not limited thereto. The material for organic EL devices may be used in any of the above layers, for example, used in a light emitting layer of a fluorescent emission unit as a host material or a dopant material, in a light emitting layer of a phosphorescent emitting unit as a host material, or in a hole transporting layer, an electron transporting layer, etc. of an emission unit.

The organic EL device in an aspect of the invention may be any of a single color emitting device of fluorescent or phosphorescent type, a white-emitting device of fluorescent-phosphorescent hybrid type, an emitting device of a simple type having a single emission unit, and an emitting device of a tandem type having two or more emission units, with the phosphorescent device being preferred. The "emission unit" referred to herein is the smallest unit for emitting light by the recombination of injected holes and injected electrons, which comprises one or more organic layers wherein at least one layer is a light emitting layer.

Representative device structures of the simple-type organic EL device are shown below.

(1) Anode/Emission Unit/Cathode

The emission unit may be a laminate comprising two or more phosphorescent emitting layers and two or more phosphorescent emitting layers. A space layer may be disposed between light emitting layers to prevent the diffusion of excitons generated in a phosphorescent emitting layer into a phosphorescent emitting layer. Representative layered structures of the emission unit are shown below:

(a) hole transporting layer/light emitting layer (/electron transporting layer);
(b) hole transporting layer/first phosphorescent emitting layer/second phosphorescent emitting layer (/electron transporting layer);
(c) hole transporting layer/phosphorescent emitting layer/space layer/phosphorescent emitting layer (/electron transporting layer);
(d) hole transporting layer/first phosphorescent emitting layer/second phosphorescent emitting layer/space layer/phosphorescent emitting layer (/electron transporting layer);
(e) hole transporting layer/first phosphorescent emitting layer/space layer/second phosphorescent emitting layer/space layer/phosphorescent emitting layer (/electron transporting layer);
(f) hole transporting layer/phosphorescent emitting layer/space layer/first phosphorescent emitting layer/second phosphorescent emitting layer (/electron transporting layer);
(g) hole transporting layer/electron blocking layer/light emitting layer (/electron transporting layer);
(h) hole transporting layer/light emitting layer/hole blocking layer (/electron transporting layer); and
(i) hole transporting layer/phosphorescent emitting layer/triplet blocking layer (/electron transporting layer).

The emission color of a phosphorescent emitting layer and that of a phosphorescent emitting layer may be different. For example, the layered structure of the laminated light emitting layer (d) may be hole transporting layer/first phosphorescent emitting layer (red)/second phosphorescent emitting layer (green)/space layer/phosphorescent emitting layer (blue)/electron transporting layer.

An electron blocking layer may be disposed between a light emitting layer and a hole transporting layer or between alight emitting layer and a space layer, if necessary. Also, a hole blocking layer may be disposed between a light emitting layer and a electron transporting layer, if necessary. With such an electron blocking layer or a hole blocking layer, electrons and holes are confined in a light emitting layer to increase the degree of charge recombination in the light emitting layer, thereby improving the lifetime.

A representative device structure of the tandem-type organic EL device is shown below:

(2) anode/first emission unit/intermediate layer/second emission unit/cathode.

The layered structures of the first emission unit and the second emission unit may be independently selected from those described above with respect to the emission unit.

Generally, the intermediate layer is also called an intermediate electrode, an intermediate conductive layer, a charge generation layer, an electron withdrawing layer, a connecting layer, or an intermediate insulating layer. The intermediate layer may be formed by a known material capable of supplying electrons to the first emission unit and holes to the second emission unit.

A schematic structure of an example of the organic EL device in an aspect of the invention is shown in FIG. 1, wherein the organic EL device 1 comprises a substrate 2, an anode 3, a cathode 4, and an emission unit 10 disposed between the anode 3 and the cathode 4. The emission unit 10 comprises a light emitting layer 5 which comprises at least one phosphorescent emitting layer comprising a phosphorescent host and a phosphorescent dopant (phosphorescent emitting material). A hole injecting/transporting layer (an anode-side organic thin film layer) 6 may be disposed between the light emitting layer 5 and the anode 3, and an electron injecting/transporting layer (a cathode-side thin film layer) 7 may be disposed between the light emitting layer 5 and the cathode 4. An electron blocking layer may be disposed on the anode 3 side of the light emitting layer 5, and a hole blocking layer may be disposed on the cathode 4 side of the light emitting layer 5. With these blocking layers, electrons and holes are confined in the light emitting layer 5 to increase the degree of exciton generation in the light emitting layer 5.

In the present invention, a host is referred to as a fluorescent host when combinedly used with a fluorescent dopant (fluorescent emitting material) and as a phosphorescent host when combinedly used with a phosphorescent dopant. Therefore, the fluorescent host and the phosphorescent host are not distinguished from each other merely by the difference in their molecular structures. Namely, in the present invention, the term "phosphorescent host" means a material for constituting a phosphorescent emitting layer containing a phosphorescent dopant and does not necessarily mean a material that cannot be used as a material for a fluorescent emitting layer. The same applies to the fluorescent host.

Substrate

The organic EL device in an aspect of the invention is formed on a light-transmissive substrate. The light-transmissive substrate serves as a support for the organic EL device and is preferably a flat substrate having a transmittance of 50% or more to 400 to 700 nm visible light. Examples of the substrate include a glass plate and a polymer plate. The glass plate may include a plate made of soda-lime glass, barium-strontium-containing glass, lead glass, aluminosilicate glass, borosilicate glass, barium borosilicate glass, or quartz. The polymer plate may include a plate made of polycarbonate, acryl, polyethylene terephthalate, polyether sulfide, or polysulfone.

Anode

The anode of organic EL device injects holes to a hole transporting layer or a light emitting layer, and an anode having a work function of 4.5 eV or more is effective. Examples of the material for anode include indium tin oxide alloy (ITO), tin oxide (NESA), indium zinc oxide alloy, gold, silver, platinum, and cupper. The anode is formed by making the material for anode into a thin film by a method, such as a vapor deposition method or a sputtering method. When getting the light emitted from a light emitting layer through the anode, the transmittance of anode to visible light is preferably 10% or more. The sheet resistance of anode is preferably several hundreds Ω/or less. The film thickness of anode depends upon the kind of material and generally 10 nm to 1 μm, preferably 10 to 200 nm.

Cathode

The cathode injects electrons to an electron injecting layer, an electron transporting layer or a light emitting layer, and formed preferably by a material having a small work function. Examples of the material for cathode include, but not limited to, indium, aluminum, magnesium, magnesium-indium alloy, magnesium-aluminum alloy, aluminum-lithium alloy, aluminum-scandium-lithium alloy, and magnesium-silver alloy. Like the anode, the cathode is formed by making the material for cathode into a thin film by a method, such as a vapor deposition method and a sputtering method. The emitted light may be taken through the cathode, if necessary.

Light Emitting Layer

The light emitting layer is an organic layer having a light emitting function and contains a host material and a dopant material when a doping system is employed. The major function of the host material is to promote the recombination of electrons and holes and confine excitons within a light emitting layer. The dopant material causes the excitons generated by recombination to emit light efficiently.

In a phosphorescent device, the major function of the host material is to confine the excitons generated on the dopant within a light emitting layer.

To control the carrier balance in a light emitting layer, the light emitting layer may be made into a double host (host/co-host) layer, for example, by combinedly using an electron transporting host and a hole transporting host.

The light emitting layer may be also made into a double dopant layer, in which two or more kinds of dopant materials having a high quantum yield are combinedly used and each dopant material emits light with its own color. For example, a yellow emission can be obtained by a light emitting layer which is formed by co-depositing a host, a red-emitting dopant, and a green-emitting dopant.

In a laminate of two or more light emitting layers, electrons and holes can be accumulated in the interface between the light emitting layers, and therefore, the recombination region is localized in the interface between the light emitting layers. With this structure, the quantum efficiency can be enhanced.

The easiness of hole injection to alight emitting layer and the easiness of electron injection to a light emitting layer may be different from each other. Also, the hole transporting ability and the electron transporting ability each being expressed by mobility of holes and electrons in a light emitting layer may be different from each other.

The phosphorescent dopant (phosphorescent emitting material) to be used in a light emitting layer is a compound which emits light by releasing the energy of excited triplet state and preferably a organometallic complex comprising at least one metal selected from Ir, Pt, Os, Au, Cu, Re, and Ru and a ligand, although not particularly limited thereto as long as emitting light by releasing the energy of excited triplet state. The ligand is preferably ortho-metallated. In view of obtaining a high phosphorescent quantum yield and further improving the external quantum efficiency of luminescent device, a metal complex comprising a metal selected from Ir, Os, and Pt is preferred, with a metal complex, such as an iridium complex, an osmium complex and a platinum complex, particularly an ortho-metallated complex being more preferred, an iridium complex and a platinum complex being still more preferred, and an ortho-metallated iridium complex being particularly preferred.

The content of the phosphorescent dopant in a light emitting layer is not particularly limited and selected according to the use of the device, and preferably 0.1 to 70% by mass, and more preferably 1 to 30% by mass. If being 0.1% by mass or more, the amount of light emission is sufficient. If being 70% by mass or less, the concentration quenching can be avoided.

Preferred examples of the organometallic complex for the phosphorescent dopant are shown below.

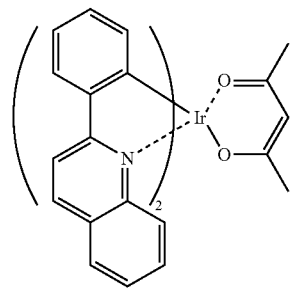

PQIr

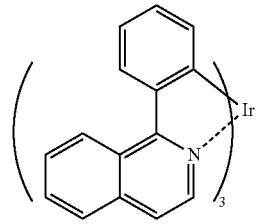

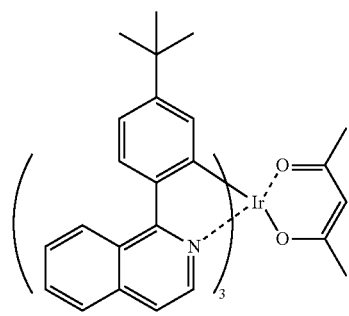

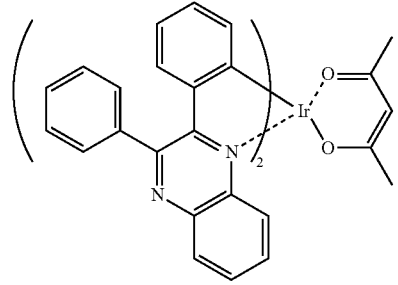

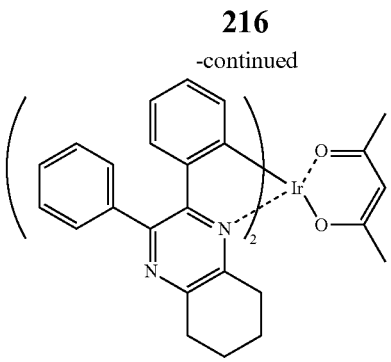

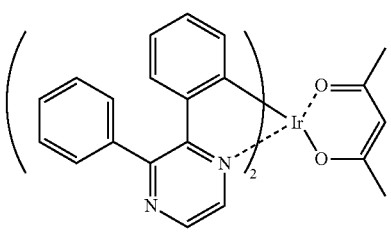

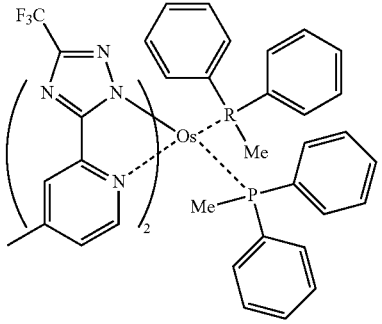

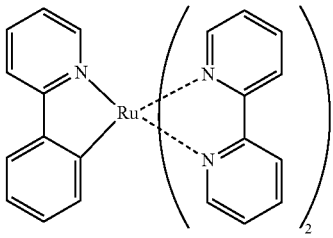

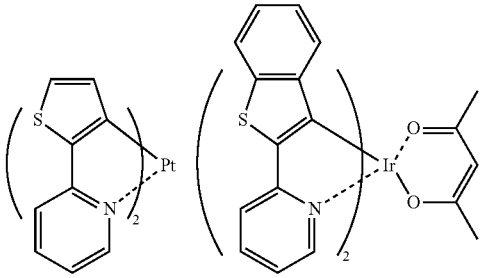

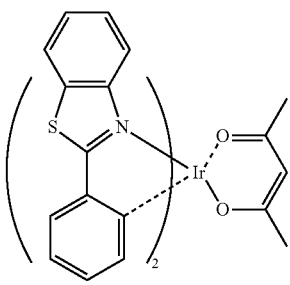

217
-continued
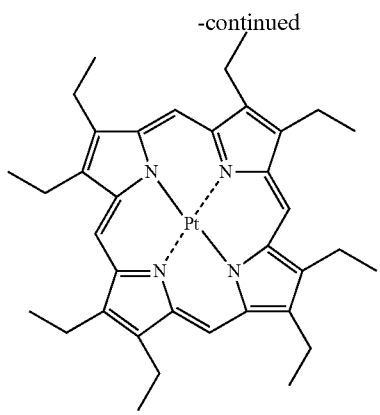
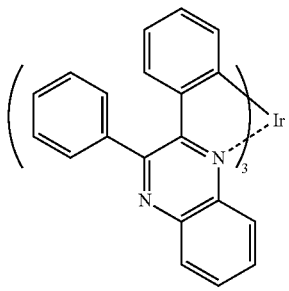
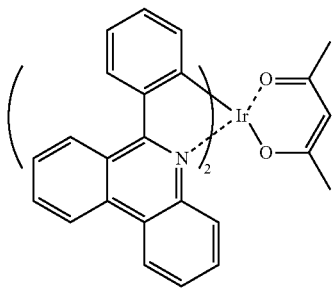
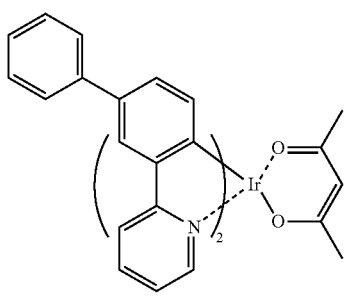
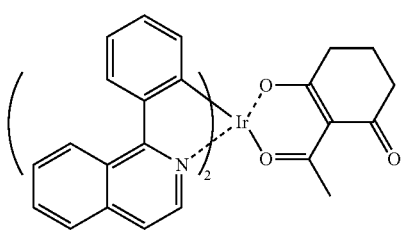
218
-continued
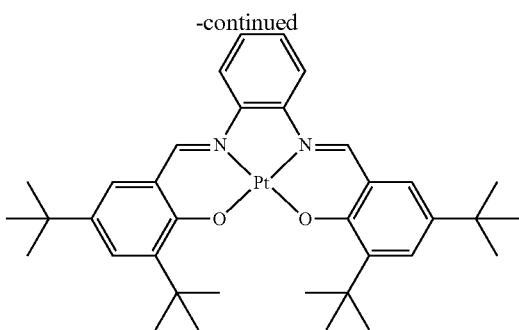
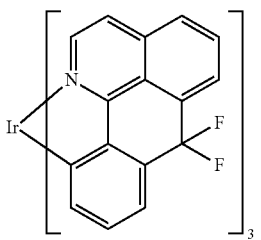
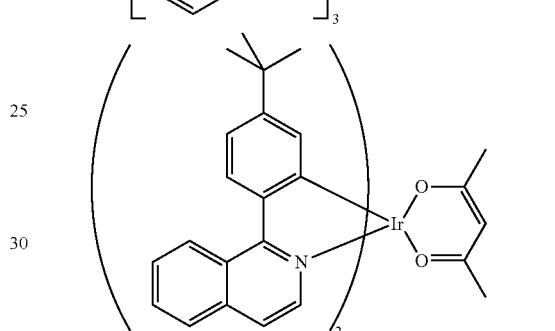
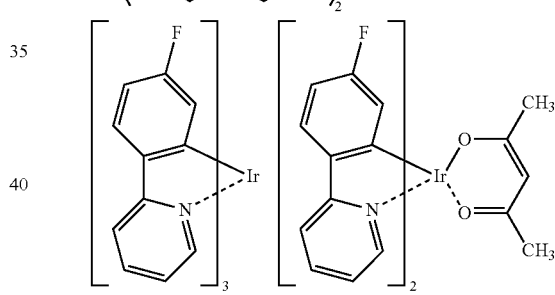
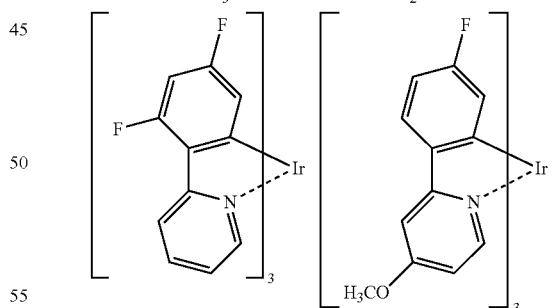
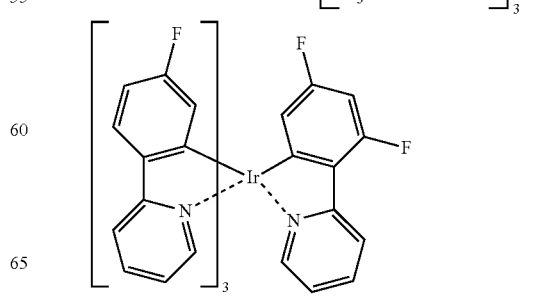

-continued
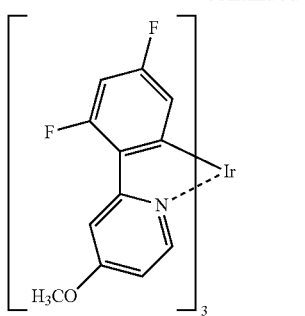
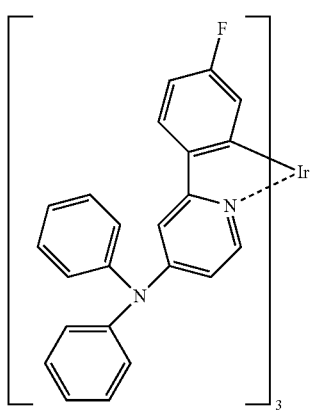
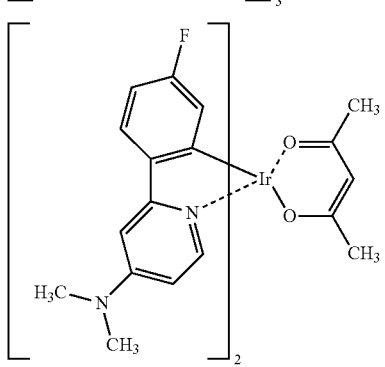
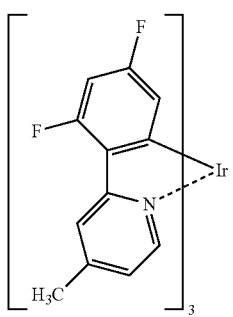
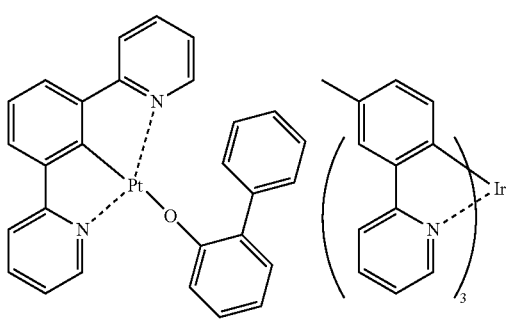
-continued
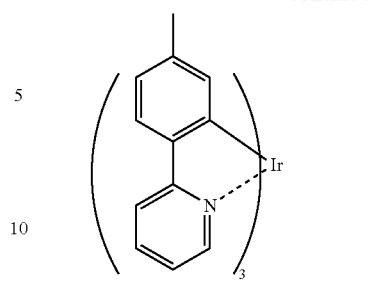
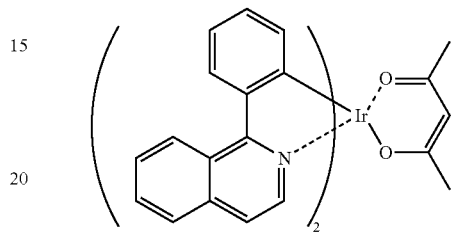
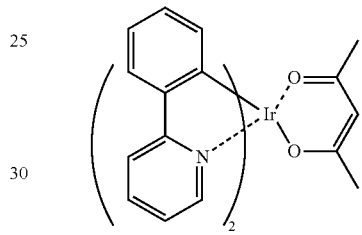
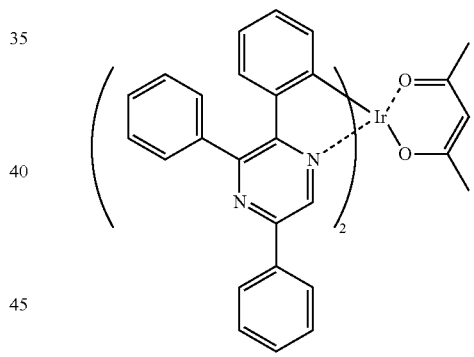
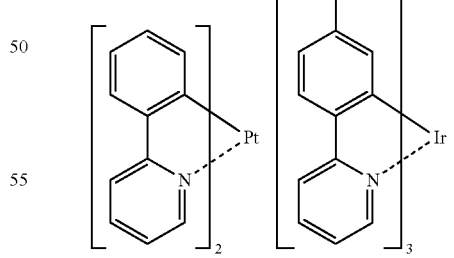
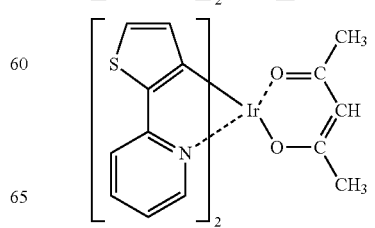

221
-continued
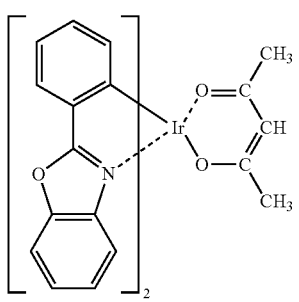
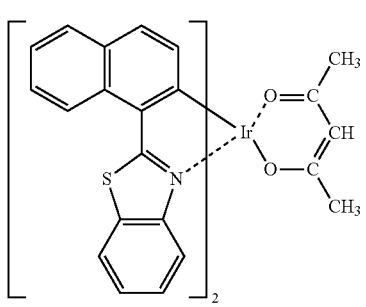
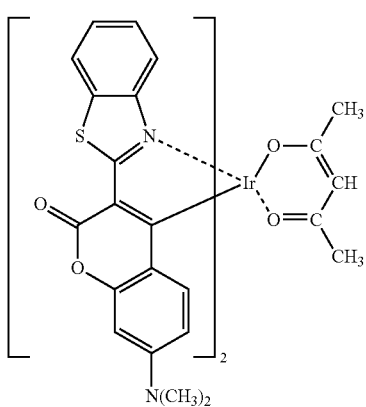
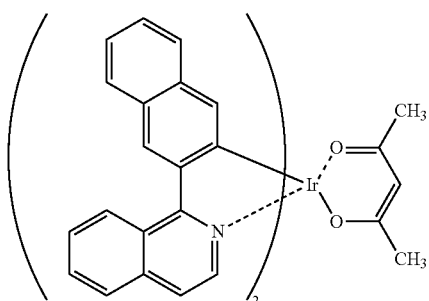
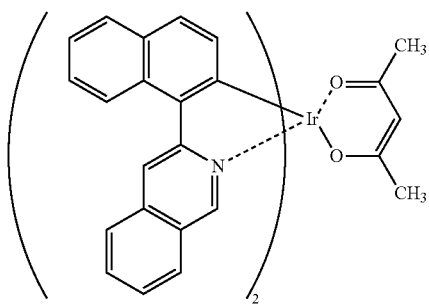
222
-continued
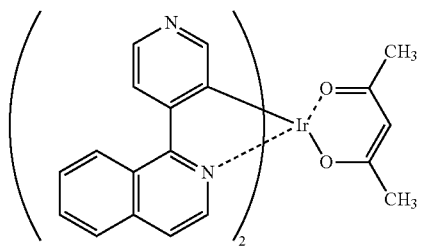
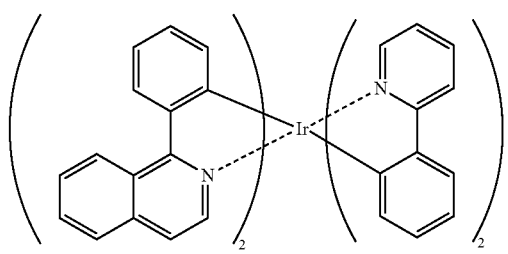
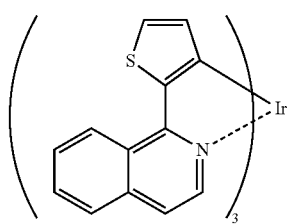
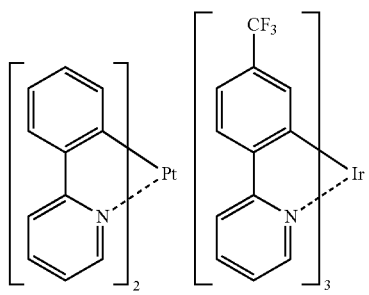
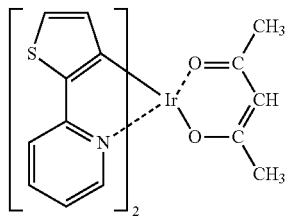
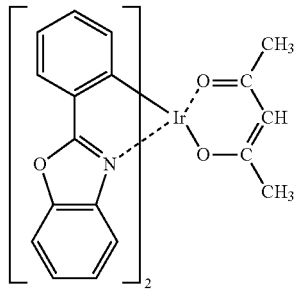

-continued

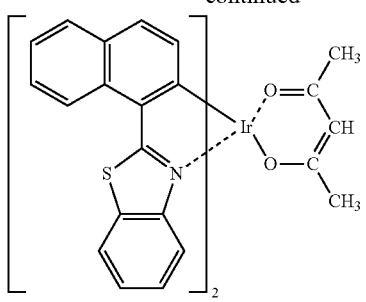

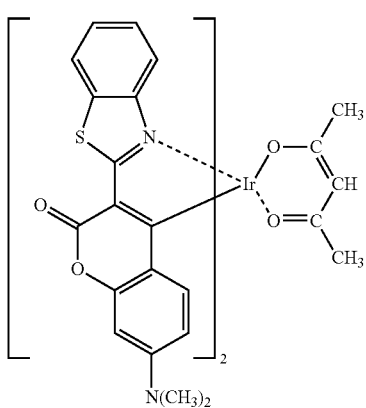

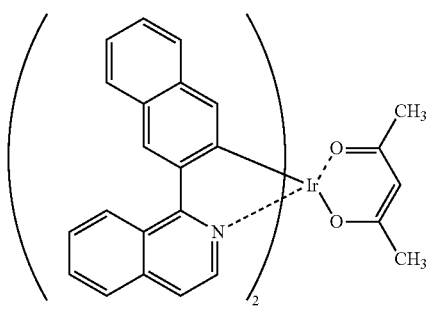

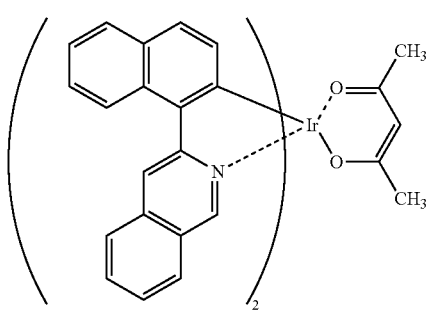

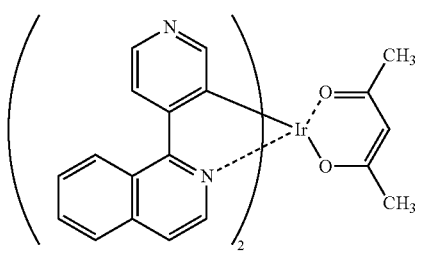

-continued

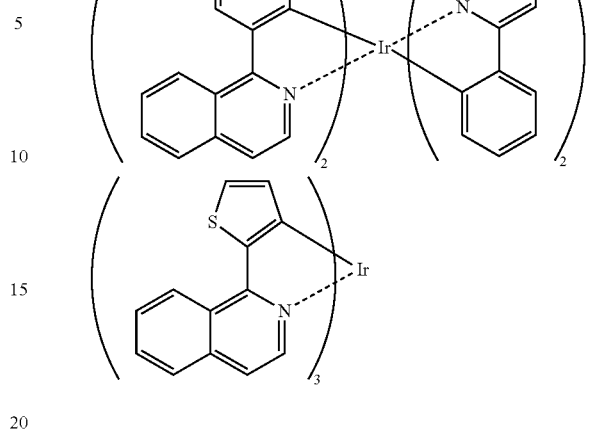

In addition, in the organic EL device in an aspect of the invention, a complex represented by formula (X) or (Y) is preferably used as the phosphorescent emitting material:

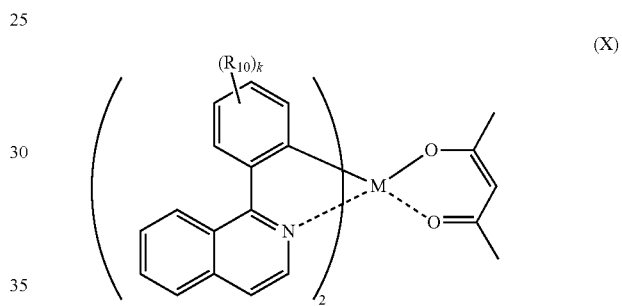

(X)

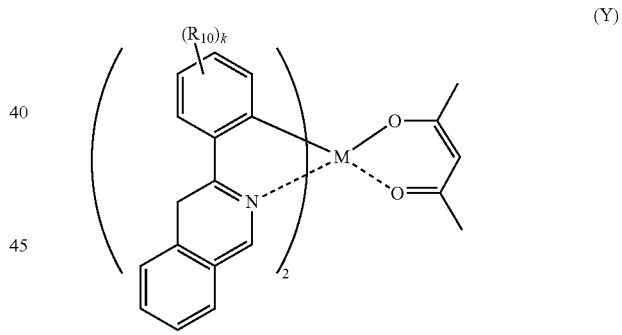

(Y)

wherein $R_{10}$ represents a hydrogen atom or a substituent, r represents an integer of 1 to 4, and M represents Ir, Os, or Pt.

Examples of the substituent represented by $R_{10}$ include those mentioned above with respect to $R_0$ to $R_8$, etc. of formula (1).

The phosphorescent host is a compound which confines the triplet energy of the phosphorescent dopant efficiently within a light emitting layer to cause the phosphorescent dopant to emit light efficiently. Although the compound and the material for organic EL device each in an aspect of the invention are useful as a phosphorescent host, a compound other than the material for organic EL device may be used as the phosphorescent host according to the use of the device. The use of the material for organic EL device in an aspect of the invention is not limited to the use as the phosphorescent host mentioned above.

The compound in an aspect of the invention and a compound other than it may be combinedly used in the same light emitting layer as the phosphorescent host materials. Alternatively, the material for organic EL device in an aspect of the invention can be used in one of light emitting layers as a phosphorescent host material and a compound other than it can be used in another of the light emitting layers as a phosphorescent host material. The material for organic EL device in an aspect of the invention may be used in an organic layer other than the light emitting layer. In this case, a compound other than the material for organic EL device may be used as a phosphorescent host of the light emitting layer.

Examples of the compound other than the material for organic EL devices in an aspect of the invention, which is suitable as a phosphorescent host, include a carbazole derivative, a triazole derivative, a oxazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, a styrylanthracene derivative, a fluorenone derivative, a hydrazone derivative, a stilbene derivative, a silazane derivative, an aromatic tertiary amine compound, a styrylamine compound, an aromatic methylidene compound, a porphyrin compound, an anthraquinodimethane derivative, an anthrone derivative, a diphenylquinone derivative, a thiopyran dioxide derivative, a carbodiimide derivative, a fluorenylidenemethane derivative, a distyrylpyrazine derivative, a tetracarboxylic anhydride of fused ring such as naphthalene and perylene, a phthalocyanine derivative, a metal complex of 8-quinolinol derivative, metal phthalocyanine, metal complexes having a ligand such as benzoxazole and benzothiazole, an electroconductive oligomer, such as a polysilane compound, a poly(N-vinylcarbazole) derivative, an aniline copolymer, thiophene oligomer, and a polythiophene, and a polymer such as a polythiophene derivative, a polyphenylene derivative, a polyphenylenevinylene derivative, and a polyfluorene derivative. These phosphorescent hosts may be used alone or in combination of two or more. Examples thereof are shown below.

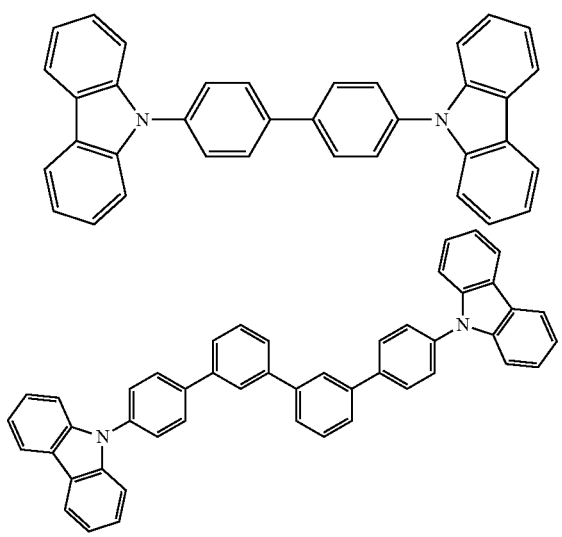

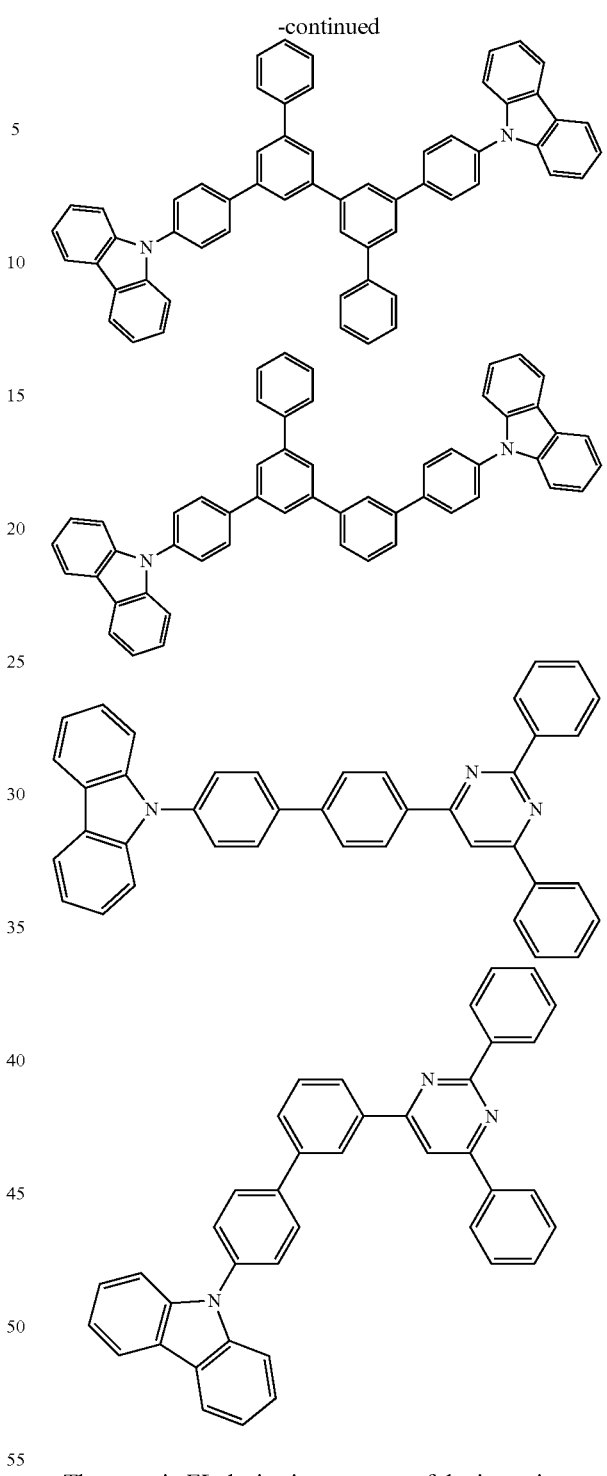

The organic EL device in an aspect of the invention may comprise a light emitting layer comprising a fluorescent material, i.e., a fluorescent emitting layer. The fluorescent emitting layer may be formed from a known fluorescent emitting material, for example, at least one material selected from an anthracene derivative, a fluoranthene derivative, a styrylamine derivative, and an arylamine derivative, with the anthracene derivative and the arylamine derivative being more preferred. In particular, the anthracene derivative is preferably used as a host material and the arylamine derivative is preferably used as a dopant. The materials described in WO 2010/134350 and WO 2010/134352 are preferably used. The material for organic EL device in an aspect of the invention may be used in a fluorescent emitting layer as a fluorescent emitting material or a host material.

Electron-Donating Dopant

The organic EL device in an aspect of the invention preferably comprises an electron-donating dopant at an interfacial region between the cathode and the emitting unit. With such a construction, the organic EL device has an improved luminance and an elongated lifetime. The electron-donating dopant comprises a metal having a work function of 3.8 eV or less and examples thereof include at least one selected from an alkali metal, an alkali metal complex, an alkali metal compound, an alkaline earth metal, an alkaline earth metal complex, an alkaline earth metal compound, a rare earth metal, a rare earth metal complex, and a rare earth metal compound.

Examples of the alkali metal include Na (work function: 2.36 eV), K (work function: 2.28 eV), Rb (work function: 2.16 eV), and Cs (work function: 1.95 eV), with those having a work function of 2.9 eV or less being particularly preferred. Of the above, preferred are K, Rb, and Cs, more preferred are Rb and Cs, and most preferred is Cs. Examples of the alkaline earth metal include Ca (work function: 2.9 eV), Sr (work function: 2.0 to 2.5 eV), and Ba (work function: 2.52 eV), with those having a work function of 2.9 eV or less being particularly preferred. Examples of the rare earth metal include Sc, Y, Ce, Tb, and Yb, with those having a work function of 2.9 eV or less being particularly preferred.

Examples of the alkali metal compound include an alkali oxide, such as $Li_2O$, $Cs_2O$, and $K_2O$, and an alkali halide, such as LiF, NaF, CsF, and KF, with LiF, $Li_2O$, and NaF being preferred. Examples of the alkaline earth metal compound include BaO, SrO, CaO, and a mixture thereof, such as $Ba_xSr_{1-x}O$ (0<x<1) and $Ba_xCa_{1-x}O$ (0<x<1), with BaO, SrO, and CaO being preferred. Examples of the rare earth metal compound include $YbF_3$, $ScF_3$, $ScO_3$, $Y_2O_3$, $Ce_2O_3$, $GdF_3$, and $TbF_3$, with $YbF_3$, $ScF_3$, and $TbF_3$ being preferred.

Examples of the alkali metal complex, the alkaline earth metal complex, and the rare earth metal are not particularly limited as long as containing at least one metal ion selected from an alkali metal ion, an alkaline earth metal ion, and a rare earth metal ion, respectively. The ligand is preferably, but not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfulborane, bipyridyl, phenanthroline, phthalocyanine, porphyrin, cyclopentadiene, β-diketones, azomethines, and derivatives thereof.

The electron-donating dopant is added to the interfacial region preferably into a form of layer or island preferably by co-depositing the electron-donating dopant together with an organic compound for forming the interfacial region (a light emitting material, an electron injecting material, etc.) by a resistance heating deposition method, thereby dispersing the electron-donating dopant into the organic compound. The disperse concentration expressed by the molar ratio of the organic compound and the electron-donating dopant is 100:1 to 1:100 and preferably 5:1 to 1:5.

When the electron-donating dopant is formed into a form of layer, a light emitting material or an electron injecting material is made into a layer to form an interfacial organic layer, and then, the electron-donating dopant alone is deposited by a resistance heating deposition method into a layer having a thickness of preferably 0.1 to 15 nm. When the electron-donating dopant is formed into a form of island, a light emitting material or an electron injecting material is made into a form of island to form an interfacial organic layer, and then, the electron-donating dopant alone is deposited by a resistance heating deposition method into a form of island having a thickness of preferably 0.05 to 1 nm.

The molar ratio of the main component and the electron-donating dopant in the organic EL device in an aspect of the invention is preferably 5:1 to 1:5 and more preferably 2:1 to 1:2.

Electron Transporting Layer

The electron transporting layer is an organic layer disposed between a light emitting layer and a cathode and transports electrons from the cathode to the light emitting layer. If two or more electron transporting layers are provided, the organic layer closer to the cathode may be defined as an electron injecting layer in some cases. The electron injecting layer injects electrons from the cathode to the organic layer unit efficiently. The compound and the material for organic EL devices in an aspect of the invention may be used in the electron transporting layer (second charge transporting layer) as an electron transporting material.

An aromatic heterocyclic compound having one or more heteroatoms in its molecule is preferably used as an electron transporting material for use in the electron transporting layer, and a nitrogen-containing ring derivative is particularly preferred. The nitrogen-containing ring derivative is preferably an aromatic ring compound having a nitrogen-containing 6- or 5-membered ring, or a fused aromatic ring compound having a nitrogen-containing 6- or 5-membered ring.

The nitrogen-containing ring derivative is preferably a metal chelate complex having a nitrogen-containing ring represented by formula (A):

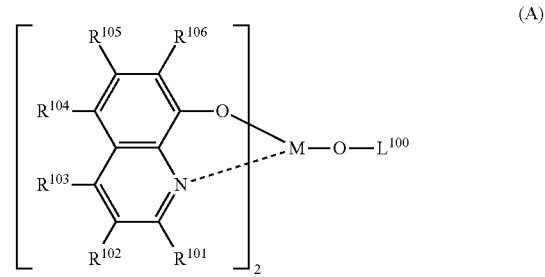

wherein $R^{101}$ to $R^{105}$ each independently represent a hydrogen atom, a halogen atom, a hydroxyl group, an amino group, a hydrocarbon group having 1 to 40, preferably 1 to 20, more preferably 1 to 10, and still more preferably 1 to 5 carbon atoms, an alkoxy group having 1 to 40, preferably 1 to 20, more preferably 1 to 10, and still more preferably 1 to 5 carbon atoms, an aryloxy group having 6 to 50, preferably 6 to 20, and more preferably 6 to 12 ring carbon atoms, an alkoxycarbonyl group having 2 to 40, preferably 2 to 20, more preferably 2 to 10, and still more preferably 2 to 5 carbon atoms, or an aromatic heterocyclic group having 5 to 50, preferably 5 to 30, and more preferably 5 to 20 ring atoms, each optionally having a substituent.

The halogen atom may include fluorine, chlorine, bromine, and iodine.

The substituted amino group may include an alkylamino group, an arylamino group, and an aralkylamino group.

The alkylamino group and the aralkylamino group are represented by $—NQ^1Q^2$. $Q^1$ and $Q^2$ each independently represent an alkyl group having 1 to 20 carbon atoms or an aralkyl group having 1 to 20 carbon atoms. One of $Q^1$ and $Q^2$ may be a hydrogen atom.

The arylamino group is represented by —NAr$^{1'}$Ar$^{2'}$, wherein Ar$^{1'}$ and Ar$^{2'}$ each independently represent a non-fused aromatic hydrocarbon group or a fused aromatic hydrocarbon group, each having 6 to 50 carbon atoms. One of Ar$^{1'}$ and Ar$^{2'}$ may be a hydrogen atom.

Examples of the hydrocarbon group having 1 to 40 carbon atoms include an alkyl group, an alkenyl group, a cycloalkyl group, an aryl group, and an aralkyl group.

The alkoxycarbonyl group is represented by —COOY', wherein Y' is an alkyl group having 1 to 20 carbon atoms.

M is aluminum (Al), gallium (Ga), or indium (In), with In being preferred.

$L^{100}$ is a group represented by formula (A') or (A"):

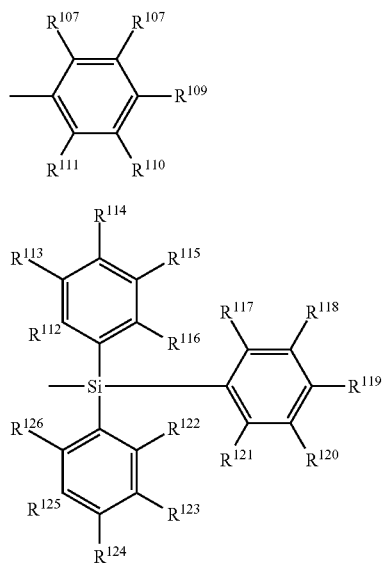

$R^{107}$ to $R^{111}$ of formula (A') each independently represent a hydrogen atom or a substituted or unsubstituted hydrocarbon group having 1 to 40, preferably 1 to 20, more preferably 1 to 10, and still more preferably 1 to 5 carbon atoms, wherein groups adjacent to each other may form a ring structure. $R^{112}$ to $R^{126}$ of formula (A") each independently represent a hydrogen atom or a substituted or unsubstituted hydrocarbon group having 1 to 40, preferably 1 to 20, more preferably 1 to 10, and still more preferably 1 to 5 carbon atoms, wherein groups adjacent to each other may form a ring structure.

Examples of the hydrocarbon group having 1 to 40 carbon atoms for $R^{107}$ to $R^{126}$ of formulae (A') and (A") are the same as those described above with respect to $R^{101}$ to $R^{106}$ of formula (A). Examples of the divalent group formed by adjacent groups selected from $R^{107}$ to $R^{111}$ which complete a ring structure include a tetramethylene group, a pentamethylene group, a hexamethylene group, a diphenylmethane-2,2'-diyl group, a diphenylethane-3,3'-diyl group, and a diphenylpropane-4,4'-diyl group.

The electron transporting compound for use in the electron transporting layer is preferably a metal complex including 8-hydroxyquinoline or its derivative, an oxadiazole derivative, or a nitrogen-containing heterocyclic derivative. Examples of the metal complex including 8-hydroxyquinoline or its derivative include a metal chelate oxinoid including a chelated oxine (generally, 8-quinolinol or 8-hydroxyquinoline), for example, tris(8-quinolinol)aluminum. Examples of the oxadiazole derivative are shown below:

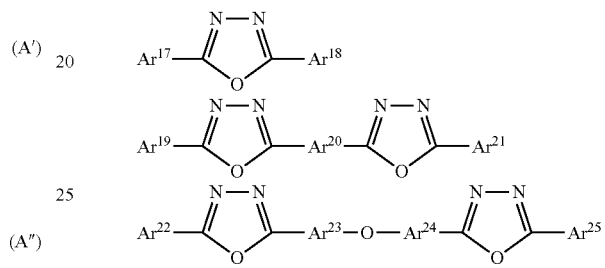

wherein Ar$^{17}$, Ar$^{18}$, Ar$^{19}$, Ar$^{21}$, Ar$^{22}$, and Ar$^{25}$ are each a substituted or unsubstituted aromatic hydrocarbon group or a substituted or unsubstituted fused aromatic hydrocarbon group each having 6 to 50 carbon atoms, and Ar$^{17}$ and Ar$^{18}$, Ar$^{19}$ and Ar$^{21}$, and Ar$^{22}$ and Ar$^{25}$ may be the same or different, respectively. Examples of the aromatic hydrocarbon group and the fused aromatic hydrocarbon group include a phenyl group, a naphthyl group, a biphenyl group, an anthranyl group, a perylenyl group, and a pyrenyl group. The optional substituent may be an alkyl group having 1 to 10 carbon atoms, an alkoxyl group having 1 to 10 carbon atoms or a cyano group.

Ar$^{20}$, Ar$^{23}$, and Ar$^{24}$ are each a substituted or unsubstituted divalent aromatic hydrocarbon group or a substituted or unsubstituted divalent fused aromatic hydrocarbon group each having 6 to 50 carbon atoms, and Ar$^{23}$ and Ar$^{24}$ may be the same or different. Examples of the divalent aromatic hydrocarbon group or the divalent fused aromatic hydrocarbon group include a phenylene group, a naphthylene group, a biphenylene group, an anthranylene group, a perylenylene group, and a pyrenylene group. The optional substituent may be an alkyl group having 1 to 10 carbon atoms, an alkoxyl group having 1 to 10 carbon atoms or a cyano group.

An electron transporting compound which has a good thin film-forming property is preferably used. Examples thereof are shown below.

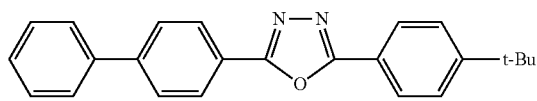

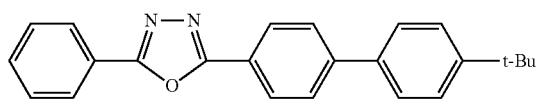

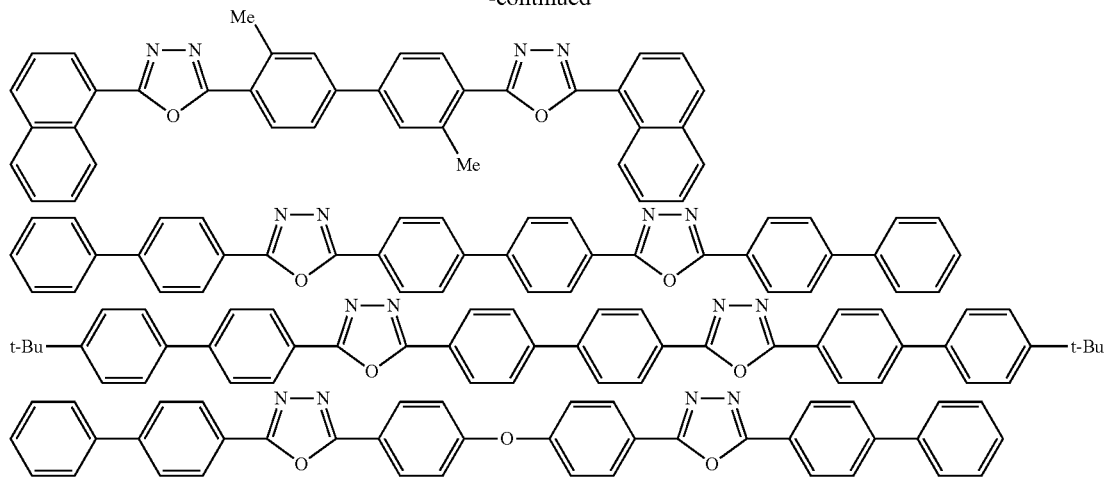

Examples of the nitrogen-containing heterocyclic derivative for use as the electron transporting compound include a nitrogen-containing heterocyclic derivative having the following formulae but exclusive of a metal complex, for example, a compound having a 5- or 6-membered ring which includes a skeleton represented by formula (B) or having a structure represented by formula (C):

(B)

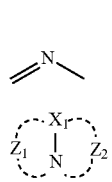

(C)

wherein $X_1$ is a carbon atom or a nitrogen atom and $Z_1$ and $Z_2$ each independently represent a group of atoms for completing the nitrogen-containing heterocyclic ring.

The nitrogen-containing heterocyclic derivative is more preferably an organic compound which has a nitrogen-containing aromatic polycyclic ring comprising a 5-membered ring or a 6-membered ring. If two or more nitrogen atoms are included, the nitrogen-containing aromatic polycyclic compound preferably has a skeleton of a combination of formulae (B) and (C) or a combination of formulae (B) and (D):

(D)

The nitrogen-containing group of the nitrogen-containing aromatic polycyclic compound is selected, for example, from the nitrogen-containing heterocyclic groups shown below:

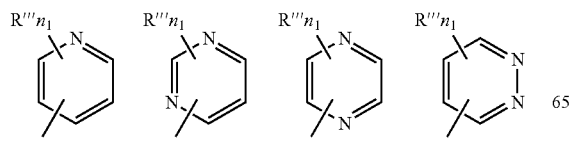

-continued

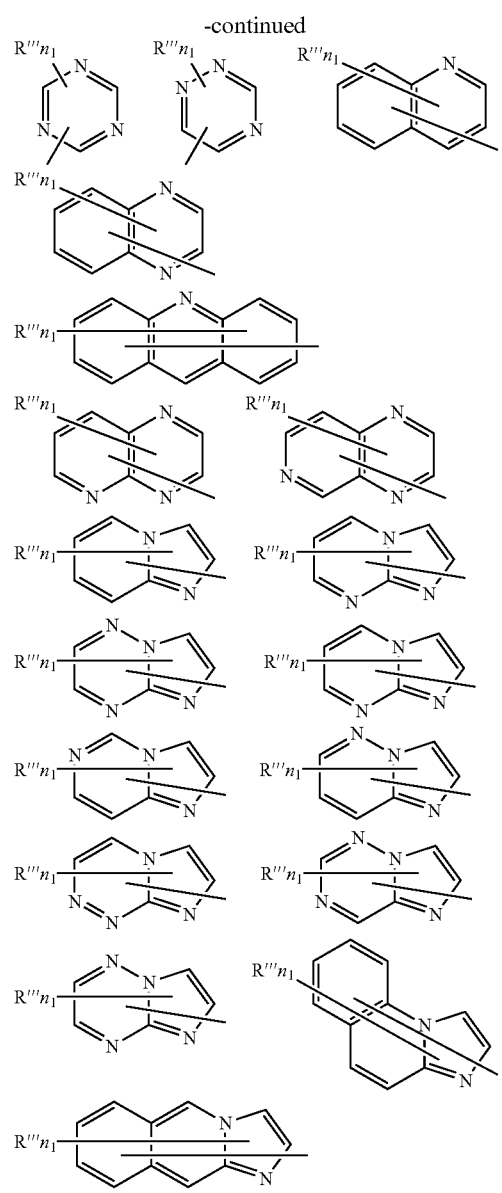

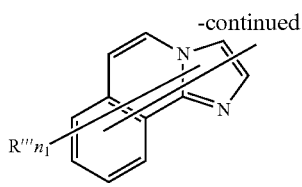

wherein R''' is an aromatic hydrocarbon group having 6 to 40, preferably 6 to 30, more preferably 6 to 20, and still more preferably 6 to 12 ring carbon atoms, a fused aromatic hydrocarbon group having 6 to 40, preferably 6 to 30, more preferably 6 to 20, and still more preferably 6 to 12 ring carbon atoms, an aromatic heterocyclic group having 5 to 40, preferably 5 to 30, more preferably 5 to 20, and still more preferably 5 to 12 ring atoms, a fused aromatic heterocyclic group having 5 to 40, preferably 5 to 30, more preferably 5 to 20, and still more preferably 5 to 12 ring atoms, an alkyl group having 1 to 20, preferably 1 to 10, and more preferably 1 to 5 carbon atoms, or an alkoxy group having 1 to 20, preferably 1 to 10, and more preferably 1 to 5 carbon atoms; $n_1$ is an integer of 0 to 5; and when $n_1$ is an integer of 2 or more, groups R''' may be the same or different.

A nitrogen-containing heterocyclic derivative represented by formula (D1) is also preferred:

wherein:

HAr is a substituted or unsubstituted nitrogen-containing heterocyclic group having 5 to 40, preferably 5 to 30, more preferably 5 to 20, and still more preferably 5 to 12 ring atoms;

$L^{101}$ is a single bond, a substituted or unsubstituted aromatic hydrocarbon group or fused aromatic hydrocarbon group each having 6 to 40, preferably 6 to 30, more preferably 6 to 20, and still more preferably 6 to 12 ring carbon atoms, a substituted or unsubstituted aromatic heterocyclic group having 5 to 40, preferably 5 to 30, more preferably 5 to 20, and still more preferably 5 to 12 ring atoms, or a substituted or unsubstituted fused aromatic heterocyclic group having 6 to 40, preferably 6 to 30, more preferably 6 to 20, and still more preferably 6 to 12 ring carbon atoms; and $Ar^{101}$ is a substituted or unsubstituted divalent aromatic hydrocarbon group having 6 to 40, preferably 6 to 30, more preferably 6 to 20, and still more preferably 6 to 12 ring carbon atoms; and $Ar^{102}$ is a substituted or unsubstituted aromatic hydrocarbon group having 6 to 40, preferably 6 to 30, more preferably 6 to 20, and still more preferably 6 to 14 ring carbon atoms, a substituted or unsubstituted fused aromatic hydrocarbon group having 6 to 40, preferably 6 to 30, more preferably 6 to 20, and still more preferably 6 to 12 ring carbon atoms, a substituted or unsubstituted aromatic heterocyclic group having 5 to 40, preferably 5 to 30, more preferably 5 to 20, and still more preferably 5 to 12 ring atoms, or a substituted or unsubstituted fused aromatic heterocyclic group having 5 to 40, preferably 5 to 30, more preferably 5 to 20, and still more preferably 5 to 12 ring atoms.

HAr is selected, for example, from the following groups:

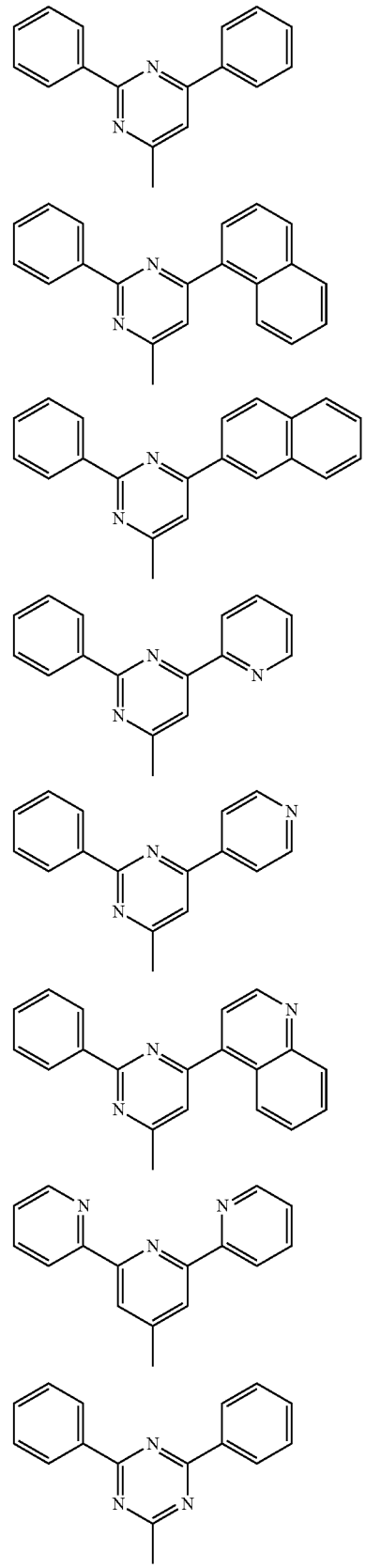

-continued

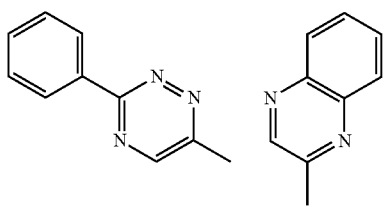
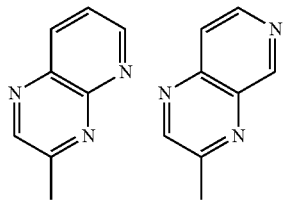
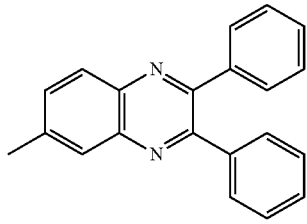
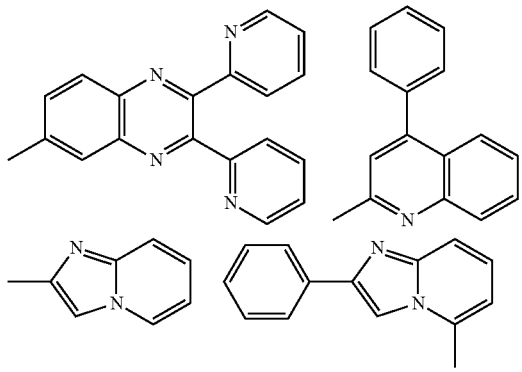
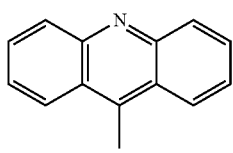
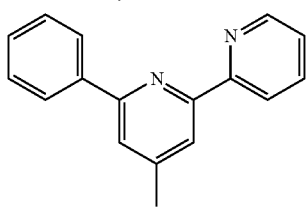

$L^{101}$ is selected, for example, from the following groups:

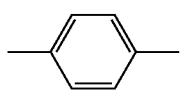

-continued

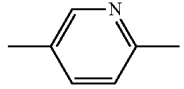

Ar$^{101}$ is selected, for example, from the group represented by formula (D2) or (D3):

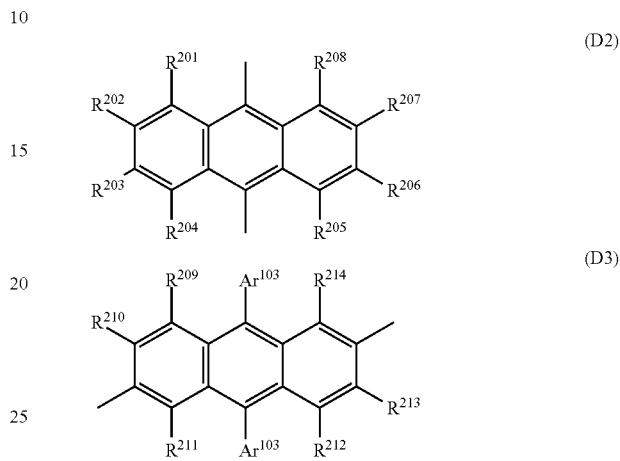

wherein:

R$^{201}$ to R$^{214}$ are each independently a hydrogen atom, a halogen atom, a substituted or unsubstituted alkyl group having 1 to 20, preferably 1 to 10, and more preferably 1 to 5 carbon atoms, a substituted or unsubstituted alkoxy group having 1 to 20, preferably 1 to 10, and more preferably 1 to 5 carbon atoms, a substituted or unsubstituted aryloxy group having 6 to 40, preferably 6 to 30, more preferably 6 to 20, and still more preferably 6 to 12 ring carbon atoms, a substituted or unsubstituted aromatic hydrocarbon group having 6 to 40, preferably 6 to 30, more preferably 6 to 20, and still more preferably 6 to 12 ring carbon atoms, a substituted or unsubstituted fused aromatic hydrocarbon group having 6 to 40, preferably 6 to 30, more preferably 6 to 20, and still more preferably 6 to 12 ring carbon atoms, a substituted or unsubstituted aromatic heterocyclic group having 5 to 40, preferably 5 to 30, more preferably 5 to 20, and still more preferably 5 to 12 ring atoms, or a substituted or unsubstituted fused aromatic heterocyclic group having 5 to 40, preferably 5 to 30, more preferably 5 to 20, and still more preferably 5 to 12 ring atoms; and Ar$^{103}$ is a substituted or unsubstituted aromatic hydrocarbon group having 6 to 40, preferably 6 to 30, more preferably 6 to 20, and still more preferably 6 to 12 ring carbon atoms, a substituted or unsubstituted fused aromatic hydrocarbon group having 6 to 40, preferably 6 to 30, more preferably 6 to 20, and still more preferably 6 to 12 ring carbon atoms, a substituted or unsubstituted aromatic heterocyclic group having 5 to 40, preferably 5 to 30, more preferably 5 to 20, and still more preferably 5 to 12 ring atoms, or a substituted or unsubstituted fused aromatic heterocyclic group having 5 to 40, preferably 5 to 30, more preferably 5 to 20, and still more preferably 5 to 12 ring atoms.

Ar¹⁰² is selected, for example, from the following groups:

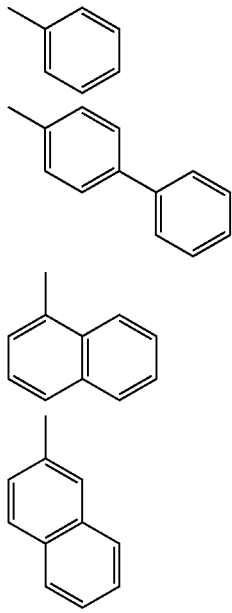

-continued

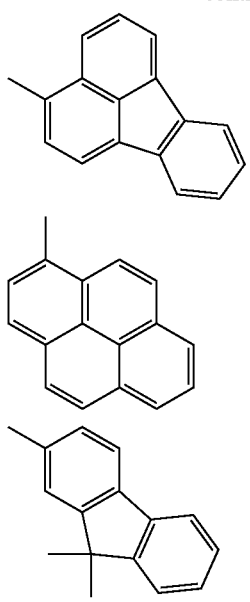

In addition, the following compound is preferably used as the nitrogen-containing aromatic polycyclic compound for use as the electron transporting compound:

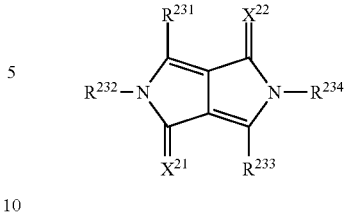

(D4)

wherein $R^{211}$ to $R^{214}$ each independently represent a hydrogen atom, a substituted or unsubstituted aliphatic group having 1 to 20 carbon atoms, a substituted or unsubstituted alicyclic group having 3 to 20 carbon atoms, a substituted or unsubstituted aromatic ring group having 6 to 50 carbon atoms, or a substituted or unsubstituted heterocyclic group having 3 to 50 carbon atoms; and $X^{21}$ and $X^{22}$ each independently represent an oxygen atom, a sulfur atom, or a dicyanomethylene group.

Further, the following compound is also suitable as the electron transporting compound:

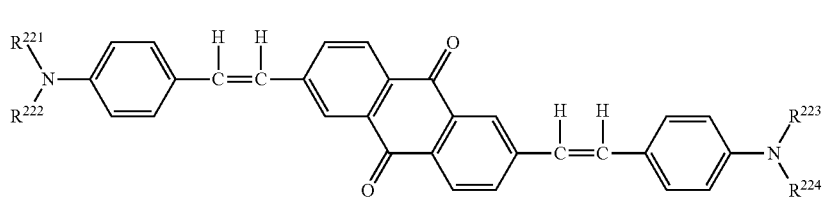

(D5)

wherein $R^{221}$, $R^{222}$, $R^{223}$, and $R^{224}$ may be the same or different and each represent an aromatic hydrocarbon group or a fused aromatic hydrocarbon group each represented by formula (D6):

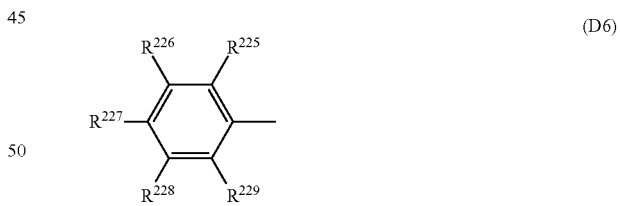

(D6)

wherein $R^{225}$, $R^{226}$, $R^{227}$, $R^{228}$, and $R^{229}$ may be the same or different and each represent a hydrogen atom, a saturated or unsaturated alkoxyl group having 1 to 20 carbon atoms, a saturated or unsaturated alkyl group having 1 to 20 carbon atoms, an amino group, or an alkylamino group having 1 to 20 carbon atoms; and at least one selected from $R^{225}$, $R^{226}$, $R^{227}$, $R^{228}$, and $R^{229}$ represents a group other than a hydrogen atom.

Further, a polymer including the nitrogen-containing heterocyclic group or the nitrogen-containing heterocyclic derivative is also usable as the electron transporting compound.

The electron transporting layer of the organic EL device in an aspect of the invention preferably comprises at least one compound selected from the nitrogen-containing heterocyclic derivatives represented by formulae (E) to (G):

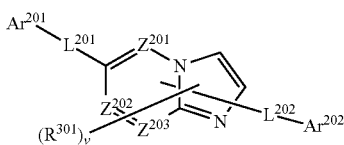
(E)

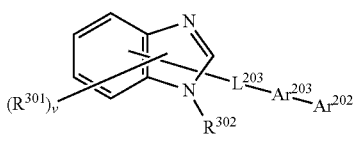
(F)

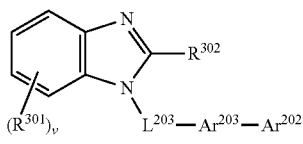
(G)

wherein $Z^{201}$, $Z^{202}$ and $Z^{203}$ each independently represent a nitrogen atom or a carbon atom;

$R^{301}$ and $R^{302}$ each independently represent a substituted or unsubstituted aryl group having 6 to 50, preferably 6 to 30, more preferably 6 to 20, and still more preferably 6 to 12 ring carbon atoms, a substituted or unsubstituted heteroaryl group having 5 to 50, preferably 5 to 30, more preferably 5 to 20, and still more preferably 5 to 12 ring atoms, a substituted or unsubstituted alkyl group having 1 to 20 carbon atoms, a substituted or unsubstituted haloalkyl group having 1 to 20 carbon atoms, or a substituted or unsubstituted alkoxy group having 1 to 20 carbon atoms;

v is an integer of 0 to 5, when v is an integer of 2 or more, groups $R^{301}$ may be the same or different, and adjacent two groups $R^{301}$ may bond to each other to form a substituted or unsubstituted hydrocarbon ring;

$Ar^{201}$ represents a substituted or unsubstituted aryl group having 6 to 50, preferably 6 to 30, more preferably 6 to 20, and still more preferably 6 to 12 ring carbon atoms or a substituted or unsubstituted heteroaryl group having 5 to 50, preferably 5 to 30, more preferably 5 to 20, and still more preferably 5 to 12 ring atoms;

$Ar^{202}$ represents a hydrogen atom, a substituted or unsubstituted alkyl group having 1 to 20, preferably 1 to 10, and more preferably 1 to 5 carbon atoms, a substituted or unsubstituted haloalkyl group having 1 to 20, preferably 1 to 10, and more preferably 1 to 5 carbon atoms, a substituted or unsubstituted alkoxy group having 1 to 20 carbon atoms, a substituted or unsubstituted aryl group having 6 to 50, preferably 6 to 30, more preferably 6 to 20, and still more preferably 6 to 12 ring carbon atoms, or a substituted or unsubstituted heteroaryl group having 5 to 50, preferably 5 to 30, more preferably 5 to 20, and still more preferably 5 to 12 ring atoms;

provided that one of $Ar^{201}$ and $Ar^{202}$ is a substituted or unsubstituted fused aromatic hydrocarbon ring group having 10 to 50, preferably 10 to 30, and more preferably 10 to 20 ring carbon atoms or a substituted or unsubstituted fused aromatic heterocyclic group having 9 to 50, preferably 9 to 30, and more preferably 9 to 20 ring atoms;

$Ar^{203}$ represents a substituted or unsubstituted arylene group having 6 to 50, preferably 6 to 30, more preferably 6 to 20, and still more preferably 6 to 12 ring carbon atoms or a substituted or unsubstituted heteroarylene group having 5 to 50, preferably 5 to 30, more preferably 5 to 20, and still more preferably 5 to 12 ring atoms; and $L^{201}$, $L^{202}$, and $L^{203}$ each independently represent a single bond, a substituted or unsubstituted arylene group having 6 to 50, preferably 6 to 30, more preferably 6 to 20, and still more preferably 6 to 12 ring carbon atoms or a substituted or unsubstituted divalent fused aromatic heterocyclic group having 9 to 50, pre 9 to 30, and more preferably 9 to 20 ring atoms.

Examples of the aryl group having 6 to 50 ring carbon atoms include a phenyl group, a naphthyl group, an anthryl group, a phenanthryl group, a naphthacenyl group, a chrysenyl group, pyrenyl group, a biphenyl group, a terphenyl group, a tolyl group, a fluoranthenyl group, and a fluorenyl group.

Examples of the heteroaryl group having 5 to 50 ring atoms include a pyrrolyl group, a furyl group, a thiophenyl group, a silolyl group, a pyridyl group, a quinolyl group, an isoquinolyl group, a benzofuryl group, an imidazolyl group, a pyrimidyl group, a carbazolyl group, a selenophenyl group, an oxadiazolyl group, a triazolyl group, a pyrazinyl group, a pyridazinyl group, a triazinyl group, a quinoxalinyl group, an acridinyl group, an imidazo[1,2-a]pyridinyl group, and an imidazo[1,2-a]pyrimidinyl.

Examples of the alkyl group having 1 to 20 carbon atoms include a methyl group, an ethyl group, a propyl group, a butyl group, a pentyl group, and a hexyl group.

Examples of the haloalkyl group having 1 to 20 carbon atoms include the groups obtained by replacing one or more hydrogen atoms of the alkyl group mentioned above with at least one halogen atom selected from fluorine, chlorine, iodine, and bromine.

Examples of the alkyl moiety of the alkoxy group having 1 to 20 carbon atoms include the alkyl group mentioned above.

Examples of the arylene groups include the groups obtained by removing one hydrogen atom from the aryl group mentioned above.

Examples of the divalent fuse aromatic heterocyclic group having 9 to 50 ring atoms include the groups obtained by removing one hydrogen atom from the fused aromatic heterocyclic group mentioned above with respect to the heteroaryl group.

The thickness of the electron transporting layer is preferably 1 to 100 nm, but not particularly limited thereto.

The electron injecting layer optionally formed adjacent to the electron transporting layer preferably comprises an inorganic compound, such as an insulating material and a semiconductor, in addition to the nitrogen-containing ring derivative. The electron injecting layer comprising the insulating material or the semiconductor effectively prevents the leak of electric current to enhance the electron injecting properties.

The insulating material is preferably at least one metal compound selected from the group consisting of an alkali metal chalcogenide, an alkaline earth metal chalcogenide, an alkali metal halide and an alkaline earth metal halide. The electron injecting properties of the electron injecting layer are further enhanced when the alkali metal chalcogenide, etc. is used in the electron injecting layer. Examples of preferred alkali metal chalcogenide include $Li_2O$, $K_2O$, $Na_2S$, $Na_2Se$ and $Na_2O$, and examples of preferred alkaline earth metal chalcogenide include CaO, BaO, SrO, BeO, BaS and CaSe. Examples of preferred alkali metal halide include LiF, NaF, KF, LiCl, KCl and NaCl. Examples of preferred alkaline earth metal halide include fluorides, such as $CaF_2$, $BaF_2$, $SrF_2$, $MgF_2$ and $BeF_2$, and halides other than fluorides.

Examples of the semiconductor include an oxide, a nitride and an oxynitride of at least one element selected from the group consisting of Ba, Ca, Sr, Yb, Al, Ga, In, Li, Na, Cd, Mg, Si, Ta, Sb and Zn. The semiconductor may be used alone or in combination of two or more. The inorganic compound included in the electron injecting layer preferably forms a microcrystalline or amorphous insulating thin film. The electron injecting layer formed from such an insulating thin film decreases the pixel defects, such as dark spots, because the insulating thin film is highly uniform. Examples of such an inorganic compound include the alkali metal chalcogenide, the alkaline earth metal chalcogenide, the alkali metal halide and the alkaline earth metal halide.

The thickness of a layer comprising the insulating material or the semiconductor is preferably about 0.1 to 15 nm. The electron injecting layer of the organic EL device in an aspect of the invention may comprise the electron-donating dopant mentioned above.

Hole Transporting Layer

The hole transporting layer is an organic layer formed between a light emitting layer and an anode and has a function of transporting holes from the anode to the light emitting layer. If two or more hole transporting layers are provided, the organic layer closer to the anode may be defined as the hole injecting layer in some cases. The hole injecting layer has a function of efficiently injecting holes from the anode to the organic layer unit. The compound and the material for organic EL devices in an aspect of the invention may be used in the hole transporting layer (first charge transporting layer) as a hole transporting material.

Another preferred material for use in the hole transporting layer may include an aromatic amine compound, for example, an aromatic amine derivative represented by formula (H):

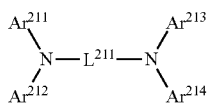

(H)

wherein:

$Ar^{211}$ to $Ar^{214}$ each represent a substituted or unsubstituted aromatic hydrocarbon group having 6 to 50, preferably 6 to 30, more preferably 6 to 20, and still more preferably 6 to 12 ring carbon atoms, a substituted or unsubstituted fused aromatic hydrocarbon group having 6 to 50, preferably 6 to 30, more preferably 6 to 20, and still more preferably 6 to 12 ring carbon atoms, a substituted or unsubstituted aromatic heterocyclic group having 5 to 50, preferably 5 to 30, more preferably 5 to 20, and still more preferably 5 to 12 ring atoms, a substituted or unsubstituted fused aromatic heterocyclic group having 5 to 50, preferably 5 to 30, more preferably 5 to 20, and still more preferably 5 to 12 ring atoms, or a group wherein the aromatic hydrocarbon group or fused aromatic hydrocarbon group is bonded to the aromatic heterocyclic group or fused aromatic heterocyclic group;

$Ar^{211}$ and $Ar^{212}$ or $Ar^{213}$ and $Ar^{214}$ may be bonded to each other to form a saturated or unsaturated ring structure; and $L^{211}$ represents a substituted or unsubstituted aromatic hydrocarbon group having 6 to 50, preferably 6 to 30, more preferably 6 to 20, and still more preferably 6 to 12 ring carbon atoms, a substituted or unsubstituted fused aromatic hydrocarbon group having 6 to 50, preferably 6 to 30, more preferably 6 to 20, and still more preferably 6 to 12 ring carbon atoms, a substituted or unsubstituted aromatic heterocyclic group having 5 to 50, preferably 5 to 30, more preferably 5 to 20, and still more preferably 5 to 12 ring atoms, or a substituted or unsubstituted fused aromatic heterocyclic group having 5 to 50, preferably 5 to 30, more preferably 5 to 20, and still more preferably 5 to 12 ring atoms.

Examples of the compound represented by formula (H) are shown below.

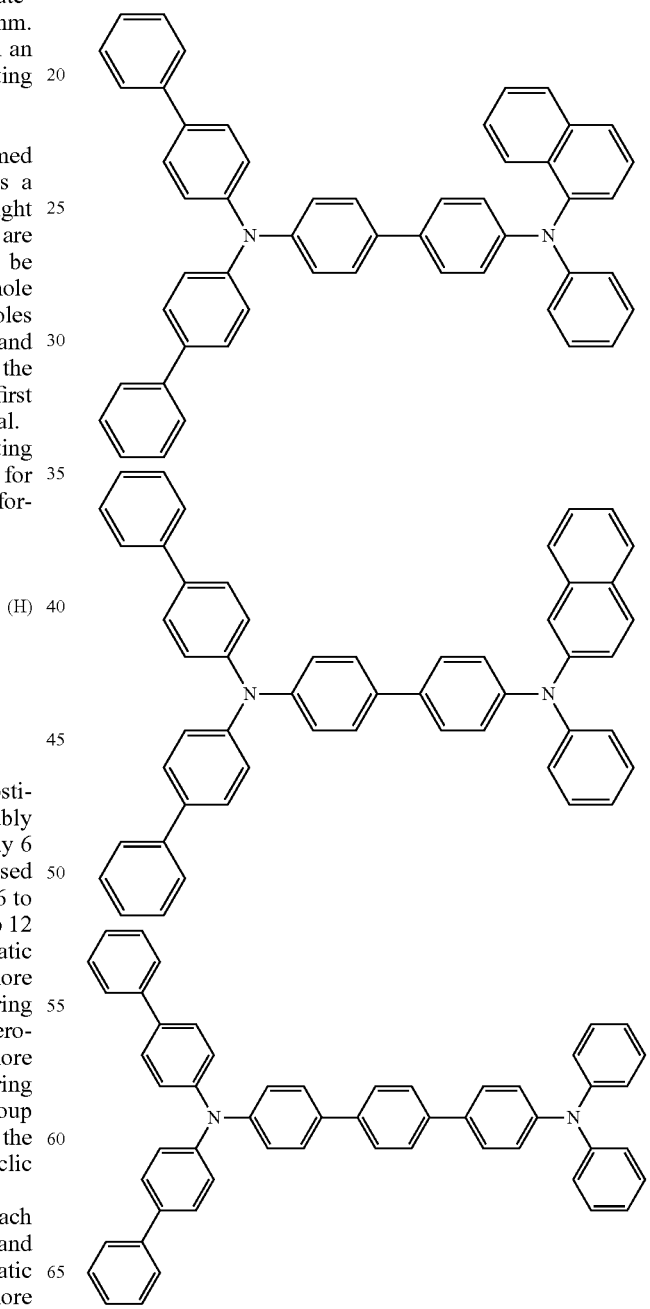

243
-continued
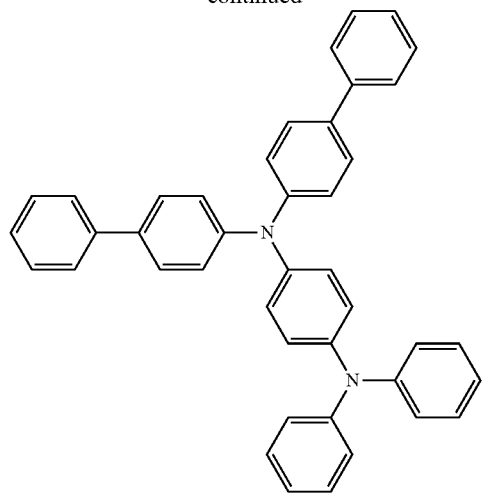
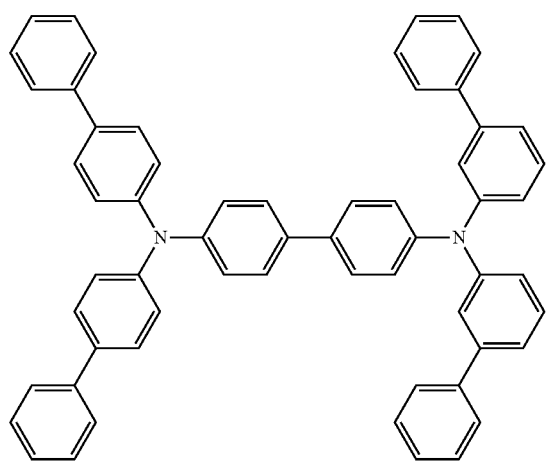
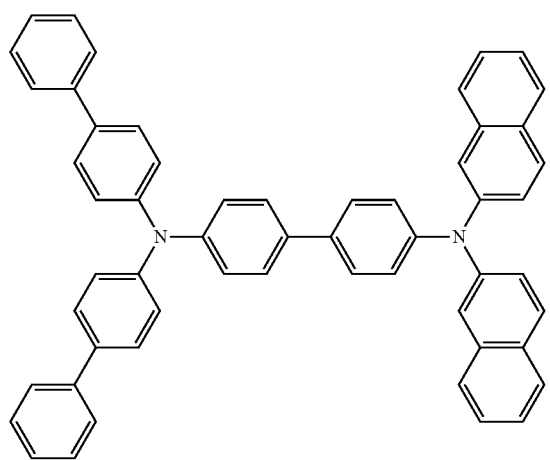
244
-continued
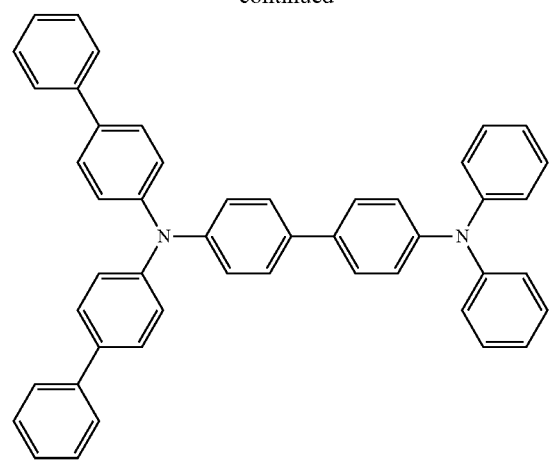
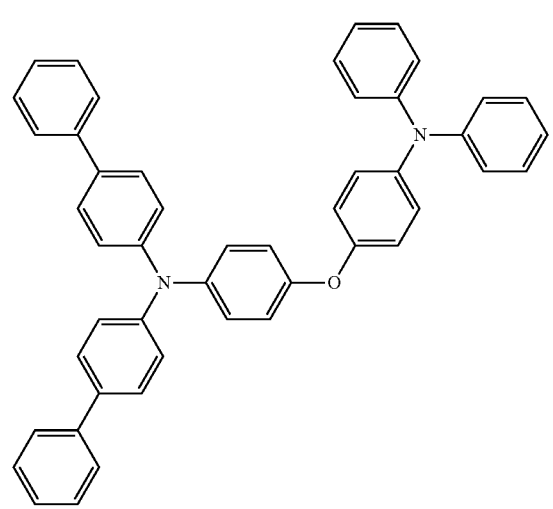
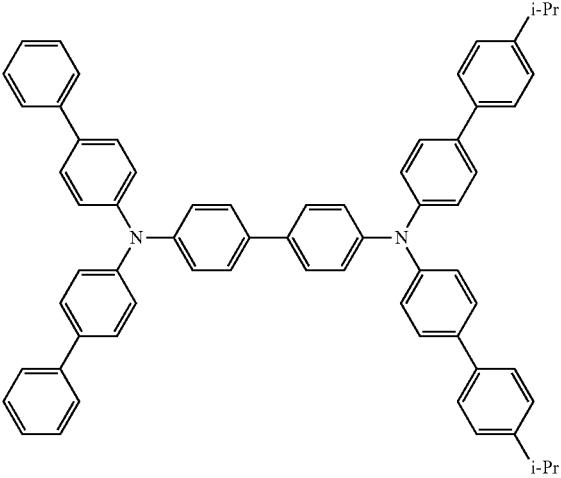

245
-continued
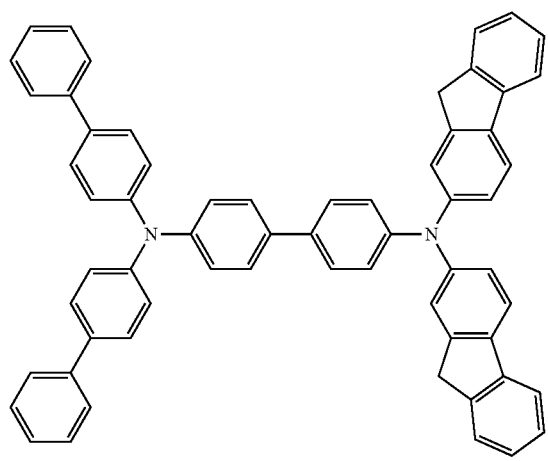
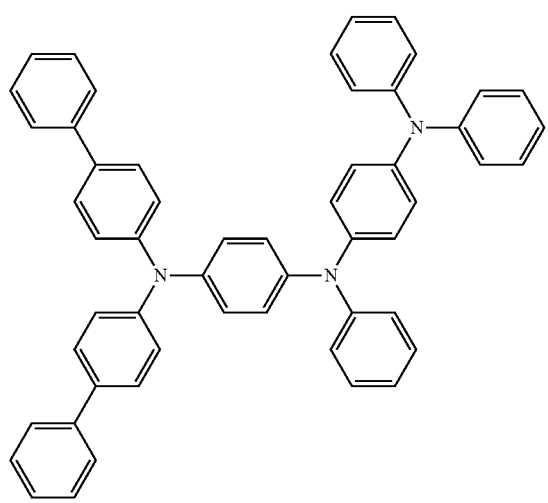
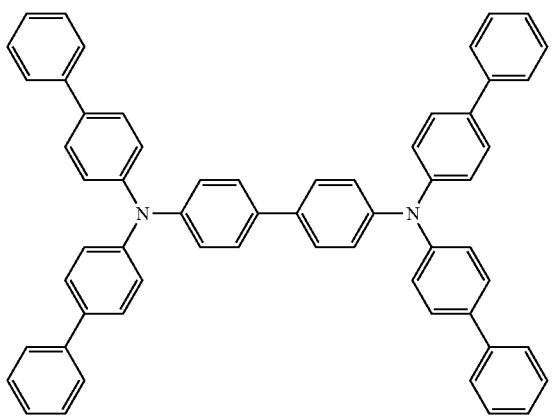
246
-continued
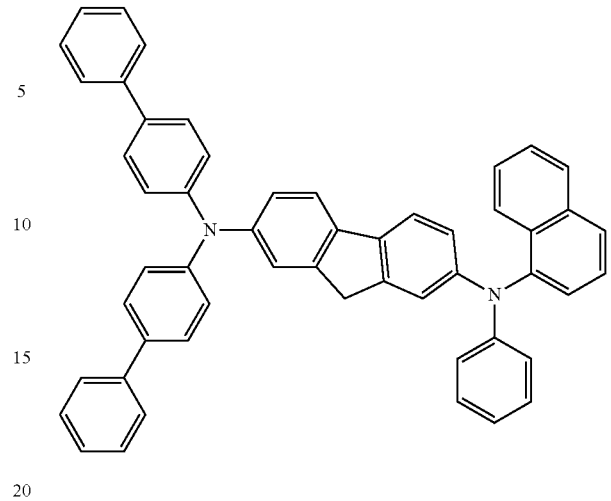
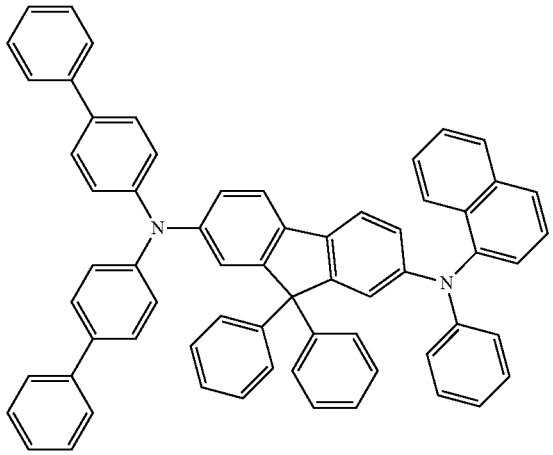
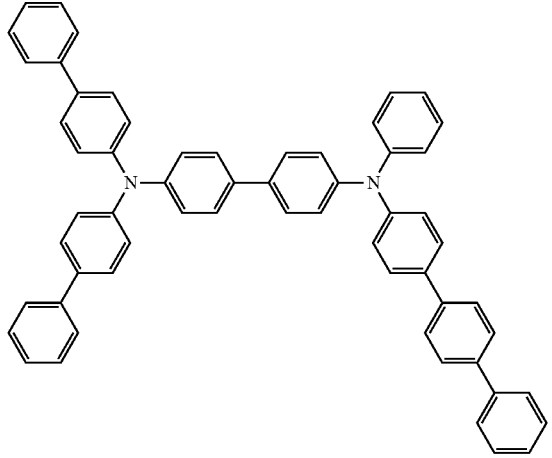

247
-continued
248
-continued
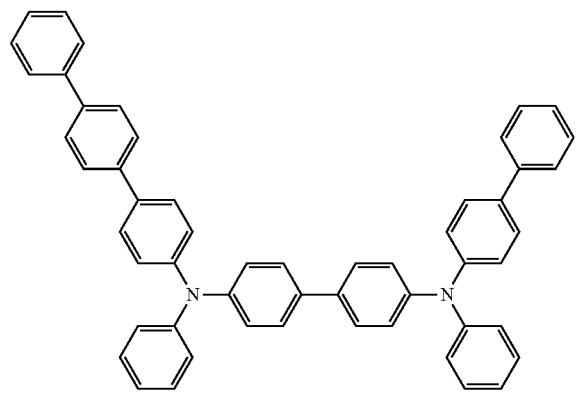
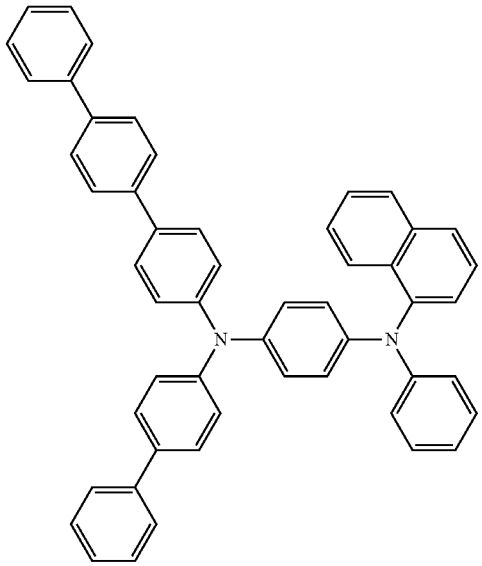
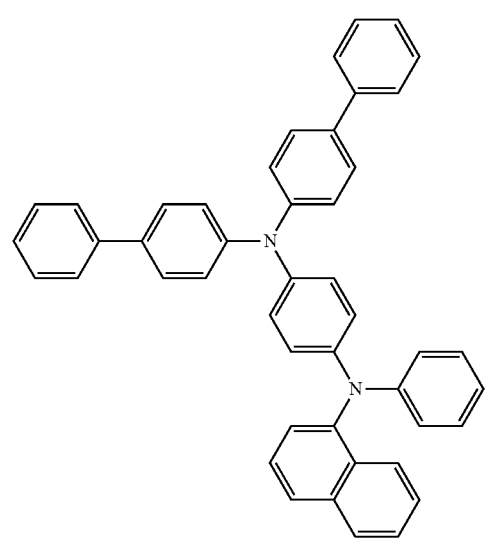
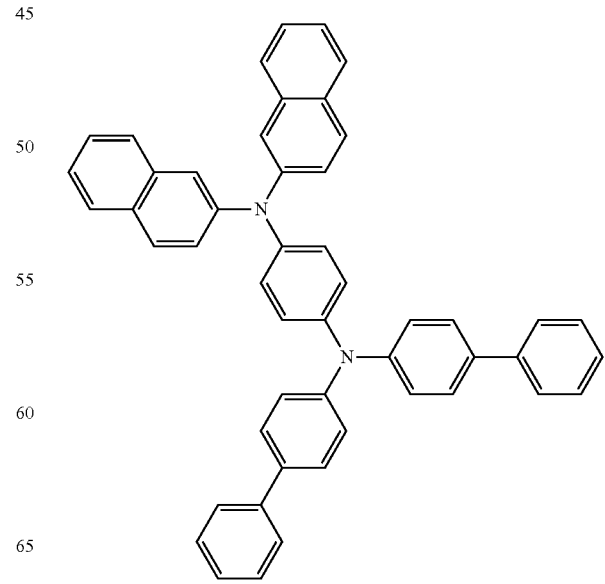

249
-continued
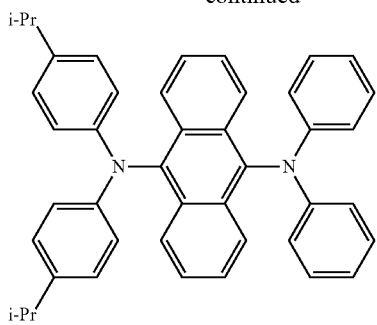
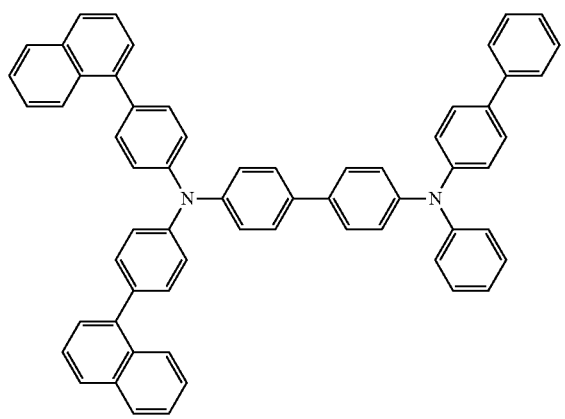
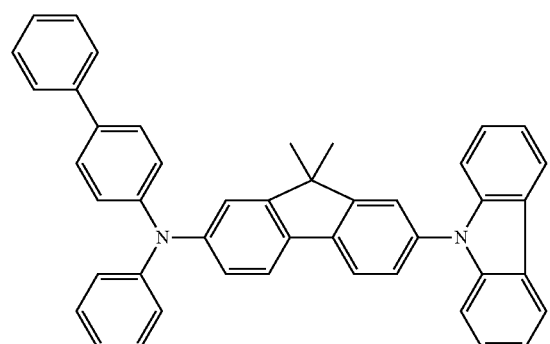
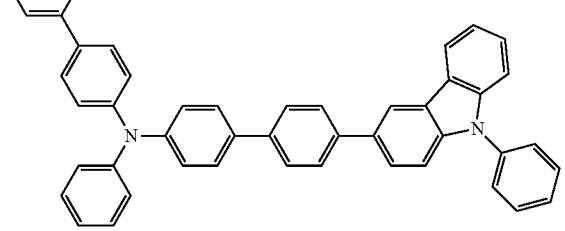
250
-continued
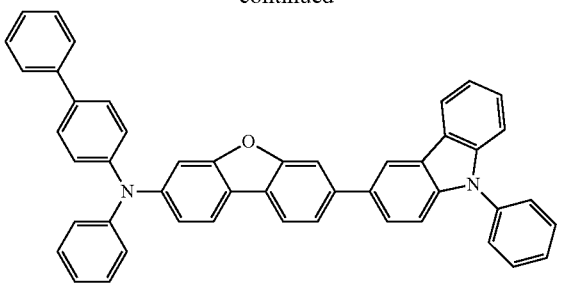
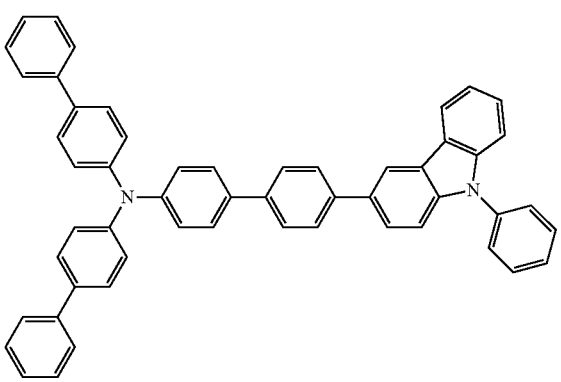
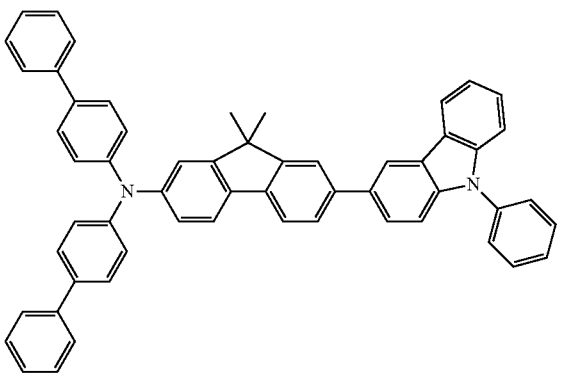
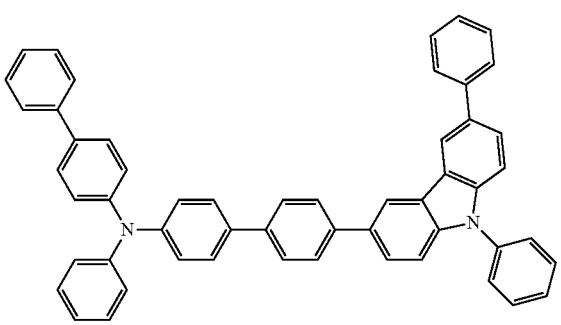

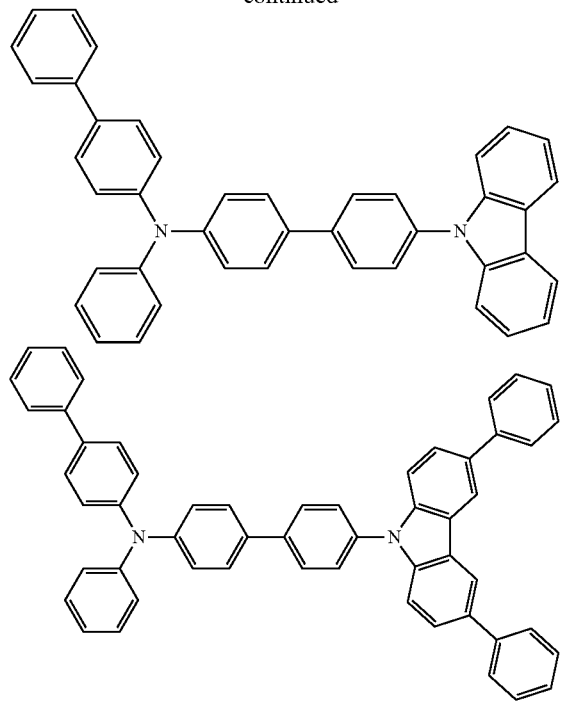
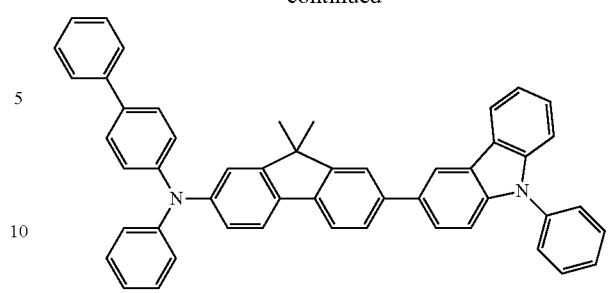
In addition, an aromatic amine represented by formula (J) is preferably used in the hole transporting layer:
(J)
wherein $Ar^{221}$ to $Ar^{223}$ are the same as defined above with respect to $Ar^{211}$ to $Ar^{214}$ of formula (H). Examples of the compound represented by formula (J) are shown below, although not limited thereto.
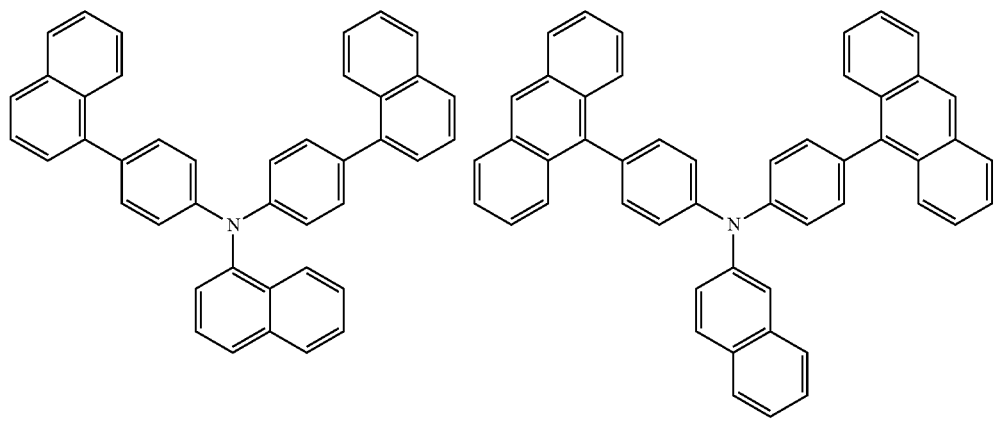
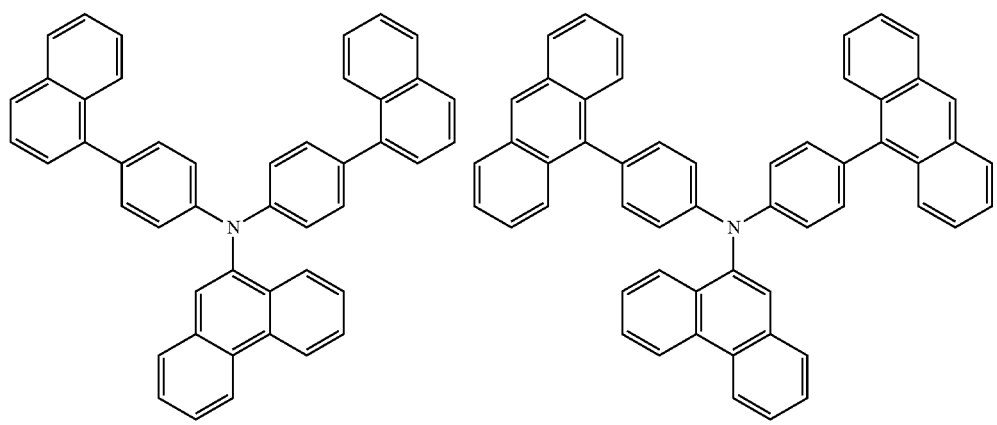

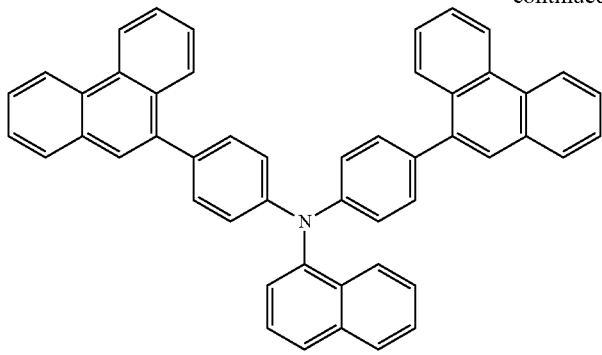
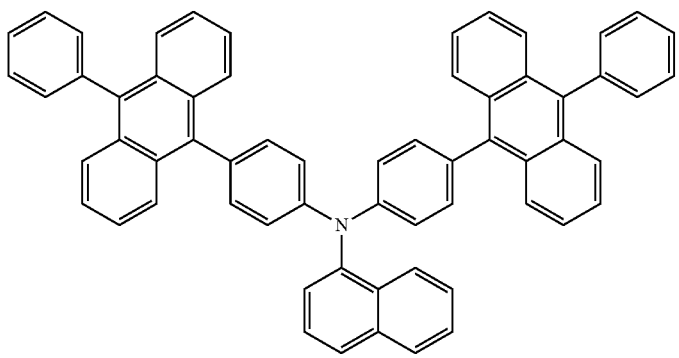
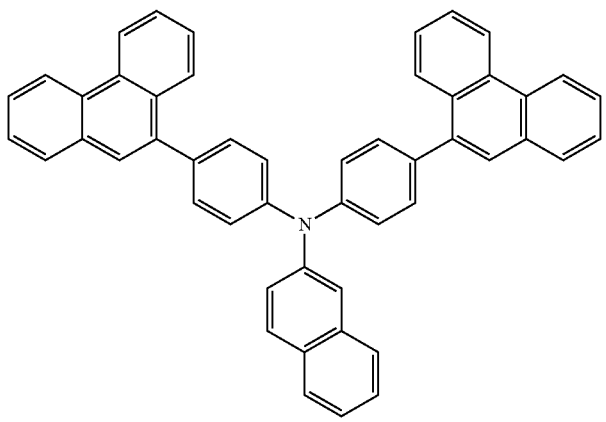
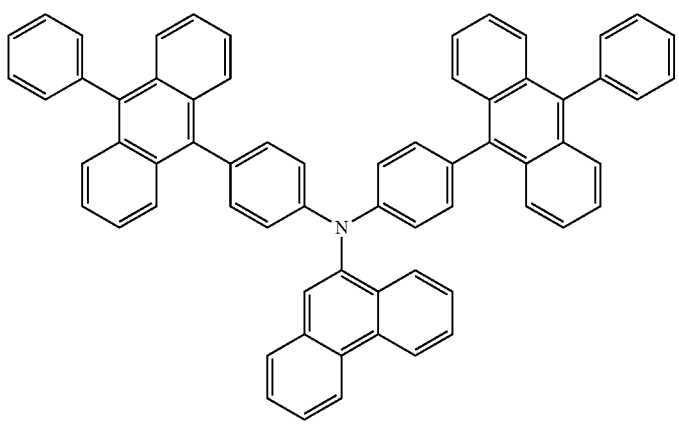

255
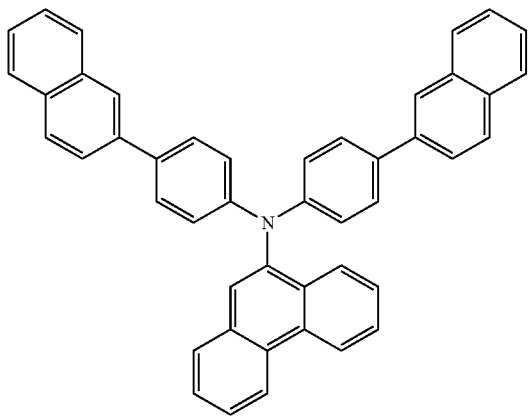
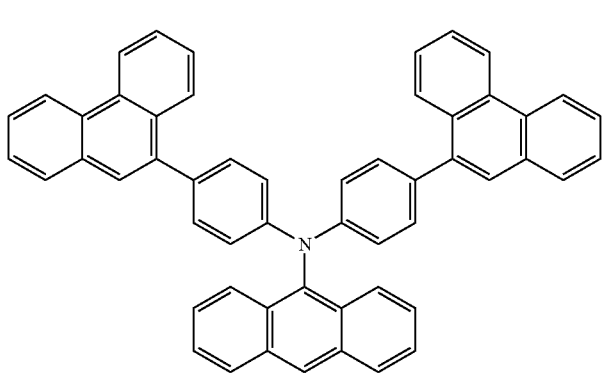
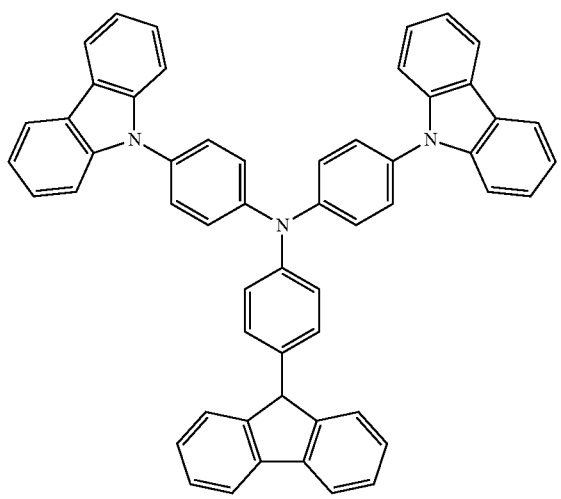
256
-continued
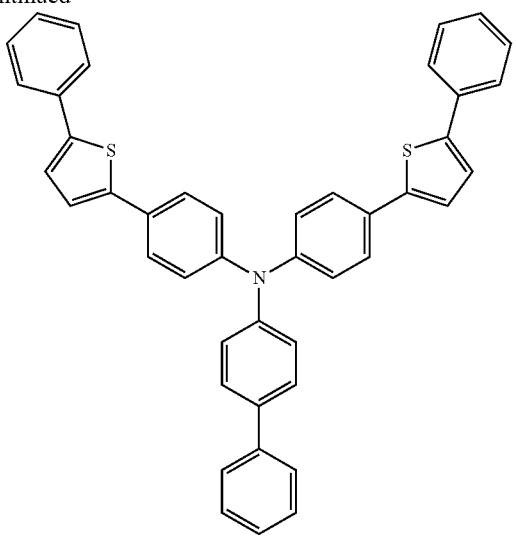
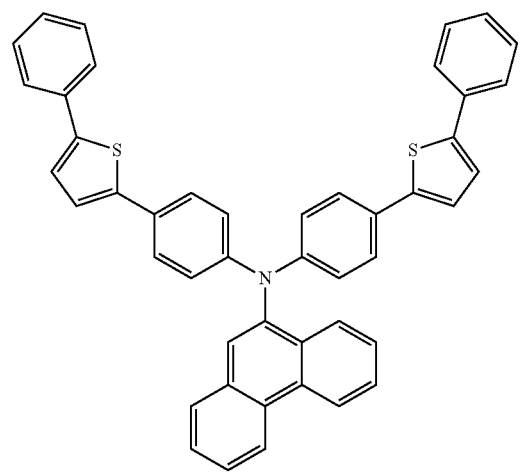
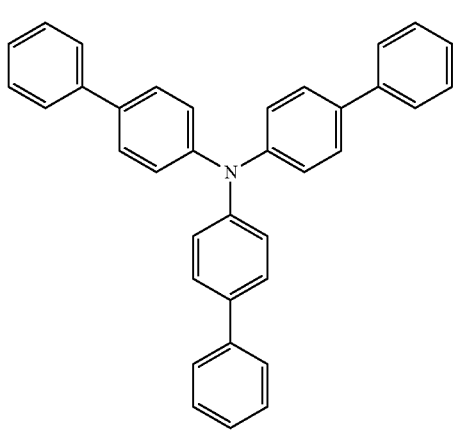

-continued
257
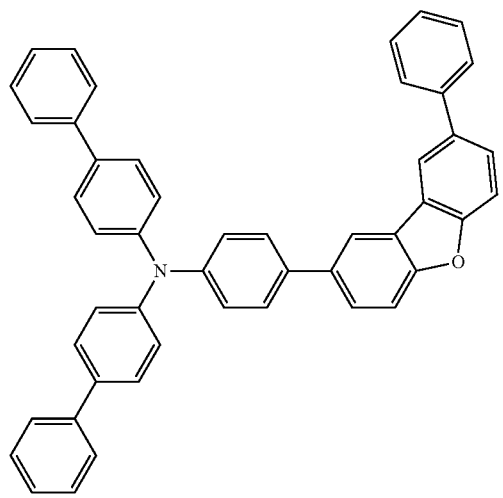
258
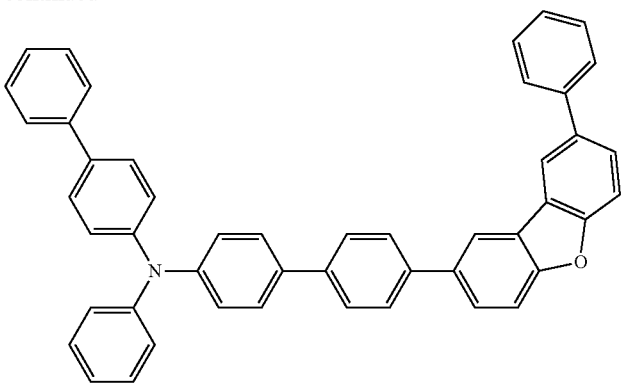
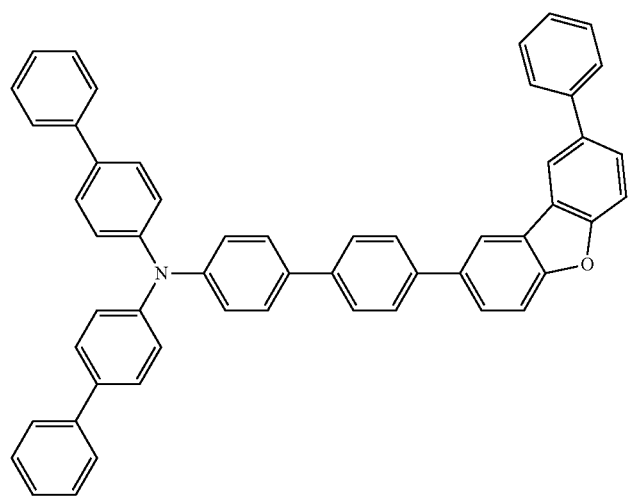

-continued
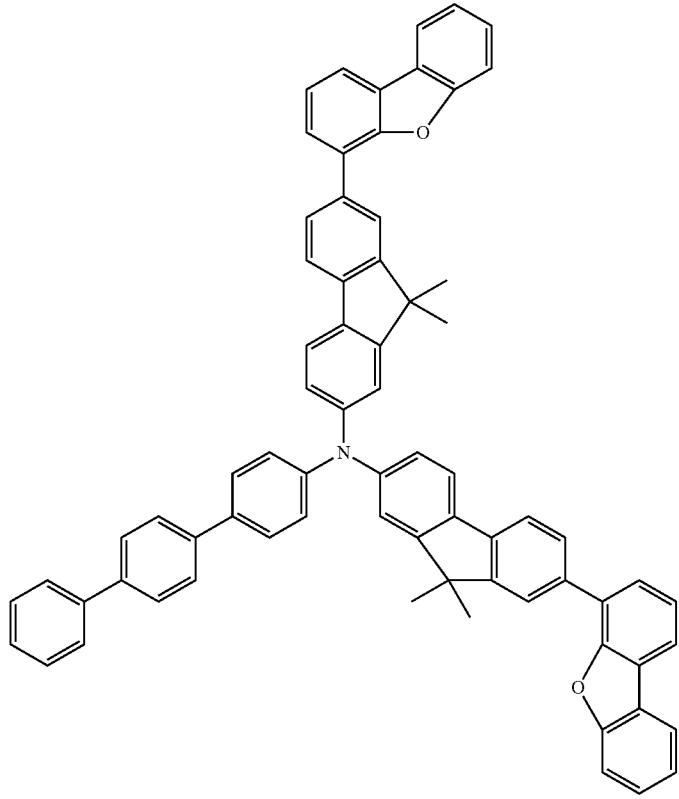
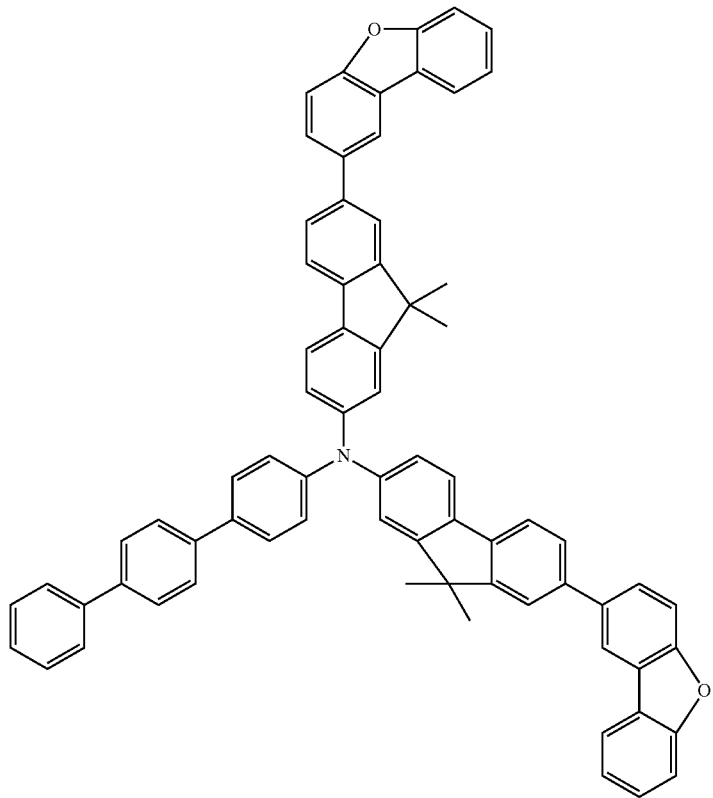

-continued
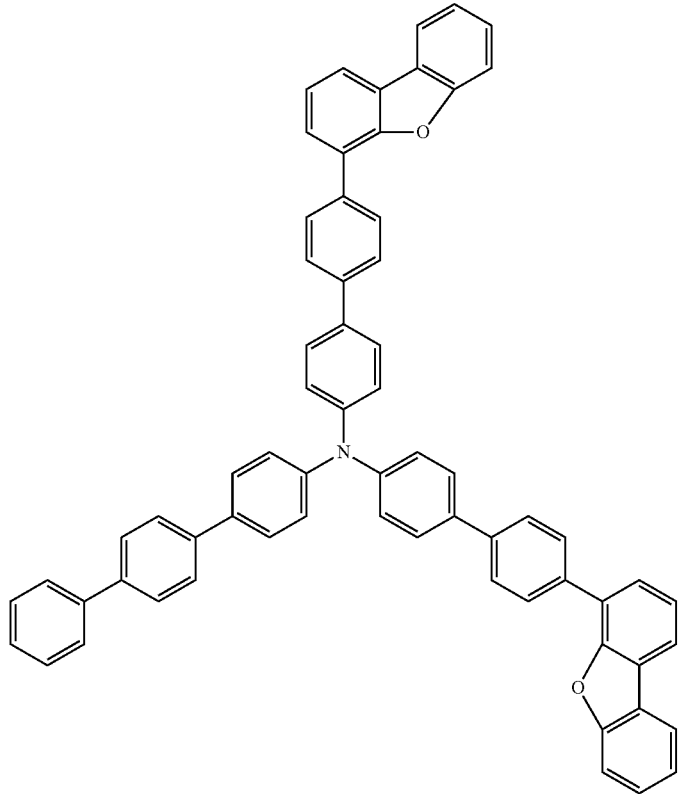
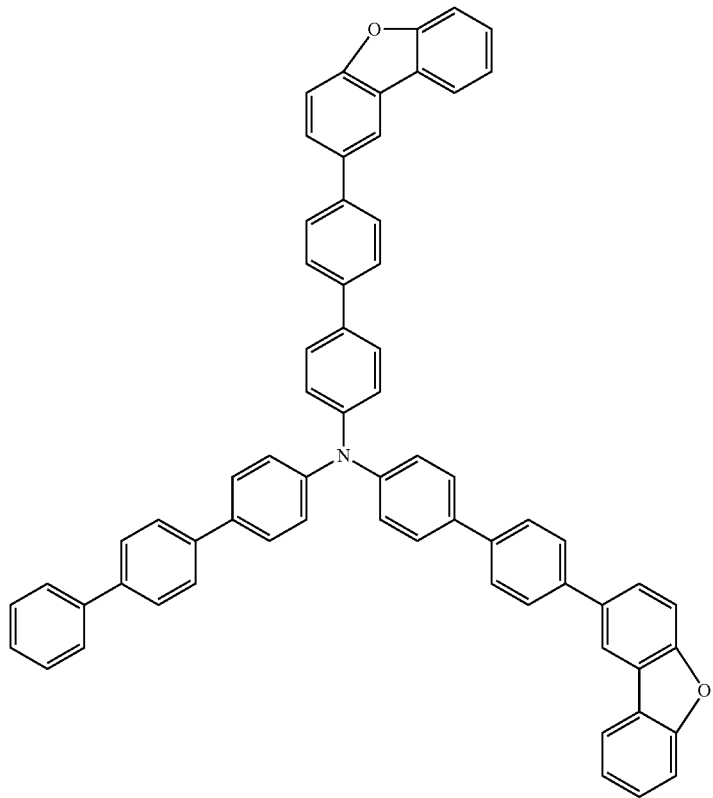

-continued
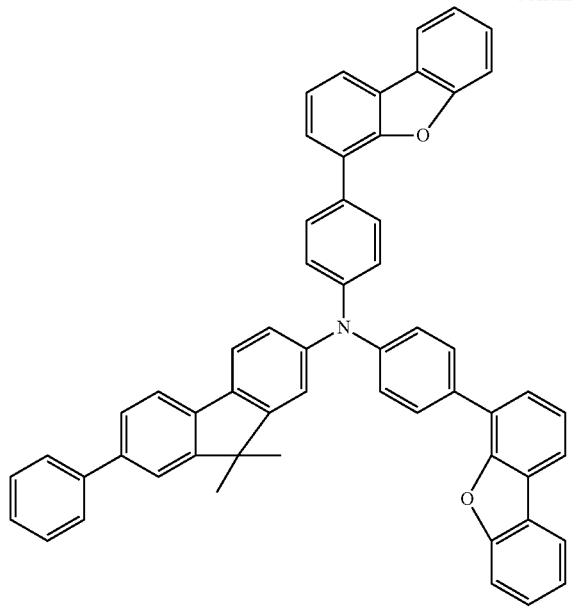
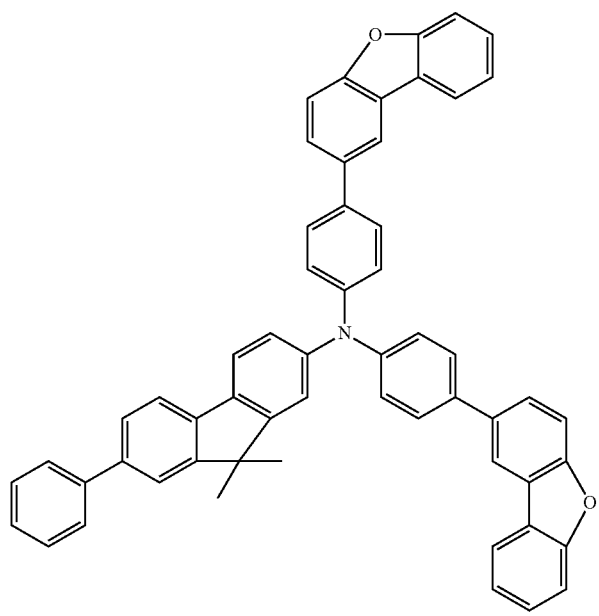

-continued
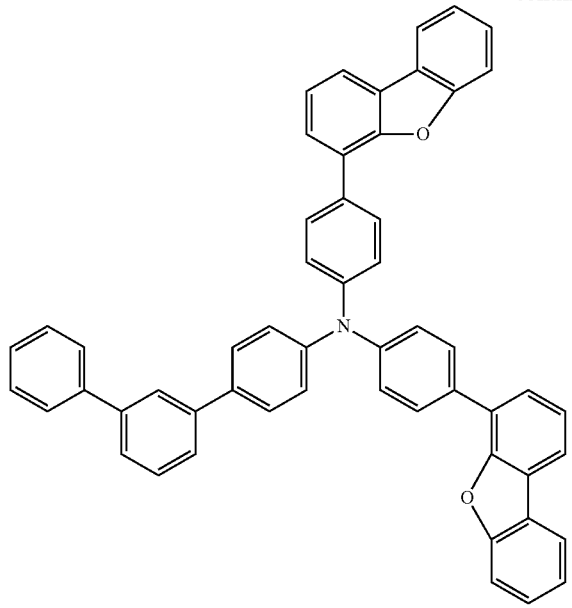
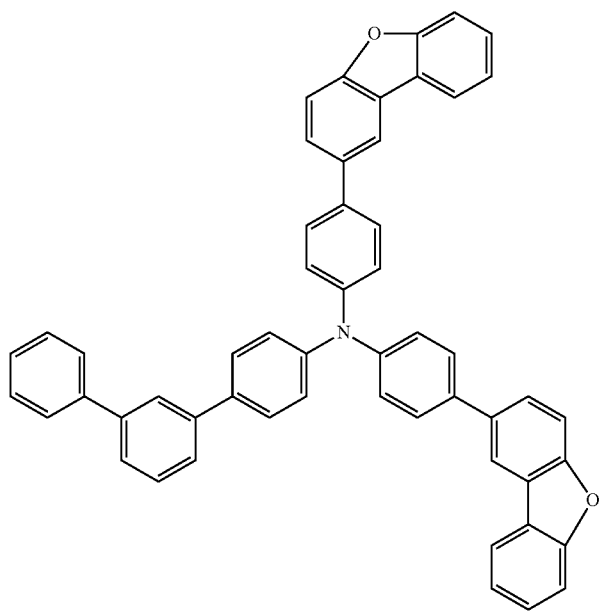 [SMILES: c1ccc(-c2cccc(-c3ccc(N(c4ccc(-c5ccc6oc7ccccc7c6c5)cc4)c4ccc(-c5ccc6oc7ccccc7c6c5)cc4)cc3)c2)cc1]

-continued
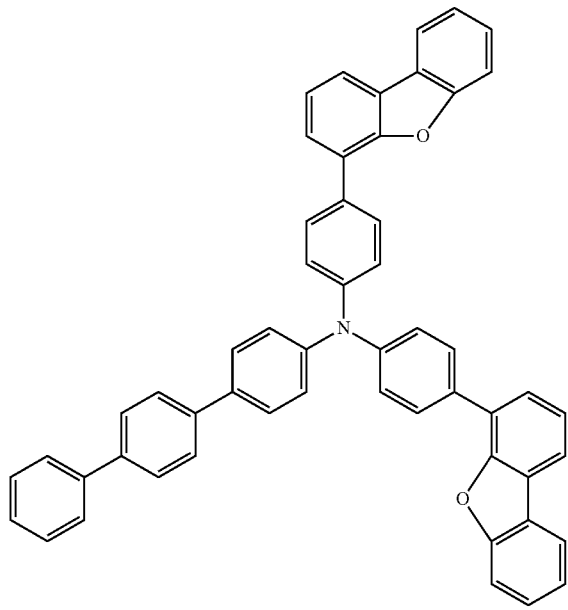
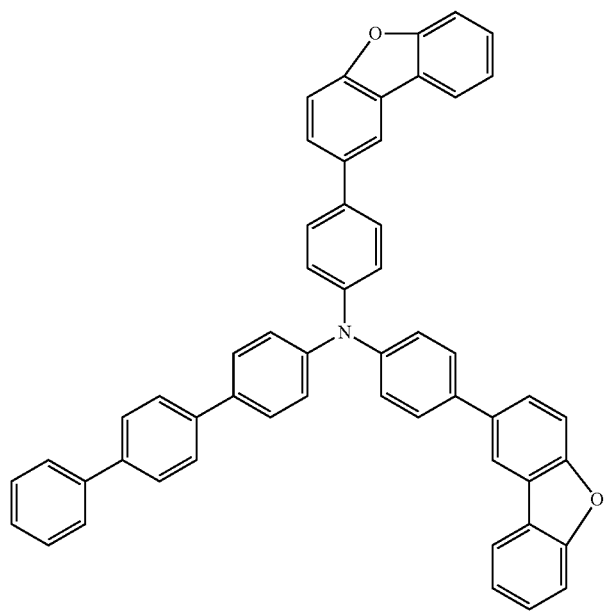

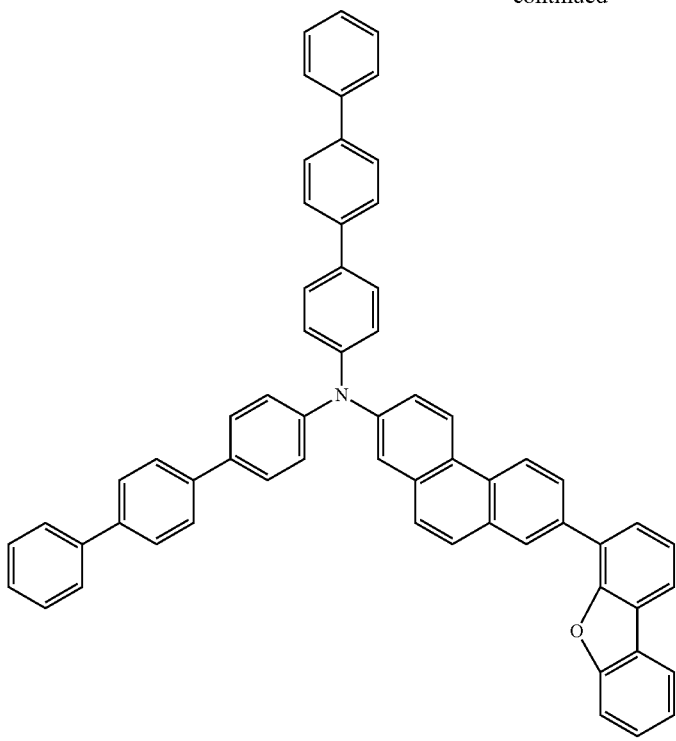
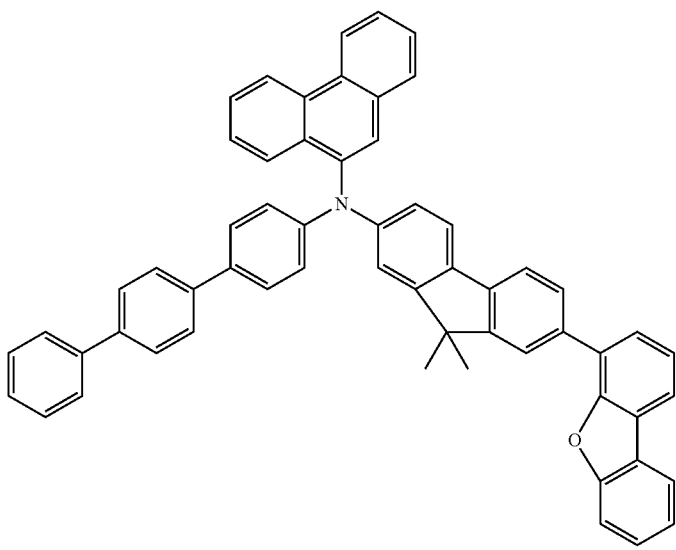

-continued
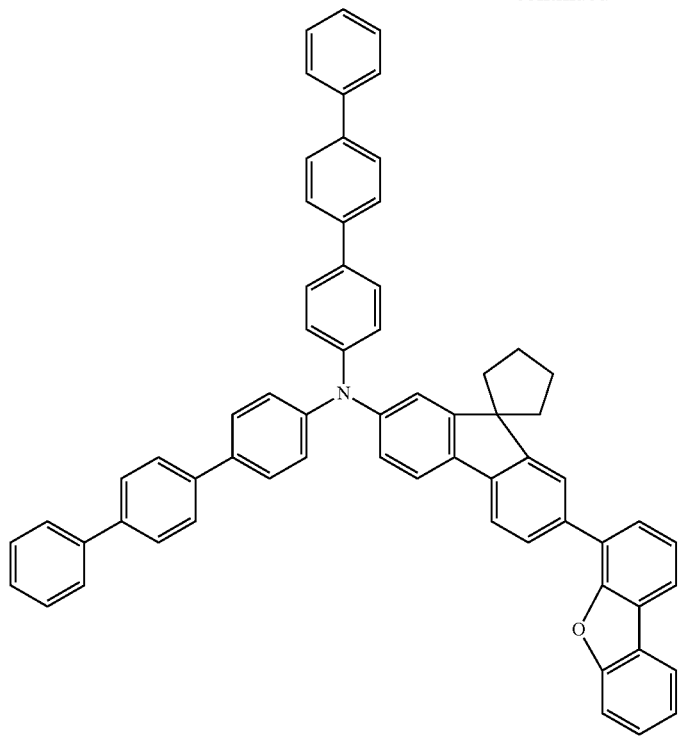
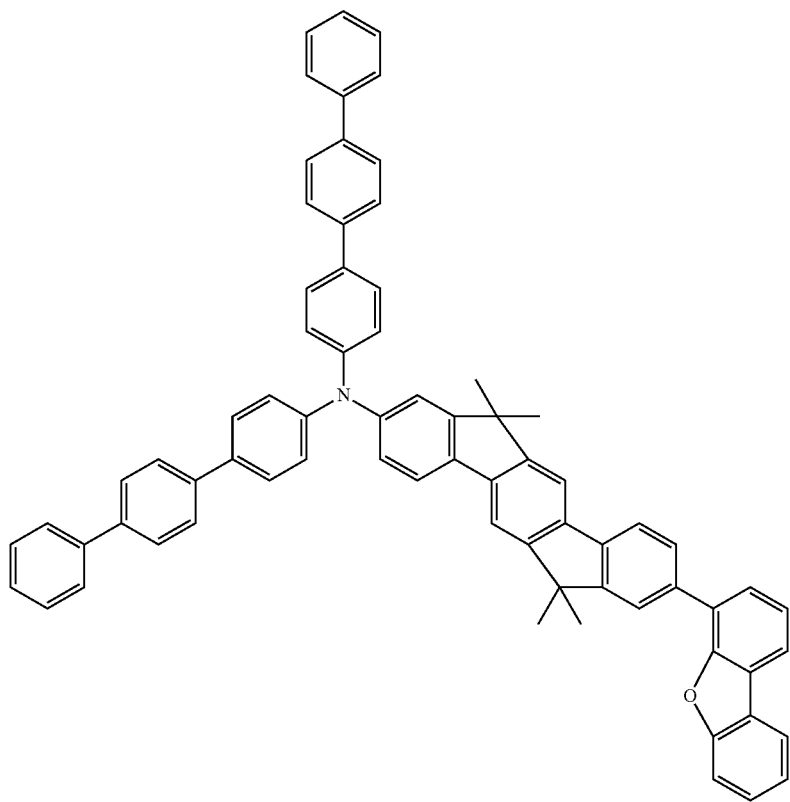

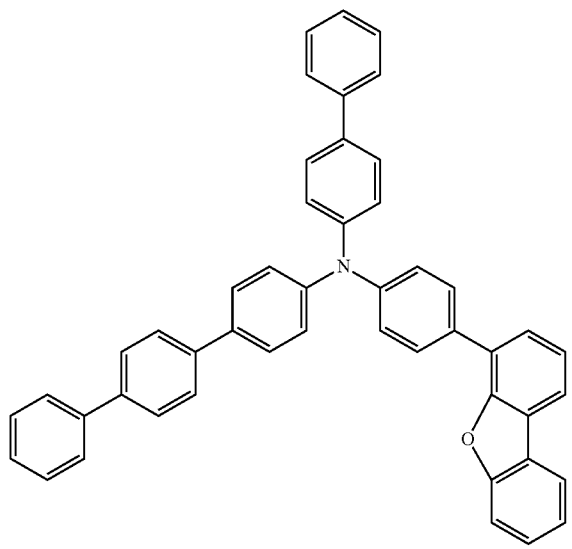
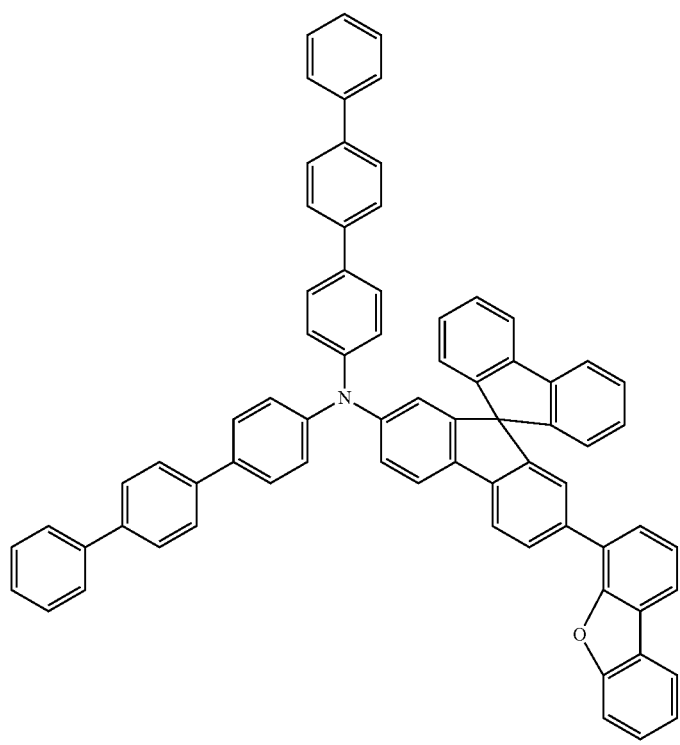

275 276
-continued
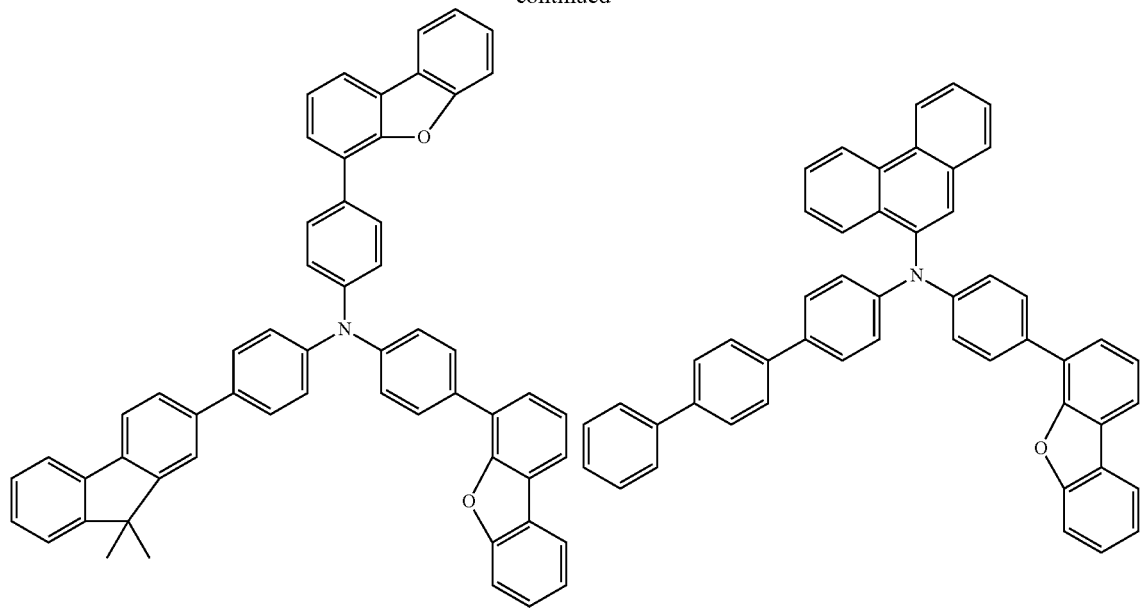
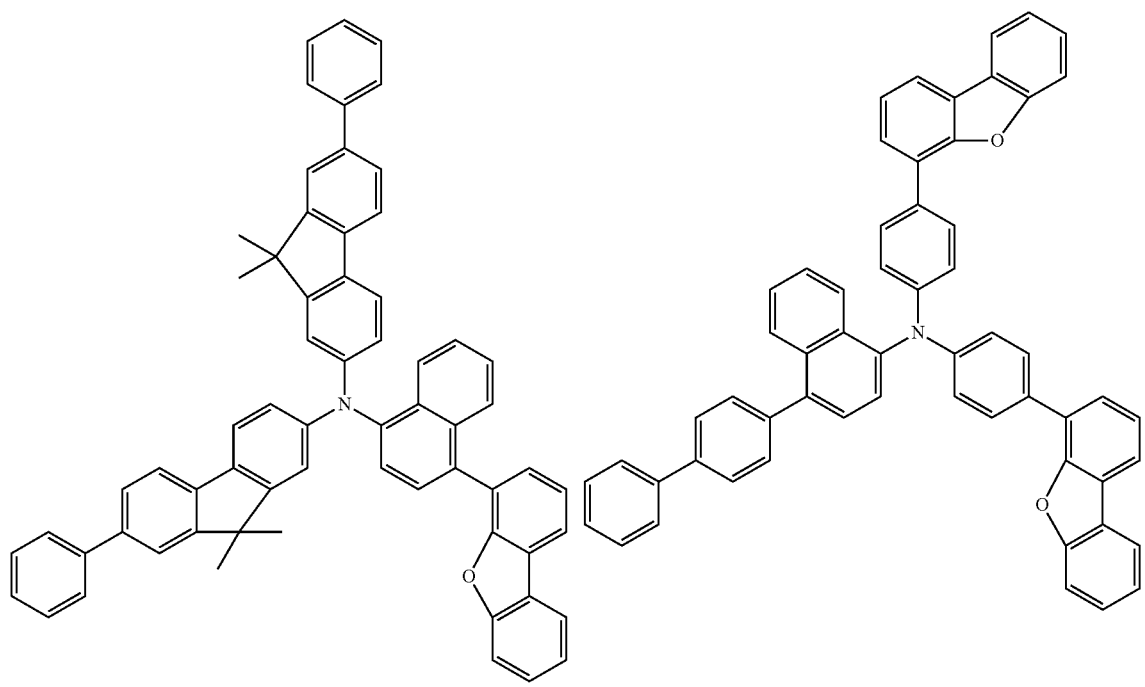

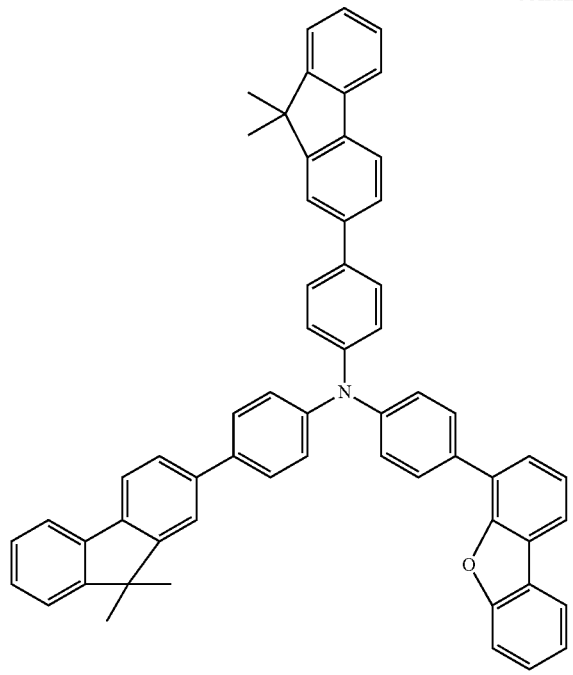
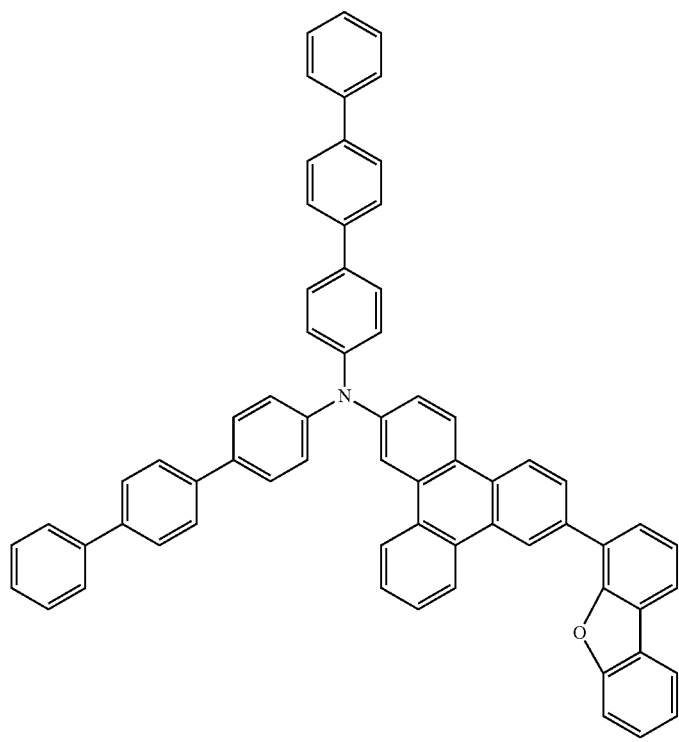

-continued

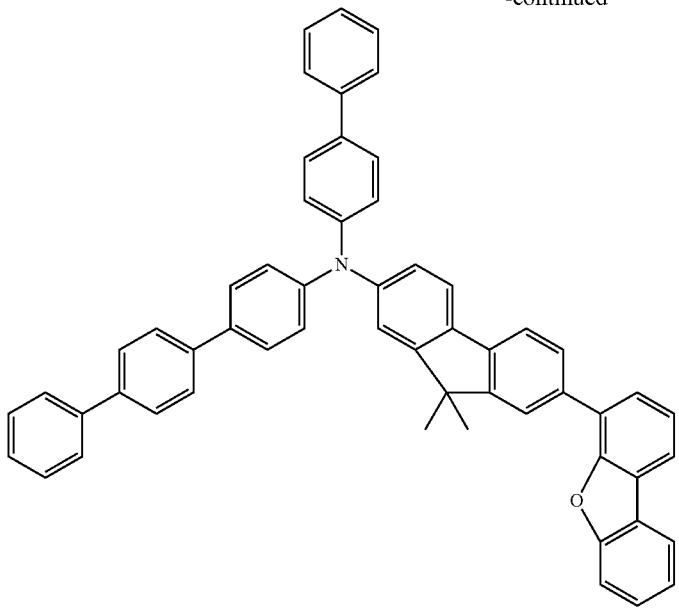

The hole transporting layer of the organic EL device in an aspect of the invention may be made into two-layered structure of a first hole transporting layer (anode side) and a second hole transporting layer (cathode side).

The thickness of the hole transporting layer is preferably 10 to 200 nm, although not particularly limited thereto.

The organic EL device in an aspect of the invention may include a layer comprising an acceptor material which is disposed in contact with the anode side of the hole transporting layer or the first hole transporting layer. With such a layer, it is expected that the driving voltage is lowered and the production cost is reduced.

The acceptor material is preferably a compound represented by formula (K):

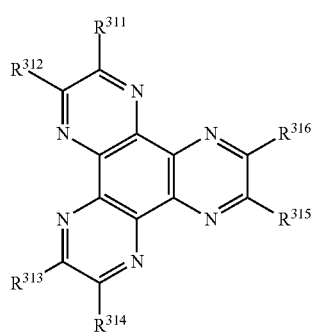

(K)

wherein $R^{311}$ to $R^{316}$ may be the same or different and each independently represent a cyano group, —$CONH_2$, a carboxyl group, or —COO $R^{317}$ wherein $R^{317}$ represents an alkyl group having 1 to 20 carbon atoms or a cycloalkyl group having 3 to 20 carbon atoms; and one or more pairs selected from $R^{311}$ and $R^{312}$, $R^{313}$ and $R^{314}$, and $R^{315}$ and $R^{316}$ may bond to each other to form a group represented by —CO—O—CO—.

Examples of $R^{317}$ include a methyl group, an ethyl group, a n-propyl group, an isopropyl group, a n-butyl group, an isobutyl group, a t-butyl group, a cyclopentyl group, and a cyclohexyl group.

The thickness of the layer comprising the acceptor material is preferably 5 to 20 nm, although not particularly limited thereto.

The following compounds may be used as the acceptor material.

281
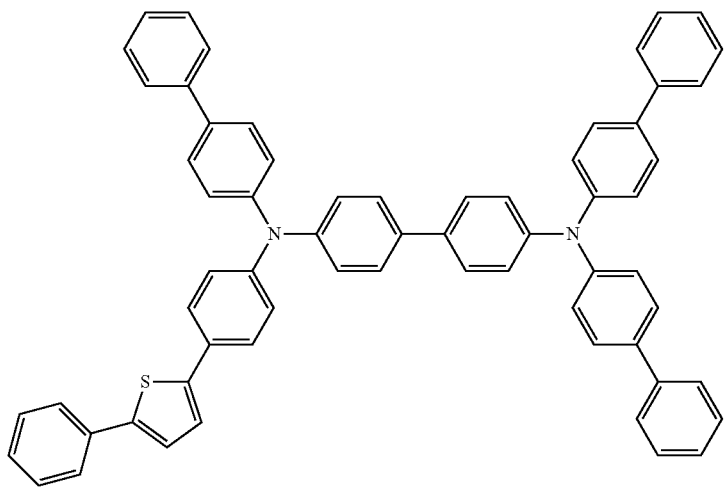
282
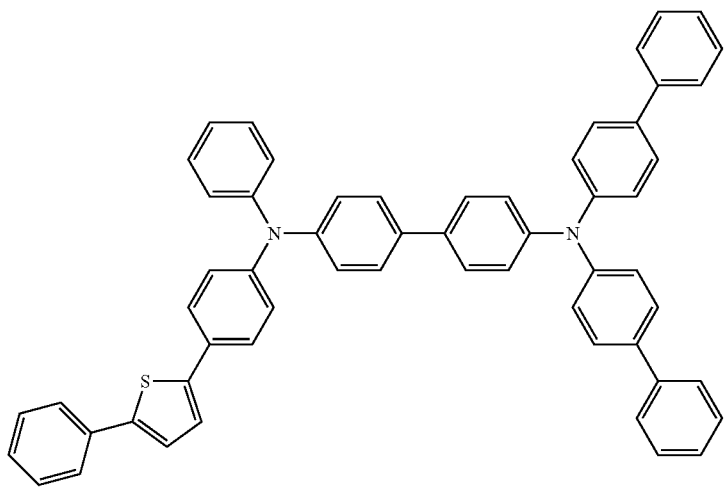
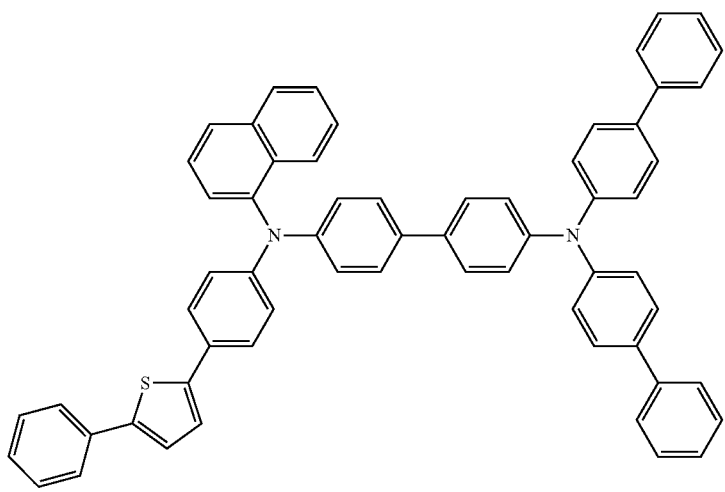

-continued
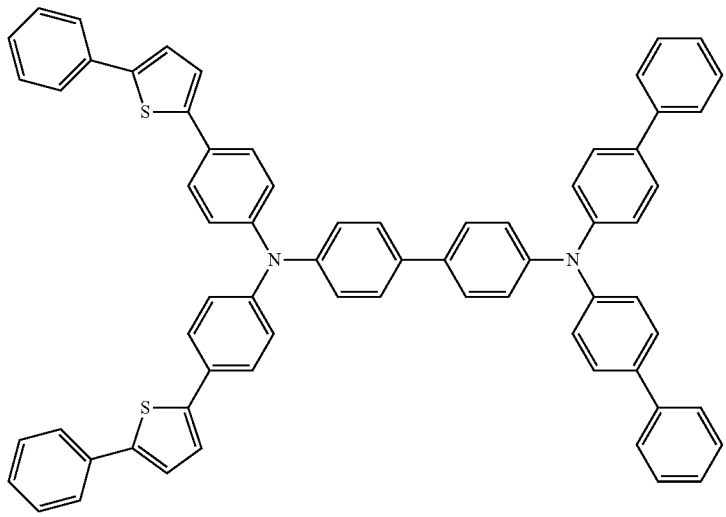
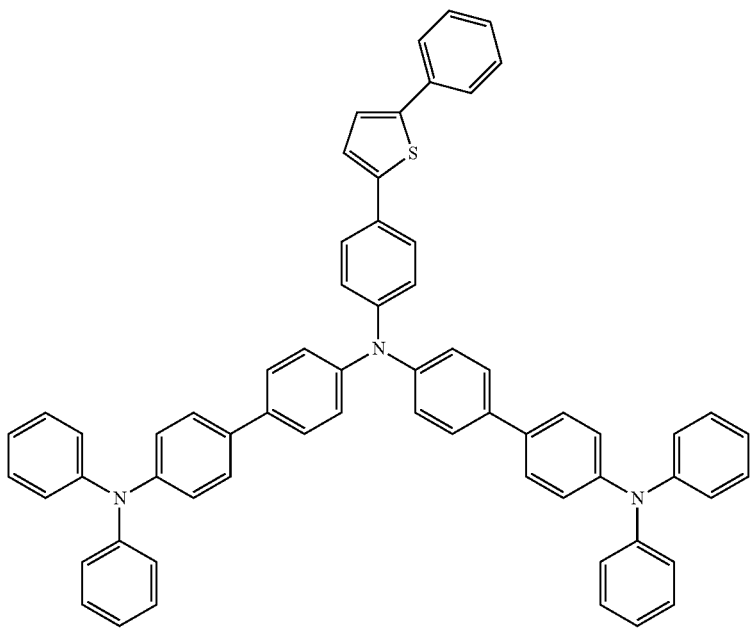
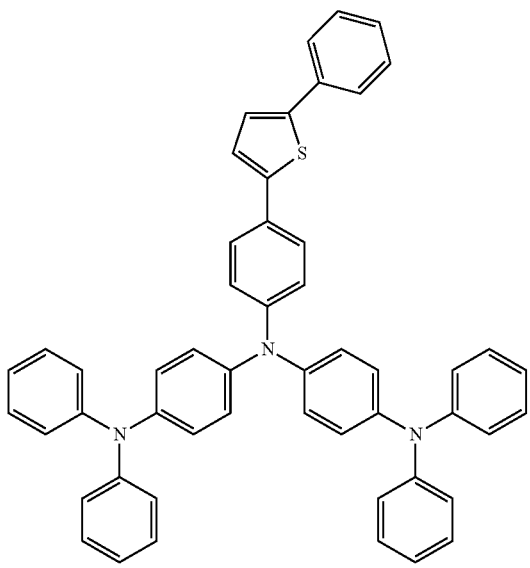

-continued
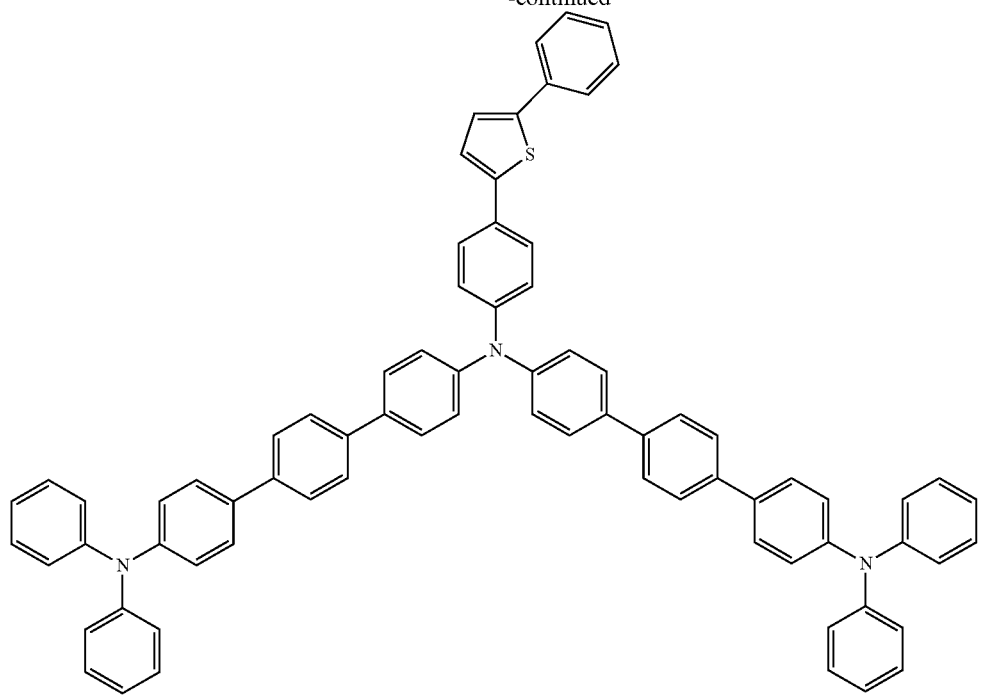
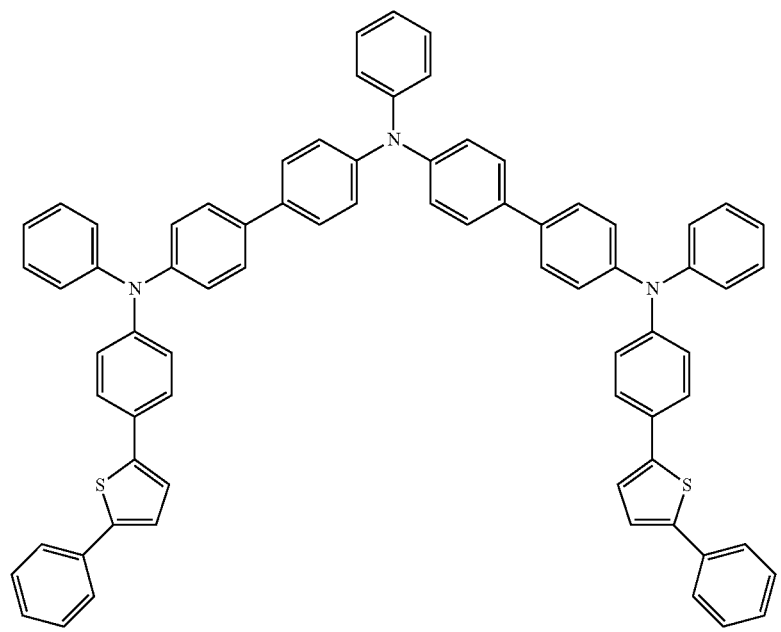

-continued
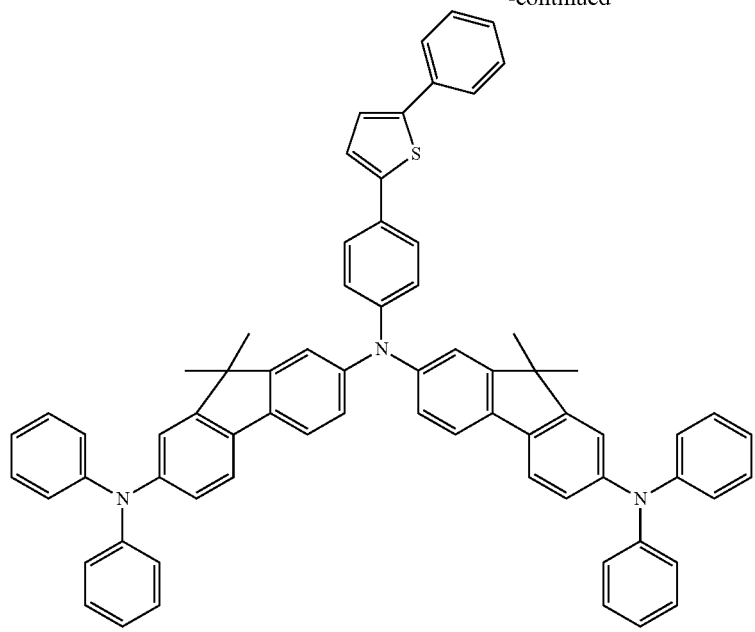
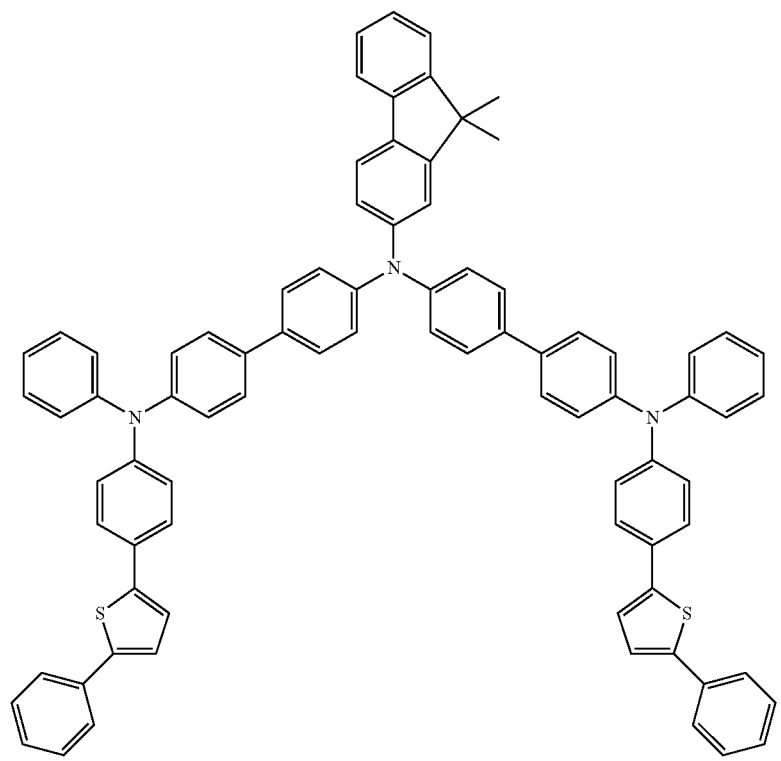

-continued
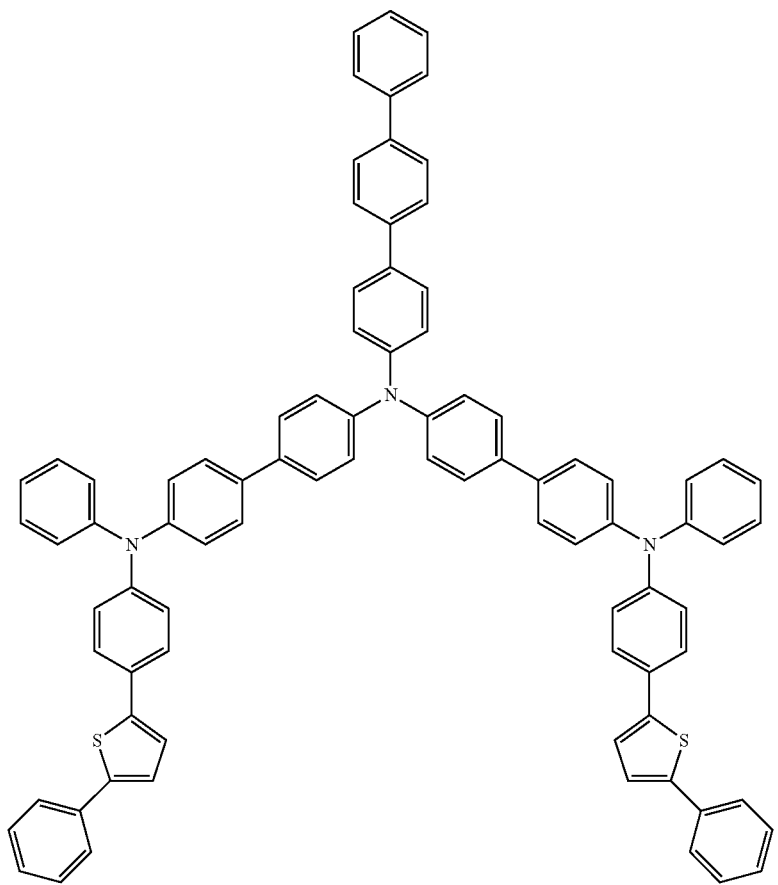
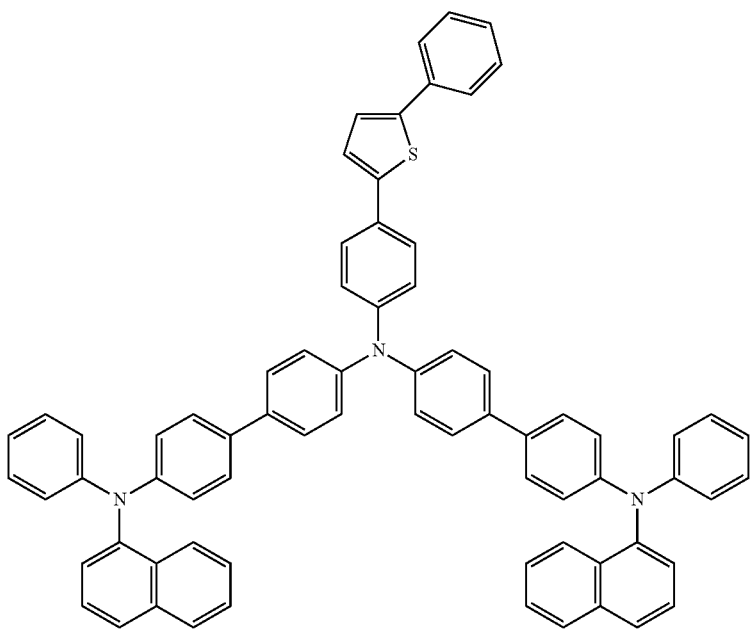

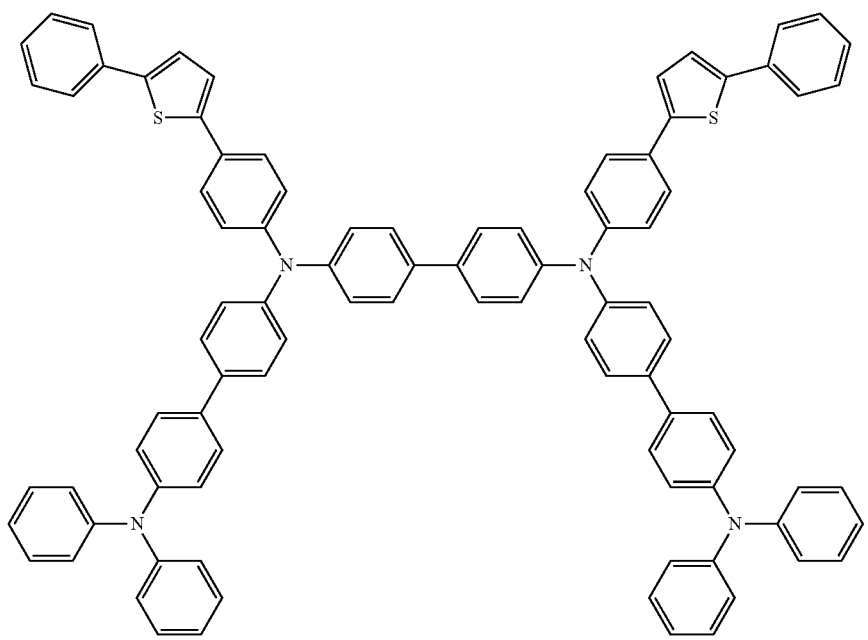
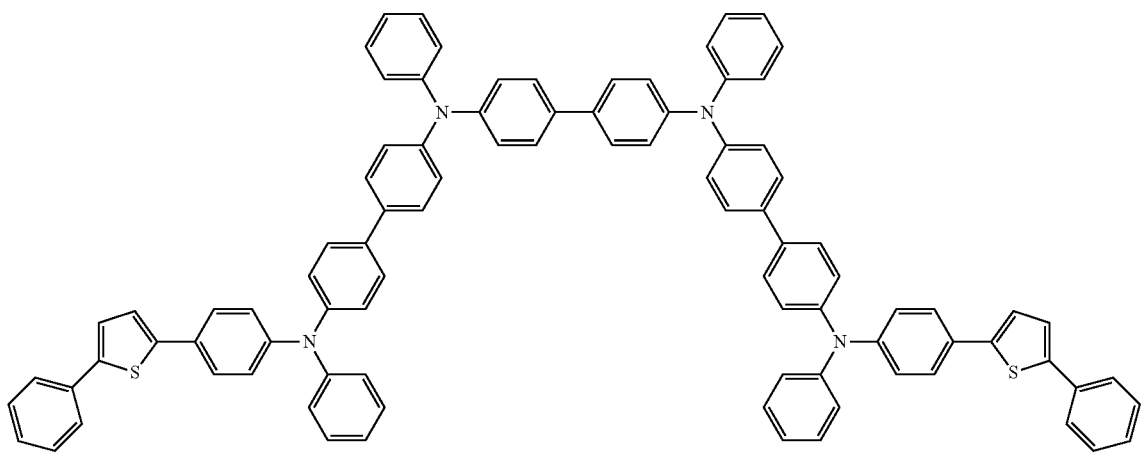
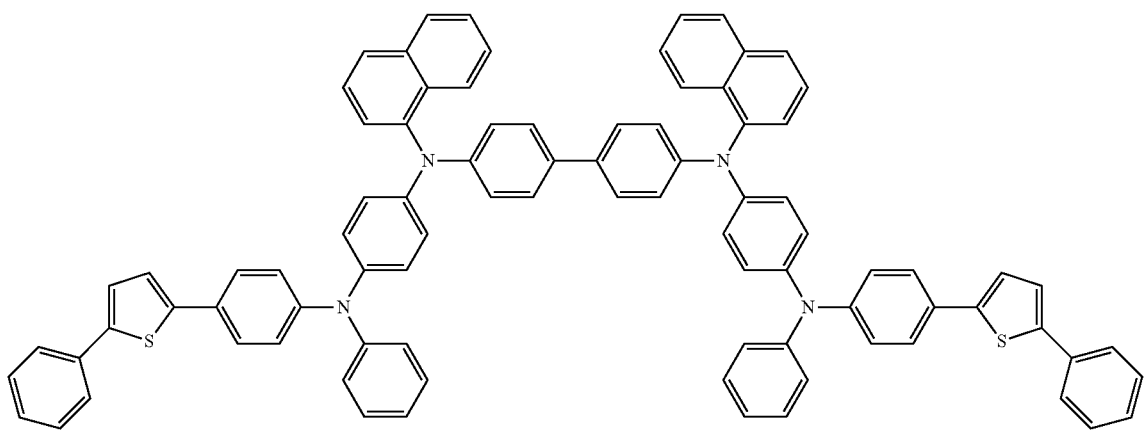

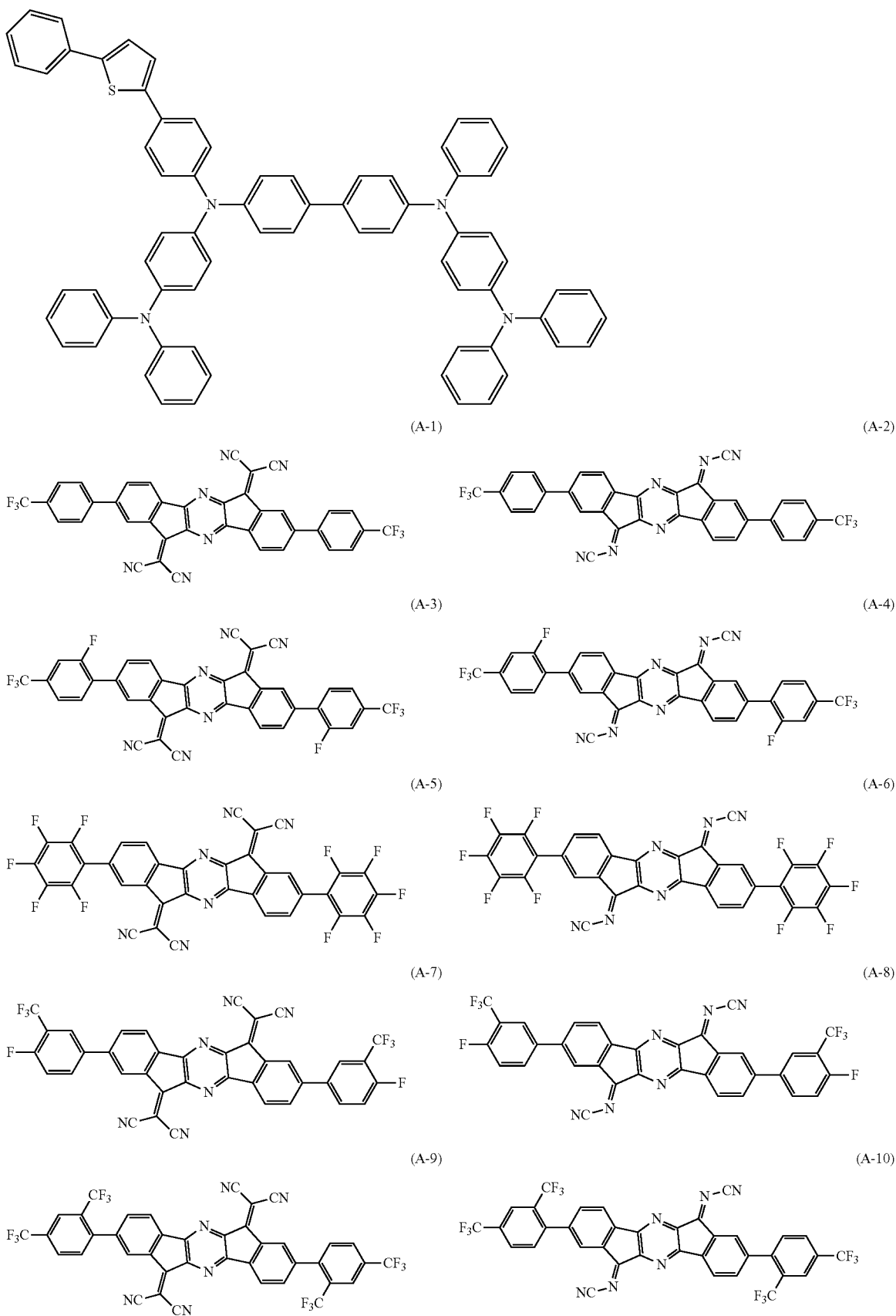

-continued
(A-11)
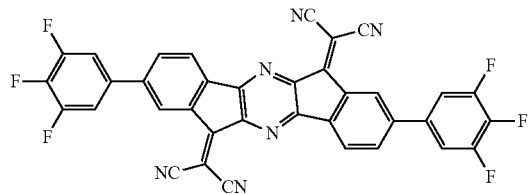
(A-12)
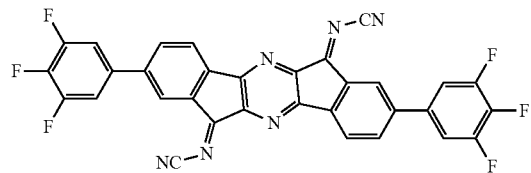
(A-13)
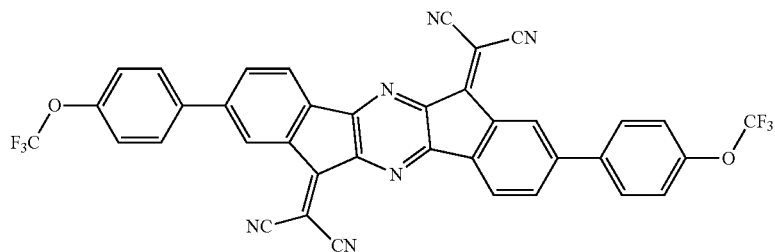
(A-14)
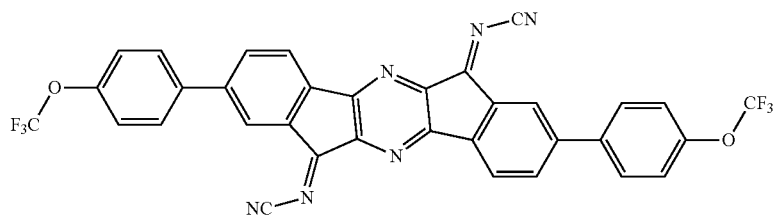
(A-15)
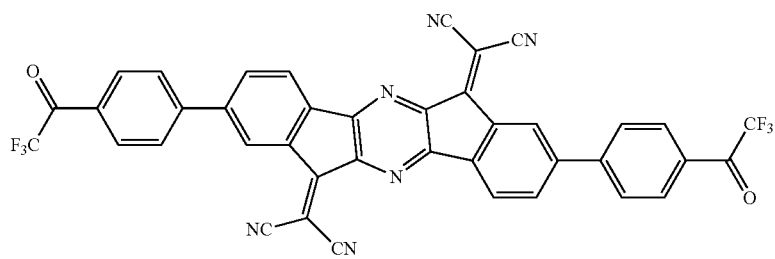
(A-16)
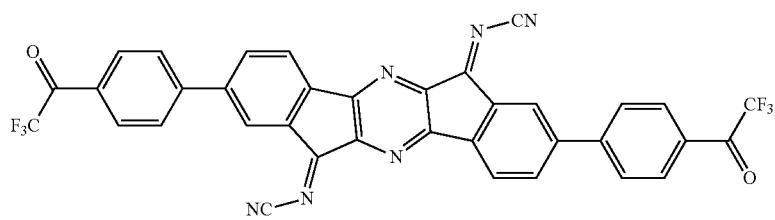
(A-17)
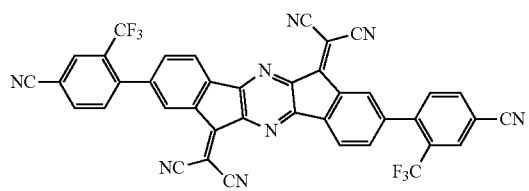
(A-18)
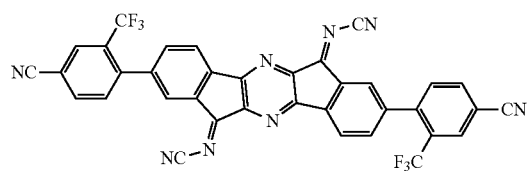

-continued
(A-19) 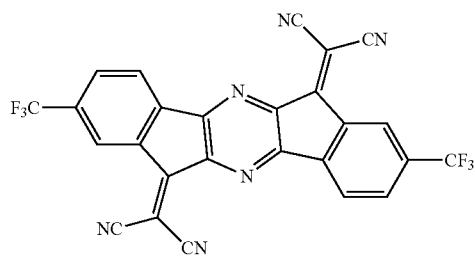
(A-20) 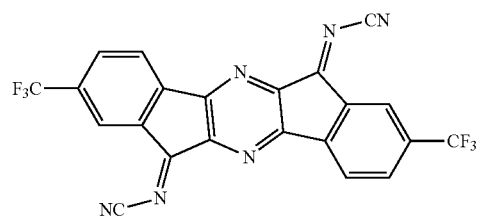
(A-21) 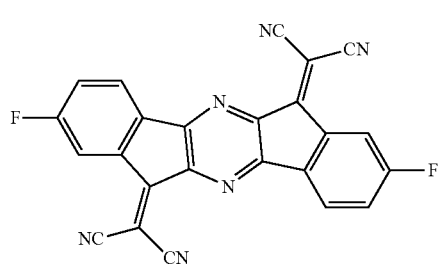
(A-22) 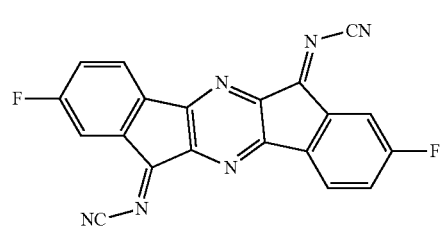
(A-23) 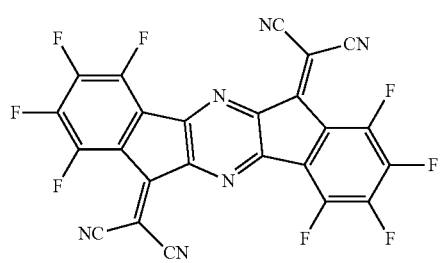
(A-24) 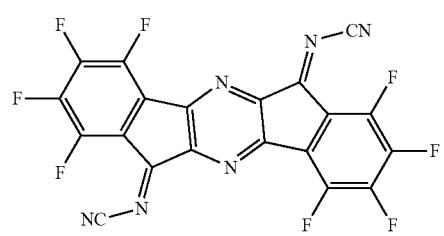
(A-25) 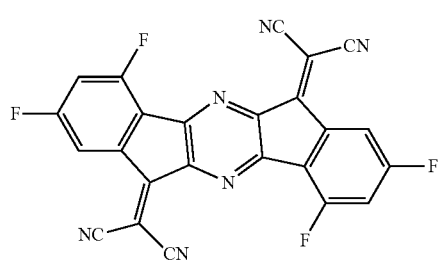
(A-26) 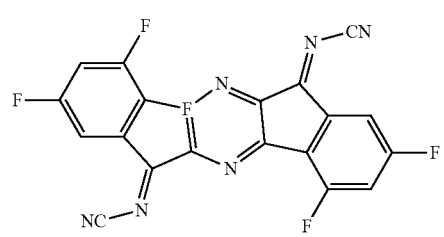
(A-27) 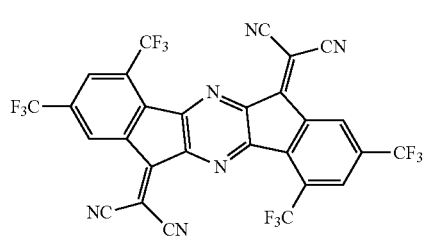
(A-28) 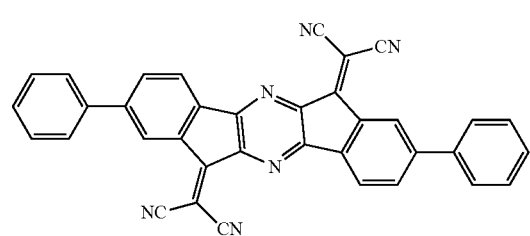

-continued
(A-29)
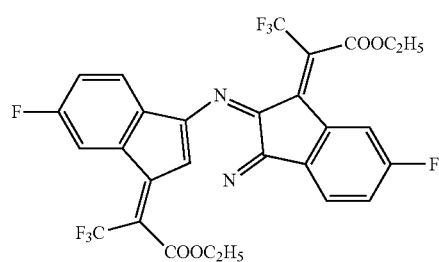
(A-30)
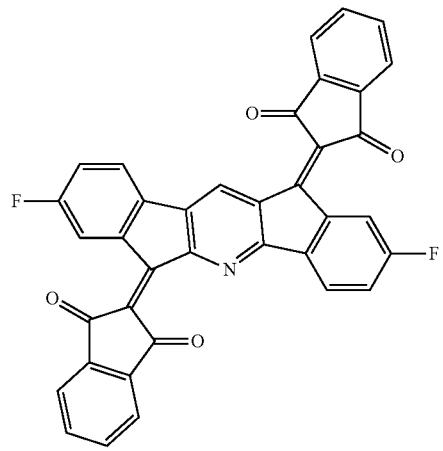
(A-31)
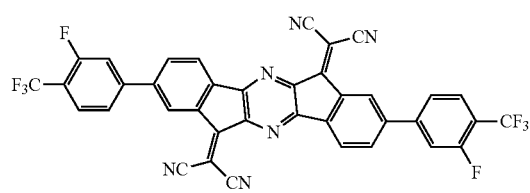
(A-32)
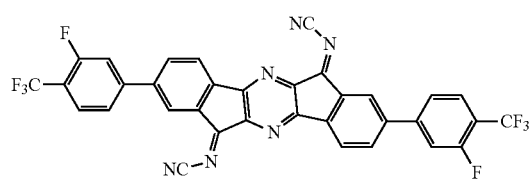
(A-33)
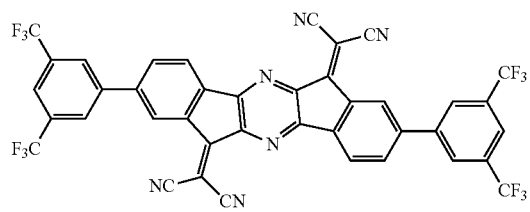
(A-34)
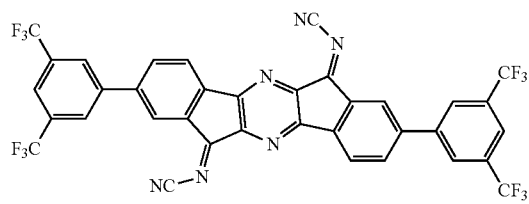
(A-35)
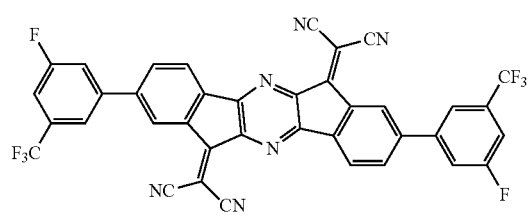
(A-36)
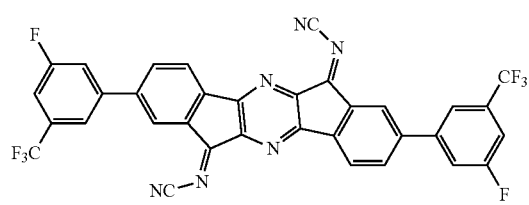
(A-37)
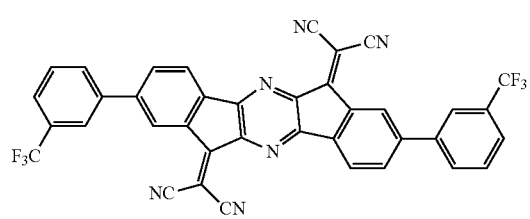
(A-38)
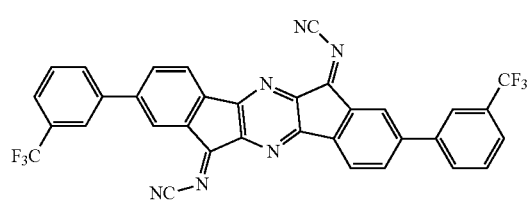
(A-39)
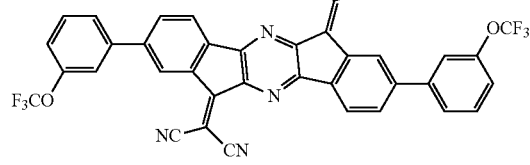
(A-40)
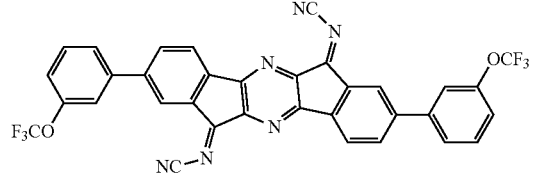

-continued
(A-41) 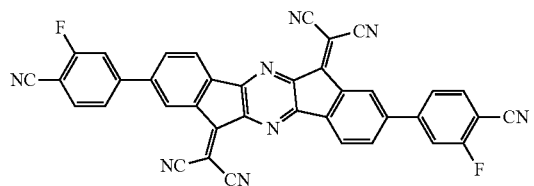
(A-42) 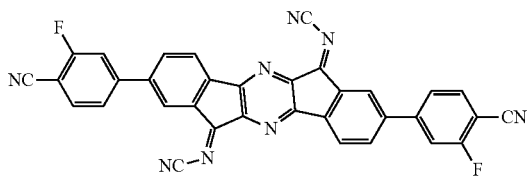
(A-43) 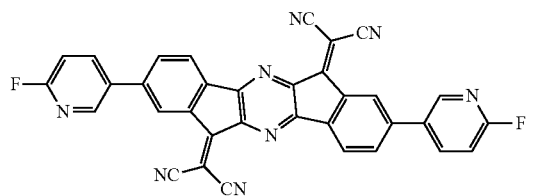
(A-44) 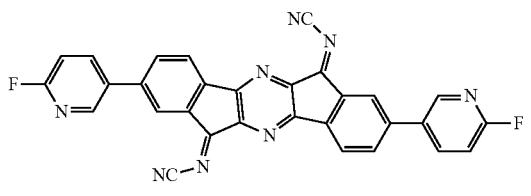
(A-45) 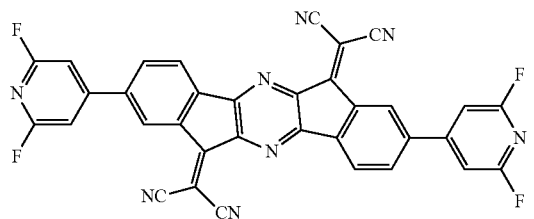
(A-46) 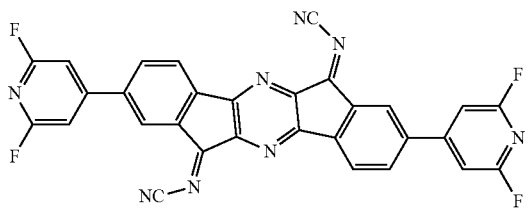
(A-47) 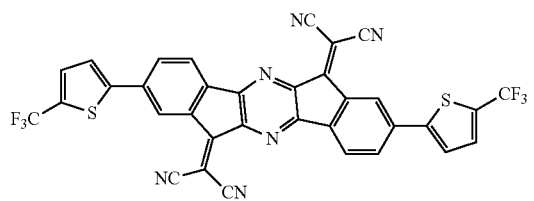
(A-48) 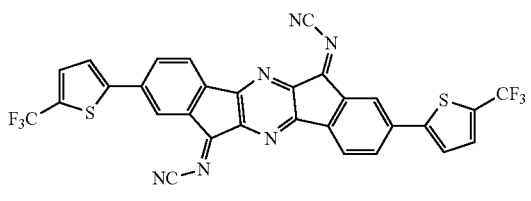
(A-49) 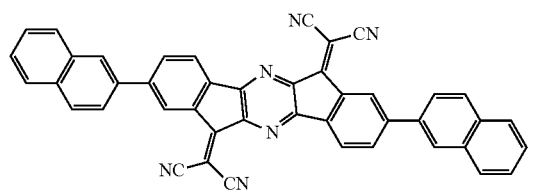
(A-50) 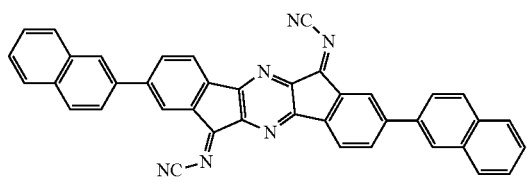
(A-51) 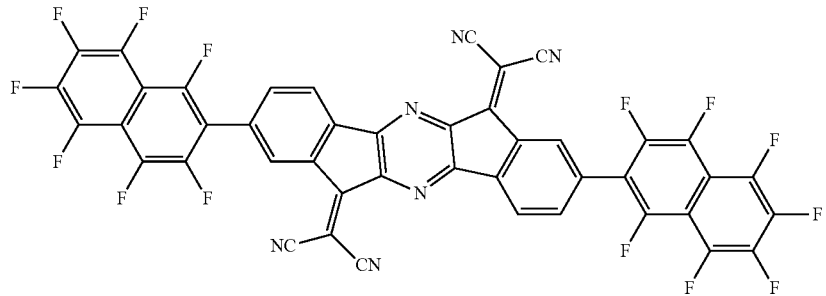

-continued
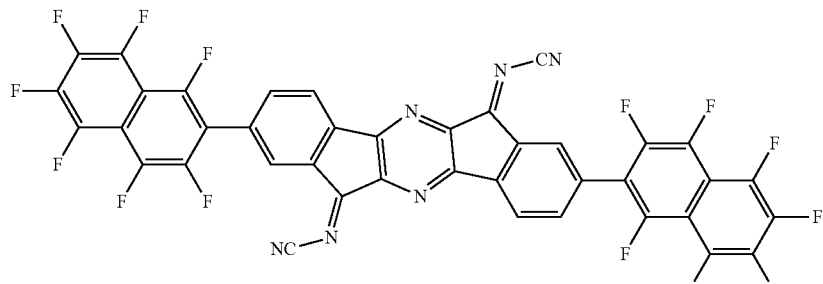
(A-52)
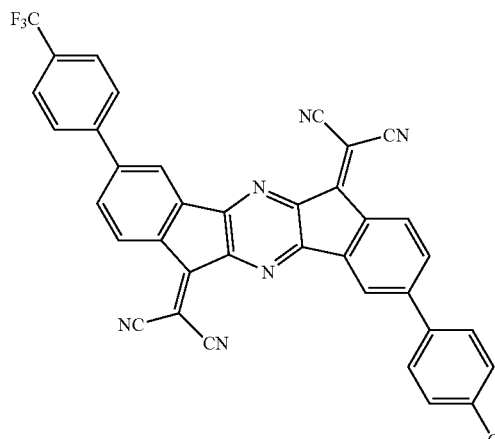
(A-53)
(A-54)
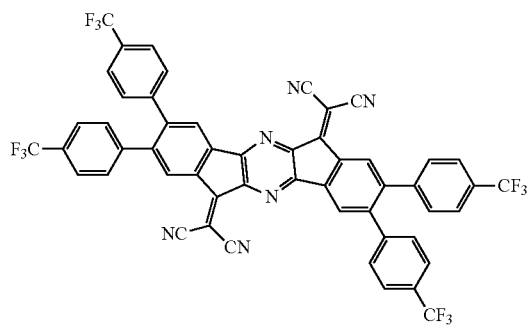
(A-55)
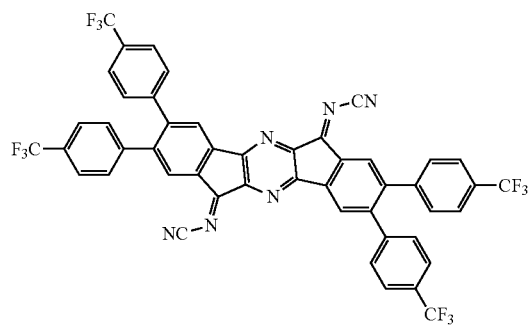
(A-56)
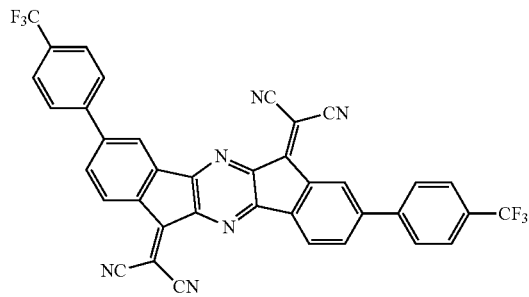
(A-57)
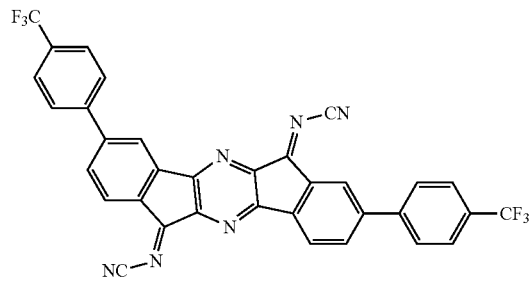
(A-58)
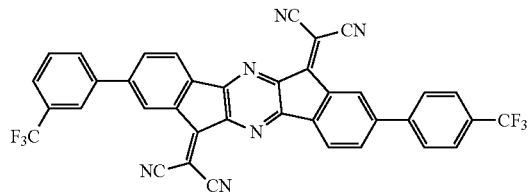
(A-59)
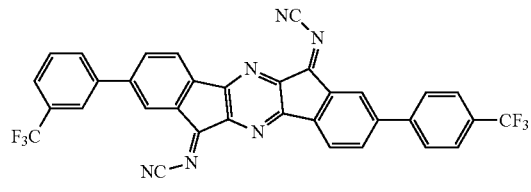
(A-60)

-continued
(A-61) 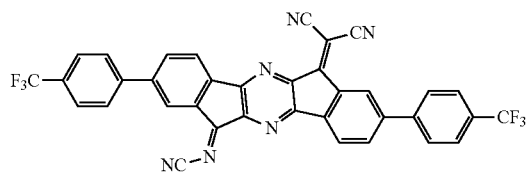
(B-1) 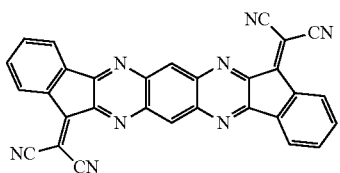
(B-2) 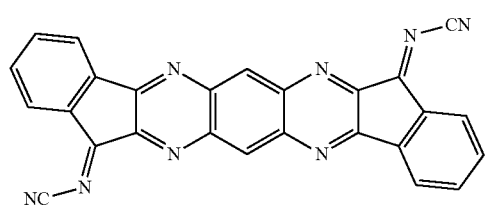
(B-3) 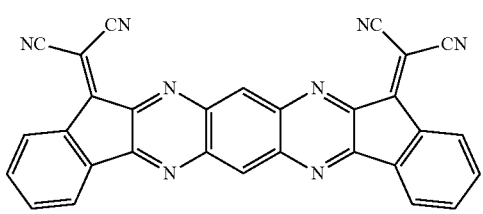
(B-4) 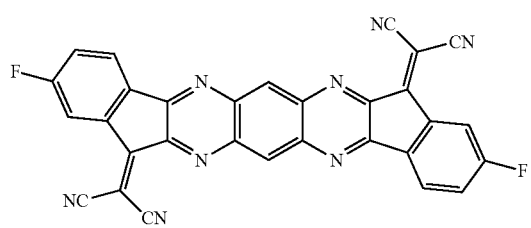
(B-5) 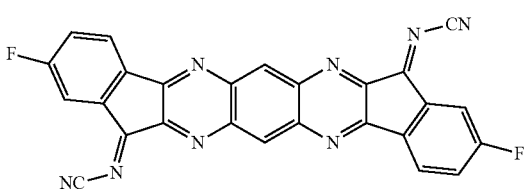
(B-6) 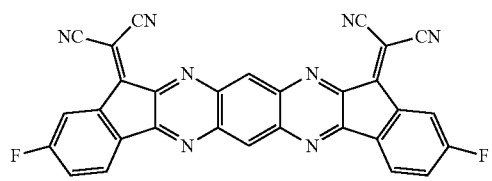
(B-7) 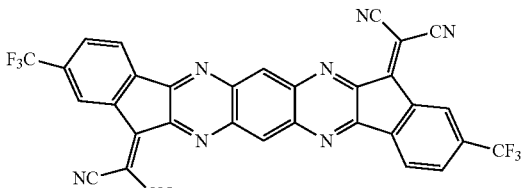
(B-8) 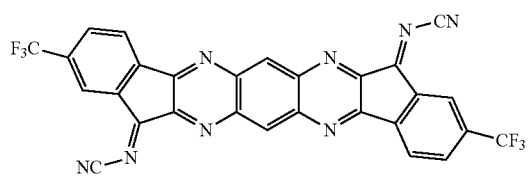
(B-9) 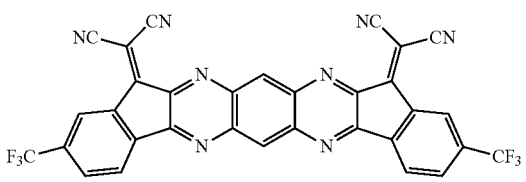
(B-10) 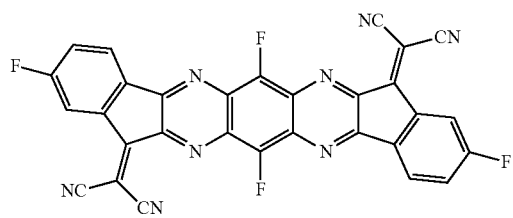
(B-11)
(B-12) 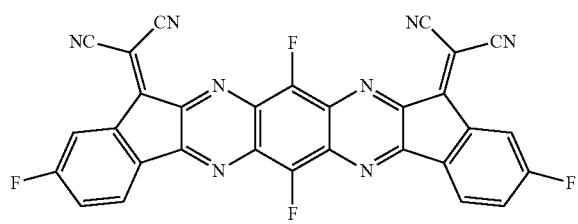

-continued
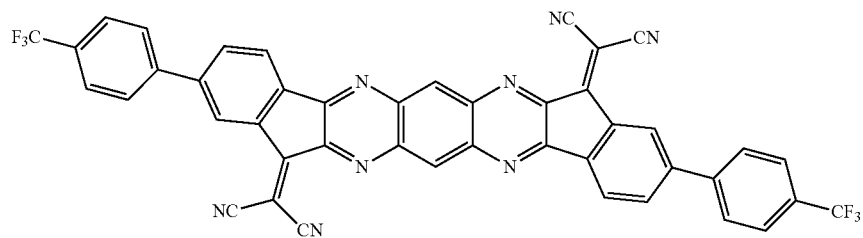
(B-13)
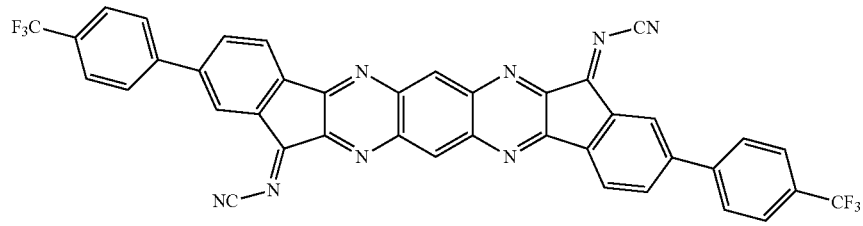
(B-14)
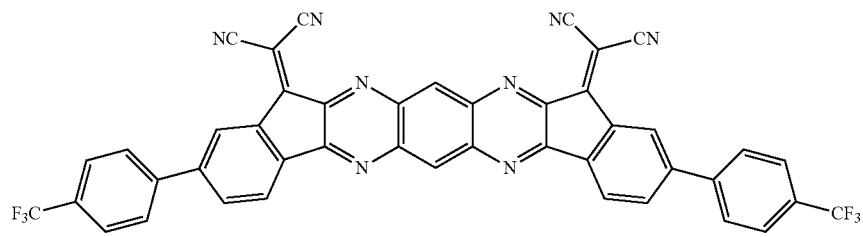
(B-15)
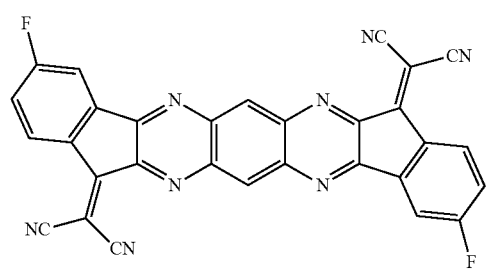
(B-16)
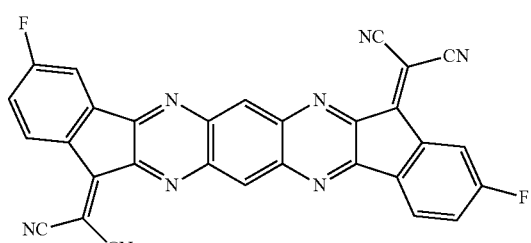
(B-17)
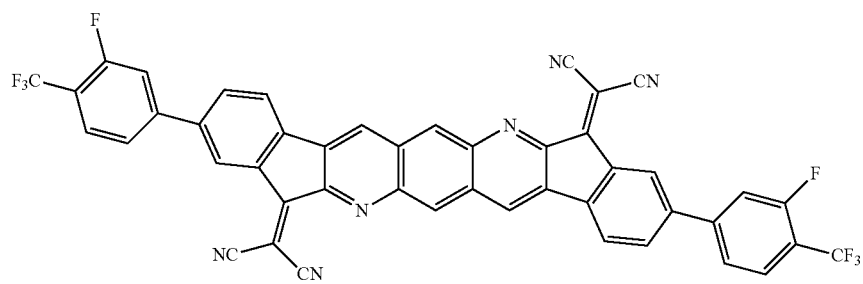
(B-18)
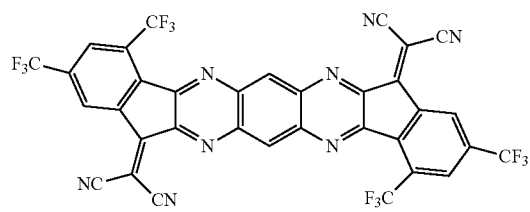
(B-19)
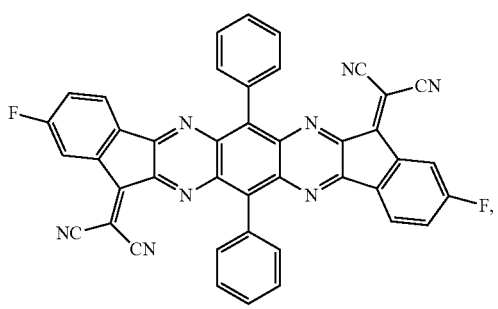
(B-20)

-continued
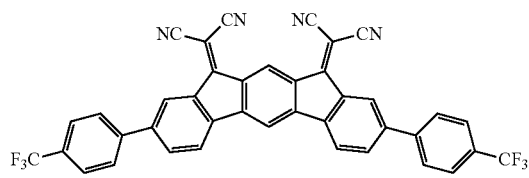
(A'-1)
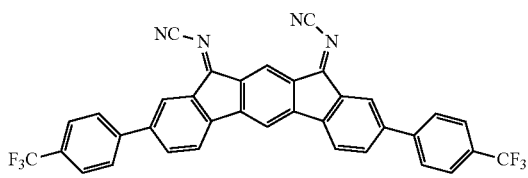
(A'-2)
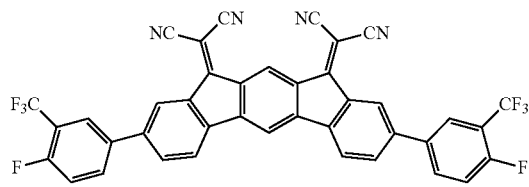
(A'-3)
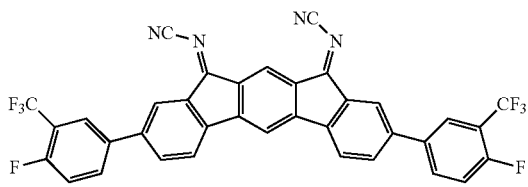
(A'-4)
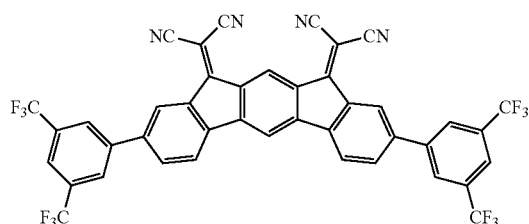
(A'-5)
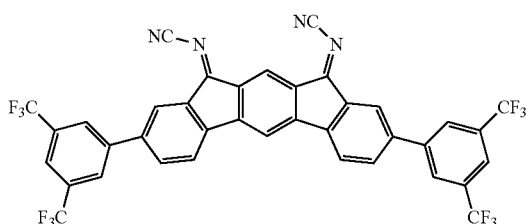
(A'-6)
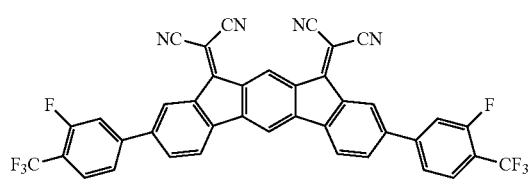
(A'-7)
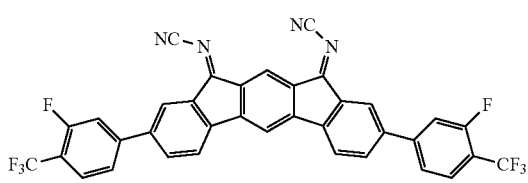
(A'-8)
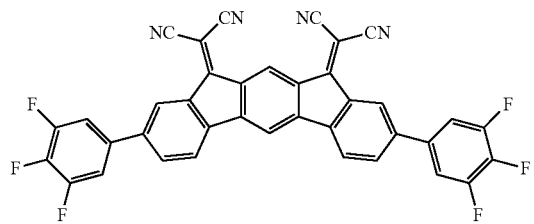
(A'-9)
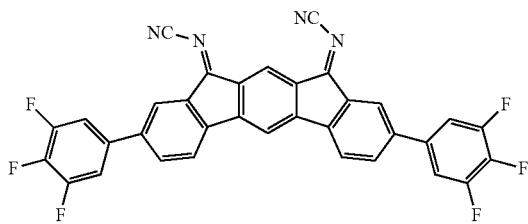
(A'-10)
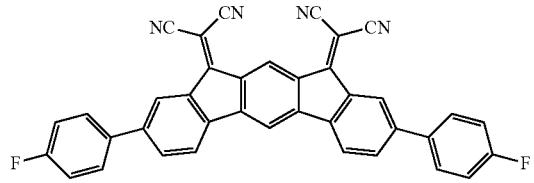
(A'-11)
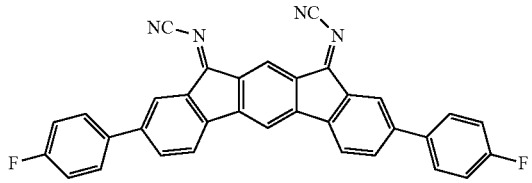
(A'-12)
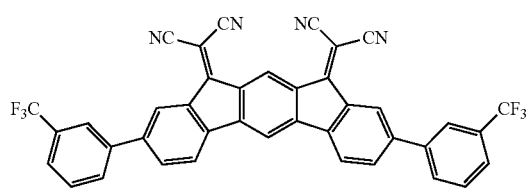
(A'-13)
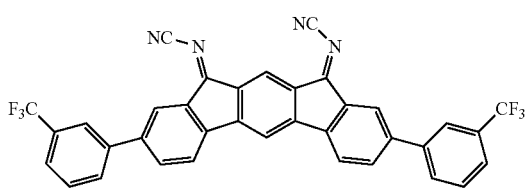
(A'-14)

-continued
(A'-15)
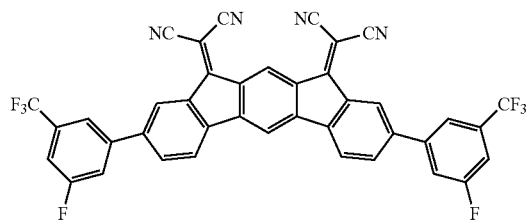
(A'-16)
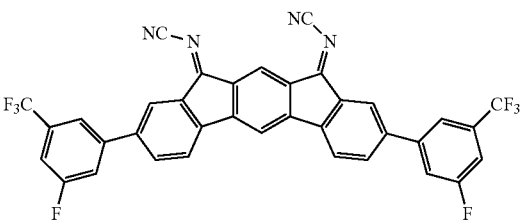
(A'-17)
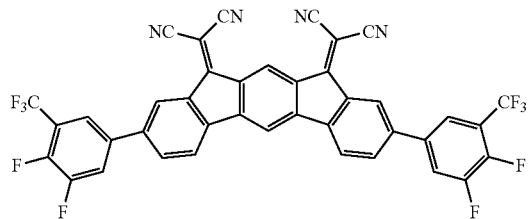
(A'-18)
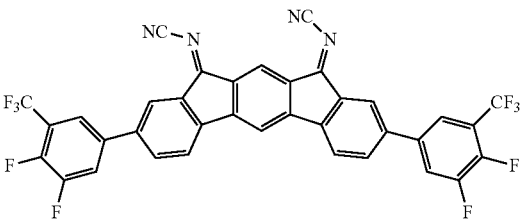
(A'-19)
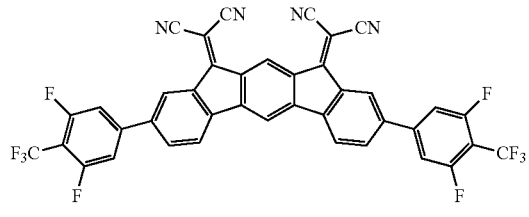
(A'-20)
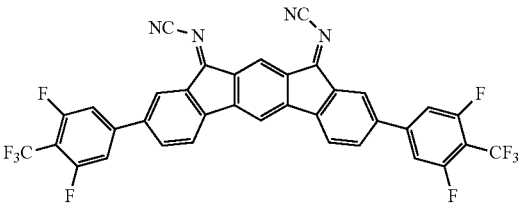
(A'-21)
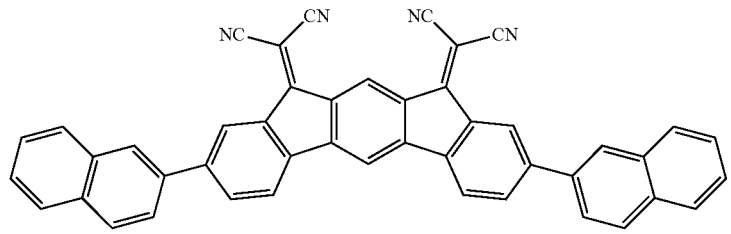
(A'-22)
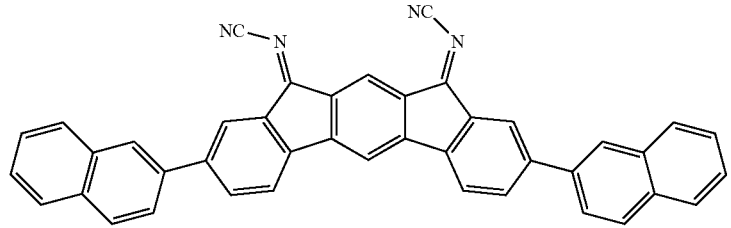
(A'-23)
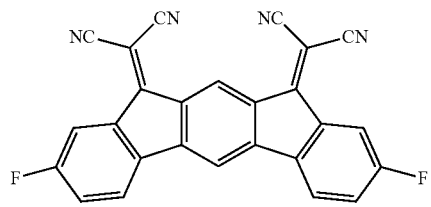
(A'-24)
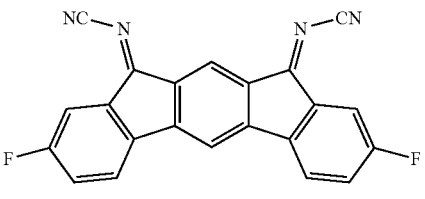
(A'-25)
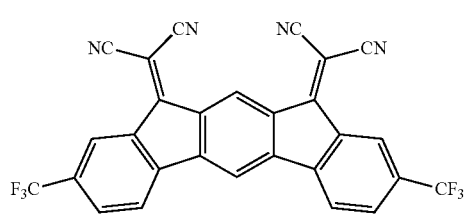
(A'-26)
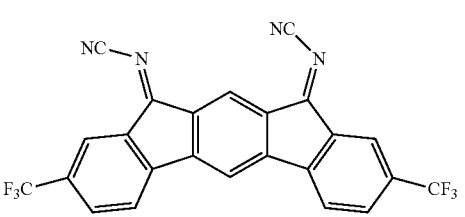

-continued
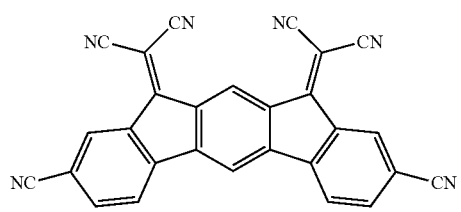 (A'-27)
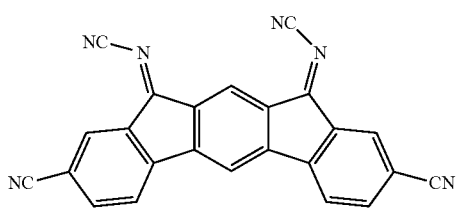 (A'-28)
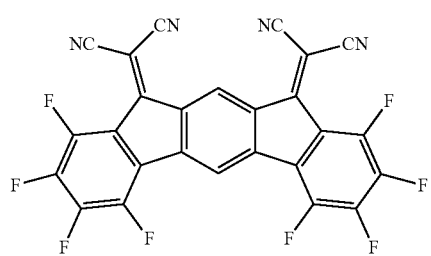 (A'-29)
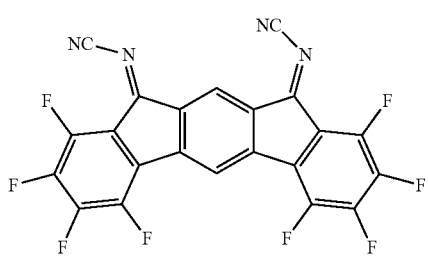 (A'-30)
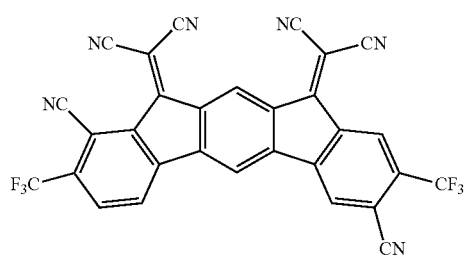 (A'-31)
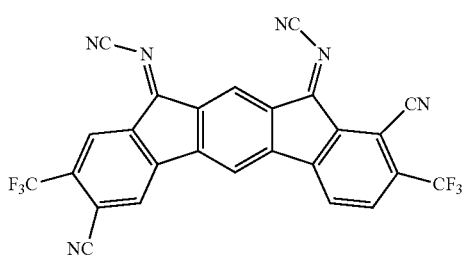 (A'-32)
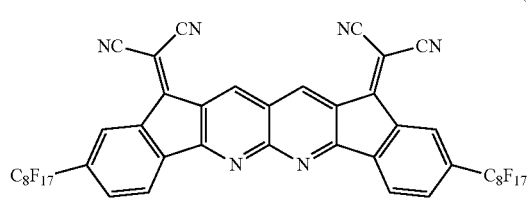 (A'-43)
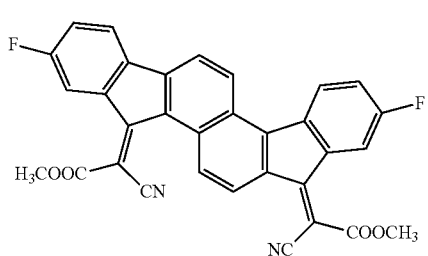 (A'-44)
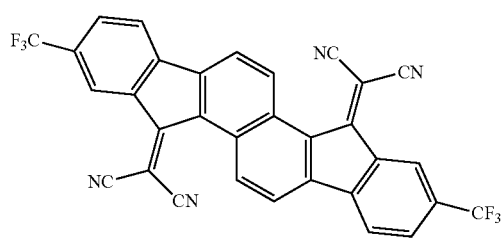 (A'-45)
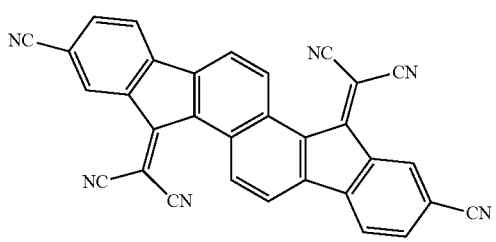 (A'-46)
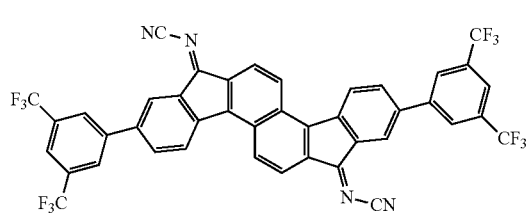 (A'-47)

-continued
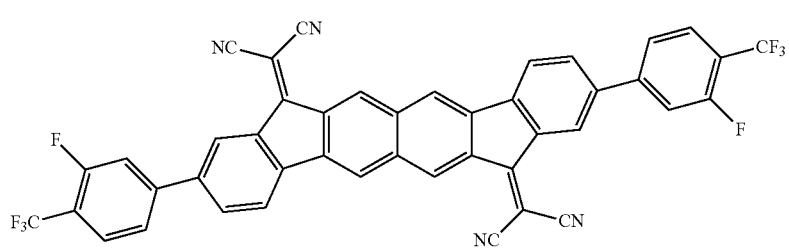
(A'-48)
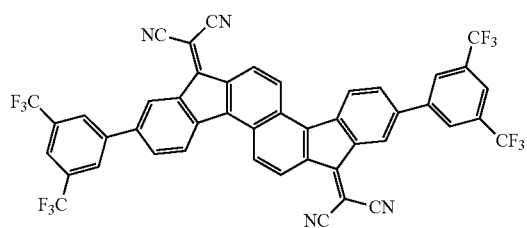
(A'-49)
(A'-50)
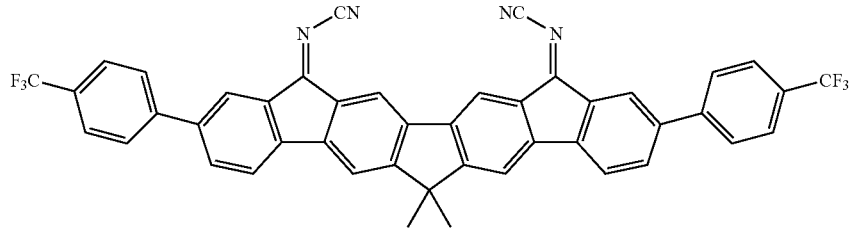
(A'-51)
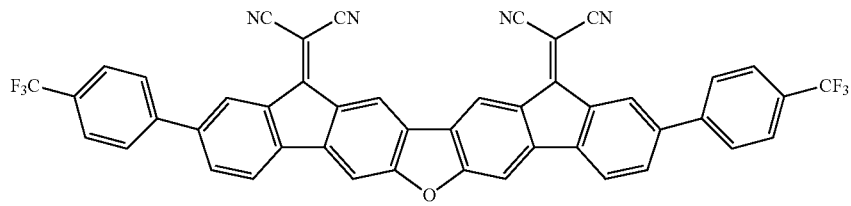
(A'-52)
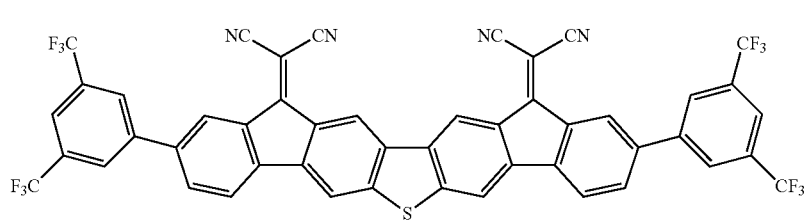
(A'-53)
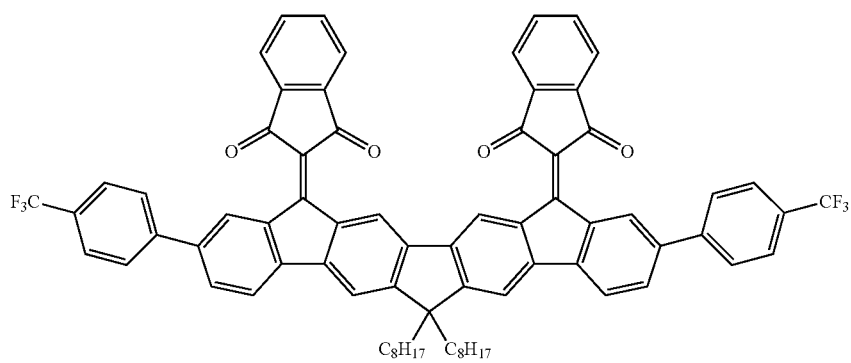
(A'-54)

-continued
(A'-55)
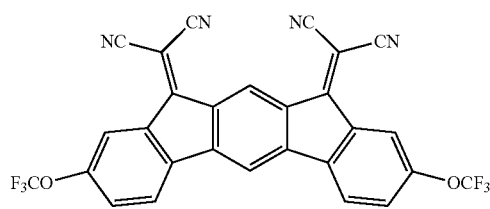
(A'-56)
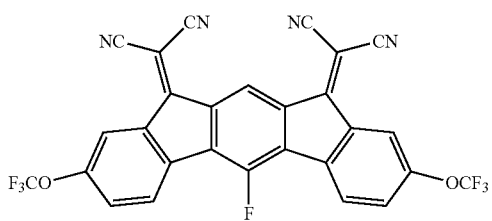
(A'-57)
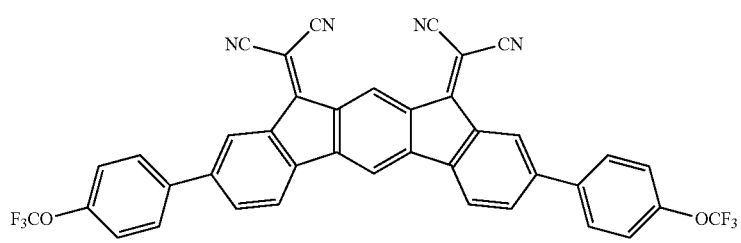
(A'-58)
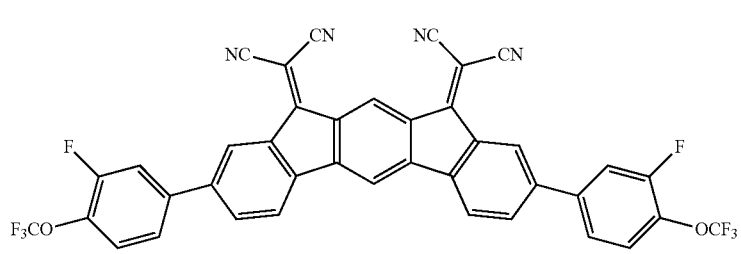
(A'-59)
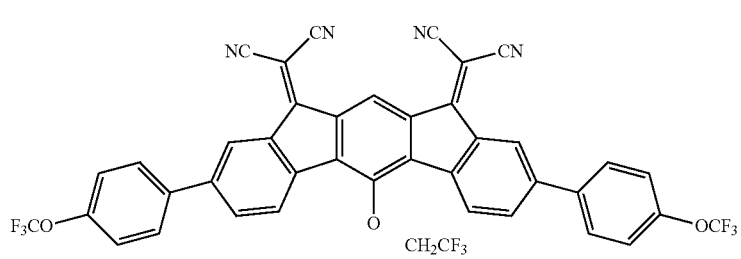
(A'-60)
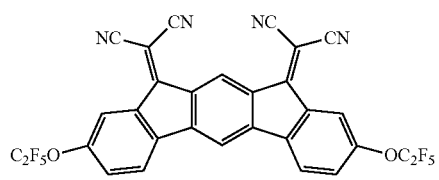
(A'-61)
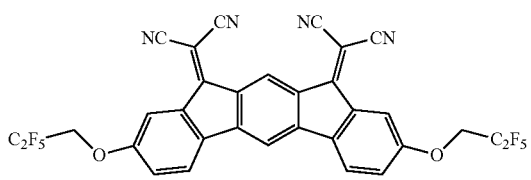
(A'-62)
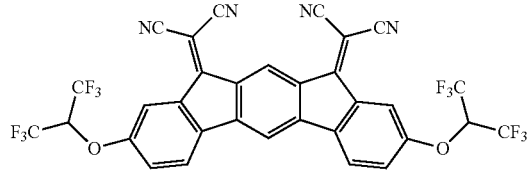
(A'-63)
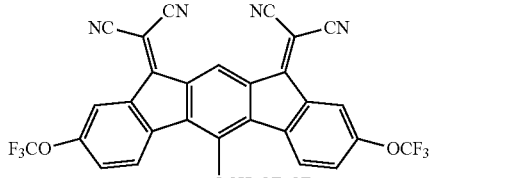
(A'-64)
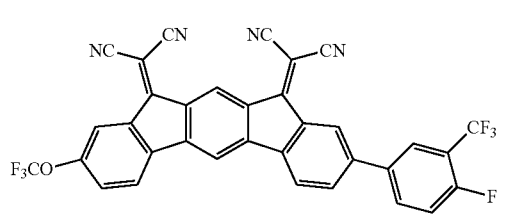
(A'-65)
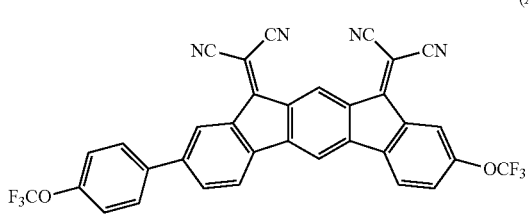

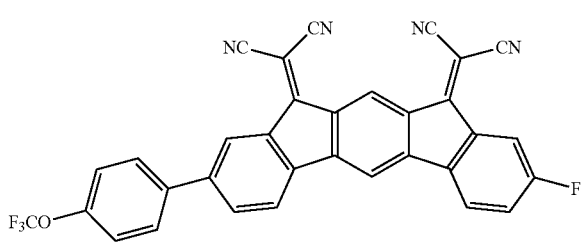

(A'-66)

N/P Doping

The carrier injecting properties of the hole transporting layer and the electron transporting layer can be controlled, as described in JP 3695714B, by the doping (n) with a donor material or the doping (p) with an acceptor material.

A typical example of the n-doping is an electron transporting material doped with a metal, such as Li and Cs, and a typical example of the p-doping is a hole transporting material doped with an acceptor material, such as $F_4TCNQ$ (2,3,5,6-Tetrafluoro-7,7,8,8-tetracyanoquinodimethane).

Space Layer

The space layer is a layer, for example, disposed between a fluorescent emitting layer and a phosphorescent emitting layer to prevent the diffusion of excitons generated in the phosphorescent emitting layer to the fluorescent emitting layer or to control the carrier balance. The space layer may be disposed between two or more phosphorescent emitting layers.

Since the space layer is disposed between the light emitting layers, a material combining the electron transporting ability and the hole transporting ability is preferably used as a material for the space layer. To prevent the diffusion of triplet energy in the adjacent phosphorescent emitting layer, the triplet energy of the material for the space layer is preferably 2.6 eV or more. The materials described above with respect to the hole transporting layer are usable as the material for the space layer. The material for organic EL device in an aspect of the invention may be used as the material for the space layer.

Blocking Layer

The organic EL device in an aspect of the invention preferably comprises a blocking layer, such as an electron blocking layer, a hole blocking layer, and a triplet blocking layer, which is disposed adjacent to a light emitting layer. The electron blocking layer is a layer which prevents the diffusion of electrons from a light emitting layer to a hole transporting layer. The hole blocking layer is a layer which prevents the diffusion of holes from a light emitting layer to an electron transporting layer. The material for organic EL device in an aspect of the invention may be used as the material for hole blocking layer.

The triplet blocking layer prevents the diffusion of triplet excitons generated in a light emitting layer to adjacent layers and has a function of confining the triplet excitons within a light emitting layer, thereby preventing the deactivation of energy on a molecule other than the emitting dopant of triplet excitons, for example, on a molecule in an electron transporting layer.

If a phosphorescent device having a triplet blocking layer satisfies the following energy relationship:

$$E^T_d < E^T_{TB}$$

wherein $E^T_d$ is the triplet energy of a phosphorescent dopant in a light emitting layer and $E^T_{TB}$ is the triplet energy of a compound forming the triplet blocking layer, the triplet excitons of phosphorescent dopant are energetically confined (not move into other molecules). Therefore, the energy deactivation process other than the emission on the phosphorescent dopant may be prevented, thereby enabling the emission with high efficiency. However, even in case of satisfying the relationship of $E^T_d < E^T_{TB}$, the triplet excitons may move into other molecules if the energy difference ($\Delta E^T = E^T_{TB} - E^T_d$) is small, because the energy difference $\Delta E^T$ may be overcome by the absorption of the ambient heat energy when a device is operated at around room temperature as generally employed in practical operation. As compared with the fluorescent emission, the phosphorescent emission is likely to be affected by the endothermic diffusion of excitons because the lifetime of triplet excitons is longer. Therefore, as for the energy difference $\Delta E^T$, the larger as compared with the heat energy of room temperature, the better, i.e., the energy difference $\Delta E^T$ is more preferably 0.1 eV or more and particularly preferably 0.2 eV or more. In fluorescent devices, the material for organic EL device in an aspect of the invention is usable as the material for triplet blocking layer of the TTF device described in WO 2010/134350A1.

The electron mobility of the material for the triplet blocking layer is preferably $10^{-6}$ cm$^2$/Vs or more at an electric field strength of 0.04 to 0.5 MV/cm. There are several methods for measuring the electron mobility of organic material, for example, Time of Flight method. In the present invention, the electron mobility is determined by an impedance spectroscopy.

The electron mobility of the electron injecting layer is preferably $10^{-6}$ cm$^2$/Vs or more at an electric field strength of 0.04 to 0.5 MV/cm. Within the above range, the injection of electrons from the cathode to the electron transporting layer is promoted and the injection of electrons to the adjacent blocking layer and the light emitting layer is also promoted, thereby enabling to drive a device at lower voltage.

Each layer of the organic EL device in an aspect of the invention may be formed by any of known methods such as a vacuum vapor deposition method and a spin coating method, although not particularly limited thereto. The organic thin-film layer comprising the compound in another aspect of the invention is formed by a known method such as a vacuum vapor deposition method, a molecular beam epitaxy method (MBE method) and a coating method using a solution of the compound of the invention in a solvent, for example, a dipping method, a spin coating method, a casting method, a bar coating method and a roll coating method.

The thickness of each organic thin film layer in the organic EL device in an aspect of the invention is not particularly limited and preferably several nanometers to 1

μm because an excessively small thickness may cause defects, such as pin holes, and an excessively large thickness may require a high applied voltage to reduce the efficiency. The layer comprising the compound in an aspect of the invention, particularly the light emitting layer, is preferably formed by forming a solution containing the compound of the invention and another material, such as a dopant, into a film.

Examples of the film-forming method include known coating methods, and preferably a spin coating method, a casting method, a microgravure coating method, a gravure coating method, a bar coating method, a roll coating method, a slit coating method, a wire bar coating method, a clip coating method, a spray coating method, a screen printing method, a flexographic printing method, an off-set printing method, an ink-jet printing method, and a nozzle printing method. When a pattern is formed, a screen printing method, a flexographic printing method, an off-set printing method, and an ink-jet printing method are preferred. The film formation by these methods can be made under the conditions well known by a skilled person.

After coating, the solvent is removed by heating (250° C. or below) and drying under vacuum, and the irradiation of light and the high temperature heating exceeding 250° C. for polymerization reaction are not needed. Therefore, the deterioration of the device in its performance due to the irradiation of light and the high temperature heating exceeding 250° C. can be prevented.

The film-forming solution contains at least one compound in an aspect of the invention and may further contain another material, for example, a hole transporting material, an electron transporting material, a light emitting material, an acceptor material, a solvent, and an additive, such as a stabilizer.

The film-forming solution may contain an additive for controlling the viscosity and/or surface tension, for example, a thickener (a high molecular weight compound, etc.), a viscosity depressant (a low molecular weight compound, etc.) and a surfactant. In addition, an antioxidant not adversely affecting the performance of the organic EL device, for example, a phenol antioxidant and a phosphine antioxidant, may be included so as to improve the storage stability.

The content of the compound in an aspect of the invention in the film-forming solution is preferably 0.1 to 15% by mass and more preferably 0.5 to 10% by mass based on the total amount of the film-forming solution.

Examples of the high molecular weight compound usable as the thickener include an insulating resin, such as polystyrene, polycarbonate, polyarylate, polyester, polyamide, polyurethane, polysulfone, polymethyl methacrylate, polymethyl acrylate, cellulose, and a copolymer thereof, a photoconductive resin, such as poly-N-vinylcarbazole and polysilane; and an electroconductive resin, such as polythiophene and polypyrrole.

Examples of the solvent for the film-forming solution include a chlorine-containing solvent, such as chloroform, methylene chloride, 1,2-dichloroethane, 1,1,2-trichloroethane, chlorobenzene, and o-dichlorobenzene; an ether solvent, such as tetrahydrofuran, dioxane, dioxolane, and anisole; an aromatic hydrocarbon solvent, such as toluene and xylene; an aliphatic hydrocarbon solvent, such as cyclohexane, methylcyclohexane, n-pentane, n-hexane, n-heptane, n-octane, n-nonane, and n-decane; a ketone solvent, such as acetone, methyl ethyl ketone, cyclohexanone, benzophenone, and acetophenone; an ester solvent, such as ethyl acetate, butyl acetate, ethyl cellosolve acetate, methyl benzoate, and phenyl acetate; a polyhydric alcohol and its derivatives, such as ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerin, and 1,2-hexanediol; an alcoholic solvent, such as methanol, ethanol, propanol, isopropanol, and cyclohexanol; a sulfoxide solvent, such as dimethyl sulfoxide; and an amide solvent, such as N-methyl-2-pyrrolidone and N,N-dimethylformamide. These solvents may be used alone or in combination of two or more.

Of the above solvents, in view of solubility, uniform film formation, viscosity, etc., preferred are the aromatic hydrocarbon solvent, the ether solvent, the aliphatic hydrocarbon solvent, the ester solvent and the ketone solvent, and more preferred are toluene, xylene, ethylbenzene, diethylbenzene, trimethylbenzene, n-propylbenzene, isopropylbenzene, n-butylbenzene, isobutylbenzene, 5-butylbenzene, n-hexylbenzene, cyclohexylbenzene, 1-methylnaphthalene, tetralin, 1,3-dioxane, 1,4-dioxane, 1,3-dioxolane, anisole, ethoxybenzene, cyclohexane, bicyclohexyl, cyclohexenylcyclohexanone, n-heptylcyclohexane, n-hexylcyclohexane, decalin, methyl benzoate, cyclohexanone, 2-propylcyclohexanone, 2-heptanone, 3-heptanone, 4-heptanone, 2-octanone, 2-nonanone, 2-decanone, dicyclohexyl ketone, acetophenone, and benzophenone.

The organic electroluminescence device in an aspect of the invention is usable in electronic equipment, for example, as display parts, such as organic EL panel module, display devices of television sets, mobile phones, personal computer, etc., and light emitting sources of lighting equipment and vehicle lighting equipment.

EXAMPLES

The present invention will be described in more detail with reference to the examples. However, it should be noted that the scope of the present invention is not limited thereto.

Synthesis Example 1 (Synthesis of Compound 1)

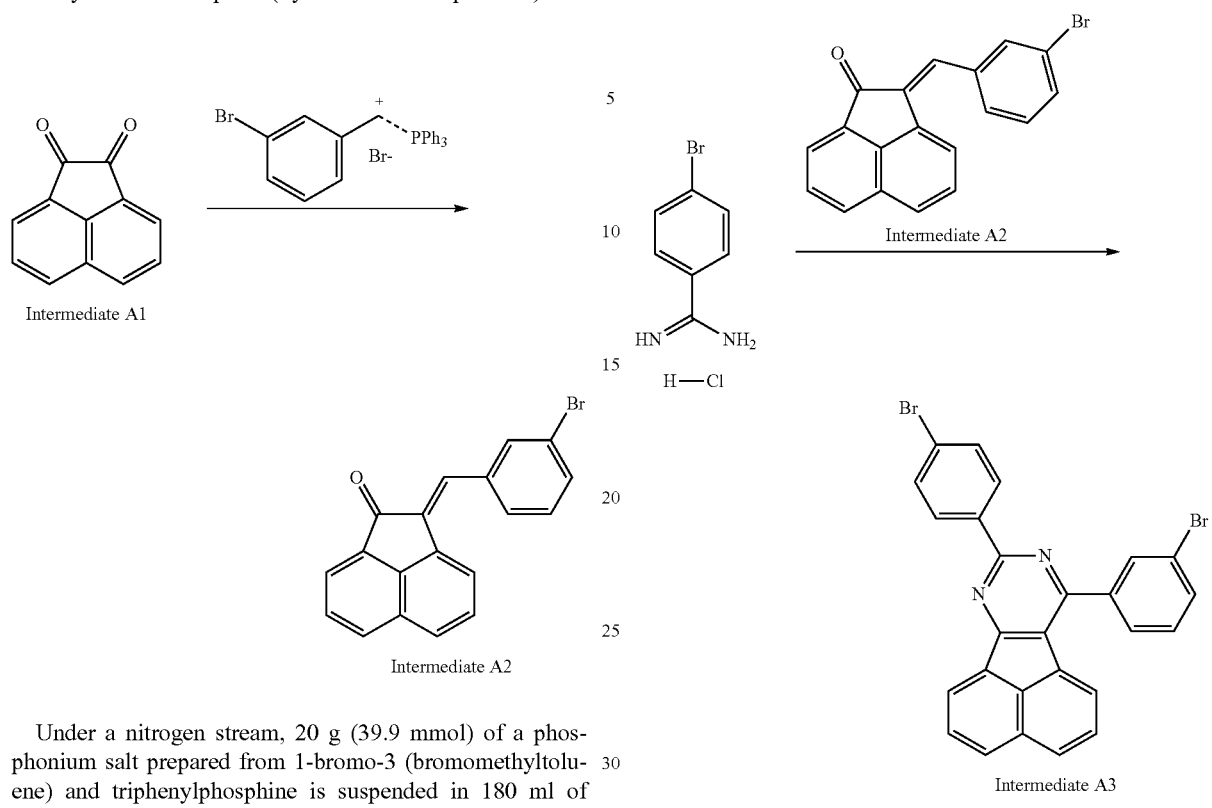

Under a nitrogen stream, 20 g (39.9 mmol) of a phosphonium salt prepared from 1-bromo-3 (bromomethyltoluene) and triphenylphosphine is suspended in 180 ml of ethanol. After adding 55 ml of a 0.001 mmol/ml ethanol solution of EtONa, the obtained mixture was stirred at room temperature for 10 min. After adding 4.01 g (22.0 mmol) of acenaphthoquinone (intermediate (A1)), the mixture was stirred at room temperature for 15 min. After adding 120 ml of ion-exchanged water, the stirring was further continued. After allowing to cool, the suspended matter was removed by filtration. The filtrate was washed with a small portion of ethanol and purified by silica gel column chromatography (ethyl acetate/hexane=1/9) to obtain the intermediate (A2) in a yield of 4.76 g.

Into 160 ml of ethanol, 1.712 g (8.602 mmol) of 4-bromobenzamidine hydrochloride was added and then 0.822 g (20.56 mmol) of sodium hydroxide was added. After further adding 2.62 g (7.82 mmol) of the intermediate (A2), the resultant mixture was refluxed for 5 h. After allowing to cool, the mixture was further cooled by ice. The precipitate was removed by filtration and the filtrate was washed with cooled water and then cooled ethanol. The solvent was removed under reduced pressure to obtain the intermediate (A3) in a yield of 1.78 g.

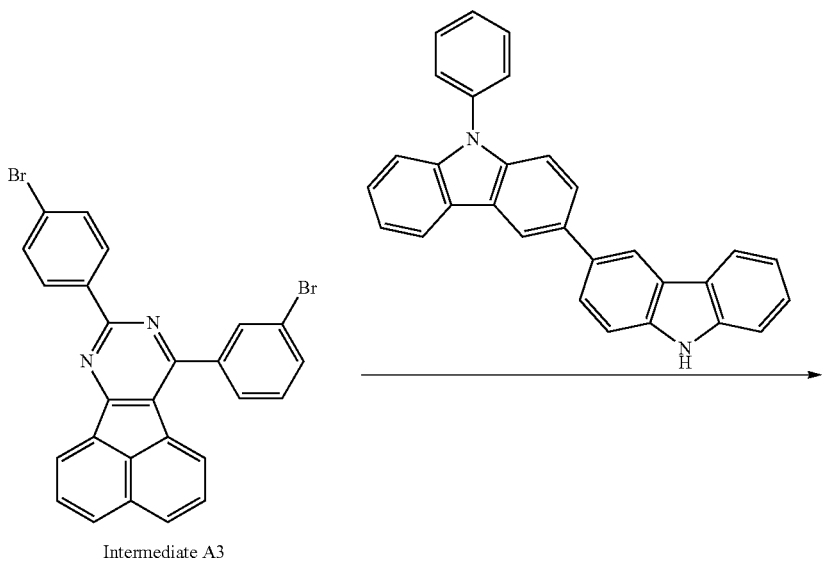

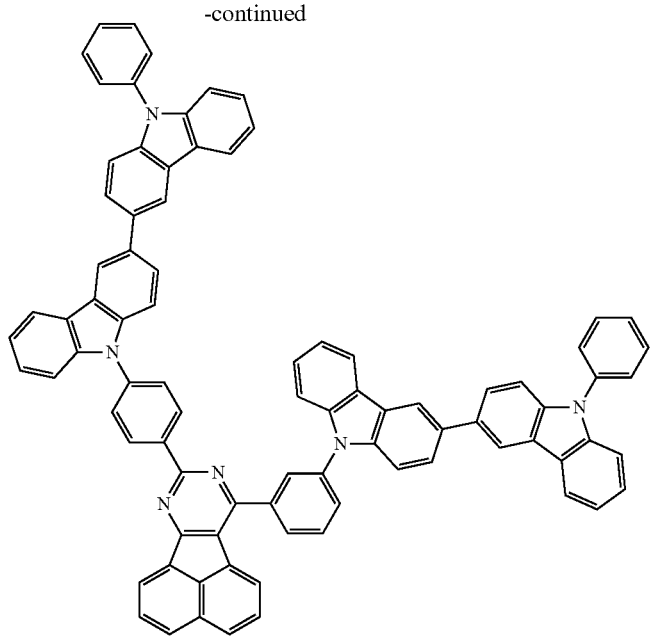

Compound 1

Under a nitrogen stream, a mixture of 1.542 g (3.0 mmol) of the intermediate (A3), 2.57 g (6.29 mmol) of 3-(9H-carbazole-3-yl)-9-phenyl-carbazole, 0.055 g (0.06 mmol) of tris(dibenzylideneacetone)dipalladium (0), 0.035 g (0.06 mmol) of xantphos, 0.875 g (8.92 mmol) of sodium tert-butoxide, and 57 ml of dehydrated xylene was refluxed under heating for 8 h. The insoluble was removed by filtration. The filtrate was passed through 60 ml of silica gel (eluent: toluene) to remove the catalyst residue. The eluted toluene solution was concentrated and 190 ml of methanol was added to precipitate a crude product, which was then purified by silica gel column chromatography (eluent: $CH_2Cl_2$/hexane=1/1) to obtain the compound 1 in a yield of 1.1 g.

The result of FD-MS (Field Desorption Mass Spectrometry) analysis is shown below.

FD-MS: calcd for $C_{86}H_{52}N_6$=1168.
found m/z=1168 ($M^+$).

Figure 2:
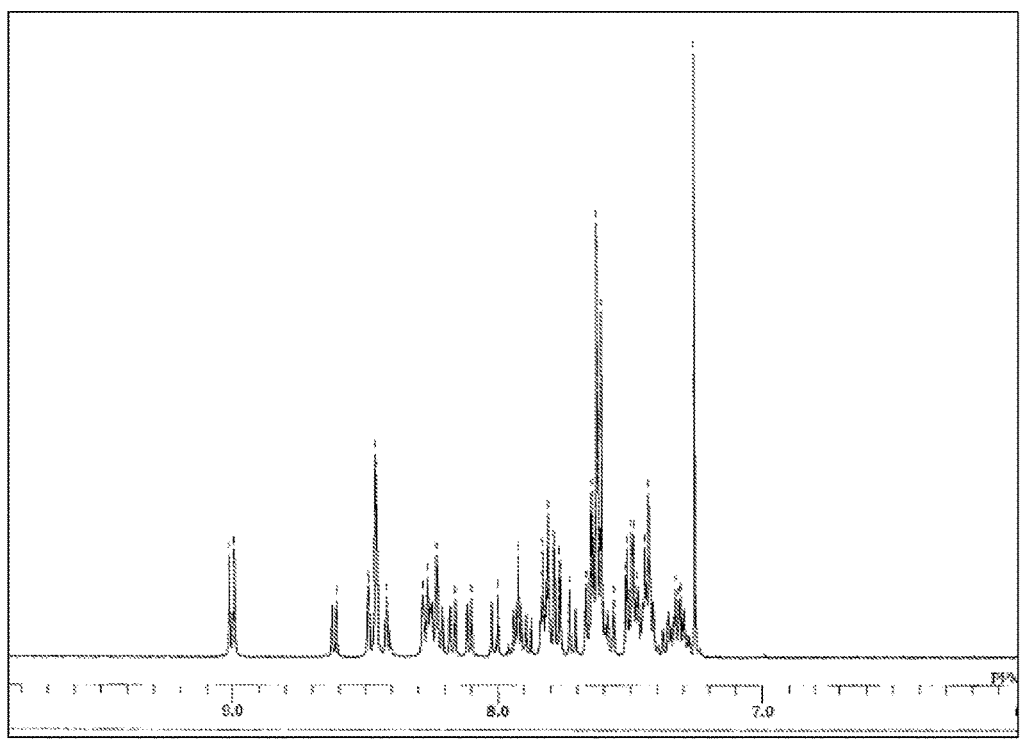
FIG. 2 is a $^1$H-NMR chart of the compound 1 obtained in Synthesis Example 1.

The $^1$H-NMR ($CDCl_3$) chart of the compound 1 is shown in FIG. 2.

Synthesis Example 2 (Synthesis of Compound 2)

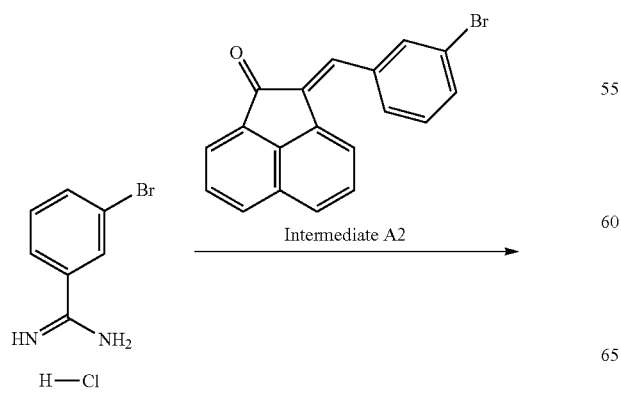

Intermediate A2

-continued

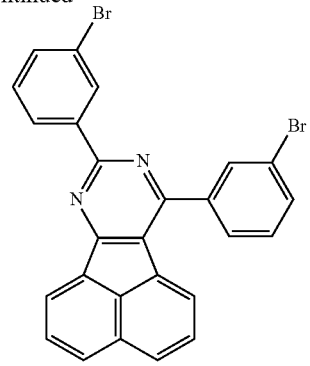

Intermediate A4

In the same manner as in the synthesis of the intermediate (A3) of Synthesis Example 1 except for using 2.583 g (12.98 mmol) of 3-bromobenzamidine hydrochloride in place of 4-bromobenzamidine hydrochloride, the intermediate (A4) was obtained in a yield of 2.91 g.

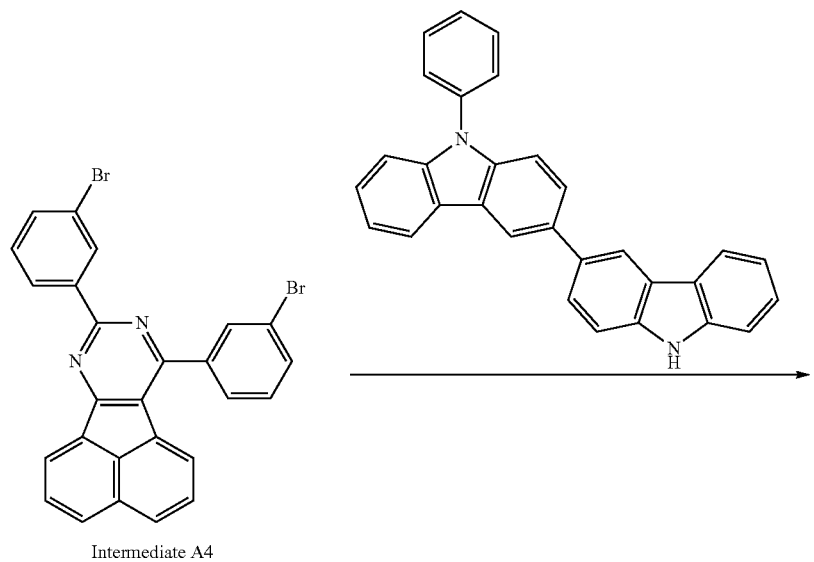

Intermediate A4

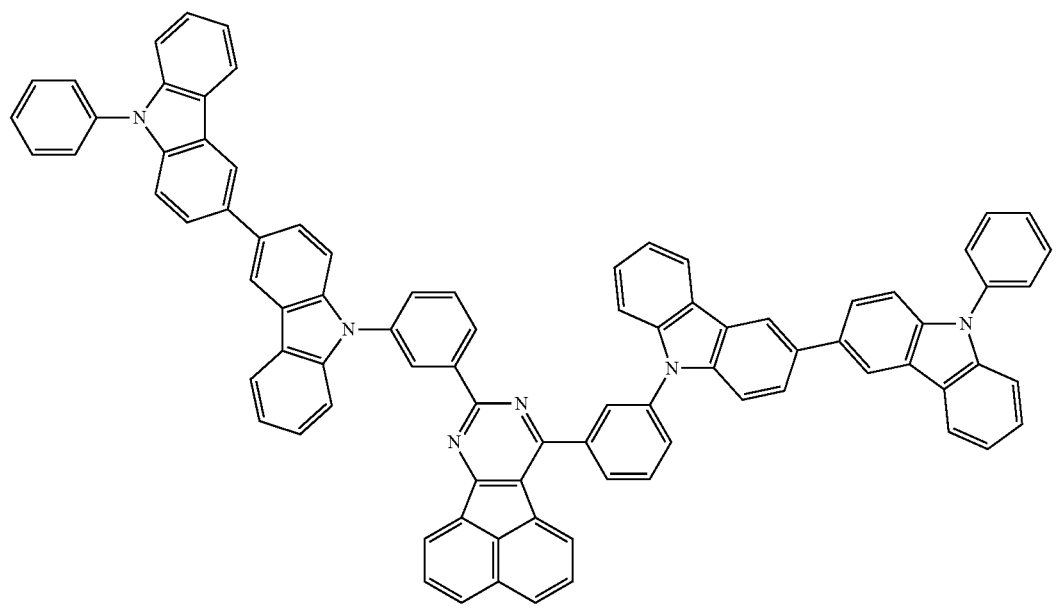

Compound 2

In the same manner as in the synthesis of the compound 1 of Synthesis Example 1 except for using 1.76 g (3.145 mmol) of the intermediate (A4) in place of the intermediate (A3), the compound 2 was obtained in a yield of 1.98 g.

The result of FD-MS analysis is shown below.

FD-MS: calcd for $C_{86}H_{52}N_6$=1168.

found m/z=1168 (M$^+$).

Figure 3:
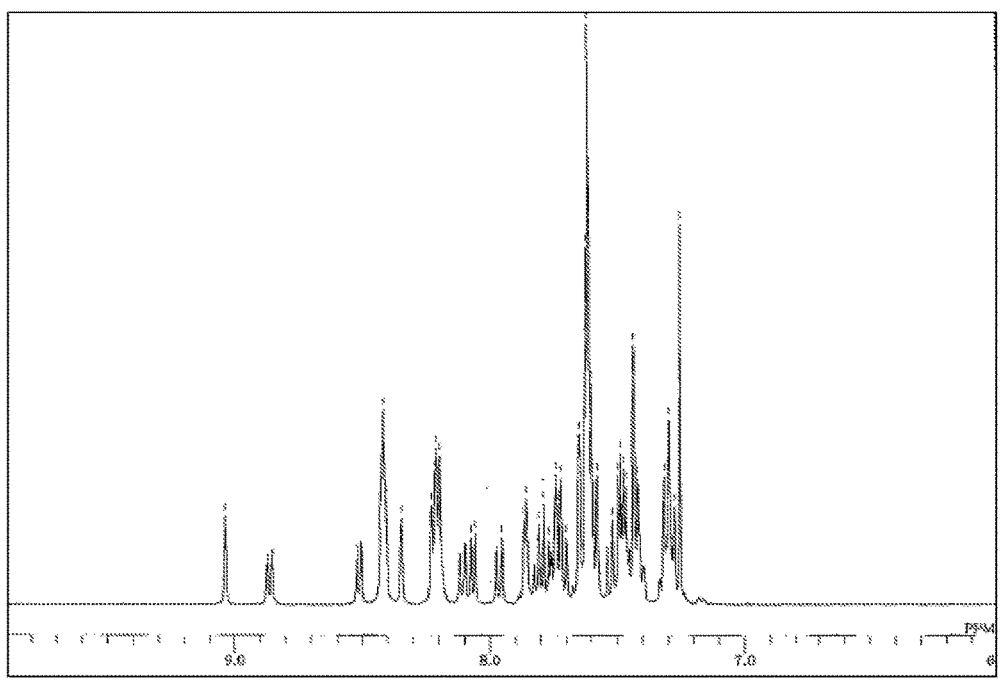
FIG. 3 is a H-NMR chart of the compound 2 obtained in Synthesis Example 2.

The $^1$H-NMR (CDCl$_3$) chart of the compound 2 is shown in FIG. 3.

Synthesis Example 3 (Synthesis of Compound 3)

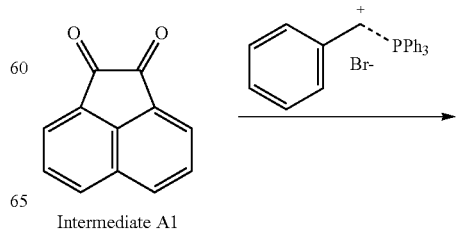

Intermediate A1

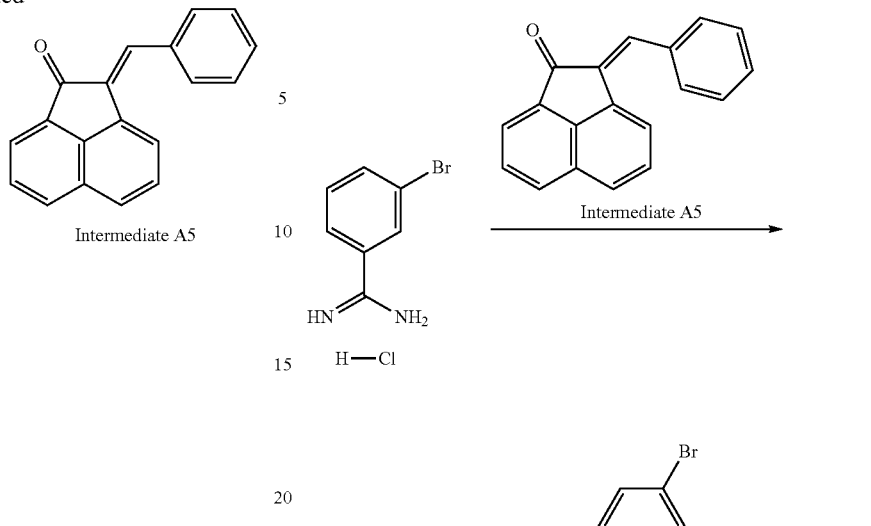

Under a nitrogen stream, 15.9 g (34.62 mmol) of the above phosphonium salt and 6.307 g (34.62 mmol) of acenaphthoquinone (intermediate (A1)) were dissolved in 400 ml of dichloromethane. A solution of 2.905 g (69.24 mmol) of lithium hydroxide monohydrate in 120 ml of ion-exchanged water was added to the dichloromethane solution and the resultant solution was vigorously stirred at room temperature for 15 min. The dichloromethane layer was washed with 500 ml of ion-exchanged water. After drying the organic layer over anhydrous magnesium sulfate, the solvent was evaporated off under reduced pressure. The residue was purified by silica gel column chromatography (eluent: ethyl acetate/hexane=1/9) to obtain the intermediate (A5) in a yield of 7.75 g.

In the same manner as in the synthesis of the intermediate (A3) of Synthesis Example 1 except for using 3 g (11.70 mmol) of the intermediate (A5) in place of the intermediate (A2) and using 3.03 g (12.87 mmol) of 3-benzamidine hydrochloride in place of 4-bromobenzamidine hydrochloride, the intermediate (A6) was obtained in a yield of 1.79 g.

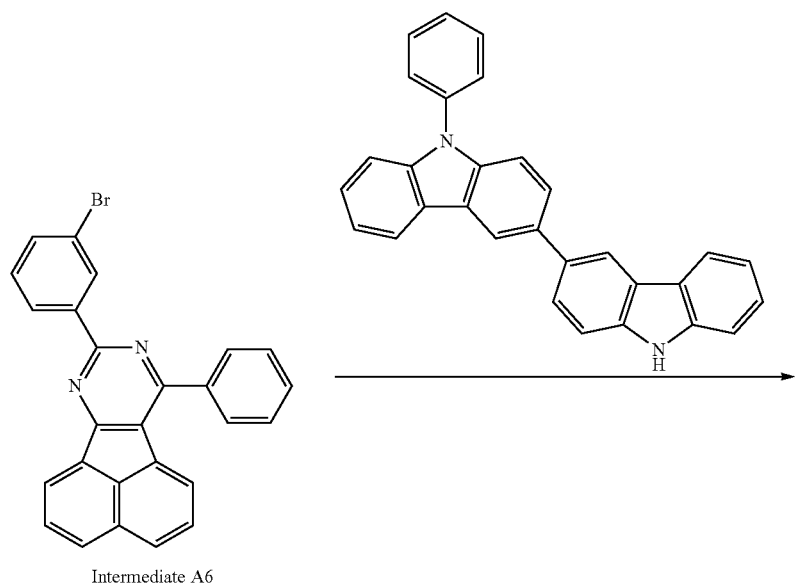

-continued

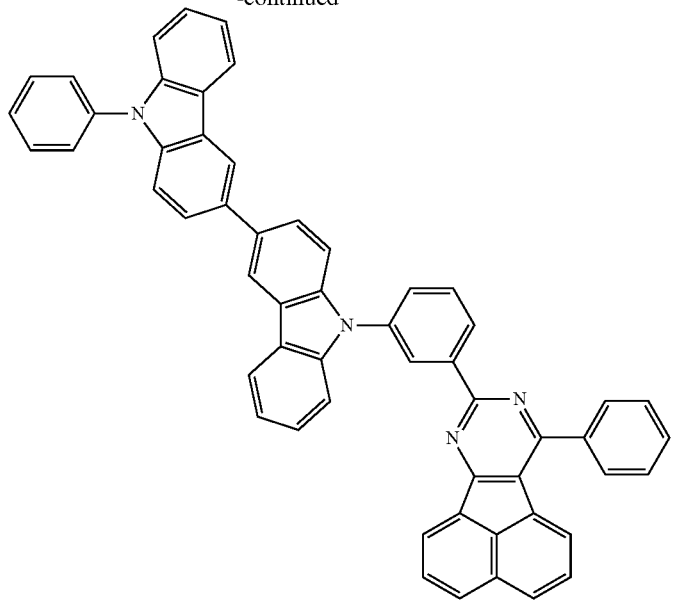

Compound 3

In the same manner as in the synthesis of the compound 1 of Synthesis Example 1 except for using 1.676 g (3.85 mmol) of the intermediate (A6) in place of the intermediate (A3), the compound 3 was obtained in a yield of 2.21 g.

The result of FD-MS is shown below.

FD-MS: calcd for $C_{56}H_{34}N_4$=762.

found m/z=762 (M$^+$).

Figure 4:
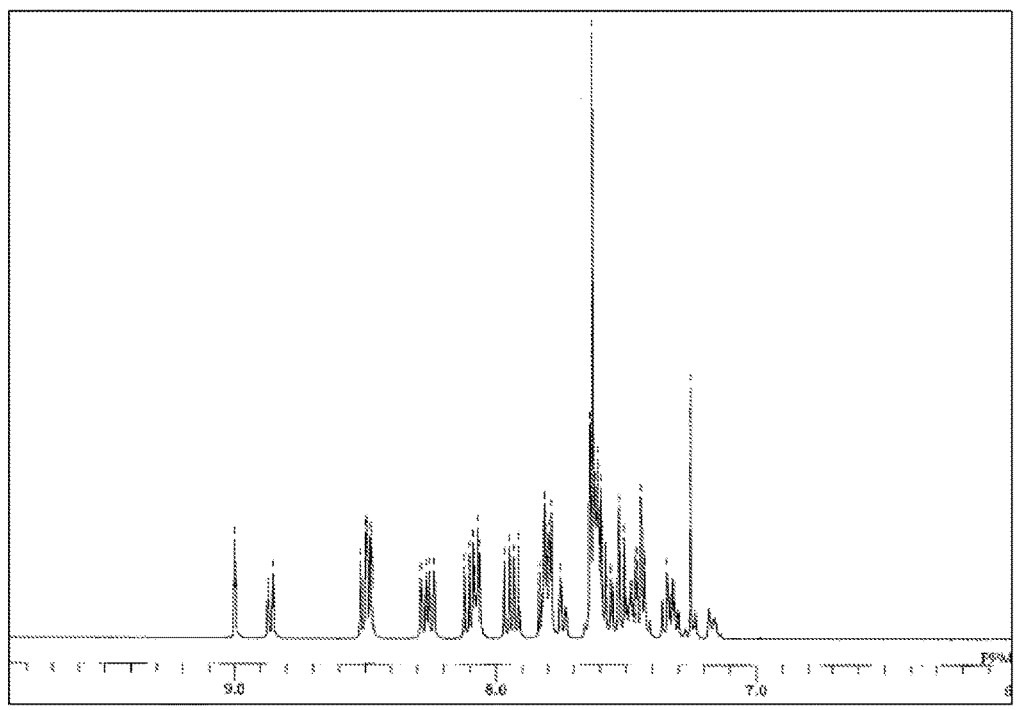
FIG. 4 is a $^1$H-NMR chart of the compound 3 obtained in Synthesis Example 3.

The $^1$H-NMR (CDCl$_3$) chart of the compound 3 is shown in FIG. 4.

Example 1

A glass substrate of 25 mm×25 mm×1.1 mm thickness having an ITO transparent electrode (product of Geomatec Company) was cleaned by ultrasonic cleaning in isopropyl alcohol for 5 min and then UV ozone cleaning for 5 min.

Clevious AI4083 (tradename) manufactured by Heraeus as a hole transporting material was spin-coated on the ITO substrate to form a hole transporting layer with a thickness of 30 nm. Thereafter, the unnecessary portion was removed by acetone and then a base substrate was produced by baking in air for 10 min on a hot plate at 200° C.

Separately, a 1.6% by mass toluene solution containing the compound 1 obtained in Synthesis Example 1 as a host material and the following compound D-1 as a dopant material was prepared in a mixing ratio of compound 1:compound D-1=95:5 by mass. The toluene solution was spin-coated on the base substrate into a thickness of 50 nm. Thereafter, the unnecessary portion was removed by toluene and then a coat-laminated substrate with a light emitting layer was obtained by drying under heating at 150° C. on a hot plate. The film-forming operations for forming the light emitting layer were all conducted in a glove box under a nitrogen atmosphere.

The coat-laminated substrate was conveyed into a vapor deposition chamber and the following compound ET-1 as an electron transporting material was vapor-deposited into a thickness of 50 nm to form an electron transporting layer. Then, lithium fluoride was vapor-deposited into a thickness of 1 nm and aluminum was vapor-deposited into a thickness of 80 nm. After completing all the vapor deposition processes, the substrate with laminated films was sealed with a bored glass in a glove box under a nitrogen atmosphere to produce an organic EL device.

By driving on a direct current, the obtained organic EL device was allowed to emit light to measure the external quantum efficiency at a current density of 10 mA/cm$^2$. The result was shown in Table 1.

Example 2

An organic EL device was produced in the same manner as in Example 1 except for using the compound 2 obtained in Synthesis Example 2 as a host material in place of the compound 1.

The obtained organic EL device was evaluated in the same manner as in Example 1 and the result thereof is shown in Table 1.

Comparative Example 1

An organic EL device was produced in the same manner as in Example 1 except for using the following comparative compound C-1 as a host material in place of the compound 1.

The obtained organic EL device was evaluated in the same manner as in Example 1 and the result thereof is shown in Table 1.

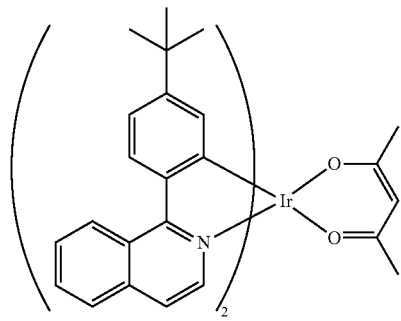

D-1

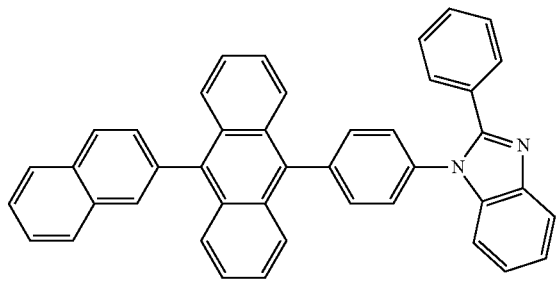

ET-1

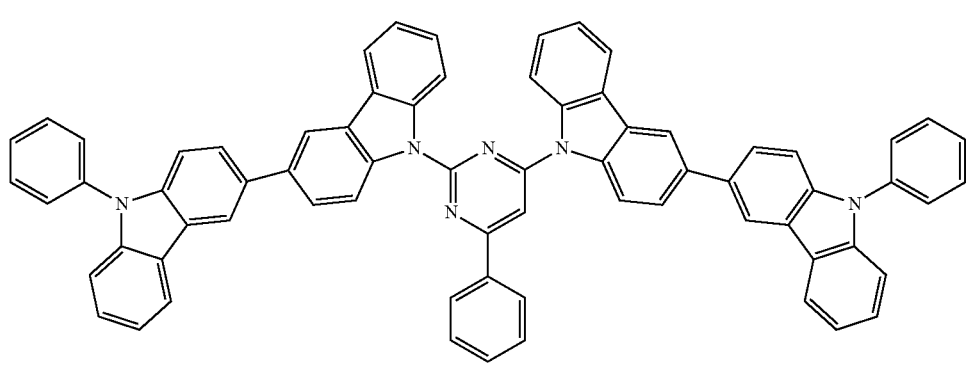

C-1

TABLE 1

|  | Host material in light emitting layer | external quantum efficiency (EQE) % |
| --- | --- | --- |
| Example 1 | Compound 1 | 9.8 |
| Example 2 | Compound 2 | 8.7 |
| Comparative Example 1 | Comparative compound C-1 | 3.4 |

Example 3

A glass substrate of 25 mm×25 mm×1.1 mm thickness having an ITO transparent electrode (product of Geomatec Company) was cleaned by ultrasonic cleaning in isopropyl alcohol for 5 min and then UV ozone cleaning for 5 min.

The cleaned glass substrate having a transparent electrode line (130 nm thick) was mounted to a substrate holder of a vacuum vapor deposition apparatus. The compound HT-1 as a first hole transporting material was vapor-deposited so as to cover the transparent electrode to form a first hole transporting layer with a thickness of 45 nm. Successively after forming the first hole transporting layer, the compound HT-2 as a second hole transporting material was vapor-deposited to form a second hole transporting layer with a thickness of 10 nm.

On the second hole transporting layer, the compound 3 obtained in Synthesis Example 3 as a host material and the compound D-1 as a phosphorescent emitting material were vapor co-deposited to form a phosphorescent emitting layer with a thickness of 40 nm. The concentration of the compound D-1 in the light emitting layer was 5.0% by mass. The co-deposited film works as a light emitting layer.

Successively after forming the light emitting layer, the compound ET-1 as an electron transporting material was vapor-deposited into a film with a thickness of 40 nm. The compound ET-1 film works as an electron transporting layer.

Then, LiF was vapor-deposited into a film with a thickness of 1 nm at a film-forming speed of 0.1 Å/min to form an electron injecting electrode (cathode). On the LiF film, metallic Al was vapor-deposited to form a metallic cathode with a thickness of 80 nm, thereby obtaining an organic EL device.

By driving on a direct current, the obtained organic EL device was allowed to emit light to measure the external quantum efficiency at a current density of 10 mA/cm$^2$. The result was shown in Table 2.

Comparative Example 2

An organic EL device was produced in the same manner as in Example 3 except for using the following comparative compound C-2 as a host material in place of the compound 3.

The obtained organic EL device was evaluated in the same manner as in Example 3 and the result thereof is shown in Table 2.

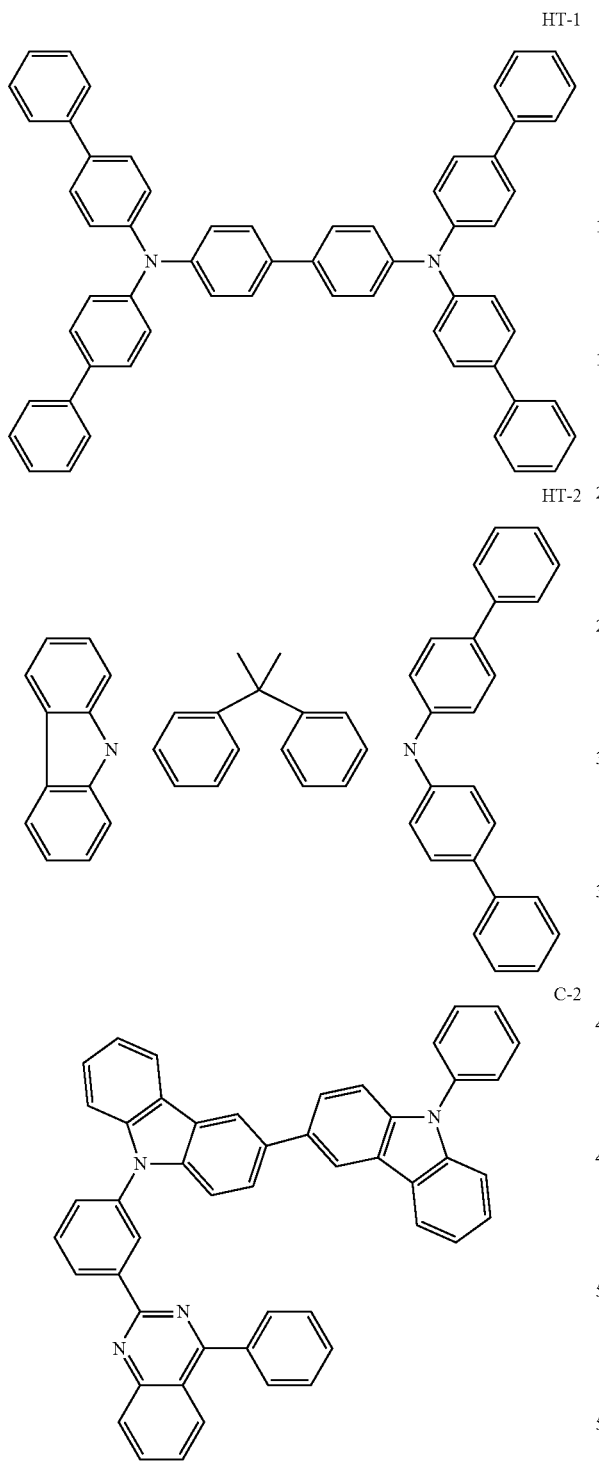

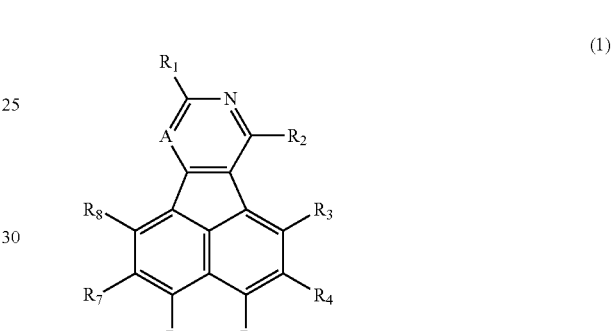

The compound comprising the azafluoranthene skeleton in an aspect of the invention broadens the nitrogen-containing conjugated system to make the transport of electrons and holes efficient. It has been found that the efficiency of an organic EL device using the compound is further improved by this effect.

REFERENCE SIGNS LIST

1: Organic EL device
2: Substrate
3: Anode
4: Cathode
5: Light emitting layer
6: Anode-side organic thin film layer
7: Cathode-side organic thin film layer
10: Emission unit

What is claimed is:

1. A compound represented by formula (1):

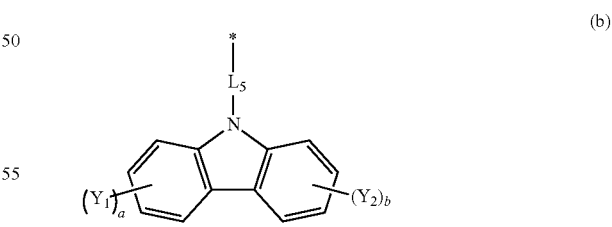

wherein:
A represents N;
one of $R_1$ or $R_2$ is represented by formula (b) and the other is selected from the group consisting of a hydrogen atom, an aryl group having 6 to 60 ring carbon atoms, and a heteroaryl group having 5 to 60 ring carbon atoms;
$R_3$, $R_4$, $R_6$, $R_7$, and $R_8$ are hydrogen,
$R_5$ is selected from the group consisting of a hydrogen atom, an aryl group having 6 to 60 ring carbon atoms, and a heteroaryl group having 5 to 60 ring carbon atoms (b)

wherein:
* represents a bonding site to the carbon atom in formula (1) to which $R_1$ or $R_2$ is bonded;
$L_5$ represents a single bond, or an arylene group having 6 to 60 ring carbon atoms;
$L_5$ may have a substituent selected from an alkyl group having 1 to 20 carbon atoms, a cycloalkyl group having 3 to 18 ring carbon atoms, an alkoxy group having 1 to 20 carbon atoms, a cycloalkoxy group having 3 to 20

TABLE 2

| | Host material in light emitting layer | external quantum efficiency (EQE) % |
|---|---|---|
| Example 3 | Compound 3 | 15.6 |
| Comparative Example 2 | Comparative compound C-2 | 14.0 | ring carbon atoms, an aryloxy group having 6 to 18 ring carbon atoms, an amino group, a silyl group, a fluorine atom, a cyano group, an aryl group having 6 to 18 ring carbon atoms, and a heteroaryl group having 5 to 18 ring atoms;

$Y_1$ and $Y_2$ each represent a hydrogen atom, an aryl group having 6 to 60 ring carbon atoms, or a heteroaryl group having 5 to 60 ring carbon atoms;

a and b each represent an integer of 1 or 2, and when a or b is 2, groups $Y_1$ or groups $Y_2$ may be the same or different; and adjacent groups $Y_1$ and adjacent groups $Y_2$ may be bonded to each other to form a saturated or unsaturated ring, respectively; and groups selected from $R_1$ to $R_8$ which are bonded to adjacent carbon atoms may be bonded to each other to form a saturated or unsaturated ring structure.

2. The compound according to claim 1, formula (b) is represented by formula (c):

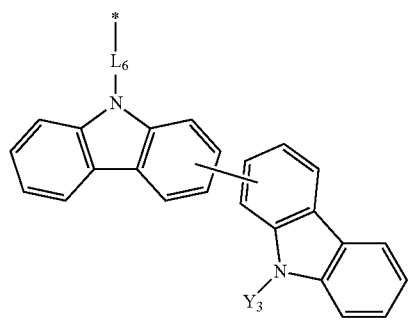

(c)

wherein:
* represents a bonding site to the carbon atom in formula (1) to which each of $R_1$ to $R_8$ is bonded;
$L_6$ represents a single bond, or an arylene group having 6 to 60 ring carbon atoms;
$L_6$ may have a substituent selected from an alkyl group having 1 to 20 carbon atoms, a cycloalkyl group having 3 to 18 ring carbon atoms, an alkoxy group having 1 to 20 carbon atoms, a cycloalkoxy group having 3 to 20 ring carbon atoms, an aryloxy group having 6 to 18 ring carbon atoms, an amino group, a silyl group, a fluorine atom, a cyano group, an aryl group having 6 to 18 ring carbon atoms, and a heteroaryl group having 5 to 18 ring atoms; and
$Y_3$ represents a hydrogen atom, an aryl group having 6 to 60 ring carbon atoms, or a heteroaryl group having 5 to 60 ring carbon atoms.

3. The compound according to claim 2, wherein two selected from $R_1$, $R_2$ and $R_5$ are represented by formula (c).

4. The compound according to claim 1, wherein formula (1) is represented by formula (3):

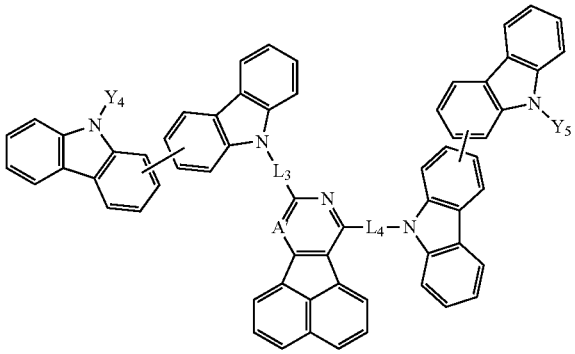

(3)

wherein:
A' represents N;
$L_3$ and $L_4$ each independently represent a single bond, an arylene group having 6 to 60 ring carbon atoms, or a heteroarylene group having 5 to 60 ring atoms;
$L_3$ and $L_4$ may have a substituent independently selected from an alkyl group having 1 to 20 carbon atoms, a cycloalkyl group having 3 to 18 ring carbon atoms, an alkoxy group having 1 to 20 carbon atoms, a cycloalkoxy group having 3 to 20 ring carbon atoms, an aryloxy group having 6 to 18 ring carbon atoms, an amino group, a silyl group, a fluorine atom, a cyano group, an aryl group having 6 to 18 ring carbon atoms, and a heteroaryl group having 5 to 18 ring atoms; and
$Y_4$ and $Y_5$ each independently represent a hydrogen atom or a substituent.

5. The compound according to claim 4, wherein formula (3) is represented by formula (6):

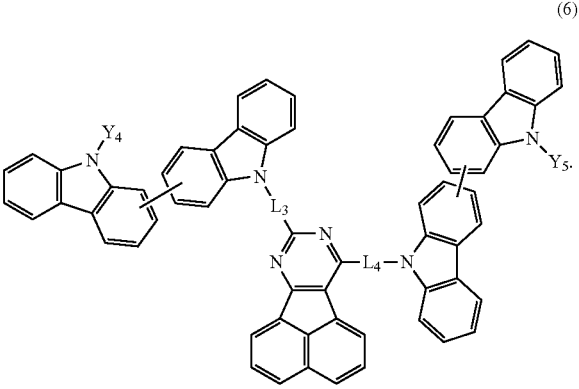

(6)

6. The compound according to claim 1, wherein three selected from $R_1$, $R_2$ and $R_5$ are represented by formula (b).

7. The compound according to claim 1, wherein formula (1) is represented by formula (7):

(7)

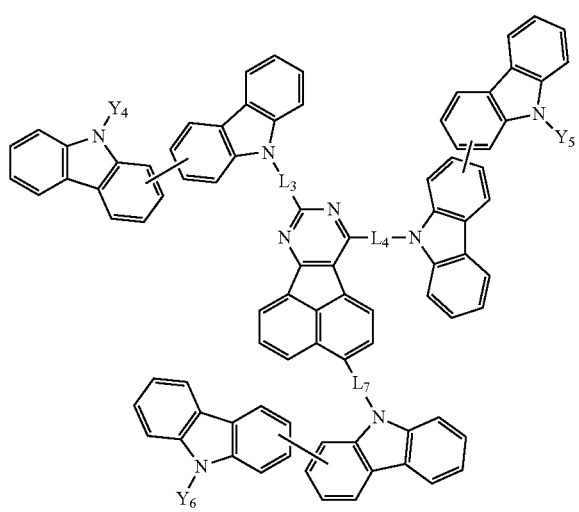

wherein:
  $L_3$, $L_4$, and $L_7$ each independently represent a single bond, an arylene group having 6 to 60 ring carbon atoms, or a heteroarylene group having 5 to 60 ring atoms;
  $L_3$, $L_4$, and $L_7$ may have a substituent independently selected from an alkyl group having 1 to 20 carbon atoms, a cycloalkyl group having 3 to 18 ring carbon atoms, an alkoxy group having 1 to 20 carbon atoms, a cycloalkoxy group having 3 to 20 ring carbon atoms, an aryloxy group having 6 to 18 ring carbon atoms, an amino group, a silyl group, a fluorine atom, a cyano group, an aryl group having 6 to 18 ring carbon atoms, and a heteroaryl group having 5 to 18 ring atoms; and
  $Y_4$, $Y_5$, and $Y_6$ each independently represent a hydrogen atom or a substituent.

8. A material comprising the compound according to claim 1.

9. An organic electroluminescence device comprising an organic thin film layer between a cathode and an anode, wherein the organic thin film layer comprises one or more layers comprising a light emitting layer, and at least one layer of the organic thin film layer comprises the compound according to claim 1.

10. The organic electroluminescence device according to claim 9, wherein the light emitting layer comprises the compound.

11. The organic electroluminescence device according to claim 9, wherein the organic electroluminescence device further comprises a first charge transporting layer between the anode and the light emitting layer, and the first charge transporting layer comprises the compound.

12. The organic electroluminescence device according to claim 9, wherein the organic electroluminescence device further comprises a second charge transporting layer between the cathode and the light emitting layer, and the second charge transporting layer comprises the compound.

13. The organic electroluminescence device according to claim 9, wherein the light emitting layer comprises a phosphorescent emitting material.

14. The organic electroluminescence device according to claim 9, wherein the light emitting layer comprises a fluorescent emitting material.

15. The organic electroluminescence device according to claim 13, wherein the phosphorescent material is an ortho-metallated complex comprising a metal selected from the group consisting of iridium (Ir), osmium (Os), and platinum (Pt).

16. The organic electroluminescence device according to claim 15, wherein the phosphorescent emitting material is a complex represented by formula (X) or (Y):

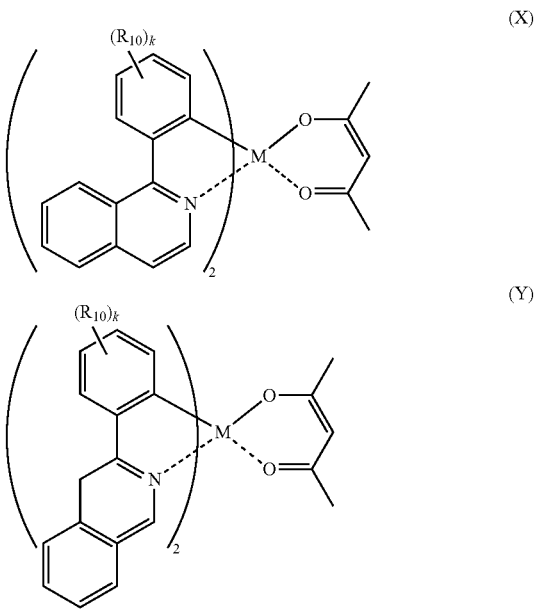

wherein $R_{10}$ represents a hydrogen atom or a substituent, k represents an integer of 1 to 4, and M represents Ir, Os, or Pt.

17. An electronic equipment comprising the organic electroluminescence device according to claim 9.

* * * * *